US011810650B2

(12) United States Patent
van der Lelie et al.

(10) Patent No.: US 11,810,650 B2
(45) Date of Patent: Nov. 7, 2023

(54) RATIONAL DESIGN OF MICROBIAL-BASED BIOTHERAPEUTICS

(71) Applicant: Gusto Global, LLC, Charlotte, NC (US)

(72) Inventors: Daniel van der Lelie, Chapel Hill, NC (US); Safiyh Taghavi, Chapel Hill, NC (US)

(73) Assignee: Gusto Global, LLC, Charlotte, NC (US)

( * ) Notice: Subject to any disclaimer, the term of this patent is extended or adjusted under 35 U.S.C. 154(b) by 752 days.

(21) Appl. No.: 16/592,070

(22) Filed: Oct. 3, 2019

(65) Prior Publication Data

US 2020/0027524 A1 Jan. 23, 2020

Related U.S. Application Data

(63) Continuation of application No. PCT/US2018/025805, filed on Apr. 3, 2018.

(60) Provisional application No. 62/620,752, filed on Jan. 23, 2018, provisional application No. 62/545,733, filed on Aug. 15, 2017, provisional application No. 62/481,062, filed on Apr. 3, 2017.

(51) Int. Cl.
| | | |
|---|---|---|
| *G06G 7/48* | (2006.01) | |
| *G16B 5/00* | (2019.01) | |
| *A61K 35/741* | (2015.01) | |
| *A61K 35/742* | (2015.01) | |
| *G16B 35/20* | (2019.01) | |
| *G16B 35/00* | (2019.01) | |
| *G16B 99/00* | (2019.01) | |

(52) U.S. Cl.
CPC .............. *G16B 5/00* (2019.02); *A61K 35/741* (2013.01); *A61K 35/742* (2013.01); *G16B 35/00* (2019.02); *G16B 35/20* (2019.02); *G16B 99/00* (2019.02)

(58) Field of Classification Search
None
See application file for complete search history.

(56) References Cited

U.S. PATENT DOCUMENTS

| 9,415,079 | B2 | 8/2016 | Honda et al. |
| 9,433,652 | B2 | 9/2016 | Honda et al. |
| 9,801,933 | B2 | 10/2017 | Honda et al. |
| 2010/0254948 | A1 | 10/2010 | Giuliani et al. |
| 2014/0147425 | A1 | 5/2014 | Henn et al. |
| 2014/0199281 | A1 | 7/2014 | Henn et al. |
| 2015/0190435 | A1 | 7/2015 | Henn et al. |
| 2016/0030494 | A1 | 2/2016 | Henn et al. |
| 2016/0193258 | A1* | 7/2016 | Berry .................. A61K 9/0053 424/93.3 |
| 2016/0206666 | A1 | 7/2016 | Falb et al. |
| 2016/0235792 | A1 | 8/2016 | Berry et al. |
| 2016/0263166 | A1 | 9/2016 | Elinav et al. |
| 2016/0271188 | A1 | 9/2016 | Berry et al. |
| 2017/0067065 | A1 | 3/2017 | Falb et al. |
| 2019/0070225 | A1 | 3/2019 | Strandwitz et al. |
| 2019/0282628 | A1* | 9/2019 | Falb ...................... A61K 35/74 |
| 2020/0016256 | A1 | 1/2020 | Gilbert et al. |
| 2020/0027524 | A1 | 1/2020 | van der Lelie et al. |
| 2020/0087660 | A1 | 3/2020 | Sommer et al. |
| 2020/0206284 | A1 | 7/2020 | Schneider et al. |

FOREIGN PATENT DOCUMENTS

| EP | 3606325 | | 2/2020 |
| WO | 2011094027 | A1 | 8/2011 |
| WO | 2011151941 | A1 | 12/2011 |
| WO | 2013080561 | A1 | 6/2013 |
| WO | 2014060555 | A1 | 4/2014 |
| WO | 2014075745 | A1 | 5/2014 |
| WO | 2014076246 | A1 | 5/2014 |
| WO | 2014107619 | A1 | 7/2014 |
| WO | 2014121298 | A2 | 8/2014 |
| WO | 2014121302 | A2 | 8/2014 |
| WO | 2014145958 | A2 | 9/2014 |
| WO | 2014159287 | A1 | 10/2014 |

(Continued)

OTHER PUBLICATIONS

Magnúsdóttir, Stefanía, et al. "Generation of genome-scale metabolic reconstructions for 773 members of the human gut microbiota." Nature biotechnology 35.1 (2017): 81-89.*

Kim, Won Jun, Hyun Uk Kim, and Sang Yup Lee. "Current state and applications of microbial genome-scale metabolic models." Current Opinion in Systems Biology 2 (2017): 10-18.*

Prasad, Kailash. "Secoisolariciresinol diglucoside from flaxseed delays the development of type 2 diabetes in Zucker rat." Journal of laboratory and clinical medicine 138.1 (2001): 32-39.*

Orth, Jeffrey D., Ines Thiele, and Bernhard Ø. Palsson. "What is flux balance analysis?." Nature Biotechnology 28.3 (2010): 245.*

(Continued)

*Primary Examiner* — Anna Skibinsky
(74) *Attorney, Agent, or Firm* — NK Patent Law

(57) ABSTRACT

Methods are provided for the rational design of stable communities of microbes for benefiting the health of a host organism, including human and/or animal health. The methods describe design of microbial consortia based on providing and/or complementing key functionalities lacking or underrepresented in the microbiome of an organism having a disorder or disease as compared to healthy subjects. The consortia are designed to possess metabolic interdependencies for improved engrafting, stability and performance of the consortium. Compositions that include the designed microbial consortia are provided for treatment of disorders/diseases involving chronic inflammation, infection, and the combination of chronic inflammation and infection including inflammatory bowel disease and related disorders. The compositions are also broadly applicable for the treatment of neurological, metabolic and oncology-related conditions.

10 Claims, 11 Drawing Sheets

Specification includes a Sequence Listing.

(56) References Cited

FOREIGN PATENT DOCUMENTS

| | | | |
|---|---|---|---|
| WO | 2014197562 | A1 | 12/2014 |
| WO | 2015006355 | A2 | 1/2015 |
| WO | 2015077794 | A1 | 5/2015 |
| WO | 2015095241 | A2 | 6/2015 |
| WO | 2015156419 | A1 | 10/2015 |
| WO | 2015184441 | A2 | 12/2015 |
| WO | 2016086205 | A2 | 6/2016 |
| WO | 2016086206 | A1 | 6/2016 |
| WO | 2016086208 | A1 | 6/2016 |
| WO | 2016086209 | A1 | 6/2016 |
| WO | 2016086210 | A1 | 6/2016 |
| WO | 2016102950 | A1 | 6/2016 |
| WO | 2016120475 | A1 | 8/2016 |
| WO | 2016183577 | A1 | 11/2016 |
| WO | 2016191356 | A1 | 12/2016 |
| WO | 2016201114 | A1 | 12/2016 |
| WO | 2016203217 | A1 | 12/2016 |
| WO | 2016203218 | A1 | 12/2016 |
| WO | 2016203220 | A1 | 12/2016 |
| WO | 2016203221 | A1 | 12/2016 |
| WO | 2016203223 | A1 | 12/2016 |
| WO | 2017008026 | A1 | 1/2017 |
| WO | 2017042347 | A1 | 3/2017 |
| WO | 2017075098 | A1 | 5/2017 |
| WO | 2017085518 | A1 | 5/2017 |
| WO | 2017085520 | A1 | 5/2017 |
| WO | 2017089794 | A1 | 6/2017 |
| WO | 2017089795 | A1 | 6/2017 |
| WO | 2017091783 | A2 | 6/2017 |
| WO | 2017148596 | A1 | 9/2017 |
| WO | 2017197364 | A1 | 11/2017 |
| WO | 2017210428 | A1 | 12/2017 |
| WO | 2017218680 | A1 | 12/2017 |
| WO | 2018011593 | A1 | 1/2018 |
| WO | 2018011594 | A1 | 1/2018 |
| WO | 2018026913 | A1 | 2/2018 |
| WO | 2018065628 | A2 | 4/2018 |
| WO | 2018071532 | A1 | 4/2018 |
| WO | 2018071534 | A1 | 4/2018 |
| WO | 2018071536 | A1 | 4/2018 |
| WO | 2018071537 | A1 | 4/2018 |
| WO | 2018081550 | A1 | 5/2018 |
| WO | 2018112360 | A1 | 6/2018 |
| WO | 2018112363 | A1 | 6/2018 |
| WO | 2018112364 | A1 | 6/2018 |
| WO | 2018112365 | A2 | 6/2018 |
| WO | 2018187272 | A1 | 10/2018 |
| WO | 2019036510 | A1 | 2/2019 |
| WO | 2019070913 | A1 | 4/2019 |

OTHER PUBLICATIONS

Berry, David, and Stefanie Widder. "Deciphering microbial interactions and detecting keystone species with co-occurrence networks." (Frontiers in Microbiology, vol. 5 (2014) pp. 1-14).*

Shaw, Grace Tzun-Wen, Yueh-Yang Pao, and Daryi Wang. "MetaMIS: a metagenomic microbial interaction simulator based on microbial community profiles." BMC bioinformatics 17.1 (2016): 1-12.*

Allen-Vercoe, Emma et al.: "*Fusobacterium nucleatum*—An emerging gut pathogen?", Gut Microbes, 2:5, 294-298; Sep./Oct. 2011, 7 pages total.

Arpaia, Nicholas et al.: "Metabolites produced by commensal bacteria promote peripheral regulatory T-cell generation", Research Letter, Dec. 19/26, 2013, vol. 504, Nature, 451-455, 6 pages total.

Atarashi, Koji et al.: "Treg induction by a rationally selected mixture of Clostridia strains from the human microbiota", Research Letter, Nature, vol. 500, Aug. 8, 2013, 232-235, 7 pages total.

Bansal, Tarun et al.: "The bacterial signal indole increases epithelial-cell tight-junction resistance and attenuates indicators of inflammation", PNAS, Jan. 5, 2010, vol. 107, No. 1, 228-233, 6 pages total.

Baron, Ellen Jo: "Bilophila wadsworthia: a Unique Gram-negative Anaerobic Rod", Anaerobe (1997) 3, 83-86, 4 pages total.

Ben-Othman, Nouha et al.: "Long-Term GABA Administration Induces Alpha Cell-Mediated Beta-like Cell Neogenesis", Cell, 168, 73-85, Jan. 12, 2017, 25 pages total.

Bhattacharjee, Surjyadipta et al.: "Alzheimer'sdiseaseandthemicrobiome", Frontiers in Cellular Neuroscience, Sep. 2013, vol. 7, Article 153, 4 pages total.

Bhowmik, Shiva et al.: "Structure and functional characterization of a bile acid 7alpha dehydratase BaiE in secondary bile acid synthesis", Proteins, 2016, 84:316-331, 16 pages total.

Boulangé, Claire L. et al.: "Impact of the gut microbiota on inflammation, obesity, and metabolic disease", Boulangé et al. Genome Medicine (2016) 8:42, 12 pages total.

Canani, Roberto Berni et al.: "Lactobacillus rhamnosus GG-supplemented formula expands butyrate-producing bacterial strains in food allergic infants", The ISME Journal (2016) 10, 742-750, 9 pages total.

Cassidy, Aedin et al.: "Isoflavones, lignans and stilbenes—origins, metabolism and potential importance to human health", J Sci Food Agric, 80:1044-1062 (2000), 19 pages total.

Chang, Pamela V. et al.: "The microbial metabolite butyrate regulates intestinal macrophage function via histone deacetylase inhibition", PNAS, Feb. 11, 2014, vol. 111, No. 6, 2247-2252, 6 pages total.

Chehoud, Christel et al.: "A Fungal Signature in the Gut Microbiota of Pediatric Patients with Inflammatory Bowel Disease", Inflamm Bowel Dis., Aug. 2015, 21(8): 1948-1956, 19 pages total.

Chimerel, Catalin et al.: "Bacterial Metabolite Indole Modulates Incretin Secretion from Intestinal Enteroendocrine L Cells", Cell Reports, 9, 1202-1208, Nov. 20, 2014, 8 pages total.

Clavel, Thomas et al.: "Phylogeny of human intestinal bacteria that activate the dietary lignan secoisolariciresinol diglucoside", FEMS Microbiol Ecol, 55 (2006) 471-478, 8 pages total.

Clavel, Thomas et al.: "*Clostridium saccharogumia* sp. nov. and *Lactonifactor longoviformis* gen. nov., sp. nov., two novel human faecal bacteria involved in the conversion of the dietary phytoestrogen secoisolariciresinol diglucoside", Systematic and Applied Microbiology, 30 (2007) 16-26, 11 pages total.

Da Silva, Sofia M. et al.: "Hydrogen as an energy source for the human pathogen Bilophila wadsworthia", Antonie van Leeuwenhoek (2008) 93:381-390, 10 pages total.

De Souza, Heitor S. P. et al.: "Immunopathogenesis of IBD: current state of the art", Nature Reviews, Gastroenterology & Hepatology, vol. 13, Jan. 2016, 13-27, 15 pages total.

Downes, J. et al.: "*Dialister invisus* sp. nov., isolated from the human oral cavity", International Journal of Systematic and Evolutionary Microbiology (2003), 53, 1937-1940, 4 pages total.

Duboc, Henri et al.: "Connecting dysbiosis, bile-acid dysmetabolism and gut inflammation in inflammatory bowel diseases", Gut, 2013, 62:531-539, 9 pages total.

El Mouzan, Mohammad et al.: "Fungal Microbiota Profile in Newly Diagnosed Treatment-naïve Children with Crohn's disease", Journal of Crohn's and Colitis, 2017, 1-7, 7 pages total.

Erickson, Alison R. et al.: "Integrated Metagenomics/Metaproteomics Reveals Human Host-Microbiota Signatures of Crohn's Disease", PLOS ONE, Nov. 2012, vol. 7, Issue 11, 14 pages total.

Eun, Chang Soo et al.: "Induction of Bacterial Antigen-Specific Colitis by a Simplified Human Microbiota Consortium in Gnotobiotic Interleukin-10-/-Mice", Infection and Immunity, Jun. 2014, vol. 82, No. 6, 2239-2246, 8 pages total.

Evrensel, Alper et al.: "The Gut-Brain Axis: The Missing Link in Depression", Clinical Psychopharmacology and Neuroscience, 2015, 13(3):239-244, 6 pages total.

Fasano, Alessio: "Zonulin and Its Regulation of Intestinal Barrier Function: The Biological Door to Inflammation, Autoimmunity, and Cancer", Physiol Rev, 91: 151-175, 2011, 25 pages total.

Field, Des et al.: "Bioengineering Lantibiotics for Therapeutic Success", Frontiers in Microbiology, Nov. 2015, vol. 6, Article 1363, 8 pages total.

Finlay, B. Brett: "The Role of the Microbiome in Early Childhood", Feb. 17, 2017, AAAS Annual Meeting, Abstract, 2 pages total.

(56) References Cited

OTHER PUBLICATIONS

Fong, Fiona Long Yan et al.: "Immunomodulation of Lactobacillus rhamnosus GG (LGG)-derived soluble factors on antigenpresenting cells of healthy blood donors", Scientific Reports, Mar. 10, 2016, 6:22845, 8 pages total.
Furusawa, Yukihiro et al.: "Commensal microbe-derived butyrate induces the differentiation of colonic regulatory T cells", Nature, 2013, vol. 000, 8 pages total.
Geva-Zatorsky, Naama et al.: "Mining the Human Gut Microbiota for Immunomodulatory Organisms", Cell, 168, 928-943, Feb. 23, 2017, 28 pages total.
Gevers, Dirk et al.: "The Treatment-Naive Microbiome in New-Onset Crohn's Disease", Cell Host & Microbe, 15, 382-392, Mar. 12, 2014, 11 pages total.
Gevers, Dirk et al.: "A Microbiome Foundation for the Study of Crohn's Disease", Cell Host & Microbe, 21, Mar. 8, 2017, 4 pages total.
Giel, Jennifer L. et al.: "Metabolism of Bile Salts in Mice Influences Spore Germination in Clostridium difficile", PLoS ONE, Jan. 2010, vol. 5, Issue 1, e8740, 7 pages total.
Göker, Markus et al.: "Complete genome sequence of Odoribacter splanchnicus type strain (1651/6T)", Standards in Genomic Sciences (2011) 4:200-209, 10 pages total.
Goodman, Andrew L. et al.: "Identifying Genetic Determinants Needed to Establish a Human Gut Symbiont in Its Habitat", Cell Host & Microbe, 6, 279-289, Sep. 17, 2009, 11 pages total.
Goriely, Stanislas et al.: "How microorganisms tip the balance between interleukin-12 family members", Nature Reviews, Immunology, vol. 8, Jan. 2008, 81-86, 6 pages total.
Halfvarson, Jonas et al.: "Dynamics of the human gut microbiome in inflammatory bowel disease", Nature Microbiology, Feb. 13, 2017, vol. 2, Article No. 17004, 7 pages total.
Henry, Christopher S. et al.: "High-throughput generation, optimization and analysis of genome-scale metabolic models", Nature Biotechnology, vol. 28, No. 9, Sep. 2010, 977-982, 8 pages total.
Hoarau, G. et al.: "Bacteriome and Mycobiome Interactions Underscore Microbial Dysbiosis in Familial Crohn's Disease", American Society for Microbiology, mBio, Sep./Oct. 2016, vol. 7, Issue 5, e01250-16, 11 pages total.
Hohnadel, Dany et al.: "Specificity of Pyoverdine-Mediated Iron Uptake among Fluorescent Pseudomonas Strains", Journal of Bacteriology, Oct. 1988, p. 4865-4873, vol. 170, No. 10, 9 pages total.
Holmstrøm, Kim et al.: "*Subdoligranulum variabile* gen. nov., sp. nov. from human feces", Anaerobe, 10 (2004) 197-203, 8 pages total.
Hubbard, Troy D. et al.: "Indole and Tryptophan Metabolism: Endogenous and Dietary Routes to Ah Receptor Activation", Drug Metab Dispos, 43:1522-1535, Oct. 2015, 14 pages total.
Hubbard, Troy D. et al.: "Adaptation of the human aryl hydrocarbon receptor to sense microbiota-derived indoles", Scientific Reports, 5:12689, Aug. 3, 2015, 13 pages total.
Joossens, Marie et al.: "Dysbiosis of the faecal microbiota in patients with Crohn's disease and their unaffected relatives", Gut, 2011, 60:631-637, 7 pages total.
Kang, Dae-Joong et al.: "Clostridium scindens baiCD and baiH genes encode stereo-specific 7α/7β-hydroxy-3-oxo-Δ4-cholenoic acid oxidoreductases", Biochimica et Biophysica Acta, 1781 (2008) 16-25, 10 pages total.
Kang, Dongwan D. et al.: "MetaBAT, an efficient tool for accurately reconstructing single genomes from complex microbial communities", PeerJ, 3:e1165, Aug. 27, 2015, 15 pages total.
Kortman, Guus A.M. et al.: "Nutritional iron turned inside out: intestinal stress from a gut microbial perspective", FEMS Microbiol Rev, 38 (2014) 1202-1234, 33 pages total.
Li, Q. et al.: "The Microbiota-Gut-Brain Axis and Its Potential Therapeutic Role in Autism Spectrum Disorder", Neuroscience, 324 (2016) 131-139, 9 pages total.
Louis, Petra et al.: "Diversity,metabolismand microbial ecologyof butyrate-producing bacteria fromthe human large intestine", FEMS Microbiol Lett, 294 (2009) 1-8, 8 pages total.

Louis, Petra et al.: "Diversity of human colonic butyrate-producing bacteria revealed by analysis of the butyryl-CoA: acetate CoA transferase gene", Environmental Microbiology (2010) 12(2), 304 314, 11 pages total.
ISA/US, International Search Report and Written Opinin for PCT Patent Application No. PCT/US2021/054944, dated Feb. 25, 2022, 15 pages.
Van Der Lelie et al.: "Rationally designed bacterial consortia to treat chronic immune-mediated colitis and restore intestinal homeostasis", Nat Commun, May 28, 2021 (May 28, 2021), vol. 12, 3105, pp. 1-17.
ISA/US; International Search Report and Written Opinion for International Patent Application No. PCT/US2018/025805, dated Aug. 29, 2018, 18 pages.
WIPO; International Preliminary Report on Patentability for International Patent Application No. PCT/US2018/025805, dated Oct. 8, 2019, 12 pages.
Zitomersky, Naamah L. et al.: "Characterization of Adherent Bacteroidales from Intestinal Biopsies of Children and Young Adults with Inflammatory Bowel Disease", PLOS ONE, Jun. 2013, vol. 8, Issue 6, e63686, 11 pages total.
Zazzeroni, Raniero et al.: "Determination of γ-Aminobutyric Acid in Food Matrices by Isotope Dilution Hydrophilic Interaction Chromatography Coupled to Mass Spectrometry", Journal of Chromatographic Science, vol. 47, Aug. 2009, 564-568, 5 pages total.
Willing, Ben P. et al.: "A Pyrosequencing Study in Twins Shows That Gastrointestinal Microbial Profiles Vary With Inflammatory Bowel Disease Phenotypes", Gastroenterology, 2010, 139:1844-1854, 12 pages total.
Sokol, Harry et al.: "*Faecalibacterium prausnitzii* is an anti-inflammatory commensal bacterium identified by gut microbiota analysis of Crohn disease patients", PNAS, Oct. 28, 2008, vol. 105, No. 43, 16731-16736, 6 pages total.
Sellon, Rance K. et al.: "Resident Enteric Bacteria Are Necessary for Development of Spontaneous Colitis and Immune System Activation in Interieukin-10-Deficient Mice", Infection and Immunity, Nov. 1998, 5224-5231, vol. 66, No. 11, 8 pages total.
Rasad, Kailash, MD, PHD, FRCPC: "Reduction of Serum Cholesterol and Hypercholesterolemic Atherosclerosis in Rabbits by Secoisolariciresinol Diglucoside Isolated From Flaxseed", Circulation, 1999, 99:1355-1362, 9 pages total.
Eeckhaut, Venessa et al.: "*Anaerostipes butyraticus* sp. nov., an anaerobic, butyrate-producing bacterium from Clostridium cluster XIVa isolated from broiler chicken caecal content, and emended description of the genus *Anaerostipes*", International Journal of Systematic and Evolutionary Microbiology (2010), 60, 1108-1112, 5 pages total.
Canani, Roberto Berni et al.: "Extensively hydrolyzed casein formula containing Lactobacillus rhamnosus GG reduces the occurrence of other allergic manifestations in children with cow's milk allergy: 3-year randomized controlled trial", J Allergy Clin Immunol, Jun. 2017, vol. 139, Issue 6, 1906-1913, 12 pages total.
Bereswill, Stefan et al.: "Novel Murine Infection Models Provide Deep Insights into the "Ménage à Trois" of Campylobacter jejuni, Microbiota and Host Innate Immunity", PLoS ONE, Jun. 2011, vol. 6, Issue 6, e20953, 13 pages total.
Bansal, Tarun et al.: "Differential Effects of Epinephrine, Norepinephrine, and Indole on *Escherichia coli* O157:H7 Chemotaxis, Colonization, and Gene Expression", Infection and Immunity, Sep. 2007, 4597-1607, vol. 75, No. 9, 11 pages total.
Chen, J. et al.: "Exposure to flaxseed or its purified lignan during suckling inhibits chemically induced rat mammary tumorigenesis", Exp Biol Med (Maywood), Sep. 1, 2003, 228(8): 951-958, Abstract, 2 pages total.
Dehghan, P. et al.: "Inulin controls inflammation and metabolic endotoxemia in women with type 2 diabetes mellitus: a randomized-controlled clinical trial", Int J Food Sci Nutr., Feb. 2014, 65(1):117-123, Abstract, 2 pages total.
Endesielder, D. et al.: "Towards a functional hypothesis relating anti-islet cell autoimmunity to the dietary impact on microbial communities and butyrate production", Microbiome, Apr. 26, 2016, 4:17, 12 pages total.

(56) References Cited

OTHER PUBLICATIONS

Hazenberg, M. P. et al.: "Antibodies to Coprococcus comes in sera of patients with Crohn's disease. Isolation and purification of the agglutinating antigen tested with an ELISA technique", J Clin Lab Immunol, Jul. 1987, 23(3): 143-148, Abstract, 2 pages total.
CIPO, Office Action for corresponding Canadian Patent Application No. 3,058,943, dated Oct. 28, 2021, 17 pages.
EPO, Extended European Search Report in European Application No. 18781289.6 dated Dec. 17, 2020.
Sakamoto, et al, hsp60 and 16S rRNA gene sequence relationships among species of the genus *Bacteroides* with the finding that *Bacteroides suis* and *Bacteroides tectus* are heterotypic synonyms of *Bacteroides pyogenes*, International Journal of Systematic and Evolutionary Microbiology, 2010, pp. 2984-2990, vol. 60.
Singh, MD, Namita, et al, Multi-Cnter Experience of Vedolizumab Effectiveness in Pediatric Inflammatory Bowel Disease, Inflamm Bowel Dis, Sep. 2016, pp. 2121-2126, vol. 22, No. 9.
Fidder, H., et al, Long-Term Safety of Infliximab in the Treatment of Inflammatory Bowel Disease: A Single Center Cohort Study, Abstracts of ECCO Congress, Innsbruck, Austria, Mar. 1-3, 2007, p. 3, No. 007.
Guidi, Luisa, et al., Update on the management of inflammatory bowel disease: specific role of adalimumab, Clinical and Experimental Gastroenterology, 2011, pp. 163-172, vol. 4.
Canadian Intellectual Property Office, Examination Report in Canadian Application No. 3,058,943 dated Sep. 25, 2020.
Luft, Vivian C. et al.: "Chronic inflammation role in the obesity-diabetes association: a case-cohort study", Diabetology & Metabolic Syndrome, 2013, 5:31, 8 pages total.
Ma, Huijuan et al.: "Bile Acids, Obesity, and the Metabolic Syndrome", Best Pract Res Clin Gastroenterol., Aug. 2014, 28(4): 573-583, 16 pages total.
Mariño, Eliana et al.: "Gut microbial metabolites limit the frequency of autoimmune T cells and protect against type 1 diabetes", Nature Immunology, vol. 18, No. 5, May 2017, 552-562, 15 pages total.
Martínes, Inés et al.: "Gut microbiome composition is linked to whole grain-induced immunological improvements", The ISME Journal (2013) 7, 269-280, 12 pages total.
Mayer, A. M.: "Determination of Indole Acetic Acid by the Salkowsky Reaction", Nature, Dec. 13, 1958, vol. 162, 1670-1671, 2 pages total.
Mazur, Witold: "Phytoestrogen content in foods", Baillière's Clinical Endocrinology and Metabolism, vol. 12, No. 4, Dec. 1998, 729-742, 14 pages total.
Mazzoli, Roberto et al.: "The Neuro-endocrinological Role of Microbial Glutamate and GABA Signaling", Frontiers in Microbiology, Nov. 2016, vol. 7, Article 1934, 17 pages total.
Moos, Walter H. et al.: "Microbiota and Neurological Disorders: A Gut Feeling", BioResearch Open Access, vol. 5.1, 2016, 137-145, 9 pages total.
Morgan, Xochitl C. et al.: "Dysfunction of the intestinal microbiome in inflammatory bowel disease and treatment", Genome Biology, 2012, 13:R79, 18 pages total.
Narushima, Seiko et al.: "Characterization of the 17 strains of regulatory T cell-inducing human-derived Clostridia", Gut Microbes, 5:3, 333-339, May/Jun. 2014, 7 pages total.
Nastasi, Claudia et al: "The effect of short-chain fatty acids on human monocyte-derived dendritic cells", Science Reports, 5:16148, Nov. 6, 2015, 10 pages total.
Neis, Evelien P. J. G. et al.: "The Role of Microbial Amino Acid Metabolism in Host Metabolism", Nutrients, 2015, 7, 2930-2946, 17 pages total.
Ning, Chong et al.: "Chicory inulin ameliorates type 2 diabetes mellitus and suppresses JNK and MAPK pathways in vivo and in vitro", Mol. Nutr. Food Res., 61, 8, 2017, 1600673, 9 pages total.
O'Callaghan, Amy et al.: "Bifidobacteria and Their Role as Members of the Human Gut Microbiota", Frontiers in Microbiology, Jun. 2016, vol. 7, Article 925, 23 pages total.
Ortega-Morales, B.O. et al.: "Characterization of extracellular polymers synthesized by tropical intertidal biofilm bacteria", Journal of Applied Microbiology, 102 (2007) 254-264, 11 pages total.
Paun, Alexandra, PHD et al.: "Modulation of type 1 and type 2 diabetes risk by the intestinal microbiome", Pediatr Diabetes, 2016, 17(7):469-477, 9 pages total.
Pellegrini, Silvia et al.: "Duodenal Mucosa of Patients With Type 1 Diabetes Shows Distinctive Inflammatory Profile and Microbiota", J Clin Endocrinol Metab, May 2017, 102(5):1468-1477, 10 pages total.
Peng, Yu et al.: "IDBA-UD: a de novo assembler for single-cell and metagenomic sequencing data with highly uneven depth", Bioinformatics, vol. 28 No. 11 2012, pp. 1420-1428, 9 pages total.
Pitt, Jonathan M. et al.: "Fine-Tuning Cancer Immunotherapy: Optimizing the Gut Microbiome", Cancer Res, 76(16) Aug. 15, 2016, 4602-4607, 7 pages total.
Prasad, Kailash: "Secoisolariciresinol diglucoside from flaxseed delays the development of type 2 diabetes in Zucker rat", J Lab Clin Med, Jul. 2001, vol. 138, No. 1, 32-39, 8 pages total.
Prawitt, Janne et al.: "Bile Acid Metabolism and the Pathogenesis of Type 2 Diabetes", Curr Diab Rep (2011) 11:160-166, 7 pages total.
Qin, Junjie et al.: "Ametagenome-wide association study of gut microbiota in type 2 diabetes", Nature, vol. 490, Oct. 4, 2012, 55-60, 6 pages total.
Ridlon, Jason M. et al.: "The human gut sterolbiome: bile acid-microbiome endocrine aspects and therapeutics", Acta Pharmaceutica Sinica B, 2015, 5(2):99-105, 7 pages total.
Ridlon, Jason M. et al.: "Identification and characterization of two bile acid coenzyme A transferases from Clostridium scindens, a bile acid 7α-dehydroxylating intestinal bacterium", Journal of Lipid Research, vol. 53, 2012, 66-76, 11 pages total.
Ridlon, Jason M. et al.: "Bile salt biotransformations by human intestinal bacteria", Journal of Lipid Research, vol. 47, 2006, 241-259, 19 pages total.
Ridlon, Jason M. et al.: "Clostridium scindens: a human gut microbe with a high potential to convert glucocorticoids into androgens", Journal of Lipid Research, vol. 54, 2013, 2437-2449, 13 pages total.
Rogers, GB et al.: "From gut dysbiosis to altered brain function and mental illness: mechanisms and pathways", Molecular Psychiatry (2016) 21, 738-748, 11 pages total.
Sadouk, Abdelkrim et al.: "Chromosome mapping in Alcaligenes eutrophus CH34", Mol Gen Genet (1993) 240:181-187, 7 pages total.
Sartor, Balfour R. et al.: "Roles for Intestinal Bacteria, Viruses, and Fungi in Pathogenesis of Inflammatory Bowel Diseases and Therapeutic Approaches", Gastroenterology, 2017, 152:327-339, 17 pages total.
Schwabe, Robert F. et al.: "The microbiome and cancer", Nature Review Cancer, vol. 13, Nov. 2013, 800-812, 13 pages total.
Seekatz, Anna Maria et al.: "Dynamics of the fecal microbiome in patients with recurrent and nonrecurrent Clostridium difficile infection", Genome Medicine (2016) 8:47, 11 pages total.
Segata, Nicola et al.: "PhyloPhlAn is a new method for improved phylogenetic and taxonomic placement of microbes", Nature Communications, 4:2304, Aug. 14, 2013, 11 pages total.
Shaw, Kelly A. et al.: "Dysbiosis, inflammation, and response to treatment: a longitudinal study of pediatric subjects with newly diagnosed inflammatory bowel disease", Genome Medicine (2016) 8:75, 13 pages total.
Shetty, Sudarshan Anand et al.: "Comparative Genome Analysis of *Megasphaera* sp. Reveals Niche Specialization and Its Potential Role in the Human Gut", PLOS ONE, Nov. 2013, vol. 8, Issue 11, e79353, 13 pages total.
Smith, Patrick M. et al.: "The Microbial Metabolites, Short-Chain Fatty Acids, Regulate Colonic Treg Cell Homeostasis", Science 341 (6145), Aug. 2, 2013, 569-573, 6 pages total.
Sokol, Harry et al.: "Fungal microbiota dysbiosis in IBD", Gut, 2016, 0:1-10, 10 pages total.
Strandwitz, Philip et al.: "GABA-modulating bacteria of the human gut microbiota", Nature Microbiology, Dec. 10, 2018, https://doi.org/10.1038/s41564-018-0307-3, 11 pages total.

(56) References Cited

OTHER PUBLICATIONS

Sun, Jun et al.: "Gut microbiota, inflammation and colorectal cancer", Genes & Diseases (2016) 3, 130-143, 14 pages total.

Truong, Duy Tin et al.: "MetaPhlAn2 for enhanced metagenomic taxonomic profiling", Nature Methods, vol. 12, No. 10, Oct. 2015, 902-903, 3 pages total.

Vaarala, Outi et al.: "The "Perfect Storm" for Type 1 Diabetes—The Complex Interplay Between Intestinal Microbiota, Gut Permeability, and Mucosal Immunity", Diabetes, vol. 57, Oct. 2008, 2555-2562, 8 pages total.

Van Immerseel, Filip et al.: "Butyric acid-producing anaerobic bacteria as a novel probiotic treatment approach for inflammatory bowel disease", JMM Editorial, 2010, 141-143, 3 pages total.

Vanderhaeghen, Sonja et al.: "Methanogen communities in stools of humans of different age and health status and co-occurrence with bacteria", FEMS Microbiology Letters, 362, 2015, fnv092, 8 pages total.

Vatanen, Tommi et al.: "Variation in Microbiome LPS Immunogenicity Contributes to Autoimmunity in Humans", Cell, 165, 842-853, May 5, 2016, 13 pages total.

Vernia, P. et al.: "Topical butyrate for acute radiation proctitis: randomised, crossover trial", The Lancet, Oct. 7, 2000, vol. 356, 1232-1235, 4 pages total.

Vernia, P. et al.: "Topical butyrate improves efficacy of 5-ASA in refractory distal ulcerative colitis: results of a multicentre trial", European Journal of Clinical Investigation (2003) 33, 244-248, 5 pages total.

Villéger, Romain et al.: "Characterization of lipoteichoic acid structures from three probiotic Bacillus strains: involvementof D-alanine in their biological activity", Antonie van Leeuwenhoek (2014) 106:693-706, 14 pages total.

Vuong, Helen E. et al.: "Emerging Roles for the Gut Microbiome in Autism Spectrum Disorder", Biological Psychiatry, Mar. 1, 2017, 81:411-423, 13 pages total.

Wright, Emily K., MD et al.: "Recent Advances in Characterizing the Gastrointestinal Microbiome in Crohn's Disease: A Systematic Review", Inflamm Bowel Dis, vol. 21, No. 6, Jun. 2015, 1219-1228, 10 pages total.

Zhou, Fang et al.: "Antidiabetic effect of enterolactone in cultured muscle cells and in type 2 diabetic model db/db mice", Cytotechnology (2017) 69:493-502, 10 pages total.

Searle, Laura J. et al.: "Variation in Siderophore Biosynthetic Gene Distribution and Production across Environmental and Faecal Populations of *Escherichia coli*", PLoS ONE 10(3): e0117906, Mar. 10, 2015, 14 pages total.

\* cited by examiner

RATIONAL DESIGN OF MICROBIAL-BASED BIOTHERAPEUTICS

CROSS-REFERENCE TO RELATED APPLICATION

This application is a continuation of PCT patent application no. PCT/US2018/025805, titled "RATIONAL DESIGN OF MICROBIAL-BASED BIOTHERAPEUTICS", filed on Apr. 3, 2018, which claims the benefit of priority of U.S. provisional patent application No. 62/481,062, titled "Rational Design of Microbial-Based Biotherapeutics", filed on Apr. 3, 2017, U.S. provisional patent application No. 62/545,733, titled "Rational Design of Microbial-Based Biotherapeutics", filed on Aug. 15, 2017, and U.S. provisional patent application No. 62/620,752, titled "Rational Design of Microbial-Based Biotherapeutics", filed on Jan. 23, 2018, all of which are incorporated herein in their entirety by this reference.

TECHNICAL FIELD

The presently disclosed subject matter relates to the rational design of microbial consortia as biotherapeutics to benefit health. More specifically, the presently disclosed subject matter includes microbial-based compositions and methods for enhancing a weakened immune system or aid in overcoming conditions of chronic inflammation caused by an overactive immune system, such as conditions of chronic inflammation of the gastrointestinal tract, Type-1 and Type-2 diabetes, oncology conditions, neurological disorders, and metabolic disorders.

BACKGROUND

Conditions of chronic inflammation of the gastrointestinal tract have been linked to a range of conditions, such as Inflammatory Bowel Diseases (IBD), Irritable Bowel Syndrome (IBS), food allergies, surgical site infections and sepsis, or as an early stage warning for development of asthma and type 1 & 2 diabetes.

Chronic intestinal inflammation can be induced by multiple exogenous and endogenous signals and mediated by multiple immune and nonimmune cells. As reviewed by de Souza and Flocchi (2016) and Sartor and Wu (2017), the epithelial translocation of exogenous substances, including dietary antigens, pathogenic microorganisms, xenobiotics including antibiotics, or a combination of them, can trigger an initial response mediated primarily by immune cells that initiates mucosal inflammation of the gastrointestinal tract. This primary inflammatory response induces a variety of processes, which triggers a secondary inflammatory response, eventually resulting in a self-sustaining cycle of chronic inflammation of the gastrointestinal tract with tissue damage and cell death, and dysbiosis of the gut microbiome. The dysbiotic gut microbiome creates an ideal environment for the establishment of (opportunistic) pathogens, which in turn will also contribute to the severity of the inflammation and its clinical symptoms. IBD encompasses two main clinical disorders: Crohn's disease and Ulcerative Colitis. Drug treatments for IBD primarily focus on inflammation control through anti-inflammatory and immunosuppressive therapies. Examples of some of the most successful biological drugs for treatment of IBD include REMICADE (Infliximab; manufactured and sold by Johnson & Johnson subsidiary Janssen Biotech), HUMIRA (Adalimumab; manufactured and sold by AbbVie), and ENTYVIO (vedolizumab; developed by Millennium Pharmaceuticals, Inc.), which target the body's immune response through key pathways to control the inflammatory process. However, these and other immune modulating drugs only work on select patient cohorts and have multiple side effects, including the increased risk for serious and potentially life-threatening infections and neoplastic safety concerns.

To treat IBD associated infections and septic complications such as abscesses, antibiotics, particularly ciprofloxacin and metronidazole, are commonly prescribed; however, this treatment with antibiotics is often unsuccessful (Gevers et al, 2017; Sartor and Wu, 2017). Furthermore, the application of broad spectrum antibiotics can be detrimental to a healthy microbiome by non-selectively eliminating bacterial populations, including protective species that prevent overgrowth of opportunistic pathogens such as *Clostridium difficile*. As such, broad spectrum antibiotics may further contribute to the dysbiotic status of the gut microbiome in IBD patients, with additional negative consequences on the regulation of the innate immune response and the conditions of chronic inflammation.

As an alternative to drugs, microbiome inspired therapeutics are being developed for the treatment of IBD and other conditions linked to chronic inflammation of the gastrointestinal tract. The focus of this work has been on the use of butyrate synthesizing bacteria, especially strains belonging to the *Clostridium* clusters IV and XIVa. Strains of *Clostridium* cluster IV and XIVa were found to be highly successful in decreasing inflammation and necrosis in rodent IBD models (Sokol et al, 2008; Eeckhaut et al, 2009). Van Immerseel et al (2010) suggested the use of Clostridial cluster IV and XIVa strains as preventive and therapeutic probiotics for IBD. Using a rodent model, Honda et al developed a 17-strain consortium for IBD treatment (U.S. Pat. No. 9,415,079 B2—Composition for inducing proliferation or accumulation of regulatory T cells; Furusawa et al, 2013; Honda et al, 2015). This consortium, comprised of *Clostridium* cluster IV, XIVa and XVIII strains, induced the recruitment/accumulation of regulatory T cells (Treg cells) in the colon. These Treg cells suppressed proliferation of effector T cells, which in turn lowered the inflammation response by the immune system in the gut (Atarashi et al, 2013). The commonly used approach for discovery of microbiome-based therapeutics has been to compare the microbiomes of healthy subjects and patients suffering from a specific condition in order to identify microorganisms lacking or under-represented in the patients. This information is then used to propose a therapeutic formulation to replenish the microorganisms that are lacking or under-represented. This approach has been used for conditions where a role of the microbiome has been implied, including immune dysregulation such as IBD (Atarashi et al, 2013; Nrushima et al, 2014; Sugiura et al, 2014; Halfvarson et al, 2017), food allergies (Canani et al, 2016) and asthma (Canani et al, 2017), neurological disorders such as Alzheimer's Disease (Bhattacharjee and Lukiw, 2013), Autism Spectrum Disorder (Li and Zhou, 2016; Vuong, 2017), dementia (Moos et al, 2016), peri-natal/post-partum depression (Rogers et al, 2016), oncology related conditions such as colon cancer (and other GI cancers) (Schwabe and Jobin, 2013; Sun and Kato, 2016), metabolic disorders (Boulange et al, 2016) including Type-1 and Type-2 diabetes (Paun and Danska, 2016), and recurrent infections with *Clostridium difficile* (Seekatz, 2016). There is currently no FDA approved microbiome-based therapeutic available for the treatment of any of these conditions; and commonly used treatments including REMICADE, HUMIRA, ENTYVIO, and biosimilars such as RENFLEXIS (Infliximab-abda; Samsung and marketing partner Merck & Co.), as well as other treatments (e.g., corticosteroids, immunomodulators, antibiotics) suffer from negative side effects including dysbiosis of the gut microbiome and risk of serious and potentially life-threatening infections.

Thus, there remains an unmet need for improved compositions and methods to treat conditions involving chronic inflammation and infection that do not have the negative side effects of contributing to the dysbiosis of the gut microbiome or increasing the risk of serious and potentially life-threatening infections. The presently disclosed subject matter provides such improved compositions and methods.

SUMMARY

In one embodiment, a method is provided for rational design of microbial consortia for benefiting the health of an organism, the method comprising: for a plurality of microbial strains each having at least one functionality in a set of functionalities absent or underrepresented in a microbiome of an organism of interest, creating for each strain using genome annotation an in silico metabolic model that predicts an auxotrophic profile for one or a combination of essential nutrients; integrating in silico the metabolic models for each of the plurality of strains to obtain a combined metabolic model for the plurality of strains; and designating a microbial consortium having a metabolic interdependency, including by optionally introducing into the plurality or removing from the plurality one or more microbial strains, wherein the metabolic interdependency of the plurality of strains in the microbial consortium includes each of the strains having at least one auxotrophy for the essential nutrient(s) and each being dependent on at least one of the other strains in the plurality for growth, wherein the microbial consortium populates and benefits the health of the organism. The set of functionalities absent or underrepresented in the microbiome can include synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, and breakdown of complex carbohydrates and proteins. The health benefited can include one or more of Ulcerative Colitis, Crohn's Disease, Inflammatory Bowel Disease, Irritable Bowel Syndrome, food allergies, asthma, neurological disorders Alzheimer's Disease, Autism Spectrum Disorder, dementia, peri-natal/post-partum depression, cancer, colon cancer, GI cancer, solid tumors, melanoma, lung cancer, breast cancer, metabolic disorders, phenylketonuria, organic acidemias, maple syrup urine disease, obesity, diabetes, arthrosclerosis, acute infections, chronic infections, recurrent infections, primary sclerosing cholangitis (PSC) as an inflammation of the bile duct, or infection with *Clostridium difficile*. The metabolic interdependency can include each of the strains having at least two auxotrophies and each being dependent on at least one of the other strains in the plurality for growth. The metabolic interdependency can also include each of the strains having three or more auxotrophies and each being dependent on at least one of the other strains in the plurality for growth. The set of functionalities absent or underrepresented in the organism can comprise one or both of conversion of secoisolariciresinol diglucoside (SDG) to enterodiol and enterolactone and the synthesis of β-fructofuranosidase to breakdown of the prebiotic fiber inulin, and the health benefited can be Type-2 diabetes. The set of functionalities absent or underrepresented in the organism can comprise synthesis of 4-amino-butyrate (GABA), and the health benefited can be Type-1 Diabetes.

In one embodiment, a method is provided for rational design of microbial consortia for benefiting the health of an organism, the method comprising: combining ex vivo a plurality of biologically pure cultures of microbial strains having at least one functionality absent or underrepresented in the microbiome of an organism having a disease or disorder, wherein each of the absent or underrepresented functionalities is present in one of the microbial strains in the plurality, and wherein each of the microbial strains has at least one auxotrophy and is dependent on at least one of the other strains in the plurality for growth to create a microbial consortium having a metabolic interdependency.

In one embodiment, a method is provided for benefiting health, comprising: administering to a human or an animal a composition comprising: i) a plurality of biologically pure cultures of microbial strains having at least one functionality absent or underrepresented in the microbiome of an organism having a disease or disorder, wherein each of the absent or underrepresented functionalities is present in at least one of the microbial strains in the plurality, and wherein each of the microbial strains has at least one auxotrophy and is dependent on at least one of the other strains in the plurality for growth; and ii) a carrier.

In one embodiment, a composition is provided for benefiting the health of an organism, comprising: i) a plurality of biologically pure cultures of microbial strains having at least one functionality absent or underrepresented in the microbiome of an organism having a disease or disorder, wherein each of the absent or underrepresented functionalities is present in at least one of the microbial strains in the plurality, and wherein each of the microbial strains has at least one auxotrophy and is dependent on at least one of the other strains in the plurality for growth; and ii) a carrier.

In one embodiment, a composition (referred to herein as "GUT-103") is provided for benefiting the health of an animal or a human, comprising: i) a biologically pure culture comprising each of: *Blautia producta* DSM2950, *Megamonas funiformis* DSM19343, *Megamonas hypermegale* DSM1672, *Acidaminococcus intestini* DSM21505, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Anaerostipes hadrus* DSM 3319/ATCC 29173, *Clostridium symbiosum* ATCC14940, *Clostridium bolteae* ATCC BAA-613, *Blautia hydrogenotrophica* DSM10507, *Marvinbryantia formatexigens* DSM14469, *Clostridium scindens* ATCC35704 and *Akkermansia muciniphila* ATCC BAA-835; and ii) one or more carriers or excipients.

In one embodiment, a composition (referred to herein as "GUT-103 consortium subset 1) is provided for benefiting the health of an animal or a human, comprising: i) a biologically pure culture comprising each of: *Blautia producta* DSM2950, *Bacteroides massiliensis* DSM17679, and *Akkermansia muciniphila* ATCC BAA-835; and ii) one or more carriers or excipients. The composition can further comprise a biologically pure culture of *Bacteroides stercoris* ATCC 43183.

In one embodiment, a composition (referred to herein as "GUT-103 consortium subset 2") is provided for benefiting the health of an animal or a human, comprising: i) a biologically pure culture comprising each of: *Subdoligranulum variabile* DSM15176, *Anaerostipes caccae* DSM14662, *Clostridium symbiosum* ATCC14940, *Clostridium bolteae* ATCC BAA-613, and *Clostridium scindens* ATCC35704;

and ii) one or more carriers or excipients. The composition can further comprise a biologically pure culture of *Megamonas funiformis* DSM1934. In one embodiment, a composition (referred to herein as "GUT-103 consortium subset 1+GUT-103 consortium subset 2") is provided for benefiting the health of an animal or a human, comprising: i) a biologically pure culture comprising each of: *Blautia producta* DSM2950, *Bacteroides massiliensis* DSM17679, *Akkermansia muciniphila* ATCC BAA-835, *Subdoligranulum variabile* DSM15176, *Anaerostipes caccae* DSM14662, *Clostridium symbiosum* ATCC14940, *Clostridium bolteae* ATCC BAA-613, and *Clostridium scindens* ATCC35704; and ii) one or more carriers or excipients. The composition can further comprise a biologically pure culture of one or both of *Bacteroides stercoris* ATCC 43183 and *Megamonas funiformis* DSM19343.

In one embodiment, a composition (referred to herein as "GUT-104") is provided for benefiting the health of an animal or a human, comprising: i) a biologically pure culture comprising each of: *Clostridium saccharogumia* DSM17460, *Clostridium ramosum* DSM1402, *Blautia producta* DSM2950, *Clostridium scindens* ATCC35704 (DSM5676), *Lactonifactor longoviformis* DSM17459, *Anaerostipes caccae* DSM14662, *Anaerostipes hadrus* DSM3319/ATCC29173, *Clostridium symbiosum* ATCC14940, *Clostridium bolteae* ATCC BAA-613, *Blautia hydrogenotrophica* DSM10507, *Faecalibacterium prausnitzii* DSM17677, *Subdoligranulum variabile* DSM15176, and *Akkermansia muciniphila* ATCC BAA-835; and ii) one or more carriers or excipients. The composition can further comprise a biologically pure culture of one or a combination of *Bacteroides massiliensis* DSM17679, *Megamonas hypermegale* DSM1672, and *Megamonas funiformis* DSM19343.

In one embodiment, a composition (referred to herein as "GUT-104 subset 3") is provided for benefiting the health of an animal or a human, comprising: i) a biologically pure culture of each of: *Clostridium saccharogumia* DSM17460, *Clostridium ramosum* DSM1402, *Blautia producta* DSM2950, *Clostridium scindens* ATCC35704 (DSM5676) and *Lactonifactor longoviformis* DSM17459; and ii) one or more carriers or excipients.

In one embodiment, a composition (referred to herein as "GUT-107") is provided for benefiting the health of an animal or a human, comprising: i) a biologically pure culture of each of: *Megamonas funiformis* DSM19343, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Clostridium symbiosum* ATCC14940, *Clostridium bolteae* ATCC BAA-613, *Blautia producta* DSM2950, *Clostridium scindens* ATCC35704 and *Akkermansia muciniphila* ATCC BAA-835; and ii) one or more carriers or excipients.

In one embodiment, a composition is provided for benefiting the health of an animal or a human, comprising: i) a plurality of biologically pure cultures of microbial strains, wherein the combined plurality of strains comprises functionalities for each of: synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, and breakdown of complex carbohydrates and proteins; and ii) a carrier. The composition can further comprise functionality for one or both of conversion of secoisolariciresinol diglucoside (SDG) to enterodiol and enterolactone and synthesis of β-fructofuranosidase for breakdown of the prebiotic fiber inulin, and the health benefited can be Type-2 diabetes. The composition can comprise further functionality for synthesis of 4-amino-butyrate (GABA), and the health benefited can be Type-1 Diabetes. The plurality of microbial strains can comprise strains from one or a combination of: *Megamonas funiformis, Megamonas hypermegale, Acidaminococcus intestini, Bacteroides massiliensis, Bacteroides stercoris, Barnesiella intestinihominis, Faecalibacterium prausnitzii, Subdoligranulum variabile, Anaerostipes caccae, Anaerostipes hadrus, Clostridium symbiosum, Clostridium scindens, Clostridium bolteae, Clostridium saccharogumia, Clostridium ramosum, Blautia producta, Blautia hydrogenotrophica, Marvinbryantia formatexigens, Lactonifactor longoviformis,* and *Akkermansia muciniphila*. The plurality of microbial strains can comprise strains from *Megamonas funiformis, Megamonas hypermegale, Acidaminococcus intestini, Bacteroides massiliensis, Bacteroides stercoris, Barnesiella intestinihominis, Faecalibacterium prausnitzii, Subdoligranulum variabile, Anaerostipes caccae, Anaerostipes hadrus, Clostridium symbiosum, Clostridium bolteae, Blautia hydrogenotrophica, Marvinbryantia formatexigens, Clostridium scindens, Blautia producta,* and *Akkermansia muciniphila*. The plurality of microbial strains can comprise strains from species of *Blautia producta, Akkermansia muciniphila,* and *Bacteroides massiliensis*. The plurality of microbial strains can comprise strains from species of *Blautia producta, Akkermansia muciniphila* and *Bacteroides massiliensis*, and further from *Bacteroides stercoris*. The plurality of microbial strains can comprise strains from species of *Clostridium symbiosum, Clostridium bolteae, Clostridium scindens, Subdoligranulum variabile* and *Anaerostipes caccae*. The plurality of microbial strains can comprise strains from species of *Clostridium symbiosum, Clostridium bolteae, Clostridium scindens, Subdoligranulum variabile* and *Anaerostipes caccae*, and further from *Megamonas funiformis*. The plurality of microbial strains can comprise strains from species of *Blautia producta, Akkermansia muciniphila, Bacteroides massiliensis, Clostridium symbiosum, Clostridium bolteae, Clostridium scindens, Subdoligranulum variabile* and *Anaerostipes caccae*. The plurality of microbial strains can comprise strains from species of *Blautia producta, Akkermansia muciniphila, Bacteroides massiliensis, Clostridium symbiosum, Clostridium bolteae, Clostridium scindens, Subdoligranulum variabile* and *Anaerostipes caccae*, and further from one or both of *Bacteroides stercoris* and *Megamonas funiformis*. The plurality of microbial strains can comprise strains from *Clostridium saccharogumia, Clostridium ramosum, Blautia producta, Clostridium scindens, Lactonifactor longoviformis, Anaerostipes caccae, Anaerostipes hadrus, Clostridium symbiosum, Clostridium bolteae, Blautia hydrogenotrophica, Faecalibacterium prausnitzii, Subdoligranulum variabile,* and *Akkermansia muciniphila*. The plurality of microbial strains can comprise strains from species of *Clostridium saccharogumia, Clostridium ramosum, Blautia producta, Clostridium scindens* and *Lactonifactor longoviformis*. The plurality of microbial strains can comprise strains from species of *Clostridium saccharogumia, Clostridium ramosum, Blautia producta, Clostridium scindens* and *Lactonifactor longoviformis* and further from species of one or a combination of *Bacteroides massiliensis, Megamonas hypermegale,* and *Megamonas funiformis*. The plurality of microbial strains can comprise strains from species of *Megamonas funiformis, Bacteroides massiliensis, Bacteroides stercoris, Barnesiella intestinihominis, Faecalibacterium prausnitzii, Subdoligranulum variabile, Anaeros-

*tipes caccae, Clostridium symbiosum, Clostridium bolteae, Blautia producta, Clostridium scindens* and *Akkermansia muciniphila*.

The compositions of the present disclosure can be formulated as a capsule, a powder, a liquid suspension, an aerosol, or a cream.

In one embodiment, a method is provided for benefiting health, comprising: administering to a human or an animal a composition comprising: i) a plurality of biologically pure cultures of microbial strains, wherein the combined plurality of strains comprises functionalities for each of: synthesis of butyrate, synthesis of propionate, synthesis of indole, deconjugation of bile salt and conversion of bile acid into secondary bile acids, synthesis of a siderophore, uptake of a heterologously produced siderophore, and synthesis of at least one bacteriocin; and ii) a carrier, wherein the plurality of microbial strains populates and benefits the health of an animal or a human. The health benefited can include one or more of Ulcerative Colitis, Crohn's Disease, Inflammatory Bowel Disease, Irritable Bowel Syndrome, food allergies, asthma, neurological disorders Alzheimer's Disease, Autism Spectrum Disorder, dementia, peri-natal/post-partum depression, cancer, colon cancer, GI cancer, solid tumors, melanoma, lung cancer, breast cancer, metabolic disorders, phenylketonuria, organic acidemias, maple syrup urine disease, obesity, diabetes, arthrosclerosis, acute infections, chronic infections, recurrent infections, primary sclerosing cholangitis (PSC) as an inflammation of the bile duct, or infection with *Clostridium difficile*. The plurality of strains can comprise GUT-103 consortium, GUT-103 consortium subset 1+GUT-103 consortium subset 2, or GUT-103 consortium subset 1 and the health benefited can be Inflammatory Bowel Disease. The composition can further comprise functionality for one or both of conversion of secoisolariciresinol diglucoside (SDG) to enterodiol and enterolactone and the synthesis of β-fructofuranosidase for the breakdown of the prebiotic fiber inulin and the health benefited can be Type-2 diabetes. The plurality of strains can comprise GUT-104 consortium or GUT-104 consortium subset 3 and the health benefited can be Type-2 diabetes. The plurality of strains can comprise GUT-107 consortium and the health benefited can be Type-1 diabetes.

In some embodiments, the compositions are administered to an animal or a human in combination with a small molecule-based drug, a corticosteroid, a macromolecule-based drug, an antibody based drug, an immunomodulator, a checkpoint inhibitor, a αPD-[L]1 targeting antibody, a αCTLA-4 targeting antibody, an αLag-3 targeting antibody, an αTim-3 targeting antibody, an αTIGIT targeting antibody, an antibiotic, an infliximab therapeutic, an adalimumab therapeutic, an vedolizumab therapeutic, or a biosimilar of a infliximab, adalimumab, or vedolizumab therapeutic.

In one embodiment, a composition comprising GUT-103 consortium, GUT-103 consortium subset 1, GUT-103 consortium 1 extended, GUT-103 consortium subset 1+GUT-103 consortium subset 2, or GUT-103 consortium subset 1+GUT-103 consortium subset 2 extended and a carrier is administered to an animal or a human in combination with a checkpoint inhibitor for the treatment of cancer.

In some embodiments, the compositions are administered to an animal or a human in combination with one or more of a food supplement, a pre-biotic, a symbiotic, a lignan, an inulin, or a secoisolariciresinol diglucoside (SDG).

In one embodiment, a composition comprising GUT-104 consortium, GUT-104 consortium subset 3, or GUT-104 consortium extended and a carrier is administered to an animal or a human in combination with one or both of inulin and secoisolariciresinol diglucoside (SDG) for the treatment of Type-2 diabetes.

In one embodiment, a composition comprising GUT-107 and a carrier is administered to an animal or a human in combination with a zonulin receptor antagonist or a larazotide acetate for the treatment of Type-1 diabetes.

In one embodiment, a composition is provided for benefiting the health of an animal or a human, comprising i) one or more carriers or excipients, and ii) a biologically pure culture of each of: a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Megamonas funiformis* DSM19343 (SEQ ID NO: 2) and genetic material encoding functionalities for synthesis of proprionate, uptake of a ferrichrome siderophore and an enterobactin siderophore, and β-fructofuranosidase activity for inulin, fructan and sucrose hydrolysis; c) a bacterium having 99% identity to 16S rRNA gene of *Megamonas hypermegale* DSM1672 (SEQ ID NO: 3) and genetic material encoding functionalities for synthesis of proprionate, uptake of a ferrichrome siderophore, and (3-fructofuranosidase activity for inulin, fructan and sucrose hydrolysis; d) a bacterium having 99% identity to 16S rRNA gene of *Acidaminococcus intestini* DSM21505 (SEQ ID NO: 4) and genetic material encoding functionalities for synthesis of butyrate; e) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; f) a bacterium having 99% identity to 16S rRNA gene of *Bacteroides stercoris* ATCC43183/DSM19555 (SEQ ID NO: 6) and genetic material encoding functionalities for synthesis of propionate, synthesis of indole, uptake of a heterologously produced siderophore and uptake of an enterobactin siderophore; g) a bacterium having 99% identity to 16S rRNA gene of *Barnesiella intestinihominis* DSM21032 (SEQ ID NO: 7) and genetic material encoding functionalities for synthesis of proprionate, uptake of a heterologously produced siderophore and uptake of an aerobactin siderophore; h) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, synthesis of a bacteriocin, and β-fructofuranosidase activity for inulin, fructan and sucrose hydrolysis; i) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin; j) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; k) a bacterium having 99% identity to 16S rRNA gene of *Anaerostipes hadrus* DSM 3319/ATCC 29173 (SEQ ID NO: 11) and genetic material encoding functionalities for synthesis of butyrate and synthesis of indole; 1) a bacterium having 99% identity to 16S rRNA gene of *Clostridium symbiosum* ATCC14940 (SEQ ID NO: 12) and genetic material encoding functionalities for synthesis of butyrate, deconjugation of bile salt and conversion of bile acid into secondary bile acids; m) a bacterium having 99% identity to 16S rRNA gene of *Clostridium bolteae* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; n) a bacterium having 99% identity to 16S rRNA gene of *Blautia hydrogenotrophica* DSM 10507 (SEQ ID NO: 15) and genetic material encoding functionalities for deconjugation of bile salt and conversion of bile acid into secondary bile acids and synthesis of a bacteriocin; o) a bacterium having 99% identity to 16S rRNA gene of *Marvinbryantia formatexigens* DSM14469 (SEQ ID NO: 16) and genetic material encoding functionalities for uptake of a heterologously produced siderophore and uptake of a ferrichrome siderophore; p) a bacterium having 99% identity to 16S rRNA gene of *Clostridium scindens* ATCC35704 (SEQ ID NO: 17) and genetic material encoding functionalities for conversion of bile acid into secondary bile acids and synthesis of a bacteriocin; and q) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore.

In one embodiment, a composition is provided for benefiting the health of an animal or a human, the composition comprising i) one or more carriers or excipients and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; and c) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore. The biologically pure culture can further comprise a biologically pure culture of a bacterium having 99% identity to 16S rRNA gene of *Bacteroides stercoris* (SEQ ID NO: 6) and genetic material encoding functionalities for indole synthesis and the uptake of heterologous siderophores including enterobactin.

In one embodiment, a composition is provided for benefiting the health of an animal or a human, the composition comprising i) one or more carriers or excipients and ii) a biologically pure culture of each of: a) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; b) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; c) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; d) a bacterium having 99% identity to 16S rRNA gene of *Clostridium bolteae* ATCC BAA-613 (SEQ ID NO: 13) genetic material encoding functionalities for synthesis of a siderophore, deconjugation of bile salt and conversion of bile acid into secondary bile acids, and synthesis of a bacteriocin; and e) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin. The biologically pure culture can further comprise a biologically pure culture of a bacterium having 99% identity to 16S rRNA gene of *Megamonas funiformis* (SEQ ID NO: 2) and genetic material encoding a β-fructofuranosidase gene.

In one embodiment, a composition is provided for benefiting the health of an animal or a human, the composition comprising: i) one or more carriers or excipients and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; c) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore; d) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; e) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; f) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; g) a bacterium having 99% identity to 16S rRNA gene of *Clostridium bolteae* ATCC BAA-613 (SEQ ID NO: 13) genetic material encoding functionalities for synthesis of a siderophore, deconjugation of bile salt and conversion of bile acid into secondary bile acids, and synthesis of a bacteriocin; and h) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin. The biologically pure culture can further comprise one or a combination of a biologically pure culture of: i) a bacterium having 99% identity to 16S rRNA gene of *Bacteroides stercoris* (SEQ ID NO: 6) and genetic material encoding functionalities for indole synthesis and the uptake of heterologous siderophores including enterobactin; and j) a bacterium having 99% identity to 16S rRNA gene of *Megamonas funiformis* (SEQ ID NO: 2) and genetic material encoding a β-fructofuranosidase gene.

In one embodiment, a composition is provided for benefiting the health of an animal or a human, comprising i) one or more carriers or excipients, and ii) a biologically pure culture of each of: a) a bacterium having 99% identity to 16S rRNA gene of *Clostridium saccharogumia* DSM17460 (SEQ ID NO: 19) and genetic material encoding functionalities for O-deglycosylation in conversion of secoisolariciresinol diglucoside (SDG) to enterodiol and enterolactone; b) a bacterium having 99% identity to 16S rRNA gene of *Clostridium ramosum* DSM1402 (SEQ ID NO: 20) and genetic material encoding functionalities for O-deglycosylation in conversion of secoisolariciresinol diglucoside (SDG) to enterodiol and enterolactone; c) a bacterium having 99% identity to 16S rRNA gene of *Blautia producta* DSM2950 (SEQ ID NO: 14) and genetic material encoding functionalities for synthesis of butyrate, uptake of a heterologously produced siderophore, uptake of a ferrichrome siderophore, and O-demethylation in conversion of secoisolariciresinol diglucoside (SDG) to enterodiol and enterolactone; d) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; e) a bacterium having 99% identity to 16S rRNA gene of *Lactonifactor longoviformis* DSM17459 (SEQ ID NO: 21) and genetic material encoding functionalities for synthesis of a bacteriocin and dehydrogenation in conversion of secoisolariciresinol diglucoside (SDG) to enterodiol and enterolactone; f) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; g) a bacterium having 99% identity to 16S rRNA gene of *Anaerostipes hadrus* DSM3319/ATCC29173 (SEQ ID NO: 11) and genetic material encoding functionalities for synthesis of butyrate and synthesis of indole; h) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; i) a bacterium having 99% identity to 16S rRNA gene of *Clostridium bolteae* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; j) a bacterium having 99% identity to 16S rRNA gene of *Blautia hydrogenotrophica* DSM10507 (SEQ ID NO: 15) and genetic material encoding functionalities for deconjugation of bile salt and conversion of bile acid into secondary bile acids and synthesis of a bacteriocin; k) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, synthesis of a bacteriocin, and β-fructofuranosidase activity for inulin, fructan and sucrose hydrolysis; l) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin; and m) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore. The biologically pure culture can further comprise one or a combination of: n) a bacterium having 99% identity to 16S rRNA gene of *Bacteroides massiliensis* (SEQ ID NO: 5) and genetic material encoding functionalities for indole synthesis and the uptake of heterologous siderophores including enterobactin; o) a bacterium having 99% identity to 16S rRNA gene of *Megamonas hypermegale* (SEQ ID NO: 3) and genetic material encoding a β-fructofuranosidase gene; and p) a bacterium having 99% identity to 16S rRNA gene of *Megamonas funiformis* (SEQ ID NO: 2) and genetic material encoding a β-fructofuranosidase gene.

In one embodiment, a composition is provided for benefiting the health of an animal or a human, the composition comprising i) one or more carriers or excipients and ii) a biologically pure culture of each of: a) a bacterium having 99% identity to 16S rRNA gene of *Clostridium saccharogumia* DSM17460 (SEQ ID NO: 19) and genetic material encoding functionalities for O-deglycosylation in conversion of secoisolariciresinol diglucoside (SDG) to enterodiol and enterolactone; b) a bacterium having 99% identity to 16S rRNA gene of *Clostridium ramosum* DSM1402 (SEQ ID NO: 20) and genetic material encoding functionalities for O-deglycosylation in conversion of secoisolariciresinol diglucoside (SDG) to enterodiol and enterolactone; c) a bacterium having 99% identity to 16S rRNA gene of *Blautia producta* DSM2950 (SEQ ID NO: 14) and genetic material encoding functionalities for synthesis of butyrate, uptake of a heterologously produced siderophore, uptake of a ferrichrome siderophore, and O-demethylation in conversion of secoisolariciresinol diglucoside (SDG) to enterodiol and enterolactone; d) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; and e) a bacterium having 99% identity to 16S rRNA gene of *Lactonifactor longoviformis* DSM17459 (SEQ ID NO: 21) and genetic material encoding functionalities for synthesis of a bacteriocin and dehydrogenation in conversion of secoisolariciresinol diglucoside (SDG) to enterodiol and enterolactone.

In one embodiment, a composition is provided for benefiting the health of an animal or a human, the composition comprising i) one or more carriers or excipients and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Megamonas funiformis* DSM19343 (SEQ ID NO: 2) and genetic material encoding functionalities for synthesis of proprionate, uptake of a ferrichrome siderophore and an enterobactin siderophore, and β-fructofuranosidase activity for inulin, fructan and sucrose hydrolysis; c) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; d) a bacterium having 99% identity to 16S rRNA gene of *Bacteroides stercoris* ATCC43183/DSM19555 (SEQ ID NO: 6) and genetic material encoding functionalities for synthesis of propionate, synthesis of indole, uptake of a heterologously produced siderophore and uptake of an enterobactin siderophore; e) a bacterium having 99% identity to 16S rRNA gene of *Barnesiella intestinihominis* DSM21032 (SEQ ID NO: 7) and genetic material encoding functionalities for synthesis of proprionate, uptake of a heterologously produced siderophore and uptake of an aerobactin siderophore; f) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, synthesis of a bacteriocin, and β-fructofuranosidase activity for inulin, fructan and sucrose hydrolysis; g) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin; h) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; i) a bacterium having 99% identity to 16S rRNA gene of *Clostridium symbiosum* ATCC14940 (SEQ ID NO: 12) and genetic material encoding functionalities for synthesis of butyrate, deconjugation of bile salt and conversion of bile acid into secondary bile acids; j) a bacterium having 99% identity to 16S rRNA gene of *Clostridium bolteae* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; k) a bacterium having 99% identity to 16S rRNA gene of *Clostridium scindens* ATCC35704 (SEQ ID NO: 17) and genetic material encoding functionalities for conversion of bile acid into secondary bile acids and synthesis of a bacteriocin; and l) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore.

BRIEF DESCRIPTION OF THE DRAWINGS

The foregoing aspects and other features of the invention are explained in the following description, taken in connection with the accompanying drawings.

DETAILED DESCRIPTION

Figure 1:
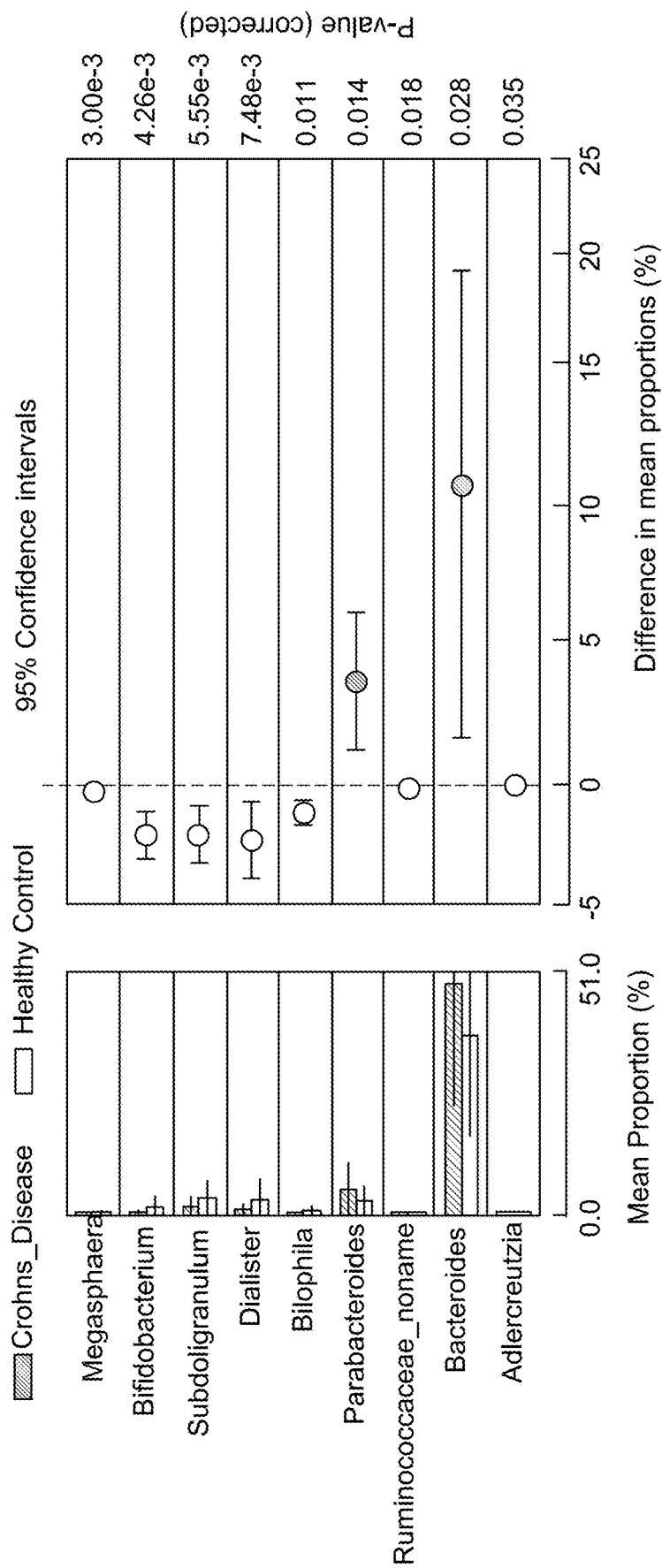
FIG. 1 is a graph showing two-way comparison of the microbiome composition between Crohn's Disease patients versus healthy individuals. A total of 9 differential features were identified on the genus level, of which the most prominent (95% confidence interval) were *Bifidobacterium* (high in Healthy), *Subdoligranulum* (high in Healthy), *Dialister* (high in Healthy), *Parabacteroides* (high in Crohn's), and *Bacteroides* (high in Crohn's).

The presently disclosed subject matter now will be described more fully hereinafter. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the descriptions provided herein. Therefore, it is to be understood that the presently disclosed subject matter is not to be limited to the specific embodiments disclosed and that modifications and other embodiments are intended to be included within the scope of the appended claims.

Following long-standing patent law convention, the terms "a," "an," and "the" refer to "one or more" when used in this application, including the claims. Thus, for example, reference to "a metabolic interdependency" includes a plurality of interdependencies, unless the context clearly is to the contrary, and so forth.

Throughout this specification and the claims, the terms "comprise," "comprises," and "comprising" are used in a non-exclusive sense, except where the context requires otherwise. Likewise, the terms "having" and "including" and their grammatical variants are intended to be non-limiting, such that recitation of items in a list is not to the exclusion of other like items that can be substituted or added to the listed items.

For the purposes of this specification and claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range. In addition, as used herein, the term "about", when referring to a value can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed compositions and methods. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Throughout this specification and the claims, the term "animal" includes humans and can be used interchangeably with the term "human".

The phrase "auxotrophic profile for one or a combination of essential nutrients" and the phrase "auxotrophy for the one or a combination of essential nutrients" are intended for the purposes of the spectification and claims to include as essential nutrients any one or more of amino acids, vitamins, co-factors, or other metabolites or nutrients that a microbial strain requires for its growth.

The phrase "microbial consortium having a metabolic interdependency" is intended for the purposes of the spectification and claims to mean that each of the strains in the microbial consortium has at least one auxotrophy for the essential nutrient(s) and each being dependent on at least one of the other strains in the plurality for growth. Metabolic interdependency is incorporated within the designed microbial-based consortia to improve engrafting and stability of the corsortium population in the gut, and performance of the consortia, through stable provision of nutrients.

The phrase "metabolic support microbial strain", is intended for the purposes of the spectification and claims to include strains capable of producing one or more nutrients including any one or more of sugars, acetate, lactate, butyrate, propionate, fatty acids, amino acids, vitamins, co-factors, or other metabolites or nutrients that aid growth of one or more microbial strains in a microbial consortium of the present disclosure, including molecules required for carbon and/or nitrogen source utilization and the ability to breakdown complex carbohydrates and proteins. In one aspect, metabolic interdependency is enhanced by inclusion of one or more metabolic support microbial strains to the consortium.

The phrase "absent or underrepresented in a microbiome of an organism" is used herein interchangeably with the phrase "absent or underrepresented functionality" and is intended to mean a metabolic function that is lacking or underrepresented in the microbiome of an organism of interest having a disorder or disease as compared to the microbiome of a healthy organism. The terms "functionality" and "metabolic functionality" are used herein interchangeably for the purposes of the spectification and claims.

As used herein, the phrase "a biologically pure culture of a microbial strain" includes one or a combination of spores and vegetative cells of the biologically pure fermentation culture of the microbial strain. By "biologically pure" is meant essentially biologically pure as it is understood in the art. In addition, the phrases "a biologically pure culture of a microbial strain" and "microbial strains" as used herein for the purposes of the specification and claims include a mutant of the microbial strain having all the identifying characteristics thereof.

Examples of absent or underrepresented functionalities include one or a combination of: synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, breakdown of complex carbohydrates and proteins, conversion of secoisolariciresinol diglucoside (SDG) to enterodiol and enterolactone, synthesis of acetylcholine, synthesis of indole-3-propionate and indole-3-aldehyde, synthesis of 4-amino-butyrate (gamma-aminobutyric acid; GABA), metabolism of acetylcholine, synthesis of a siderophore not inhibited by Lipocalin-2, synthesis of one or both of EPS and LTA compounds with immune modulating properties, conversion of formate into acetate, pathway for breakdown of host metabolites for urea cycle disorder, pathway for breakdown of host metabolites for phenylketonuria, pathway for breakdown of host metabolites for organic acidemias, pathway for breakdown of host metabolites for maple syrup urine disease, and pathway for breakdown or activation of a drug molecule.

The presently disclosed subject matter describes the rational design of communities of microbes (i.e, microbial consortia) for use in benefiting the health of organisms. In one embodiment, the described microbial-based biotherapeutics are useful for benefiting human and animal health. In one embodiment, the described microbial-based biotherapeutics are useful for benefiting plant health. The methods describe design of microbial consortia based on complementing and/or replacing key functionalities that are lacking or underrepresented in an organism. In addition, the consortia are designed to possess critical metabolic interdependencies which results in improved engrafting, stability and performance of the consortium in the organism.

In one aspect, the new approach described herein is based on rationally designed microbial consortia to reduce inflammation and control infection. In contrast to prior art microbiome-derived therapeutics, the microbial consortia described herein are designed to control inflammation and/or to attack pathogens in the gut via antagonistic mechanisms, as well as to stably populate the host organism. The stability of the microbial consortia is achieved by creating combinations of microbes that have metabolic interdependencies. In one embodiment, "designer" microbial consortia are provided for the combined treatment of inflammation and infection. In addition, in another embodiment, the approach for the rational design of microbial-based biotherapeutics based on providing functionality and stability of the consortia is broadly applicable for the treatment of other conditions including neurological, metabolic and oncology-related conditions. In one embodiment, the designer microbial consortia are useful for benefiting the health of an organism even in the absence of symptoms of a particular disease or disorder. Thus, the term "therapeutic", as it is used herein to describe the microbial-based compositions and methods for design thereof, is meant to be interpreted in its broadest sense to include microbial-based compositions for use in organisms that do not show symptoms of a disease or disorder to benefit the health of those organisms.

One mechanism is proposed herein that a dysbiotic gut microbiome can provide an ideal niche for the establishment of (opportunistic) pathogenic bacteria and fungi. It follows then, that it is important to include treatment of chronic inflammation in treatment for multi-pathogen based infections (i.e., infections composed of bacteria and/or fungi). Unfortunately, as described in the Background section of this document, treatment of infections involving both bacterial and fungal pathogens through administration of antibiotics is often unsuccessful and detrimental to a healthy microbiome. Broad spectrum antibiotics may further contribute to the dysbiotic status of the gut microbiome, with additional negative consequences on the regulation of the innate immune response and the conditions of chronic inflammation.

The deterioration of the gut microbiome can negatively affect the innate immune response, which is regulated by a healthy gut microbiome; this is turn can have a further negative effect on the severity of the self-sustaining cycle of chronic inflammation of the gastrointestinal tract as well as other parts of the body, affecting many therapeutic treatments, including oncology related conditions. In addition, a dysbiotic gut microbiome creates an ideal environment for the establishment of (opportunistic) pathogens, which in turn can also contribute to the severity of inflammation and its clinical symptoms.

Based on observations in the literature describing the elevation and/or association of opportunistic pathogenic bacteria and fungi with chronic inflammatory conditions including Inflammatory Bowel Diseases (IBD), Crohn's Disease, Ulcerative Colitis, Irritable Bowel Syndrome (IBS), Type 1&2 diabetes, and asthma, the present inventors provide a process for rational design of microbial consortia, driven by critical functionalities, to benefit the health of organisms including treatment of conditions of chronic inflammation and infection. In one aspect, the process for rational design of microbial consortia provided herein includes designating a combination of microbes that simultaneously resets the immune system, targets or controls a pathogenic infection, and which also possess critical metabolic interdependencies to optimize strain engrafting and stability and performance of the consortium in the organism. More specifically, the combination of microbes (the designer consortium) includes functionalities to reset the immune system by lowering (pre)inflammatory interleukins and to addresses a pathogenic infection by both targeting the immune response towards pathogen clearance and by providing antagonistic compounds for additional pathogen control in the gut. In addition, the designer consortia overcome the metabolic deficiencies of a dysbiosic gut microbiome, which can have a negative impact on engrafting and performance of the therapeutic strains, while the designed metabolic interdependencies of the consortium members provides for its stability in the host organism.

The approach to the rational design of microbial-based therapeutics provided herein differs from the prior art. For example, the commonly used approach for microbiome-derived therapeutics has been to compare the microbiomes of healthy subjects and patients suffering from a specific condition in order to identify microorganisms lacking or under-represented in the patients with the condition. This information is then used to propose a therapeutic formulation to replenish the microorganisms that are lacking or under-represented in the microbiome. This approach has been used for conditions where a role of the microbiome has been implied, including immune dysregulation such as IBD (Atarashi et al, 2013; Nsrushima et al, 2014; Halfvarson et al, 2017), food allergies (Canani et al, 2016) and asthma (Canani et al, 2017), neurological disorders such as Alzheimer's Disease (Bhattacharjee and Lukiw, 2013), Autism Spectrum Disorder (Li and Zhou, 2016; Vuong, 2017), dementia (Moos et al, 2016), peri-natal/post-partum depression (Rogers et al, 2016), oncology related conditions such as colon cancer (and other GI cancers) (Schwabe and Jobin, 2013; Sun and Kato, 2016), solid tumors, melanoma, lung cancer, breast cancer, metabolic disorders (Boulange et al, 2016) including Type-1 and Type-2 diabetes (Paun and Danska, 2016), and recurrent infections with *Clostridium difficile* (Seekatz, 2016). However, as can be concluded from the review by Wright et al (2015), which compared the gastrointestinal microbiome of patients with Crohn's disease, significant differences between the composition of dysbiotic microbiomes in Crohn's disease patients were observed between various studies, making it difficult to define which missing or underrepresented microorganisms should be replenished.

In contrast to the prior art, the methods described herein focus on replacement of missing functionalities rather than on replacing missing microorganisms. In addition, the consortia described herein are designed to have critical metabolic interdependencies for improved engrafting, stability and performance of the consortium in the organism. One hypothesis of the present invention, without being limited to any one mechanism of action, is that one of the direct effects of a dysbiotic gut microbiome is an underrepresentation of commensal gut bacteria that provide critical metabolites in support of the health and stability of the gut microbiome. More specifically, rational design of microbial-based communities to treat specific conditions is provided herein that focuses on both therapeutic functionality and critical support functions for strain interdependence (e.g. with regard to providing essential nutrients/metabolites to overcome auxotrophic phenotypes). In this manner, designer consortia are provided where the functions of engrafting and performance are not omitted from the process. Addressing both therapeutic functionality and critical metabolic strain interdependencies enhances engrafting of strains in a broader selection of cohorts regardless of the levels of dysbiosis of the gut microbiome, and enhances therapeutic performance of the rationally designed consortium. These designer consortia provided herein for human therapy can be based on microorganisms isolated from the human microbiome or specifically from the human gut microbiome, and can also be supplemented with microorganisms isolated from other environments, including the microbiome of animals and plants, and also from fermented foods and soils. These designer consortia can be comprised of bacteria, archaea, fungi and viruses, and combinations thereof.

In one aspect, in addition, to that described above for IBD, the present disclosure describes the design of a microbial therapeutic consortium that provides and/or complements key functionalities that are lacking or underrepresented in the dysbiotic gut microbiome of patients having a wide range of disorders or diseases as compared to healthy subjects. The list of critical functionalities provided by the various designed therapeutic consortia can be tailored to the disease or disorder as described herein. In every case, metabolic interdependency is incorporated into the designed consortia to improve engrafting, stability of the corsortium population in the gut, and performance of the consortia, through stable provision of essential nutrients.

Figure 2:
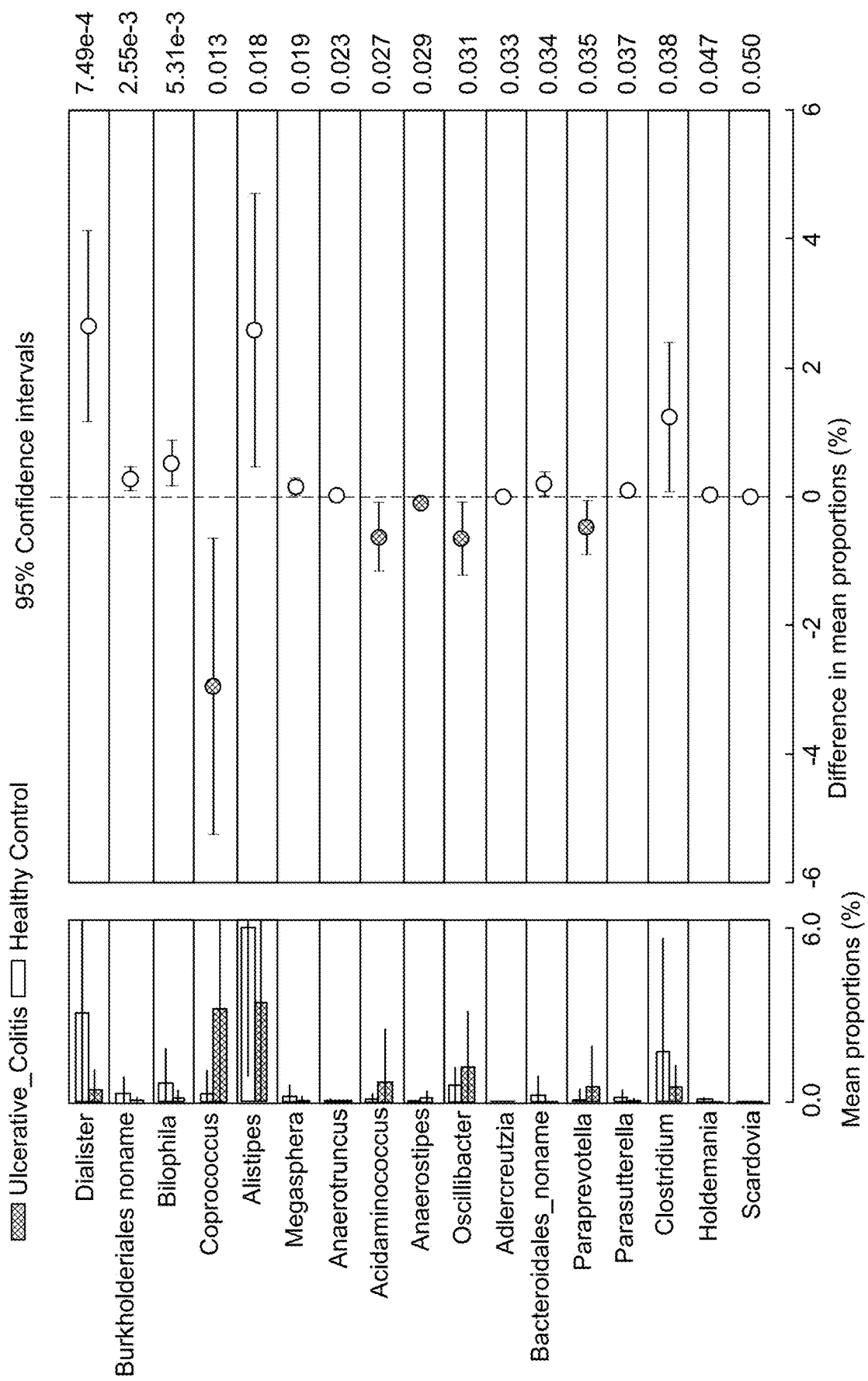
FIG. 2 is a graph showing two-way comparison of the microbiome composition between Ulcerative Colitis patients versus healthy individuals. A total of 17 differential features was identified on the genus level, of which the most prominent (95% confidence interval) were *Dialister* (high in Healthy), *Alistipes* (high in Healthy), *Clostridium* (high in Healthy), and *Coprococcus* (high in UC).
Figure 3:
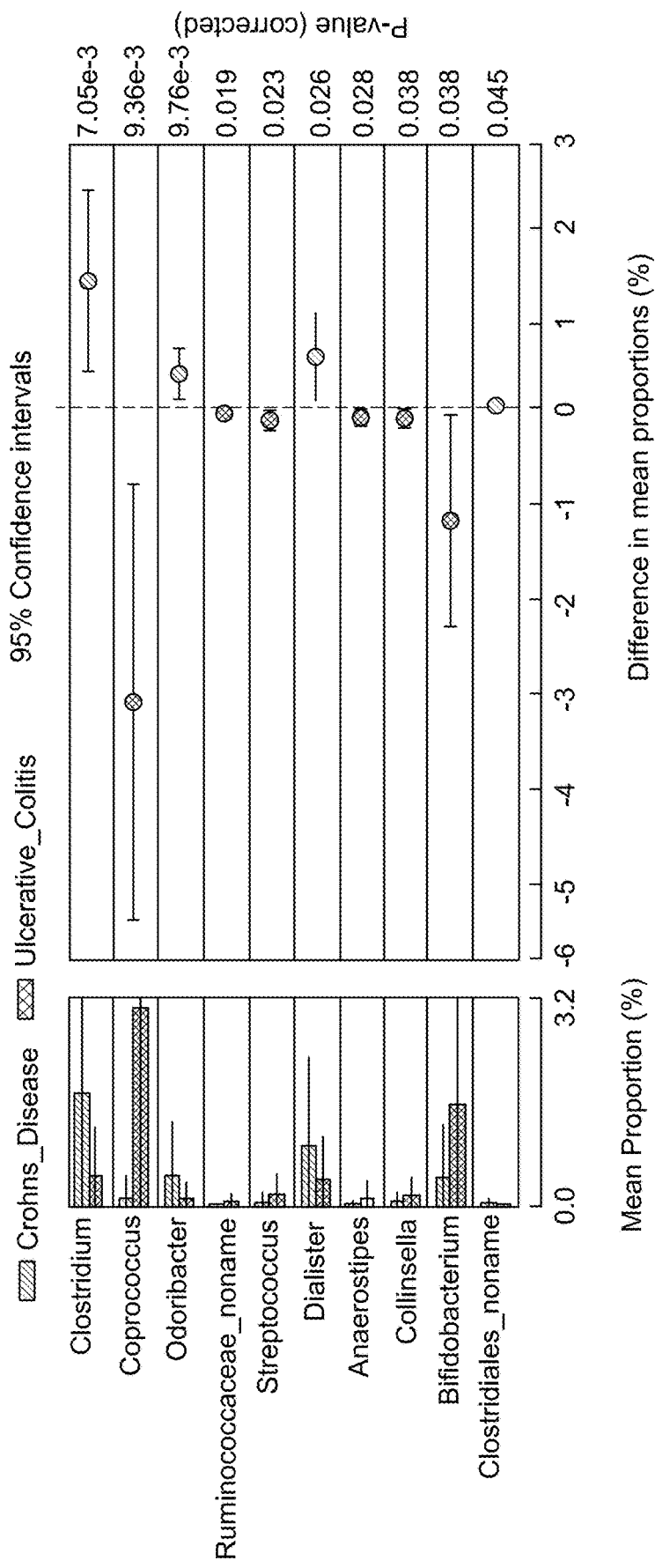
FIG. 3 is a two-way comparison of the microbiome composition between Crohn's Disease patients versus Ulcerative Colitis patients. A total of 10 differential features was identified on the genus level, of which the most prominent were *Clostridium* (high in Crohn's), *Dialister* (high in Crohn's), *Coprococcus* (high in UC), and *Bifidobacterium* (high in UC).
Figure 4:
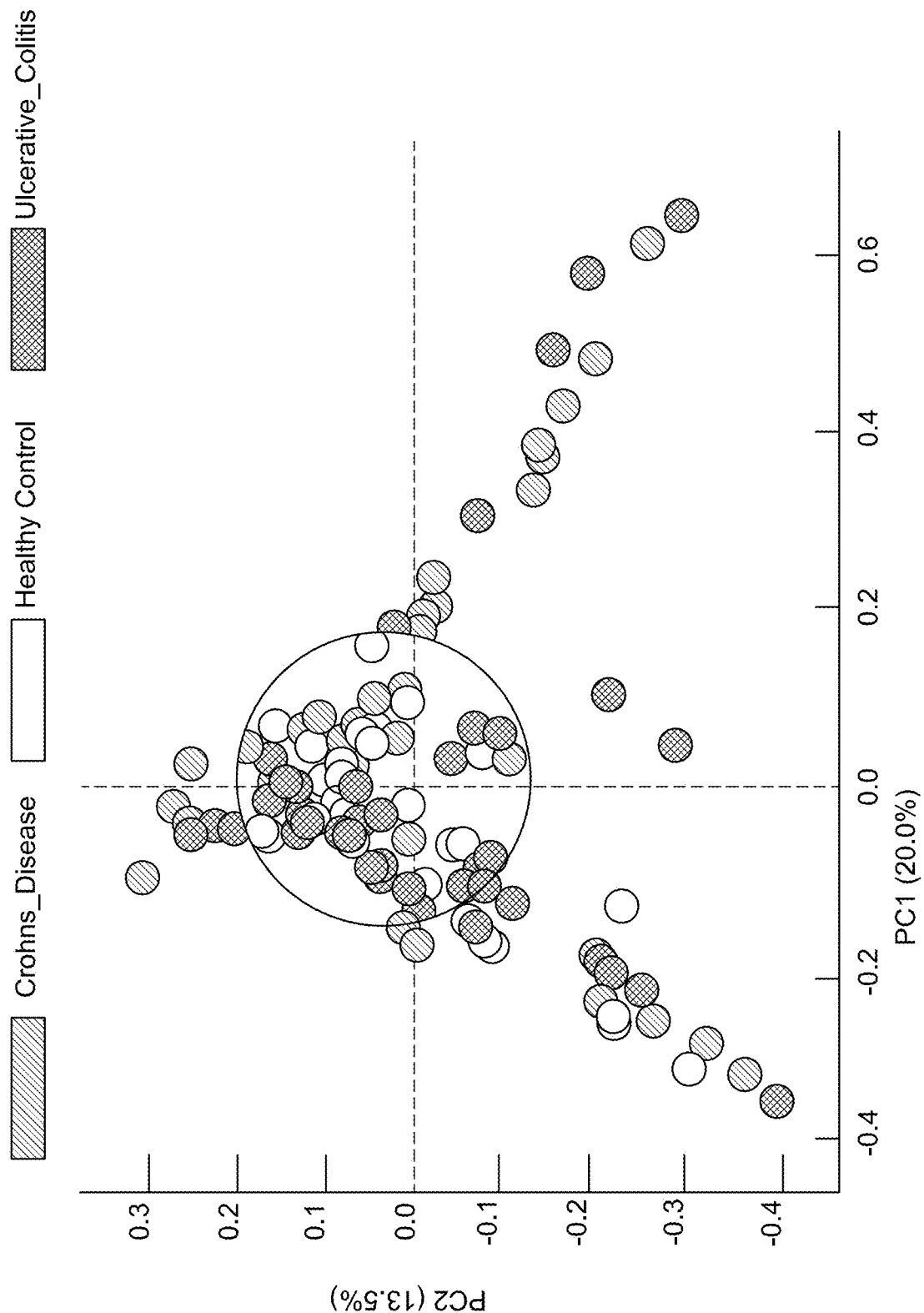
FIG. 4 is a graph showing principle compound analysis at the genus/species level of the microbiomes of healthy individuals and patients suffering from Crohn's disease or Ulcerative Colitis, respectively. For healthy individuals, 4 out of 50 microbiomes were found outside the cluster defined by the circle, while for Crohn's disease and Ulcerative Colitis 23 and 17 out of 50 microbiomes, respectively, were placed outside the cluster.

The identification of the altered functionalities of a disbiotic gut is described in one aspect in EXAMPLE 1 herein, through comparative gut metagenome analysis between healthy individuals and patients with Crohn's disease or Ulcerative Colitis. The statistically significant differences in the microbiomes at the genus level are shown in FIGS. 1-3. FIG. 1 shows a two-way comparison of the microbiome composition between Crohn's Disease Patients versus Healthy Individuals. FIG. 2 shows a two-way comparison of the microbiome composition between Ulcerative Colitis patients versus Healthy Individuals. FIG. 3 shows a two-way comparison of the microbiome composition between Crohn's Disease patients versus Ulcerative Colitis patients. Principal component analysis was performed in an attempt to understand the significance of the differences observed in the levels of microorganisms at the genus and/or species level in the normal versus diseased samples. The results are shown in FIG. 4. Surprisingly, the data in FIG. 4 show that the species that are increased in the Crohn's and Ulcerative Colitis patients do not seem to be a major factor contributing to the dysbiosis of the gut. These species are often not the same among the various Crohn's and Ulcerative Colitis patients and, thus, are not predictive of the disease. Often there is no link between the composition of the dysbiotic gut microbiome and the disease. This result is confirmed in the literature by the diverse outcomes of various studies as reviewed by Wright et al (2015).

Therefore, in one embodiment, the present methods describe design of a microbial consortia that focus on complementing key functionalities that are lacking or underrepresented in the dysbiotic gut microbiome of IBD patients as compared to healthy subjects, rather than trying to replace missing species. In one embodiment, the critical functionalities for treatment of IBD and for general maintenance of a healthy gut microbiome include: synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, and breakdown of complex carbohydrates and proteins.

The microbial consortia of the present disclosure include one or more of the key functionalities listed above. The key functionalities are described in further detail below. EXAMPLE 2 describes assays for characterization of the functionalities for strains of interest. EXAMPLES 3-10 and Tables 1-13 herein describe the design of microbial consortia based on functionality and critical metabolic interdependencies, and their application as a stand-alone biotherapeutic or as a companion treatment. The rational design of microbial-based biotherapeutics based on functionality and stability of the consortia is broadly applicable for the treatment of conditions involving chronic inflammation and infection, and also for conditions including neurological, metabolic and oncology related conditions. The health benefit for the microbial-based biotherapeutics can be one or more of Ulcerative Colitis, Crohn's Disease, Inflammatory Bowel Diseases, Irritable Bowel Syndrome, food allergies, asthma, neurological disorders, Alzheimer's Disease, Autism Spectrum Disorder, dementia, peri-natal/post-partum depression, cancer, colon cancer, GI cancer, solid tumors, melanoma, lung cancer, breast cancer, metabolic disorders, phenylketonuria, organic acidemias, maple syrup urine disease, obesity, diabetes, arthrosclerosis, acute infections, chronic infections, recurrent infections, primary sclerosing cholangitis (PSC) as an inflammation of the bile duct, or infection with *Clostridium difficile*.

EXAMPLES 3-7 describe the methods used in the rational design and EXAMPLES 8, 9 and 10, describe the rational design of microbial consortia for IBD, for Type-2 diabetes, and for Type-1 diabetes, respectively. In that the consortia of the present invention can benefit the general health of the host microbiome and reduce inflammatory pathology, these consortia can be useful for the treatment and/or prevention of a wide range of diseases and disorders in addition to IBD and Type-1 and Type-2 diabetes including oncology conditions, neurological disorders, and metabolic disorders. The consortia of the present disclosure are designated as GUT-103, GUT-104, and GUT-107, designed for the treatment of IBD (see EXAMPLE 8), Type-2 diabetes (see EXAMPLE 9), and Type-1 diabetes (see EXAMPLE 10), respectivley. However, as mentioned above, the various consortia can be useful for a wide range of diseases and disorders in addition to IBD and Type-1 and Type-2 diabetes including oncology conditions, neurological disorders, and metabolic disorders.

In addition, subsets of strains of the GUT-103 and GUT-104 consortia can be useful for benefiting the general health of an animal or a human and for reducing inflammatory pathology. Thus, these consortia can be useful for the treatment and/or prevention of a wide range of diseases and disorders in addition to IBD and Type-2 diabetes including oncology conditions, neurological disorders, and metabolic disorders. The subsets of strains of the GUT-103 consortia are described in EXAMPLE 8 and are designated as GUT-103 consortium subset 1, GUT-103 consortium subset 2, and GUT-103 consortium subset 1+GUT-103 consortium subset 2. The subset of strains of the GUT-104 consortia is described in EXAMPLE 9 and is designated as GUT-104 consortium subset 3.

The key functionalities absent or underrepresented in a microbiome of an organism of interest that are used for the rational design of microbial consortia for benefiting the health of an organism are described in further detail below.

Synthesis of short chain fatty acids. Several animal studies have highlighted the role for short chain fatty acids, especially propionate and butyrate, in regulatory T cell recruitment and function (Arpaia et al, 2013; Smith et al, 2013). The recruitment in the colon and extra-thymic conditioning of regulatory T cell response by SCFA make these molecules an important link in the cross-talk between the gut microbiome and the immune system. Of the few clinical studies that have applied SCFA therapeutically in inflammatory disease in a controlled trial setting, improvements in clinical and histological indices of IBD and therapeutic efficacy in acute radiation proctitis have been observed supporting a direct anti-inflammatory role of butyrate at sites of inflammation (Vernia et al, 2000; Vernia et al, 2003). Thus, in one embodiment, both butyrate and propionate synthesis are included as key functionalities in the rational design process of a microbial-based therapeutic. In one embodiment, these functionalities are useful for control of chronic inflammation.

Indole synthesis. Several studies have shown the role of indole, a metabolite produced from tryptophan, in reducing pathogenic *E. coli* from attaching to epithelial cells (Bansal et al, 2007), in strengthening the mucosal barrier and mucin production (Bansal et al 2010), and modulating the secretion of the glucagon-like peptide-1 (GLP-1) (Chimerel et al 2014). Indole synthesis can also induce the synthesis of the anti-inflammatory IL22, which can have a beneficial effect on metabolic disorders such as Type-2 diabetes, via the AHR pathway (Hubbard et al, 2015 a&b), as well as that of other compounds including interleukin-6 (IL6), cytochrome P450 1A1 (CYP1A1), cytochrome P450 1B1 (CYP1B1), vascular endothelial growth factor A (VEGFA), and prostaglandin G/H synthase 2 (PTGS2). Thus, in one embodiment, indole synthesis is included as a key functionality in the rational design process of a microbial-based therapeutic. In one embodiment, these functionalities are useful for control of chronic inflammation and infections.

Bile acid deconjugation and conversion. A dysbiotic gut environment can result in the inefficient microbial conversion of bile salts into their primary and secondary bile acids, thus creating an ideal environment for pathogenic microorganisms, such as *C. difficile*, to thrive. As demonstrated by Antunes et al (2011), administration of antibiotics resulted in a large shift in the bile acid pool in the cecum of mice, which lead to *C. difficile* spore germination (Antunes et al, 2011; Giel et al, 2010). IBD patients characterized by dysbiosis of their gut microbiome due to inflammation were also found to have lower concentrations of secondary bile acids in the feces and periphery as well as more conjugated bile acids in the feces compared to healthy subjects (Duboc et al, 2013). In addition, bile acid levels and distribution are altered in Type-2 diabetes and increased following bariatric procedures, in parallel with reduced body weight and improved insulin sensitivity and glycemic control (Ma and Patti, 2014). Thus, in one embodiment, conversion of conjugated bile acids, especially the conversion of cholic acid and chenodeoxycholic acid via a multistep process that includes 7-alpha-dehydroxylation as encoded by 7-alpha dehydratase activity (7-α-DH) or 7-alpha-hydroxysteroid dehydrogenase activity (7-α-HSD), are included as key functionalities for a microbial-based therapeutic. In one embodiment, these functionalities are useful for control of chronic inflammation and infections, as well as treatment of metabolic syndromes including obesity, Type-2 diabetes, and other components of the metabolic syndromes.

Competition for critical nutrients, such as iron. Competition for iron is one of the key functions driving the competitiveness and establishments of microorganisms (Kortman et al, 2014). A rationally-designed consortium can include one or several strains that synthesize one or more siderophores (molecules with high affinity to bind ferrous iron) under iron-limiting conditions. Ideally, these siderophores are insensitive to inhibition by Lipocalin-2, a peptide which inhibits specific siderophores and their uptake, and is a major defense system in the colon triggered by bacterial infections. Lipocalin-2 is especially effective to inhibit strains that produce the siderophore Enterobactin, a catechol-type siderophore produced by several Enterobacteria. A rationally-designed consortium can include one or several strains that have uptake systems for heterologously produced siderophores. The presence of such systems allows strains to compete for ferrous iron using siderophores produced by other microorganisms, providing them with a competitive advantage. This approach can be used to compete against both pathogenic bacteria and fungi. Thus, the presence of a ferrichrome uptake system in addition to the synthesis of a Lipocalin-2 insensitive siderophore, can be included as a criterion in the consortium design to allow for enhanced competition with opportunistic pathogenic fungi. In one embodiment, these functionalities are useful for control of chronic inflammation and infections.

Antagonistic metabolites, lantibiotics, bacteriocins. Bacteriocins, of which lantibiotics are considered a specific class, have shown great promise as new antibiotics for therapeutic application, as reviewed by Field et al (2015). A major drawback that has yet to be overcome with respect to therapeutic use is the sensitivity of lantibiotics to proteolytic cleavage by intestinal enzymes. However, it can be hypothesized that the bacteriocins and lantibiotics, synthesized by commensal gut bacteria, have been adapted to resist breakdown by intestinal proteases. Thus, bacteriocin synthesis can be included as a key functionality in the rational design process of a microbial-based therapeutic. In one embodiment, this functionality is useful for control of infections.

Production of endocrine molecules. The "sterolbiome" describes the genetic potential of the gut microbiome to produce endocrine molecules from endogenous and exogenous steroids. The sterobiome includes the secondary bile acids, derived from microbial conversion of bile salts, as well as other molecules. In addition to its bile acid 7-alpha-dehydroxylating activity, C. scindens ATCC 35704 was found to also metabolize host glucocorticoids into C-19 androgens (Ridlon et al, 2013); this reaction is carried out as the result of steroid-17,20-desmolase activity and results in the formation of 11β-hydroxyandrosten-3,17-dione, a primary adrenal steroid in the human host that has an osteotropic effect (stimulating bone formation). In addition, lignans are phyto-oestrogens that in order to provide their beneficial health effects need first to be metabolized by intestinal bacteria (Cassidy et al, 2000). Secoisolariciresinol diglucoside (SDG) is one of the most abundant dietary lignans and is of interest because of its implications for the prevention of breast and colon cancer (Chen et al, 2003), atherosclerosis (Prasad, 1999) and diabetes (Prasad, 2001). The human intestinal microbiome is essential for the conversion of the dietary lignan secoisolariciresinol diglucoside (SDG) via secoisolariciresinol (SECO) to the enterolignans enterodiol (ED) and enterolactone (EL). Thus, conversion of lignan, especially secoisolariciresinol diglucoside, can be included as a key functionality in the rational design process of a microbial-based therapeutic. In one embodiment, this functionality is useful for treatment or prevention of diabetes and providing beneficial health effects.

Breakdown of complex biomolecules. A healthy gut microbiome is critical for the efficient breakdown of complex carbohydrates and proteins into their basic building blocks, such as C5 and C6 sugars and their fermentation products, peptides or amino sugars and amino acids. Thus, one of the direct effects of a dysbiotic gut microbiome is an underrepresentation of commensal gut bacteria that provide critical metabolites in support of the health and stability of the gut microbiome. Consequently, strains belonging to but not limited to the genera Alistipes, Megamonas or Bacteroides that are known for their efficient breakdown of complex biomolecules, are included in the rational design of a microbial-based therapeutic. An additional advantage is that these strains can also help to break down food-specific allergens, thus helping to prevent or diminish an immune reaction against these allergens that could trigger an inflammatory response in the gastrointestinal track or beyond. Thus, breakdown of complex biomolecules, can be included as a key functionality in the rational design process of a microbial-based therapeutic. In one embodiment, this functionality is useful for enhancing engraftment and performance of therapeutic strains. In one embodiment, strains that efficiently breakdown complex biomolecules are referred to as "metabolic support microbial strains". Synthesis and metabolism of neurotransmitters: 4-amino-butyrate (gamma-aminobutyric acid; GABA), acetylcholine and tryptophan. Intestinal bacteria can send chemical messages to the brain and some strains of gut bacteria can secrete neurotransmitters such as acetylcholine, 4-amino-butyrate (GABA) and tryptophan (Mazzoli and Pessione, 2016). Because of this activity, dysbiosis of the intestinal microbiome has been implemented in various neuropsychiatric disorders such as schizophrenia, autistic disorders, anxiety disorders and major depressive disorders (for review see, Evrensel and Ceylan, 2015). For instance, decreased levels of GABA have been associated with depression and anxiety. Thus, both the synthesis and metabolism of acetylcholine, 4-amino-butyrate (GABA), and tryptophan can be included as key functionalities in the rational design process of a microbial-based therapeutic. In one embodiment, these functionalities are useful for control of chronic inflammation.

Synthesis of extracellular polysaccharides and lipoteichoic acid. Activation of pathogen recognition receptors is crucial for the initiation of innate immunity, which plays a key role in first-line defense until more specific adaptive immunity is developed. Two key bacterial metabolites, extracellular polysaccharides (EPS) and lipoteichoic acid (LTA), are recognized by pathogen recognition receptors. While recognition of EPS and LTA from pathogenic microorganisms will trigger a strong immune cascade, the same molecules from beneficiary gut bacteria can help to condition the innate immune response to promote type-1 pro-inflammatory responsiveness. Thus, both EPS and LTA synthesis can be included as key functionalities in the rational design process of a microbial-based therapeutic. In one embodiment, these functionalities are useful for control of chronic inflammation.

Overcoming other undesirable metabolic effects. Relatively little is known about the role of formate in the gut. It has been linked to methanogenesis and appears to be elevated in inflammatory conditions (Vanderhaeghen et al, 2015; Bereswill et al, 2011). Thus, conversion of formate into acetate can be included as key functionalities in the rational design process of a microbial-based therapeutic.

Methods are provided for the rational design of microbial consortia possessing the functionalities necessary for therapeutic treatment and/or maintaining and optimizing health. The phrase "therapeutic treatment" or "biotherapeutic" for the purposes of the specification and claims are herein used interchangeably with the phrase "therapeutic treatment and/ or maintaining and optimizing health". Thus, the purposes of maintaining or optimizing health or preventing the on-set of a particular disease or discorder are all included in the meaning of "therapeutic treatment" or "biotherapeutic".

In the methods for rational design of microbial consortia, machine learning approaches can be used for network optimization, to make predictions on beneficial strain adaptations, or to define the effects of external perturbations on consortium stability and performance. More specifically, in one embodiment, a method is provided for rational design of microbial consortia for benefiting the health of an organism, that includes, for a plurality of microbial strains each having at least one functionality in a set of functionalities absent or underrepresented in a microbiome of an organism of interest, creating for each strain using genome annotation an in silico metabolic model that predicts an auxotrophic profile for one or a combination of essential nutrients. The next step is integrating in silico the metabolic models for each of the plurality of strains to obtain a combined metabolic model for the plurality of strains, and designating a microbial consortium having a metabolic interdependency. The designating of a microbial consortium having a metabolic interdependency can include optionally introducing into the plurality or removing from the plurality one or more microbial strains. The metabolic interdependency of the plurality of strains in the microbial consortium includes each of the strains having at least one auxotrophy for the essential nutrient(s) and each being dependent on at least one of the other strains in the plurality for growth. In this manner, microbial consortia are designed to populate and benefit the health of the organism. The creatation of in silico metabolic models for individual strains using genome annotation to predict auxotrophic profiles, integration in silico of the metabolic models to obtain a combined metabolic model for the plurality of strains, and designation of a microbial consortium having a metabolic interdependency are described in EXAMPLES 3-7.

In one embodiment, a method is provided for rational design of microbial consortia for benefiting the health of an organism, the method comprising: for a plurality of microbial strains each having at least one functionality in a set of functionalities absent or underrepresented in a microbiome of an organism of interest, creating for each strain using genome annotation an in silico metabolic model that predicts an auxotrophic profile for one or a combination of essential nutrients; integrating in silico the metabolic models for each of the plurality of strains to obtain a combined metabolic model for the plurality of strains; and designating a microbial consortium having a metabolic interdependency, including by optionally introducing into the plurality or removing from the plurality one or more microbial strains, wherein the metabolic interdependency of the plurality of strains in the microbial consortium includes each of the strains having at least one auxotrophy for the essential nutrient(s) and each being dependent on at least one of the other strains in the plurality for growth, wherein the microbial consortium populates and benefits the health of the organism.

In one embodiment, a method is provided for rational design of microbial consortia for benefiting the health of an organism, the method comprising: combining ex vivo a plurality of biologically pure cultures of microbial strains having at least one functionality absent or underrepresented in the microbiome of an organism having a disease or disorder. Each of the absent or underrepresented functionalities is present in at least one of the microbial strains in the plurality, and each of the microbial strains has at least one auxotrophy and is dependent on at least one of the other strains in the plurality for growth. This creates a microbial consortium having a metabolic interdependency enabling it to populate and benefit the health of the organism with the disease or disorder. The metabolic interdependency can include each of the strains having at least two auxotrophies and each being dependent on at least one of the other strains in the plurality for growth. The metabolic interdependency can also include each of the strains having three or more auxotrophies and each being dependent on at least one of the other strains in the plurality for growth.

The one or a combination of essential nutrients can include amino acids, vitamins, or co-factors. The modeling in silico for each strain further can also include modeling of the carbon and nitrogen source utilization. The methods may further include introducing by mutagenesis one or more auxotrophies into a biologically pure culture of one or more of the microbial strains to enhance the metabolic interdependency and the stability of the microbial consortium. The auxotrophy for one or more of the plurality of the microbial strains may be confirmed in vitro. Similarly, the metabolic interdependency of the microbial consortium may be confirmed by growing the plurality of microbial strains together in vitro in a non-selective medium under optimal growth conditions.

The methods may further include introducing one or more additional in silico metabolic models corresponding to one or more metabolic support microbial strains to enhance the metabolic interdependency of the microbial consortium. The metabolic support microbial strain(s) do not necessarily have at least one absent or underrepresented functionality.

In one embodiment, compositions produced by the process described above are provided for benefiting the health of an organism. More specifically, a composition is provided for benefiting the health of an organism, the composition comprising: a microbial consortium for benefiting the health of an organism; and a carrier, the microbial consortium produced by a process comprising: for a plurality of microbial strains each having at least one functionality in a set of functionalities absent or underrepresented in a microbiome of an organism of interest, creating for each strain using genome annotation an in silico metabolic model that predicts an auxotrophic profile for one or a combination of essential nutrients; integrating in silico the metabolic models for each of the plurality of strains to obtain a combined metabolic model for the plurality of strains; and designating a microbial consortium having a metabolic interdependency, including by optionally introducing into the plurality or removing from the plurality one or more microbial strains, wherein the metabolic interdependency of the plurality of strains in the microbial consortium includes each of the strains having at least one auxotrophy for the essential nutrient(s) and each being dependent on at least one of the other strains in the plurality for growth, wherein the microbial consortium populates and benefits the health of the organism.

In one embodiment, a composition is provided for benefiting the health of an organism that includes: i) a plurality of biologically pure cultures of microbial strains having at least one functionality absent or underrepresented in the microbiome of an organism having a disease or disorder, wherein each of the absent or underrepresented functionalities is present in at least one of the microbial strains in the plurality, and wherein each of the microbial strains has at least one auxotrophy and is dependent on at least one of the other strains in the plurality for growth; and ii) a carrier.

In one embodiment, one or more of the plurality of microbial strains in the microbial consortia of the present disclosure can be a genetically modified strain, for example, to improve or enhance one (or more) metabolic functionality of the strain(s).

The microbial strains can be comprised of a combination of bacteria, archaea, or fungi. The microbial strains may be derived from an animal or a human gut microbiome, a plant microbiome, a soil, a food, or a fermented food.

In the compositions and methods of the present disclosure, the microbial strains may include strains from one or a combination of: Gram-positive species, Gram negative species, species of the phylum Firmicutes, species of the phylum Actinobacteria, species of the phylum Proteobacteria, species of the phylum Bacteroidetes, species of the phylum Verrucomicrobia, species of the class Negativicutes, species of the class Clostridiales, species of *Clostridium* cluster IV, species of *Clostridium* cluster XIVa, species of *Clostridium* cluster XVIII, species of *Eubacterium*, species of the Ruminococcaceae, species of *Ruminococcus, Ruminicoccus bromii*, species of *Anaerofilum*, species of *Coprococcus*, species of *Dorea*, species of *Lachnospira*, species of *Roseburia*, species of *Butyrivibrio*, species of *Lactobacillus*, species of *Clostridium*, species of Lachnospiraceae, species of Selenomonadales, species of Selenomonadaceae, species of Sporomusaceae, species of Acidaminococcales, species of Acidaminococcaceae, species of Vellionellales, species of Vellionellaceae, species of *Megamonas*, species of *Acidaminococcus*, species of *Succinispira*, species of *Megasphaera*, species of *Lactonifactor*, species of *Dialister*, species of Pelosiunus, species of *Veillonella, Acidamonas intestini, Megamonas funiformis, Megamonas hypermegale, Megamonas rupellensis*, species of Verrucomicrobiales, species of the family Verrucomicrobiaceae, species of the genus *Akkermansiaceae*, species of *Akkermansia, Akkermansia muciniphila*, species of the order Bifidobacteriales, species of the family Bifidobacteriaceae, species of *Bifidobacterium, Bifidobacterium adolescentis*, species of the family Erysipelotrichaceae, species of the family Prevotellaceae, species of the family Rikenellaceae, species of the family Porphyromonadaceae, species of the family Lactobacillaceae, species of the family Bacteroidaceae, species of *Rikenella*, species of *Alistipes, Alistipes putredinis*, species of Anaerocella, species of *Porphyromonas*, species of *Prevotella*, species of *Hallella*, species of *Alloprevotella*, species of *Bacteroides*, species of *Marvinbryantia*, or species of *Dielma*. In the compositions and methods of the present disclosure, the microbial strains can include strains from one or a combination of: *Megamonas funiformis, Megamonas hypermegale, Acidaminococcus intestini, Bacteroides massiliensis, Bacteroides stercoris, Barnesiella intestinihominis, Faecalibacterium prausnitzii, Subdoligranulum variabile, Anaerostipes caccae, Anaerostipes hadrus, Clostridium symbiosum, Clostridium scindens, Clostridium bolteae, Clostridium saccharogumia, Clostridium ramosum, Blautia producta, Blautia hydrogenotrophica, Marvinbryantia formatexigens, Lactonifactor longoviformis*, and *Akkermansia muciniphila*.

In one embodiment, the organism can be a human or an animal and the set of functionalities absent or underrepresented in the microbiome can include one or a combination of: synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, breakdown of complex carbohydrates and proteins, synthesis of β-fructofuranosidase activity for the breakdown of the dietary prebiotic fiber inulin, conversion of secoisolariciresinol diglucoside (SDG) to enterodiol and enterolactone, synthesis of acetylcholine, synthesis of indole-3-propionate and indole-3-aldehyde, synthesis of 4-amino-butyrate (gamma-aminobutyric acid; GABA), metabolism of acetylcholine, synthesis of a siderophore not inhibited by Lipocalin-2, synthesis of one or both of EPS and LTA compounds with immune modulating properties, conversion of formate into acetate, pathway for breakdown of host metabolites for urea cycle disorder, pathway for breakdown of host metabolites for phenylketonuria, pathway for breakdown of host metabolites for organic acidemias, pathway for breakdown of host metabolites for maple syrup urine disease, or pathway for breakdown or activation of a drug molecule. In the example of pathway for breakdown or activation of a drug molecule, this is used to overcome the negative side effects of certain therapies, or as a trigger to activate an orally provided drug in the GI track. In this case, the drug may be administered as a modified compound that is, by unlimited example, either in a more stable or less toxic form. Only in the GI track the activity of at least one of the consortium members would result in drug breakdown/activation. The concept of microbial drug activation can be extended to the microbiome environment of a tumor, e.g. breast cancer or solid tumors in general, where the inactive form of the drug is intravenously administered and only activated by microbial activity of organisms residing in the microbiome environment of the tumor.

EXAMPLE 8 describes the design of the consortium GUT-103 for the treatment of IBD based on providing key functionalities that are lacking or underrepresented in the dysbiotic gut microbiome of IBD patients. The GUT 103 consortium is comprised of biologically pure cultures of *Megamonas funiformis* DSM19343, *Megamonas hypermegale* DSM1672, *Acidaminococcus intestini* DSM21505, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Anaerostipes hadrus* DSM 3319/ATCC 29173, *Clostridium symbiosum* ATCC14940, *Clostridium bolteae* ATCC BAA-613, *Blautia hydrogenotrophica* DSM 10507, *Marvinbryantia formatexigens* DSM14469, *Clostridium scindens* ATCC35704, *Blautia producta* DSM2950, and *Akkermansia muciniphila* ATCC BAA-835.

As described in EXAMPLE 8, two subsets of strains of the GUT-103 consortium become established in the intestinal tract of a mouse model of IBD. The first subset is designated GUT-103 consortium subset 1 and is comprised of *Bacteroides massiliensis* DSM17679, *Blautia producta* DSM2950, and *Akkermansia muciniphila* ATCC BAA-835. These three bacteria form a stable network that can break down complex food polymers and mucus consumed by and produced by the host, and provide synthesis of butyrate, propionate and indole, each of which have a key role in interacting with the host to reduce the inflammatory pathology. In addition, the three strains can complement each others auxotrophies, thus creating a stable network of interdependent strains that can drive engraftment of the consortium in the host microbiome.

Figure 5:
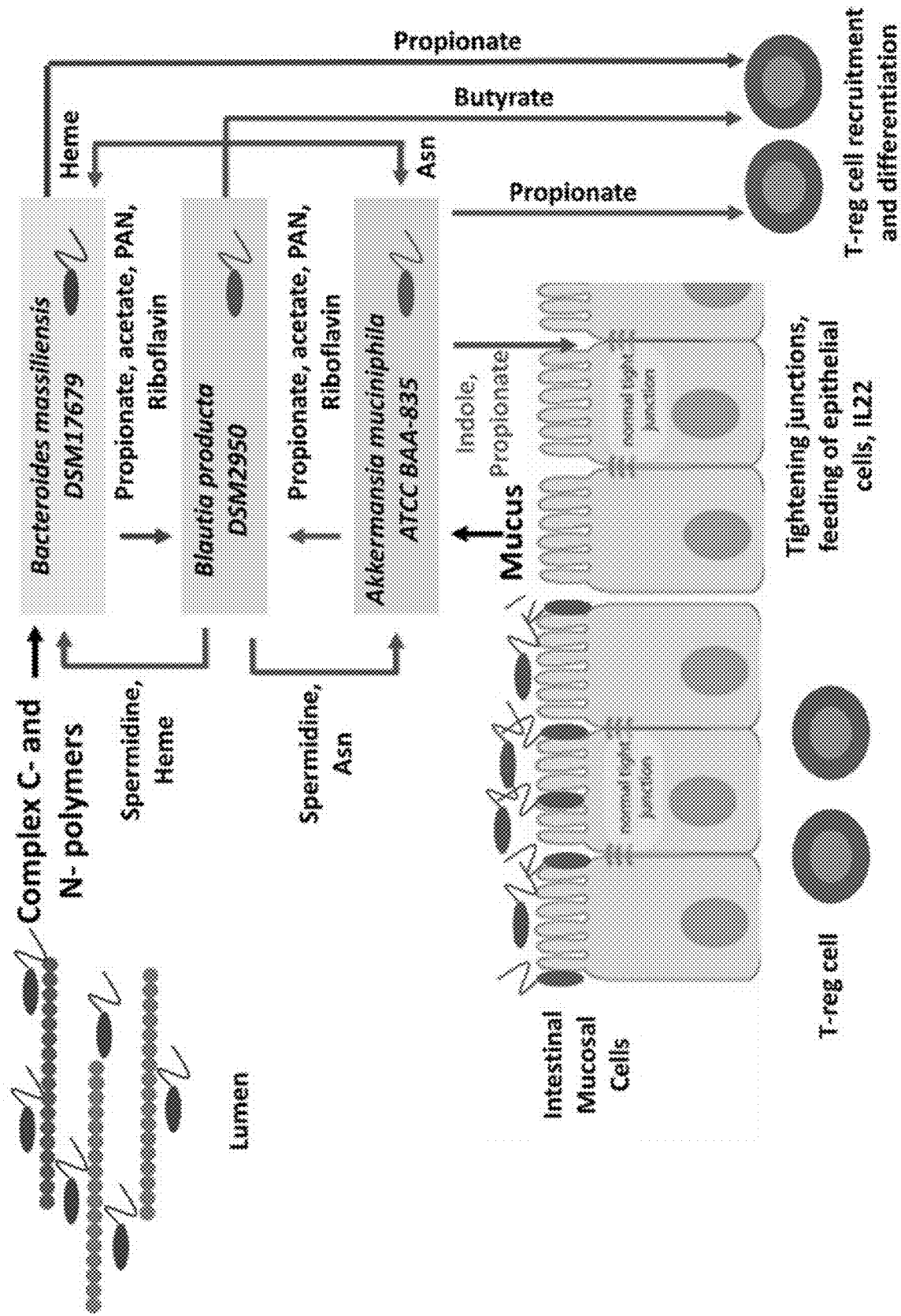
FIG. 5 is a schematic representation of the roles and metabolic interdependencies between *Bacteroides massiliensis* DSM17679, *Blautia producta* DSM2950, and *Akkermansia muciniphila* ATCC BAA-835. *Bacteroides massiliensis* DSM17679 plays a key role in the degradation of complex food polymers in the gut lumen, while *Akkermansia muciniphila* ATCC BAA-835 is capable of using mucus, produced by the epithelial cells, as a carbon, nitrogen and energy source. Both strains provide carbon (propionate, acetate) and the essential nutrients panthoate (PAN) and riboflavin to *Blautia producta* DSM2950, which in return provides spermidine, heme and asparagine (Asn) to strains DSM17679 and ATCC BAA-835, respectively. Furthermore, the propionate (DSM17679; ATCC BAA-835) and butyrate (DSM2950) produced by this three-strain consortium can help with the recruitment and differentiation of T-reg cells and impact the integrity and activity of the epithelial cell lining (e.g. via propionate and indole synthesized by *Akkermansia muciniphila* ATCC BAA-835). In addition, the indole, synthesized by strain ATCC BAA-835, can affect the synthesis of the anti-inflammatory IL22 via the AHR pathway.
Figure 6A:
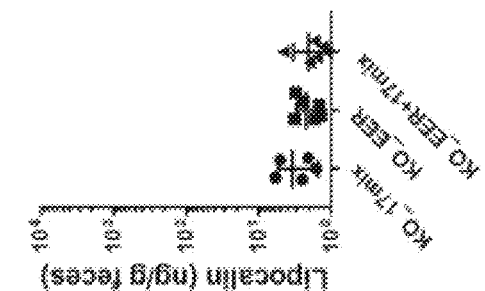
FIG. 6A is a graph showing the levels of lipocalin in log scale in the stool of germ free strain 129 IL10−/− knock-out mice determined before gavage treatment with GUT-103 (KO_17 mix), EER (KO_EER), or EER plus GUT-103 (KO_EER+17mix; GUT-103 was administered after a 2 week delay).
Figure 6B:
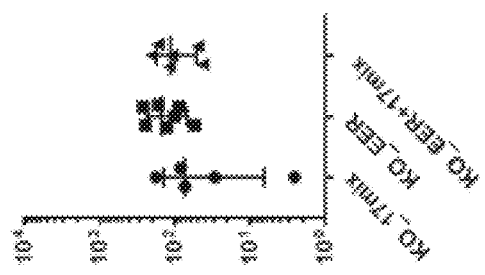
FIG. 6B is a graph showing the levels of lipocalin in log scale in the stool of germ free strain 129 IL10−/− knock-out mice determined 2 weeks after the first gavage treatment with GUT-103 (KO_17 mix), EER (KO_EER), or EER plus GUT-103 (KO_EER+17mix; GUT-103 was administered after a 2 week delay).
Figure 6C:
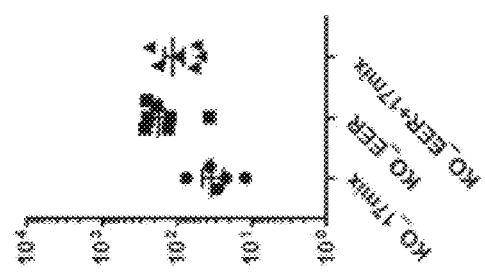
FIG. 6C is a graph showing the levels of lipocalin in log scale in the stool of germ free strain 129 IL10−/− knock-out mice determined 3 weeks after the first gavage treatment with GUT-103 (KO_17 mix), EER (KO_EER), or EER plus GUT-103 (KO_EER+17mix; GUT-103 was administered after a 2 week delay).
Figure 6D:
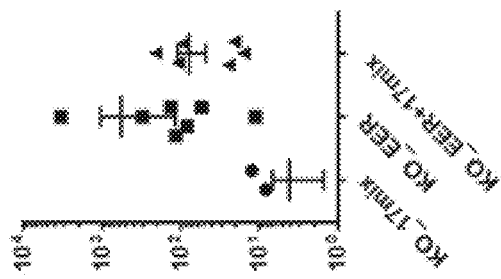
FIG. 6D is a graph showing the levels of lipocalin in log scale in the stool of germ free strain 129 IL10−/− knock-out mice determined 4 weeks after the first gavage treatment with GUT-103 (KO_17 mix), EER (KO_EER), or EER plus GUT-103 (KO_EER+17mix; GUT-103 was administered after a 2 week delay).
Figure 7:
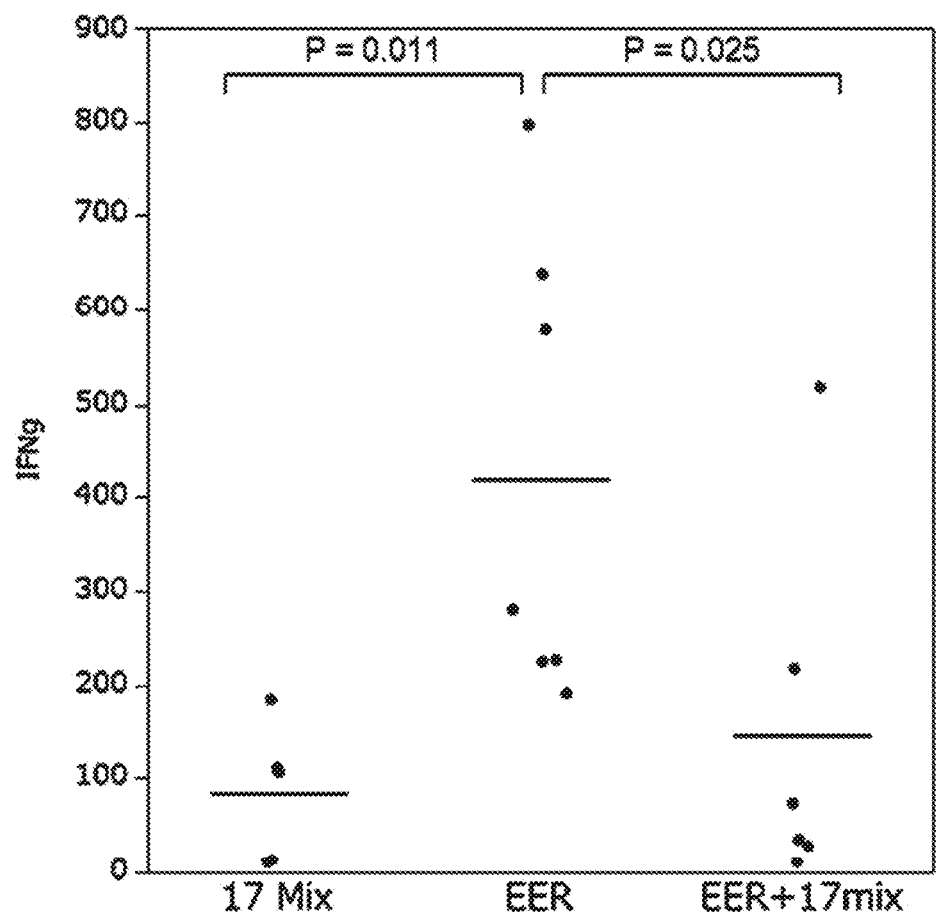
FIG. 7 is a graph of in vivo synthesis of IFNγ by $T_H1$ cells after 28 days in cecal tissue of germ free strain 129 IL10−/− knock-out mice that were treated with GUT-103 (17 mix), EER (EER), and EER plus GUT-103 (EER+17mix). P values indicate the statistical significance in IFNγ between treatments.

FIG. 5 shows a schematic representation of the roles and metabolic interdependencies between the strains in GUT-103 consortium subset 1. *Bacteroides massiliensis* DSM17679 plays a key role in the degradation of complex food polymers in the gut lumen, while *Akkermansia muciniphila* ATCC BAA-835 is capable of using mucus, produced by the epithelial cells, as a carbon, nitrogen and energy source. Both strains provide carbon (propionate, acetate) and the essential nutrients panthoate (PAN) and riboflavin to *Blautia producta* DSM2950, which in return provides spermidine, heme and asparagine (Asn) to strains DSM17679 and ATCC BAA-835, respectively. Furthermore, the propionate (DSM17679; ATCC BAA-835) and butyrate (DSM2950) produced by this three-strain consortium can help with the recruitment and differentiation of T-reg cells and impact the integrity and activity of the epithelial cell lining (e.g. via propionate and indole synthesized by *Akkermansia muciniphila* ATCC BAA-835). In addition, the indole, synthesized by strain ATCC BAA-835, can affect the synthesis of the anti-inflammatory IL22 via the AHR pathway.

The GUT-103 consortium subset 1 can be used for other applications beyond IBD, such as, but not limited to, treatment of diabetes or oncology therapies that require the establishment of strains to cover missing functionalities such as indole, butyrate and propionate synthesis. The second subset is designated GUT-103 consortium subset 2 and is comprised of *Clostridium symbiosum* ATCC 14940, *Clostridium bolteae* ATCC BAA-613, and *Clostridium scindens* ATCC 35704, *Subdoligranulum variabile* DSM15176, and *Anaerostipes caccae* DSM14662. GUT-103 consortium subset 2 covers the conversion of bile salts in secondary bile acids and steroids, and also contributes to the management of ferric iron via the synthesis of siderophores and the uptake of several heterologously produced siderophores, including a yersiniabactin siderophore insensitive to inhibition by Lipocalin-2 (*Anaerostipes caccae* DSM14662). GUT-103 consortium subset 2 is metabolically supported by GUT-103 consortium subset 1.

The eight bacterial strains in the combined GUT-103 consortium subset 1 and GUT-103 consortium subset 2 provide the key functionalities that are frequently lacking or underrepresented in the dysbiotic gut microbiome of an animal or a human afflicted with a wide range of diseases or disorders. Specifically, the GUT-103 consortium subset 1+GUT-103 consortium subset 2 provides the key functionalities of: synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, and breakdown of complex carbohydrates and proteins.

In addition, the GUT-103 consortium subset 1 can further include the strain *Bacteroides stercoris* ATCC 43183 and the GUT-103 consortium subset 2 can further include the strain *Megamonas funiformis* DSM19343. The GUT-103 consortium subset 1+GUT-103 consortium subset 2 can further include one or a combination of *Bacteroides stercoris* ATCC 43183 and *Megamonas funiformis* DSM19343. These additional strains can add to the metabolic interdependency and extend the functionality of the consortia. The GUT-103 consortium consortium subset 1 further including the strain *Bacteroides stercoris* ATCC 43183 is referred to herein as "GUT-103 consortium 1 extended". The GUT-103 consortium consortium subset 2 further including the strain *Megamonas funiformis* DSM19343 is referred to herein as "GUT-103 consortium 2 extended". The GUT-103 consortium subset 1+GUT-103 consortium subset 2 further including one or both of strains *Bacteroides stercoris* ATCC 43183 and *Megamonas funiformis* DSM19343 is referred to herein as "GUT-103 consortium subset 1+GUT-103 consortium subset 2 extended".

Overall, when designing an artificial microbe-based therapeutic consortium, a network of strains is created, not only based on therapeutic functionalities but also based on critical strain interdependencies. To avoid the collapse of such networks by putting too much pressure (energy cost) on a single strain to provide a critical metabolite to the other members of the consortium, redundancies of critical interdependencies are included when designing such a consortium. For example, if one or more strains is auxotrophic for folate, then one or more members of the consortium have the ability to produce folate. Furthermore, the folate synthesizing strains have at least one other auxotrophy, e.g. for one or more essential amino acids, to avoid outcompeting strains that depend on them for folate biosynthesis. Combining strains with different auxotrophies results in a network of critical metabolic interdependencies which forces the consortium to reach an equilibrium under a given environmental condition. This network resembles a neurological network, where each of the strains represents a unique node that is connected to other nodes via critical metabolite fluxes. Once such a network has been defined, it can be further enhanced by integrating novel functionalities by including new therapeutic or metabolic support strains.

As described in EXAMPLE 8, the ability was determined of the GUT-103 consortium to therapeutically treat chronic, immune-mediated experimental colitis in a model of IBD. This was determined by comparing the level of inflammation in ex-germ-free IL-10−/− mice selectively colonized with GUT-103 (negative control for experimental colitis), EER (positive control for the onset of colitis), and EER plus GUT-103 (therapeutic protocol with GUT-103 being applied 2 weeks after the onset of colitis induced by EER application). The results are shown in FIGS. 6A-6D and FIG. 7. After four weeks (see FIG. 6D), the average lipocalin 2 levels in the stool of the mice treated with GUT-103, EER, and EER plus GUT-103 were 4.2 ng/g, 579.2 ng/g and 78.9 ng/g, respectively. This indicates that the application of GUT-103 two weeks after the initial gavage with EER resulted in a reversal of the level of colonic inflammation. In addition, application of the GUT-103 consortium to the mice having an established EER community and resulting inflammation in their gut resulted in a statistically significant decrease in IFNγ synthesis (mean 150 pg/ml IFNγ, compared to 430 pg/ml IFNγ). Further, histological scoring of the severity of inflammation in the colon of the experimental mice resulted in scores of 0.9±0.65, 3.5±1.4 and 2.167±0.91 for mice treated with GUT-103, EER, and EER plus GUT-103, respectively. These results demonstrate the therapeutic effect of the GUT-103 consortium for treating chronic, immune-modulated ulcerative colitis.

EXAMPLE 9 describes the design of the consortium GUT-104 for the treatment of Type-2 diabetes based on providing key functionalities that are lacking or underrepresented in the dysbiotic gut microbiome of patients suffering from (the onset of) Type-2 diabetes. The GUT 104 consortium is comprised of a biologically pure culture of each of *Clostridium saccharogumia* DSM17460, *Clostridium ramosum* DSM1402, *Blautia producta* DSM2950, *Clostridium scindens* ATCC35704 (DSM5676), *Lactonifactor longoviformis* DSM17459, *Anaerostipes caccae* DSM14662, *Anaerostipes hadrus* DSM3319/ATCC29173, *Clostridium symbiosum* ATCC14940, *Clostridium bolteae* ATCC BAA-613, *Blautia hydrogenotrophica* DSM10507, *Faecalibacterium prausnitzii* DSM17677, *Subdoligranulum variabile* DSM15176, and *Akkermansia muciniphila* ATCC BAA-835.

Figure 8A:
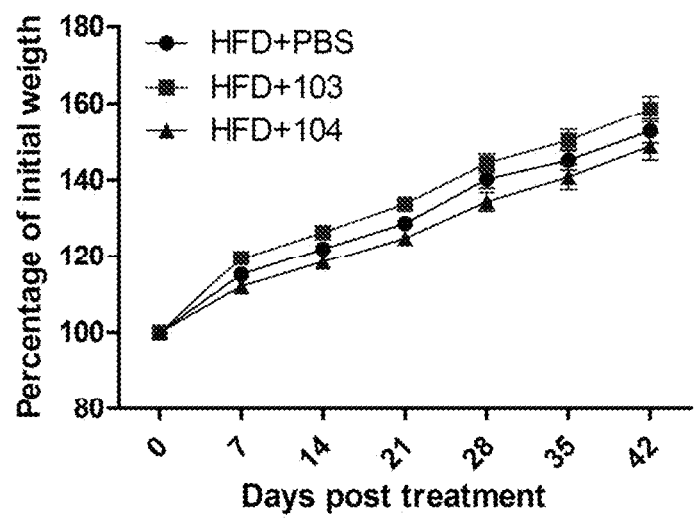
FIG. 8A is a graph showing increase in body weight for C57 BL/6 mice on a high fat diet receiving the GUT-104 consortium (HFD+104) in comparison to mice that received the GUT-103 consortium (HFD+103) or PBS (HFD+PBS). Body weight was determined as percentage of the original body weight before the animals were placed on a high fat diet. GUT-103, GUT-104 and PBS were applied three times a week for a forty two day period via oral gavage.
Figure 8B:
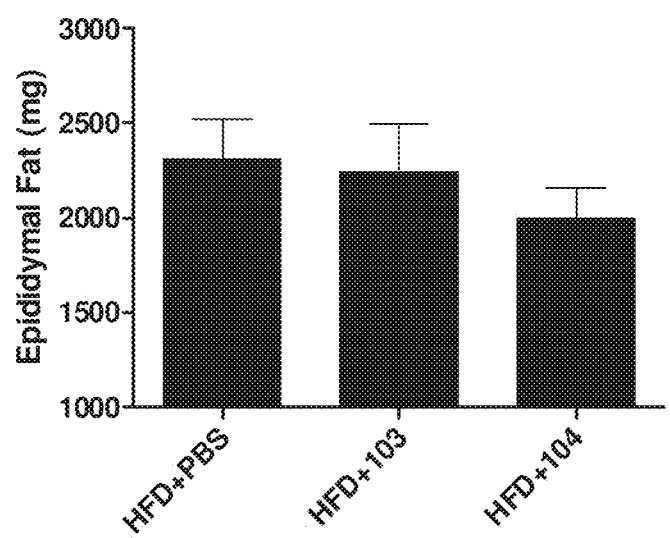
FIG. 8B is a graph showing effect of the application of the GUT-104 consortium (HFD+104) on the accumulation of bodyfat in C57 BL/6 mice on a high fat diet in comparison to mice that received the GUT-103 (HFD+103) consortium or PBS (HFD+PBS). Weight of the epididymal fat pad was determined in mice that were placed for fortytwo days on a high fat diet. GUT-103, GUT-104 and PBS were applied three times a week for a forty two day period via oral gavage.
Figure 8C:
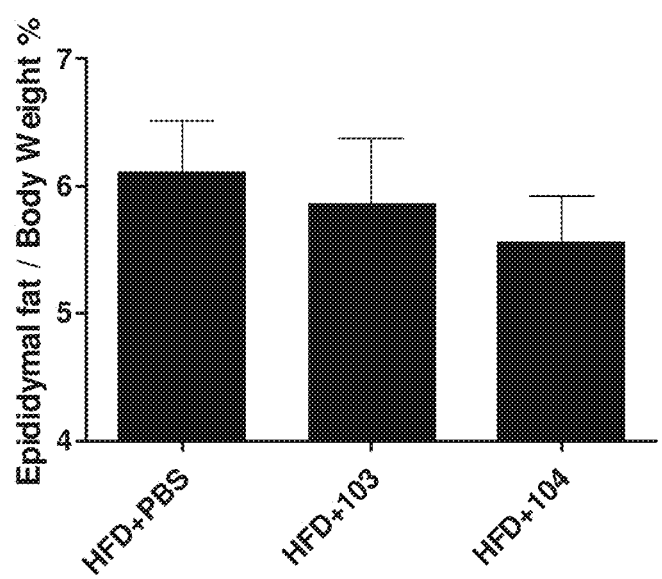
FIG. 8C is a graph showing effect of the application of the GUT-104 consortium (HFD+104) on the accumulation of bodyfat in C57 BL/6 mice on a high fat diet in comparison to mice that received the GUT-103 consortium (HFD+103) or PBS (HFD+PBS). Relative weight of the epididymal fat pad as a percentage of total body weight was determined in mice that were placed for forty two days on a high fat diet. GUT-103, GUT-104 and PBS were applied three times a week for a forty two day period via oral gavage.
Figure 9A:
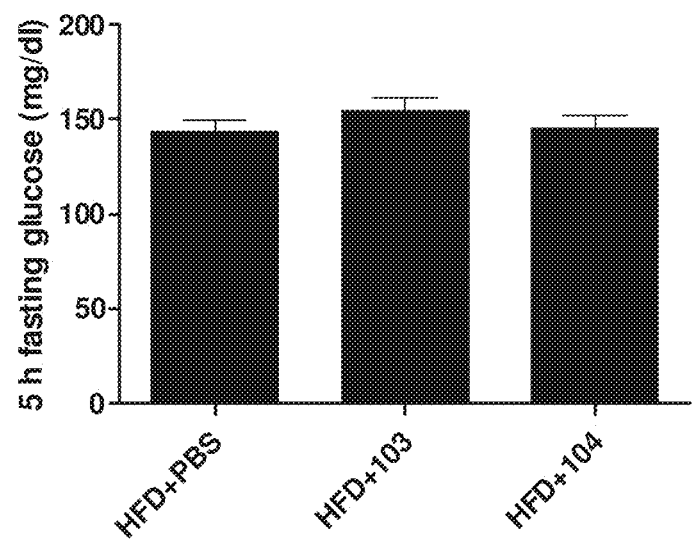
FIG. 9A is a graph showing the effect of the application of the GUT-104 consortium (HFD+104) on glucose levels in the blood of fasting C57 BL/6 mice in comparison to mice that received the GUT-103 (HFD+103) consortium or PBS (HFD+PBS). The mice were fasted for 5 hours before the glucose levels in the blood were measured. GUT-103, GUT-104 and PBS were applied three times a week for a forty two day period via oral gavage.
Figure 9B:
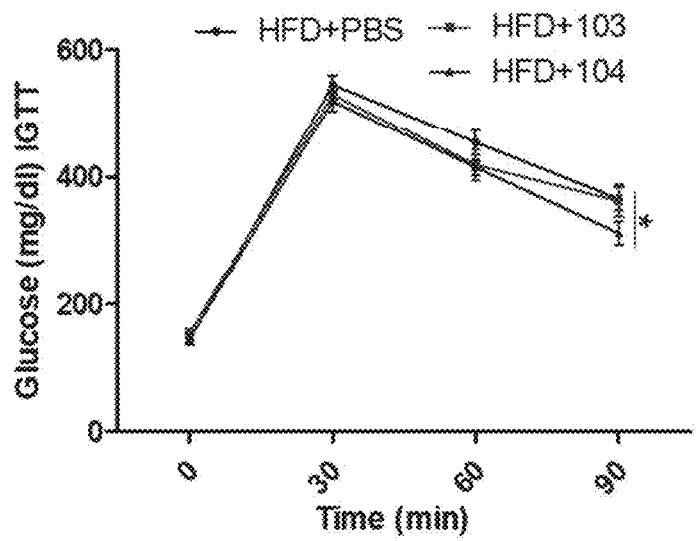
FIG. 9B is a graph showing the effect of the application of the GUT-104 consortium (HFD+104) on glucose levels in the blood of C57 BL/6 mice after intraperitoneal injection of glucose, in comparison to mice that received the GUT-103 consortium (HFD+103) or PBS (HFD+PBS). The mice were fasted for 5 hours before intraperitoneal injection of glucose, after with blood glucose levels were measured. GUT-103, GUT-104 and PBS were applied three times a week for a forty two day period via oral gavage. * indicates that the differences were statistically significant (P<0.05).
Figure 10A:
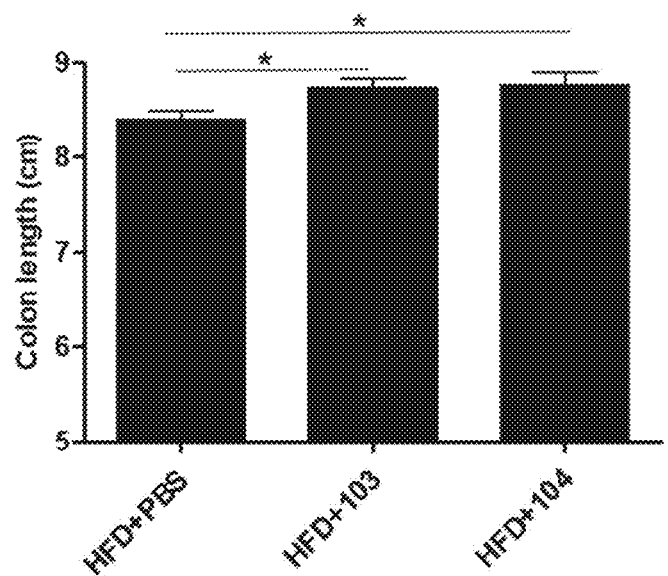
FIG. 10A is a graph showing the effect of the application of the GUT-104 consortium (HFD+104) on the development of the colon of mice placed on a high fat diet, in comparison to mice that received the GUT-103 consortium (HFD+103) or PBS (HFD+PBS). GUT-103, GUT-104 and PBS were applied three times a week for a forty two day period via oral gavage, after which the mice were sacrificed and the length of their colon was determined. * indicates that the differences were statistically significant (P<0.05).
Figure 10B:
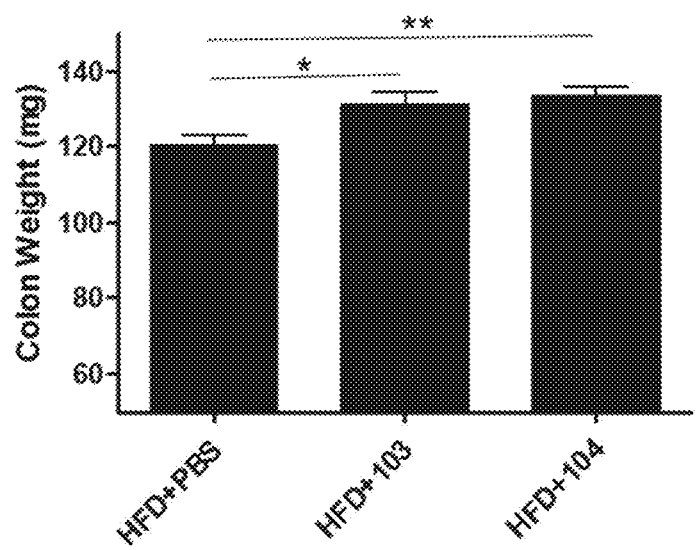
FIG. 10B is a graph showing the effect of the application of the GUT-104 consortium (HFD+104) on the development of the colon of mice placed on a high fat diet, in comparison to mice that received the GUT-103 consortium (HFD+103) or PBS (HFD+PBS). GUT-103, GUT-104 and PBS were applied three times a week for a forty two day period via oral gavage, after which the mice were sacrificed and the weight of their colon was determined. * and ** indicates that the differences were statistically significant (P<0.05 and P<0.01, respectively).

The effect of the GUT-104 consortium on the onset of Type-2 diabetes was evaluated in a mouse model of Type-2 diabetes. GUT-103 was also included in the evaluation as a positive control for reducing inflammation, and as a negative control for glucose tolerance. As described herein above, GUT-103 was rationally designed to control inflammation; however, the GUT-103 consortium lacks the functionalities for the synthesis of endocrine molecules with antidiabetic activity from endogenous and exogenous steroids. The results of the animal model experiment for onset of Type-2 diabetes are shown in FIGS. 8A-8C, 9A-9B, and 10A-10B. The results show that the application of GUT-104 resulted in a slower increase in body weight as measured over a forty two-day period (FIG. 8A). In addition, application of GUT-104 also resulted in a smaller epididymal fat pad, both in absolute weight (FIG. 8B) and as a function of total body weight (FIG. 8C). These results show that GUT-104 can be useful for decreasing the rate of development of obesity. In addition, the application of GUT-104 had no effect on the blood glucose levels of the mice that were fasted for 5 hours (FIG. 9A). However, after intraperitoneal injection of glucose, mice treated with GUT-104 showed a faster drop in blood glucose levels, indicating that GUT-104 can provide better glucose tolerance compared to GUT-103 or control (FIG. 9B).

As described in EXAMPLE 9, a subset of strains of GUT-104 (designated GUT-104 subset 3) is provided that is comprised of *Clostridium saccharogumia* DSM17460, *Clostridium ramosum* DSM1402, *Blautia producta* DSM2950, *Clostridium scindens* ATCC35704 (DSM5676) and *Lactonifactor longoviformis* DSM17459 for synthesis of endocrine molecules from endogenous and exogenous steroids. GUT-104 subset 3 can have a beneficial effect on the development and severity of metabolic disorder.

In addition, the GUT-104 consortium can further include the strain *Bacteroides massiliensis* DSM17679. This strain, together with *Blautia producta* DSM2950 and *Akkermansia muciniphila* ATCC BAA-835 forms a stable network that breaks down complex food polymers and mucus, and covers the synthesis of butyrate, propionate and indole. In another embodiment, dietary fiber such as inulin can be included in a formulation of the GUT-104 consortium as a prebiotic. Use of inulin as a carbon and energy source is dependent on the presence of the enzyme β-fructofuranosidase. Based on genome annotation, β-fructofuranosidase is present in *Faecalibacterium prausnitzii* DSM17677, a member of GUT-104. To broaden the number of strains with β-fructofuranosidase activity, the GUT-104 can further include one or more strains that encode a β-fructofuranosidase gene such as, for example, *Megamonas hypermegale* DSM1672 and *Megamonas funiformis* DSM19343. The GUT-104 consortium further including one or a combination of the strains *Bacteroides massiliensis* DSM17679, *Megamonas hypermegale* DSM1672, and *Megamonas funiformis* DSM19343 is referred to herein as "GUT-104 consortium extended".

EXAMPLE 10 describes the design of the consortium GUT-107 for the treatment of Type-1 diabetes based on providing key functionalities that are lacking or underrepresented in the dysbiotic gut microbiome of patients suffering from Type-1 diabetes. The GUT 107 consortium is comprised of a biologically pure culture of each of *Megamonas funiformis* DSM19343, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Clostridium symbiosum* ATCC14940, *Clostridium bolteae* ATCC BAA-613, *Blautia producta* DSM2950, *Clostridium scindens* ATCC35704, and *Akkermansia muciniphila* ATCC BAA-835.

In one embodiment, a method is provided for benefiting health, comprising: administering to a human or an animal a composition comprising: i) a plurality of biologically pure cultures of microbial strains having at least one functionality absent or underrepresented in the microbiome of an organism having a disease or disorder, wherein each of the absent or underrepresented functionalities is present in at least one of the microbial strains in the plurality, and wherein each of the microbial strains has at least one auxotrophy and is dependent on at least one of the other strains in the plurality for growth; and ii) a carrier, wherein the microbial consortium populates and benefits the health of an animal or a human.

In one embodiment, a method is provided for benefiting health, comprising: administering to a human or an animal a composition comprising: i) a plurality of biologically pure cultures of microbial strains, wherein the combined plurality of strains comprises functionalities for each of: synthesis of butyrate, synthesis of propionate, synthesis of indole, deconjugation of bile salt and conversion of bile acid into secondary bile acids, synthesis of a siderophore, uptake of a heterologously produced siderophore, and synthesis of at least one bacteriocin; and ii) a carrier, wherein the plurality of microbial strains populates and benefits the health of an animal or a human.

The compositions administered in the present methods for benefiting the health of an animal or a human can include one or a combination of GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, GUT-103 consortium subset 1+GUT-103 consortium subset 2 extended, GUT-104 consortium, GUT-104 consortium extended, GUT-104 consortium subset 3, and GUT-107.

In addition to being used as a stand-alone biotherapeutic, the GUT-103 consortium, GUT-104 consortium, GUT-107 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, GUT-103 consortium subset 1+GUT-103 consortium subset 2 extended, GUT-104 consortium subset 3, and GUT-104 consortium extended or any other rationally designed consortia according to the methods described herein can also be used as a companion therapy to complement the activity or help to improve the therapeutic outcome of another drug or active agent. Several studies have shown the importance of the gut microbiome for the success of check point inhibitor (CPI) treatment, and it has been suggested that dysbiosis of the intestinal microbiome also influences the outcome of cancer immunotherapy. For instance, Pitt et al (2016) observed that specific gut-resident bacteria determine the immunotherapeutic responses associated with CTLA-4 checkpoint blockade. This new evidence indicates that interindividual differences in the microbiome may account for the significant heterogeneity in therapeutic and immunopathologic responses to immune checkpoint therapies. CPIs represent a new class of compounds for the treatment of various forms of cancer, including solid state tumors, melanomas, bladder and lung cancer. CPIs drugs are a rapidly developing field and include targets such as CTLA-4, PD-L1, PD-R1, Lag-3, Tim-3, and TIGIT, all of which are co-inhibitory receptors with specialized functions in immune regulation. The latest developments are the personalized genomic vaccines to treat solid tumors.

Therefore, similar to that described in EXAMPLE 1 for IBD, methods and compositions are provided focused on key functionalities that are underrepresented or missing from the dysbiotic gut microbiome of cancer patients compared to healthy subjects. This is in order to counteract the weakened immune response in cancer patients that can negatively contribute to the success of cancer treatment. In one embodiment, the rationally-designed microbial therapeutics of the present disclosure can be administered to patients in combination with CPI therapeutics to enhance their performance over a broader cohort range.

For example, each of the GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, and GUT-103 consortium subset 1+GUT-103 consortium subset 2 extended consortia could potentially be used for the treatment of IBD in combination with an anti-inflammatory drug, where the drug treats the inflammatory process, and the particular consortium provides missing or underrepresented functionalities to the dysbiotic gut microbiome. This combination therapy can result in multiple beneficial effects by: 1. Providing missing or underrepresented functionalities in the dysbiotic gut microbiome, the risk of relapse after cessation of the drug treatment can be decreased by addressing the underlying effects; 2. Restoring the immunoregulatory cells while inhibiting effector cells that enhance the inflammation; 3. Restoring the epithelial barrier function; and 4. The microbial-based therapeutic, through its positive effect on the innate immune response, can aid in overcoming the serious side effects previously reported for commonly used treatments including REMICADE, HUMIRA, ENTYVIO, their biosimilars such as RENFLEXIS, as well as other treatments (e.g., corticosteroids, immunomodulators, antibiotics). The negative side effects patients may suffer from these existing treatments include dysbiosis of the gut microbiome and risk of serious and potentially life-threatening infections.

The GUT-104 consortium, GUT-104 consortium subset 3, and GUT-104 consortium extended can also be used as a combination therapy to complement the activity of therapeutics for the treatment of Type-2 diabetes. For example, it can be used used synergisticly with glucagon-like peptide-1 (GLP-1) receptor agonists such as Trulicity (dulaglutide; produced and distributed by Lilly); or with a prebiotic, such as inulin, indicate to have beneficial effects in animal studies (e.g. Ning et al, 2017) and on patients with Type-2 diabetes (Dehghan et al, 2014).

Other examples of combination therapies include treatments that combine the application of the GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, GUT-103 consortium subset 1+GUT-103 consortium subset 2 extended, GUT-104 consortium, GUT-104 consortium extended, or GUT-107 consortia with molecules that decrease the activity of Zonulin, a protein that regulates tight junctions between epithelial cells, and whose activity has been implicated in a range of conditions, including inflammation, autoimmune disorders, and cancer, ranging from IBD, food allergies, celiac disease and Type-1 diabetes (Fasano, 2011). More specifically, rationally designed consortia such as GUT-103 consortium, GUT-103 consortium subset 1, GUT-103 consortium subset 1 extended, GUT-103 consortium subset 1+GUT-103 consortium subset 2, GUT-103 consortium subset 1+GUT-103 consortium subset 2 extended, GUT-104 consortiym, GUT-104 consortium extended and GUT-107 consortium which include indole synthesis as a functionality to stimulate improved intestinal barrier function, can be combined with a zonulin receptor antagonist, such as larazotide acetate (INNOVATE BIOPHARMACEUTICALS INC.), In one embodiment, a composition of the present disclosure is administered to a human or an animal in combination with one or a combination of a therapeutic selected from the group consisting of: a small molecule-based drug, a corticosteroid, a macromolecule based drug, a antibody based drug, an immunomodulator, a checkpoint inhibitor, an αPD-[L]1 targeting antibody, an αCTLA-4 targeting antibody, an αLag-3 targeting antibody, an αTim-3 targeting antibody, or an αTIGIT targeting antibody, an antibiotic, an infliximab therapeutic, an adalimumab therapeutic, an vedolizumab therapeutic, or a biosimilar of an infliximab, an adalimumab, or an avedolizumab therapeutic.

In one embodiment, the compositions of the present disclosure are administered to a human or an animal in combination with one or a combination of a food supplement, a pre-biotic, a symbiotic, a lignan, an inulin, or a secoisolariciresinol diglucoside (SDG). In one embodiment, the compositions administered in the present methods for benefiting the health of an animal or a human are one or a combination of GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, or GUT-103 consortium subset 1+GUT-103 consortium subset 2 extended, and the health benefited is for the treatment of Ulcerative Colitis, Crohn's Disease, Inflammatory Bowel Diseases, or Irritable Bowel Syndrome. The administering of the composition can be in combination with one or a combination of a corticosteroid, an antibiotic, an infliximab therapeutic, an adalimumab therapeutic, a vedolizumab therapeutic, or a biosimilar of a infliximab, adalimumab, or vedolizumab therapeutic.

In one embodiment, the compositions administered in the present methods for benefiting the health of an animal or a human are one or a combination of GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, or GUT-103 consortium subset 1+GUT-103 consortium subset 2 extended, and the health benefited is for the treatment of cancer. The administering of the composition can be in combination with one or a combination of a checkpoint inhibitor, an αPD-[L]1 targeting antibody, an αCTLA-4 targeting antibody, an αLag-3 targeting antibody, an αTim-3 targeting antibody, or an αTIGIT targeting antibody.

In one embodiment, the compositions administered in the present methods for benefiting the health of an animal or a human are one or a combination of GUT-104 consortium, GUT-104 consortium subset 3, or GUT-104 consortium extended, and the health benefited is for the treatment of type-2 diabetes. The administering of the composition can be in combination with one or a combination of a food supplement, a glucagon-like peptide-1 (GLP-1) receptor agonist, a dulaglutide, a prebiotic, a symbiotic, a lignan, an inulin, or a secoisolariciresinol diglucoside (SDG).

In one embodiment, the compositions administered in the present methods for benefiting the health of an animal or a human are one or a combination of GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, or GUT-103 consortium subset 1+GUT-103 consortium subset 2 extended, GUT-104 consortium, GUT-104 consortium subset 3, GUT-104 consortium extended, or GUT-107, and the health benefited is for improved intestinal barrier function. The administering of the composition can be in combination with one or a combination of a zonulin receptor antagonist or a larazotide acetate.

In one embodiment, the compositions administered in the present methods for benefiting the health of an animal or a human are one or a combination of GUT-103 consortium, GUT-103 consortium subset 1, GUT-103 consortium subset 1 extended, GUT-103 consortium subset 2, GUT-103 consortium subset 2 extended, GUT-103 consortium subset 1+GUT-103 consortium subset 2, or GUT-103 consortium subset 1+GUT-103 consortium subset 2 extended, or GUT-107, and the health benefited is for type-1 diabetes. The administering of the composition can be in combination with one or a combination of a zonulin receptor antagonist or a larazotide acetate.

The compositions of the present disclosure can be formulated as a capsule, a powder, a liquid suspension, an aerosol, or a cream.

In the methods for benefiting health, comprising administering to an animal or a human a composition comprising the microbial strains of the present disclosure, each of the microbial strains can be present in an amount of from about $1 \times 10^{+4}$ to about $1 \times 10^{+12}$ cfu per strain. In one embodiment, each of the microbial strains is present in an amount of at least about $2 \times 10^{+7}$ cfu per strain.

In one embodiment of the compositions and methods of the present disclosure, the health benefit is one or more of Ulcerative Colitis, Crohn's Disease, Inflammatory Bowel Diseases, or Irritable Bowel Syndrome and the combined plurality of strains comprises functionalities for: synthesis of butyrate, synthesis of propionate, synthesis of indole, deconjugation of bile salt and conversion of bile acid into secondary bile acids, synthesis of a siderophore, uptake of a heterologously produced siderophore, and synthesis of at least one bacteriocin. The combined plurality of strains can further include functionality for breakdown of complex carbohydrates and breakdown of proteins. In one embodiment the animal is a human.

In one embodiment of the compositions and methods of the present disclosure, the health benefit is Type-2 Diabetes and the combined plurality of strains further includes functionality for conversion of secoisolariciresinol diglucoside (SDG) to enterodiol and enterolactone. The combined plurality of strains can further include functionality for breakdown of complex carbohydrates, the synthesis of β-fructofuranosidase for the breakdown of the prebiotic fiber inulin, and breakdown of proteins. In one embodiment the animal is a human. In one embodiment, a method is provided for benefiting health, comprising: administering to a human or an animal a composition comprising: i) a plurality of biologically pure cultures of microbial strains having at least one functionality absent or underrepresented in the microbiome of an animal or a human having a disease or disorder, wherein each of the absent or underrepresented functionalities is present in at least one of the microbial strains in the plurality, and wherein each of the microbial strains has at least one auxotrophy and is dependent on at least one of the other strains in the plurality for growth; and ii) a carrier, wherein the microbial consortium benefits the health of the animal or a human.

In one embodiment, a composition is provided for benefiting the health of an organism, the composition comprising: i) a plurality of biologically pure cultures of microbial strains having at least one functionality absent or underrepresented in the microbiome of an organism having a disease or disorder, wherein each of the absent or underrepresented functionalities is present in at least one of the microbial strains in the plurality, and wherein each of the microbial strains has at least one auxotrophy and is dependent on at least one of the other strains in the plurality for growth; and ii) a carrier.

In one embodiment, a composition is provided for benefiting the health of an animal or a human, the composition comprising: i) a plurality of biologically pure cultures of microbial strains, wherein the combined plurality of strains comprises functionalities for each of: synthesis of butyrate, synthesis of propionate, synthesis of indole, deconjugation of bile salt and conversion of bile acid into secondary bile acids, synthesis of a siderophore, uptake of a heterologously produced siderophore, synthesis of at least one bacteriocin, and breakdown of complex carbohydrates and proteins, and wherein each of the microbial strains has at least one auxotrophy and is dependent on at least one of the other strains in the plurality for growth; and ii) a carrier. The functionalities can further comprise conversion of secoisolariciresinol diglucoside (SDG) to enterodiol and enterolactone. The functionalities can further comprise one or a combination of: the synthesis of β-fructofuranosidase, synthesis of acetylcholine, synthesis of indole-3-propionate and indole-3-aldehyde, synthesis of 4-amino-butyrate (gamma-aminobutyric acid; GABA), metabolism of acetylcholine, synthesis of a siderophore not inhibited by Lipocalin-2, synthesis of one or both of EPS and LTA compounds with immune modulating properties, conversion of formate into acetate, pathway for breakdown of host metabolites for urea cycle disorder, pathway for breakdown of host metabolites for phenylketonuria, pathway for breakdown of host metabolites for organic acidemias, pathway for breakdown of host metabolites for maple syrup urine disease, or pathway for breakdown or activation of a drug molecule.

In one embodiment of the compositions and methods of the present disclosure, the plurality of microbial strains comprise strains from one or a combination of: *Megamonas funiformis, Megamonas hypermegale, Acidaminococcus intestini, Bacteroides massiliensis, Bacteroides stercoris, Barnesiella intestinihominis, Faecalibacterium prausnitzii, Subdoligranulum variabile, Anaerostipes caccae, Anaerostipes hadrus, Clostridium symbiosum, Clostridium scindens, Clostridium bolteae, Clostridium saccharogumia, Clostridium ramosum, Blautia producta, Blautia hydrogenotrophica, Marvinbryantia formatexigens, Lactonifactor longoviformis*, and *Akkermansia muciniphila*.

In one embodiment of the compositions and methods of the present disclosure, the plurality of microbial strains comprise or consist of strains from *Megamonas funiformis, Megamonas hypermegale, Acidaminococcus intestini, Bacteroides massiliensis, Bacteroides stercoris, Barnesiella intestinihominis, Faecalibacterium prausnitzii, Subdoligranulum variabile, Anaerostipes caccae, Anaerostipes hadrus, Clostridium symbiosum, Clostridium bolteae, Blautia hydrogenotrophica, Marvinbryantia formatexigens, Clostridium scindens, Blautia producta*, and *Akkermansia muciniphila*.

In one embodiment of the compositions and methods of the present disclosure, the plurality of microbial strains comprise or consist of strains from species of *Blautia producta, Akkermansia muciniphila*, and *Bacteroides massiliensis*. The plurality of microbial strains can comprise strains from species of *Blautia producta, Akkermansia muciniphila* and *Bacteroides massiliensis,* and further from *Bacteroides stercoris.*

In one embodiment of the compositions and methods of the present disclosure, the plurality of microbial strains comprise or consist of strains from species of *Clostridium symbiosum, Clostridium bolteae, Clostridium scindens, Subdoligranulum variabile* and *Anaerostipes caccae.* The plurality of microbial strains can comprise strains from species of *Clostridium symbiosum, Clostridium bolteae, Clostridium scindens, Subdoligranulum variabile* and *Anaerostipes caccae,* and further from *Megamonas funiformis.*

In one embodiment of the compositions and methods of the present disclosure, the plurality of microbial strains comprise or consist of strains from species of *Blautia producta, Akkermansia muciniphila, Bacteroides massiliensis, Clostridium symbiosum, Clostridium bolteae, Clostridium scindens, Subdoligranulum variabile* and *Anaerostipes caccae.* The plurality of microbial strains can comprise strains from species of *Blautia producta, Akkermansia muciniphila, Bacteroides massiliensis, Clostridium symbiosum, Clostridium bolteae, Clostridium scindens, Subdoligranulum variabile* and *Anaerostipes caccae,* and further from one or both of *Bacteroides stercoris* and *Megamonas funiformis.* In one embodiment of the compositions and methods of the present disclosure, the plurality of microbial strains comprise or consist of strains from *Clostridium saccharogumia, Clostridium ramosum, Blautia producta, Clostridium scindens, Lactonifactor longoviformis, Anaerostipes caccae, Anaerostipes hadrus, Clostridium symbiosum, Clostridium bolteae, Blautia hydrogenotrophica, Faecalibacterium prausnitzii, Subdoligranulum variabile,* and *Akkermansia muciniphila.*

In one embodiment of the compositions and methods of the present disclosure, the plurality of microbial strains comprise or consist of strains from species of *Clostridium saccharogumia, Clostridium ramosum, Blautia producta, Clostridium scindens* and *Lactonifactor longoviformis.* The plurality of microbial strains can comprise strains from species of *Clostridium saccharogumia, Clostridium ramosum, Blautia producta, Clostridium scindens* and *Lactonifactor longoviformis* and further from species of one or a combination of *Bacteroides massiliensis, Megamonas hypermegale,* and *Megamonas funiformis.*

In one embodiment of the compositions and methods of the present disclosure, the plurality of microbial strains comprise or consist of strains from species of *Megamonas funiformis, Bacteroides massiliensis, Bacteroides stercoris, Barnesiella intestinihominis, Faecalibacterium prausnitzii, Subdoligranulum variabile, Anaerostipes caccae, Clostridium symbiosum, Clostridium bolteae, Blautia producta, Clostridium scindens* and *Akkermansia muciniphila.*

In one embodiment, a composition (referred to herein as "GUT-103") is provided for benefiting the health of an animal or a human, comprising: i) a biologically pure culture of each of *Blautia producta* DSM2950, *Megamonas funiformis* DSM19343, *Megamonas hypermegale* DSM1672, *Acidaminococcus intestini* DSM21505, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Anaerostipes hadrus* DSM 3319/ATCC 29173, *Clostridium symbiosum* ATCC14940, *Clostridium bolteae* ATCC BAA-613, *Blautia hydrogenotrophica* DSM 10507, *Marvinbryantia formatexigens* DSM14469, *Clostridium scindens* ATCC35704 and *Akkermansia muciniphila* ATCC BAA-835; and ii) one or more carriers or excipients.

In one embodiment, a composition (referred to herein as "GUT-104") is provided for benefiting the health of an animal or a human, comprising: i) a biologically pure culture of each of: *Clostridium saccharogumia* DSM17460, *Clostridium ramosum* DSM1402, *Blautia producta* DSM2950, *Clostridium scindens* ATCC35704 (DSM5676), *Lactonifactor longoviformis* DSM17459, *Anaerostipes caccae* DSM14662, *Anaerostipes hadrus* DSM3319/ATCC29173, *Clostridium symbiosum* ATCC14940, *Clostridium bolteae* ATCC BAA-613, *Blautia hydrogenotrophica* DSM10507, *Faecalibacterium prausnitzii* DSM17677, *Subdoligranulum variabile* DSM15176, and *Akkermansia muciniphila* ATCC BAA-835; and ii) one or more carriers or excipients. The composition may further comprise one or a combination of a biologically pure culture of *Bacteroides massiliensis* DSM17679, *Megamonas hypermegale* DSM1672, and *Megamonas funiformis* DSM19343.

In one embodiment, a composition (referred to herein as "GUT-107") is provided for benefiting the health of an animal or a human, comprising: i) a biologically pure culture of each of: *Megamonas funiformis* DSM19343, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Clostridium symbiosum* ATCC14940, *Clostridium bolteae* ATCC BAA-613, *Blautia producta* DSM2950, *Clostridium scindens* ATCC35704 and *Akkermansia muciniphila* ATCC BAA-835; and ii) one or more carriers or excipients.

In one embodiment, a composition (referred to herein as "GUT-103 consortium subset 1) is provided for benefiting the health of an animal or a human, comprising: i) a biologically pure culture of each of: *Blautia producta* DSM2950, *Bacteroides massiliensis* DSM17679, and *Akkermansia muciniphila* ATCC BAA-835; and ii) one or more carriers or excipients. The composition can further comprise a biologically pure culture of *Bacteroides stercoris* ATCC 43183.

In one embodiment, a composition (referred to herein as "GUT-103 consortium subset 2") is provided for benefiting the health of an animal or a human, comprising: i) a biologically pure culture of each of: *Subdoligranulum variabile* DSM15176, *Anaerostipes caccae* DSM14662, *Clostridium symbiosum* ATCC14940, *Clostridium bolteae* ATCC BAA-613, and *Clostridium scindens* ATCC35704; and ii) one or more carriers or excipients. The composition can further comprise a biologically pure culture of *Megamonas funiformis* DSM1934.

In one embodiment, a composition (referred to herein as "GUT-103 consortium subset 1+GUT-103 consortium subset 2") is provided for benefiting the health of an animal or a human, comprising: i) a biologically pure culture of each of: *Blautia producta* DSM2950, *Bacteroides massiliensis* DSM17679, *Akkermansia muciniphila* ATCC BAA-835, *Subdoligranulum variabile* DSM15176, *Anaerostipes caccae* DSM14662, *Clostridium symbiosum* ATCC14940, *Clostridium bolteae* ATCC BAA-613, and *Clostridium scindens* ATCC35704 and; and ii) one or more carriers or excipients. The composition can further comprise a biologically pure culture of one or both of *Bacteroides stercoris* ATCC 43183 and *Megamonas funiformis* DSM19343.

In one embodiment, a composition (referred to herein as "GUT-104 consortium subset 3) is provided for benefiting the health of an animal or a human, comprising: i) a biologically pure culture of each of: *Clostridium saccharogumia* DSM17460, *Clostridium ramosum* DSM1402, *Blautia producta* DSM2950, *Clostridium scindens* ATCC35704 (DSM5676) and *Lactonifactor longoviformis* DSM17459; and ii) one or more carriers or excipients.

In one embodiment, a composition is provided for benefiting the health of an animal or a human, comprising i) one or more carriers or excipients, and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Megamonas funiformis* DSM19343 (SEQ ID NO: 2) and genetic material encoding functionalities for synthesis of proprionate, uptake of a ferrichrome siderophore and an enterobactin siderophore, and β-fructofuranosidase activity for inulin, fructan and sucrose hydrolysis; c) a bacterium having 99% identity to 16S rRNA gene of *Megamonas hypermegale* DSM1672 (SEQ ID NO: 3) and genetic material encoding functionalities for synthesis of proprionate, uptake of a ferrichrome siderophore, and (3-fructofuranosidase activity for inulin, fructan and sucrose hydrolysis; d) a bacterium having 99% identity to 16S rRNA gene of *Acidaminococcus intestini* DSM21505 (SEQ ID NO: 4) and genetic material encoding functionalities for synthesis of butyrate; e) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; f) a bacterium having 99% identity to 16S rRNA gene of *Bacteroides stercoris* ATCC43183/DSM19555 (SEQ ID NO: 6) and genetic material encoding functionalities for synthesis of propionate, synthesis of indole, uptake of a heterologously produced siderophore and uptake of an enterobactin siderophore; g) a bacterium having 99% identity to 16S rRNA gene of *Barnesiella intestinihominis* DSM21032 (SEQ ID NO: 7) and genetic material encoding functionalities for synthesis of proprionate, uptake of a heterologously produced siderophore and uptake of an aerobactin siderophore; h) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, synthesis of a bacteriocin, and β-fructofuranosidase activity for inulin, fructan and sucrose hydrolysis; i) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin; j) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; k) a bacterium having 99% identity to 16S rRNA gene of *Anaerostipes hadrus* DSM 3319/ATCC 29173 (SEQ ID NO: 11) and genetic material encoding functionalities for synthesis of butyrate and synthesis of indole; 1) a bacterium having 99% identity to 16S rRNA gene of *Clostridium symbiosum* ATCC14940 (SEQ ID NO: 12) and genetic material encoding functionalities for synthesis of butyrate, deconjugation of bile salt and conversion of bile acid into secondary bile acids; m) a bacterium having 99% identity to 16S rRNA gene of *Clostridium bolteae* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; n) a bacterium having 99% identity to 16S rRNA gene of *Blautia hydrogenotrophica* DSM 10507 (SEQ ID NO: 15) and genetic material encoding functionalities for deconjugation of bile salt and conversion of bile acid into secondary bile acids and synthesis of a bacteriocin; o) a bacterium having 99% identity to 16S rRNA gene of *Marvinbryantia formatexigens* DSM14469 (SEQ ID NO: 16) and genetic material encoding functionalities for uptake of a heterologously produced siderophore and uptake of a ferrichrome siderophore; p) a bacterium having 99% identity to 16S rRNA gene of *Clostridium scindens* ATCC35704 (SEQ ID NO: 17) and genetic material encoding functionalities for conversion of bile acid into secondary bile acids and synthesis of a bacteriocin; and q) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore.

In one embodiment, a composition is provided for benefiting the health of an animal or a human, the composition comprising i) one or more carriers or excipients and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; and c) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore. The biologically pure culture can further comprise a bacterium having 99% identity to 16S rRNA gene of *Bacteroides stercoris* (SEQ ID NO: 6) and genetic material encoding functionalities for indole synthesis and the uptake of heterologous siderophores including enterobactin.

In one embodiment, a composition is provided for benefiting the health of an animal or a human, the composition comprising i) one or more carriers or excipients and ii) a biologically pure culture of each of: a) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; b) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; c) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; d) a bacterium having 99% identity to 16S rRNA gene of *Clostridium bolteae* ATCC BAA-613 (SEQ ID NO: 13) genetic material encoding functionalities for synthesis of a siderophore, deconjugation of bile salt and conversion of bile acid into secondary bile acids, and synthesis of a bacteriocin; and e) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin. The biologically pure culture can further comprise a bacterium having 99% identity to 16S rRNA gene of *Megamonas funiformis* (SEQ ID NO: 2) and genetic material encoding a β-fructofuranosidase gene.

In one embodiment, a composition is provided for benefiting the health of an animal or a human, the composition comprising: i) one or more carriers or excipients and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; c) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore; d) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; e) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; f) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; g) a bacterium having 99% identity to 16S rRNA gene of *Clostridium bolteae* ATCC BAA-613 (SEQ ID NO: 13) genetic material encoding functionalities for synthesis of a siderophore, deconjugation of bile salt and conversion of bile acid into secondary bile acids, and synthesis of a bacteriocin; and h) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin. The biologically pure culture can further comprise one or a combination of a bacterium having 99% identity to 16S rRNA gene of *Bacteroides stercoris* (SEQ ID NO: 6) and genetic material encoding functionalities for indole synthesis and the uptake of heterologous siderophores including enterobactin; and a bacterium having 99% identity to 16S rRNA gene of *Megamonas funiformis* (SEQ ID NO: 2) and genetic material encoding a β-fructofuranosidase gene.

In one embodiment, a composition is provided for benefiting the health of an animal or a human, comprising i) one or more carriers or excipients, and ii) a biologically pure culture of each of: a) a bacterium having 99% identity to 16S rRNA gene of *Clostridium saccharogumia* DSM17460 (SEQ ID NO: 19) and genetic material encoding functionalities for O-deglycosylation in conversion of secoisolariciresinol diglucoside (SDG) to enterodiol and enterolactone; b) a bacterium having 99% identity to 16S rRNA gene of *Clostridium ramosum* DSM1402 (SEQ ID NO: 20) and genetic material encoding functionalities for O-deglycosylation in conversion of secoisolariciresinol diglucoside (SDG) to enterodiol and enterolactone; c) a bacterium having 99% identity to 16S rRNA gene of *Blautia producta* DSM2950 (SEQ ID NO: 14) and genetic material encoding functionalities for synthesis of butyrate, uptake of a heterologously produced siderophore, uptake of a ferrichrome siderophore, and O-demethylation in conversion of secoisolariciresinol diglucoside (SDG) to enterodiol and enterolactone; d) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; e) a bacterium having 99% identity to 16S rRNA gene of *Lactonifactor longoviformis* DSM17459 (SEQ ID NO: 21) and genetic material encoding functionalities for synthesis of a bacteriocin and dehydrogenation in conversion of secoisolariciresinol diglucoside (SDG) to enterodiol and enterolactone; f) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; g) a bacterium having 99% identity to 16S rRNA gene of *Anaerostipes hadrus* DSM3319/ATCC29173 (SEQ ID NO: 11) and genetic material encoding functionalities for synthesis of butyrate and synthesis of indole; h) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; i) a bacterium having 99% identity to 16S rRNA gene of *Clostridium bolteae* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; j) a bacterium having 99% identity to 16S rRNA gene of *Blautia hydrogenotrophica* DSM10507 (SEQ ID NO: 15) and genetic material encoding functionalities for deconjugation of bile salt and conversion of bile acid into secondary bile acids and synthesis of a bacteriocin; k) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, synthesis of a bacteriocin, and β-fructofuranosidase activity for inulin, fructan and sucrose hydrolysis; l) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin; and m) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore. The biologically pure culture can further comprise one or a combination of a bacterium having 99% identity to 16S rRNA gene of *Bacteroides massiliensis* (SEQ ID NO: 5) and genetic material encoding functionalities for indole synthesis and the uptake of heterologous siderophores including enterobactin; a bacterium having 99% identity to 16S rRNA gene of *Megamonas hypermegale* (SEQ ID NO: 3) and genetic material encoding a β-fructofuranosidase gene; and a bacterium having 99% identity to 16S rRNA gene of *Megamonas funiformis* (SEQ ID NO: 2) and genetic material encoding a β-fructofuranosidase gene.

In one embodiment, a composition is provided for benefiting the health of an animal or a human, comprising i) one or more carriers or excipients, and ii) a biologically pure culture of each of: a) a bacterium having 99% identity to 16S rRNA gene of *Clostridium saccharogumia* DSM17460 (SEQ ID NO: 19) and genetic material encoding functionalities for O-deglycosylation in conversion of secoisolariciresinol diglucoside (SDG) to enterodiol and enterolactone; b) a bacterium having 99% identity to 16S rRNA gene of *Clostridium ramosum* DSM1402 (SEQ ID NO: 20) and genetic material encoding functionalities for O-deglycosylation in conversion of secoisolariciresinol diglucoside (SDG) to enterodiol and enterolactone; c) a bacterium having 99% identity to 16S rRNA gene of *Blautia producta* DSM2950 (SEQ ID NO: 14) and genetic material encoding functionalities for synthesis of butyrate, uptake of a heterologously produced siderophore, uptake of a ferrichrome siderophore, and O-demethylation in conversion of secoisolariciresinol diglucoside (SDG) to enterodiol and enterolactone; d) a bacterium having 99% identity to 16S rRNA gene of *Clostridium scindens* ATCC35704 (DSM5676) (SEQ ID NO: 17) and genetic material encoding functionalities for conversion of bile acid into secondary bile acids, synthesis of a bacteriocin, and dehydrogenation in conversion of secoisolariciresinol diglucoside (SDG) to enterodiol and enterolactone; and e) a bacterium having 99% identity to 16S rRNA gene of *Lactonifactor longoviformis* DSM17459 (SEQ ID NO: 21) and genetic material encoding functionalities for synthesis of a bacteriocin and dehydrogenation in conversion of secoisolariciresinol diglucoside (SDG) to enterodiol and enterolactone.

In one embodiment, a composition is provided for benefiting the health of an animal or a human, comprising i) one or more carriers or excipients, and ii) a biologically pure culture of each of: a) a bacterium having 99% identity to 16S rRNA gene of *Blautia producta* DSM2950 (SEQ ID NO: 14) and genetic material encoding functionalities for synthesis of butyrate and uptake of a heterologously produced siderophore and uptake of a ferrichrome siderophore; b) a bacterium having 99% identity to 16S rRNA gene of *Megamonas funiformis* DSM19343 (SEQ ID NO: 2) and genetic material encoding functionalities for synthesis of proprionate, uptake of a ferrichrome siderophore and an enterobactin siderophore, and β-fructofuranosidase activity for inulin, fructan and sucrose hydrolysis; c) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; d) a bacterium having 99% identity to 16S rRNA gene of *Bacteroides stercoris* ATCC43183/DSM19555 (SEQ ID NO: 6) and genetic material encoding functionalities for synthesis of proprionate, synthesis of indole, uptake of a heterologously produced siderophore and uptake of an enterobactin siderophore; e) a bacterium having 99% identity to 16S rRNA gene of *Barnesiella intestinihominis* DSM21032 (SEQ ID NO: 7) and genetic material encoding functionalities for synthesis of proprionate, uptake of a heterologously produced siderophore and uptake of an aerobactin siderophore; f) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, synthesis of a bacteriocin, and β-fructofuranosidase activity for inulin, fructan and sucrose hydrolysis; g) a bacterium having 99% identity to 16S rRNA gene of *Subdoligranulum variabile* DSM15176 (SEQ ID NO: 9) and genetic material encoding functionalities for synthesis of butyrate and synthesis of a bacteriocin; h) a bacterium having 99% identity to 16S rRNA gene of *Anaerostipes caccae* DSM14662 (SEQ ID NO: 10) and genetic material encoding functionalities for synthesis of butyrate, uptake of a heterologously produced siderophore, uptake of a ferrichrome siderophore, synthesis of a yersiniabactin siderophore, deconjugation of bile salt and conversion of bile acid into secondary bile acids, and synthesis of a bacteriocin; i) a bacterium having 99% identity to 16S rRNA gene of *Clostridium symbiosum* ATCC14940 (SEQ ID NO: 12) and genetic material encoding functionalities for synthesis of butyrate, deconjugation of bile salt and conversion of bile acid into secondary bile acids; j) a bacterium having 99% identity to 16S rRNA gene of *Clostridium bolteae* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; k) a bacterium having 99% identity to 16S rRNA gene of *Clostridium scindens* ATCC35704 (SEQ ID NO: 17) and genetic material encoding functionalities for conversion of bile acid into secondary bile acids and synthesis of a bacteriocin; and 1) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore.

In one embodiment, a composition is provided for benefiting the health of an animal, comprising i) one or more carriers or excipients, and ii) a biologically pure culture of each of: a) a bacterium having 99% identity to 16S rRNA gene of *Dialister succinatiphilus* DSM21274 (SEQ ID NO: 1) and genetic material encoding functionalities for synthesis of proprionate and synthesis of a ferrichrome siderophore; b) a bacterium having 99% identity to 16S rRNA gene of *Megamonas funiformis* DSM19343 (SEQ ID NO: 2) and genetic material encoding functionalities for synthesis of proprionate and synthesis of a ferrichrome siderophore and a enterobactin siderophore; c) a bacterium having 99% identity to 16S rRNA gene of *Megamonas hypermegale* DSM1672 (SEQ ID NO: 3) and genetic material encoding functionalities for synthesis of proprionate and synthesis of a ferrichrome siderophore; d) a bacterium having 99% identity to 16S rRNA gene of *Acidaminococcus intestini* DSM21505 (SEQ ID NO: 4) and genetic materialtc material encoding functionalities for synthesis of butyrate; e) a bacterium having 99% identity to 16S rRNA gene of *Bacteroides massiliensis* DSM17679 (SEQ ID NO: 5) and genetic material encoding functionalities for synthesis of proprionate and uptake of a heterologously produced siderophore; f) a bacterium having 99% identity to 16S rRNA gene of *Bacteroides stercoris* ATCC43183/DSM19555 (SEQ ID NO: 6) and genetic material encoding functionalities for synthesis of propionate, synthesis of indole, uptake of a heterologously produced siderophore and synthesis of an enterobactin siderophore; g) a bacterium having 99% identity to 16S rRNA gene of *Barnesiella intestinihominis* DSM21032 (SEQ ID NO: 7) and genetic material encoding functionalities for synthesis of proprionate, uptake of a heterologously produced siderophore and synthesis of an aerobactin siderophore; h) a bacterium having 99% identity to 16S rRNA gene of *Faecalibacterium prausnitzii* DSM17677 (SEQ ID NO: 8) and genetic material encoding functionalities for synthesis of butyrate, uptake of a heterologously produced siderophore, and synthesis of a bacteriocin; i) a bacterium having 99% identity to 16S rRNA gene of *Subdoligranulum variabile* DSM15176 (SEQ ID NO: 9) genetic material encoding functionalities for synthesis of butyrate and synthesis of a bacteriocin; j) a bacterium having 99% identity to 16S rRNA gene of *Anaerostipes caccae* DSM14662 (SEQ ID NO: 10) genetic material encoding functionalities for synthesis of butyrate, uptake of a heterologously produced siderophore, synthesis of a ferrichrome siderophore, synthesis of a yersiniabactin siderophore, deconjugation of bile salt and conversion of bile acid into secondary bile acids, and synthesis of a bacteriocin; k) a bacterium having 99% identity to 16S rRNA gene of *Anaerostipes hadrus* DSM 3319/ATCC 29173 (SEQ ID NO: 11) genetic material encoding functionalities for synthesis of butyrate and synthesis of indole; 1) a bacterium having 99% identity to 16S rRNA gene of *Clostridium symbiosum* ATCC14940 (SEQ ID NO: 12) and genetic material encoding functionalities for synthesis of butyrate and deconjugation of bile salt and conversion of bile acid into secondary bile acids; m) a bacterium having 99% identity to 16S rRNA gene of *Clostridium boltea* ATCC BAA-613 (SEQ ID NO: 13) and genetic material encoding functionalities for synthesis of a siderophore, deconjugation of bile salt and conversion of bile acid into secondary bile acids, and synthesis of a bacteriocin; n) a bacterium having 99% identity to 16S rRNA gene of *Blautia hydrogenotrophica* DSM 10507 (SEQ ID NO: 15) and genetic material encoding functionalities for deconjugation of bile salt and conversion of bile acid into secondary bile acids and synthesis of a bacteriocin; o) a bacterium having 99% identity to 16S rRNA gene of *Marvinbryantia formatexigens* DSM14469 (SEQ ID NO: 16) and genetic material encoding functionalities for uptake of a heterologously produced siderophore and synthesis of a ferrichrome siderophore; p) a bacterium having 99% identity to 16S rRNA gene of *Clostridium scindens* ATCC35704 (SEQ ID NO: 17) and genetic material encoding functionalities for deconjugation of bile salt and conversion of bile acid into secondary bile acids and synthesis of a bacteriocin; and q) a bacterium having 99% identity to 16S rRNA gene of *Akkermansia muciniphila* ATCC BAA-835 (SEQ ID NO: 18) and genetic material encoding functionalities for synthesis of propionate, synthesis of indole, and uptake of a heterologously produced siderophore. The composition can further comprise a bacterium having 99% identity to 16S rRNA gene of *Blautia producta* DSM2950 (SEQ ID NO: 14) and genetic material encoding functionalities for uptake of a heterologously produced siderophore and synthesis of a ferrichrome siderophore.

In one embodiment, a method is provided for benefiting health, comprising: administering to an organism a composition having a microbial consortium and a carrier, the microbial consortium produced by a process comprising: for a plurality of microbial strains each having at least one functionality in a set of functionalities absent or underrepresented in a microbiome of an organism of interest, creating for each strain using genome annotation an in silico metabolic model that predicts an auxotrophic profile for one or a combination of essential nutrients; integrating in silico the metabolic models for each of the plurality of strains to obtain a combined metabolic model for the plurality of strains; and designating a microbial consortium having a metabolic interdependency, including by optionally introducing into the plurality or removing from the plurality one or more microbial strains, wherein the metabolic interdependency of the plurality of strains in the microbial consortium includes each of the strains having at least one auxotrophy for the essential nutrient(s) and each being dependent on at least one of the other strains in the plurality for growth.

In one embodiment, a method is provided for benefiting health, comprising: administering to an organism a composition having a microbial consortium and a carrier, the microbial consortium produced by a process comprising: for a plurality of microbial strains, the combined plurality of strains comprising functionalities for: synthesis of butyrate, synthesis of propionate, synthesis of indole, deconjugation of bile salt and conversion of bile acid into secondary bile acids, synthesis of a siderophore, uptake of a heterologously produced siderophore, and synthesis of at least one bacteriocin, wherein each individual functionality is present in at least one of the strains in the plurality, creating for each strain using genome annotation an in silico metabolic model that predicts an auxotrophic profile for one or a combination of essential nutrients; integrating in silico the metabolic models for each of the plurality of strains to obtain a combined metabolic model for the plurality of strains; and designating a microbial consortium having a metabolic interdependency, including by optionally introducing into the plurality or removing from the plurality one or more microbial strains, wherein the metabolic interdependency of the plurality of strains in the microbial consortium includes each of the strains having at least one auxotrophy for the essential nutrient(s) and each being dependent on at least one of the other strains in the plurality for growth, wherein the microbial consortium populates and benefits the health of the organism.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Comparative Gut Metagenome Analysis Between Healthy Individuals and Patients with Crohn's Disease or Ulcerative Colitis The following experiment was performed to analyze the microbiomes from healthy individuals and patients with Crohn's disease or Ulcerative Colitis. Metagenome sequencing sets for 60 healthy individuals, 60 Crohn's disease patients, and 60 Ulcerative Colitis patients were downloaded from the "Inflammatory Bowel Disease Multi'omics Database" (https://ibdmdb.org/tunnel/public/summary html).

The 180 datasets representing the three cohorts were assembled into contigs using IDBA-UD (Peng et al, 2012) iterating from k-mer 41-61 and the best assembly was selected on the assembly statistics like N50 and assembly size. The aim was to use 60 metagenome samples from each cohort, but unfortunately some of the data-sets ended up in assembly size less than 20 Mb. Those were removed as it would be hard to compare between assembly size ranging between 1 Gb and 20 Mb. A final quality data set was utilized that contained 50 metagenomes from each cohort, for a total of 150 samples.

Subsequently, the contigs were binned using MetaBAT (Metagenome Binning with Abundance and Tetra-nucleotide frequencies) (Kang et al, 2015) in order to obtain separate clusters of contigs representing one species/strain. These bins were further assigned taxonomical status using PhyloPhlAn (Segata et al, 2013) using a set of 400 conserved markers. Additionally, the raw metagenome reads from each sample were also taxonomically characterized using MetaPhlAn 2 (Truong et al, 2015). Furthermore, the contigs were annotated in KBase using the RAST nomenclature. Following the taxonomical characterization and annotations, datasets for the three cohorts were analyzed to identify: 1) The statistically significant differentially represented OTU between each cohort (healthy vs UC, UC vs Crohn's, healthy vs Crohn's and multigroup i.e. UC vs Crohn's vs Healthy); 2) The conserved and variable functions in each cohort; and 3) The statistically significant differentially represented functions between each cohort (healthy vs UC, UC vs Crohn's, healthy vs Crohn's, and multigroup i.e. UC vs Crohn's vs Healthy). The multigroup analyses were performed using ANOVA with Bonferroni correction at P-value filter of >0.05. The two group analyses were done using two-sided Welch's t-test with Bonferroni correction and P-value >0.05. These datasets were used to predict missing functionalities from the dysbiotic gut microbiome of IBD patients. In total, 16 differentially abundant genera (P-value <0.005; 95% confidence interval) were identified.

Two-way comparisons between Crohn's Disease patients versus healthy individuals, Ulcerative Colitis patients versus healthy individuals, and Crohn's Disease patients versus Ulcerative Colitis patients are shown in FIGS. 1, 2 and 3. FIG. 1 is a graph showing two-way comparison of the microbiome composition between Crohn's Disease patients versus healthy individuals. A total of 9 differential features were identified on the genus level, of which the most prominent (95% confidence interval) were *Bifidobacterium* (high in Healthy), *Subdoligranulum* (high in Healthy), *Dialister* (high in Healthy), *Parabacteroides* (high in Crohn's), and *Bacteroides* (high in Crohn's). FIG. 2 is a graph showing two-way comparison of the microbiome composition between Ulcerative Colitis patients versus healthy individuals. A total of 17 differential features was identified on the genus level, of which the most prominent (95% confidence interval) were *Dialister* (high in Healthy), *Alistipes* (high in Healthy), *Clostridium* (high in Healthy), and *Coprococcus* (high in UC). FIG. 3 is a two-way comparison of the microbiome composition between Crohn's Disease patients versus Ulcerative Colitis patients. A total of 10 differential features was identified on the genus level, of which the most prominent were *Clostridium* (high in Crohn's), *Dialister* (high in Crohn's), *Coprococcus* (high in UC), and *Bifidobacterium* (high in UC). The results confirm the differences between the gut microbiomes of Crohn's disease patients and patients suffering from Ulcerative Colitis, which reflects the physiological differences between these two forms of IBD.

Based on this comparative analysis of 150 microbiomes representing three cohorts, the following conclusions were made regarding differences in species abundancies between the two disease states and healthy individuals. Overall, patients with Crohn's disease and Ulcerative Colitis should be treated as two separate cohorts instead of a single "IBD" patient cohort. Patients with Ulcerative Colitis had a noticeable decrease in *Clostridium* species. Based on the results presented in FIGS. 1, 2, and 3 the major differences between the bacterial species present in the microbiomes of healthy individuals compared to the microbiomes of Crohn's Disease and Ulcerative Colitis patients included noticeable decreases in members of the genera *Subdoligranulum, Dialister, Megasphaera, Bifidobacterium, Alistipes* and *Bilophilia*. Members of the genera *Parabacteroides, Bacteroides, Odoribacter* and *Acidaminococcus* were relatively increased in patients with Crohn's disease, while Ulcerative Colitis patients tended to have increased populations of *Parabacteroides* and *Coprococcus*. Neither the microbiome in the patients with Crohn's Disease or Ulcerative Colitis was dominated by putatively opportunistic pathogenic species.

Principal component analysis was performed in an attempt to understand the significance of the differences observed in the levels of microorganisms at the species level in the normal versus diseased samples. The data are shown FIG. 4 which is a graph showing principle compound analysis at the genus/species level of the microbiomes of healthy individuals and patients suffering from Crohn's disease or Ulcerative Colitis, respectively. For healthy individuals, 4 out of 50 microbiomes were found outside the cluster defined by the circle, while for Crohn's disease and Ulcerative Colitis 23 and 17 out of 50 microbiomes, respectively, were placed outside the cluster. The data indicate that, surprisingly, although the microbiomes of healthy individuals seem to cluster based on species composition, the microbiomes of patients suffering from Crohn's disease or Ulcerative Colitis show no clear grouping. Surprisingly, the data in FIG. 4 show that the species that are increased in the Crohn's and UC patients do not seem to be a major factor in contributing to the dysbiosis of the gut. This indicates that the major trends in microbiome compositions of the dysbiotic gut are often not the same among the various Crohn's and Ulcerative Colitis patients and, thus, are not predictive of the disease. Instead, the species that are absent or decreased in the patients as compared to the normal samples (see FIGS. 1 and 2) have a strong correlation with the disease state.

Using published literature, the following functionalities were assigned to the species of the genera whose relative abundance was found to decrease in the gut microbiomes of patients with Crohn's disease or Ulcerative Colitis compared to healthy subjects:

Key Genera that are Decreased in IBD Patients and their Identified Effect on Gut Health and Functionality Members of the genus *Subdoligranulum*, which is part of the family Ruminococcaceae. The genus *Subdoligranulum* is closely related to the genus *Faecalibacterium* and like this genus, belongs to the *Clostridium* cluster IV. The representative strain for *Subdoligranulum* is *S. variabile* (DSM 15176), a known producer of butyrate (Holmstrom et al, 2004). Thus, a decrease of members of the genus *Subdoligranulum* is hypothesized to result in lower levels of butyrate synthesis in the gut of IBD patients compared to healthy individuals. However, butyrate synthesis is often not a homogenous feature of all members of a genus (Louis et al, 2009; 2010).

Members of the genus *Dialister*, belonging to the family of the Vellionellaceae, which falls within the class of the Negativicutes. Increased levels of *Dialister* have been associated with immunological improvement (Martinez et al, 2013). *Dialister invisus* (*D. invisus*) is capable of generating both acetate and propionate (Downes et al, 2003), and the abundance of this bacterium is reduced in patients with CD (Joossens et al, 2013). Further analysis on the species level confirmed that the decrease in *Dialister* could indeed be attributed to *D. invisus*. Thus, a decrease in members of the genus *Dialister*, predominantly *D. invisus*, is identified as contributing to lower levels of propionate synthesis in the gut of IBD patients compared to healthy individuals.

Members of the *Megasphaera* have been reported to produce important metabolites, and their role points to a potential healthy influence on the host. Analysis of two human gut isolates, NM10 and BL, revealed the presence of diverse and unique sets of Carbohydrate-Active enzymes (CAZymes) amongst these isolates, critical for the breakdown of complex carbohydrates. In silico analysis and in vitro experimentation indicates the ability of these isolates to produce important metabolites like short chain fatty acids (butyrate, acetate, formate, and caproate), vitamins and essential amino acids (Shetty et al, 2013).

Members of the genus *Bifidobacterium* are among the first microbes to colonize the human gastrointestinal tract and are believed to exert positive health benefits on their host. Due to their purported health-promoting properties, Bifidobacteria have been incorporated into many functional foods as active ingredients. Bifidobacteria possess many specific adaptations to be competitive in the human gut microbiome (O'Callaghan and van Sinderen, 2016). Based on the determination of genome sequences described above, genetic attributes were identified that may explain bifidobacterial ecological fitness, such as metabolic abilities including the breakdown of complex carbohydrates, cross-feeding of carbohydrates to other gut microbiome species including acetate and lactate that is used by other bacteria, including *Clostridium* species, for the synthesis of SCFA, evasion of the host adaptive immune system, and colonization of the host through specific appendages. Thus, a decrease of members of the genus *Bifidobacterium* was identified as resulting in less efficient breakdown of complex carbohydrates, fermentation of sugars to acetate and lactate, and ultimately a decrease of SCFA synthesis in the gut of IBD patients compared to healthy individuals.

Members of the genus *Alistipes*, which belongs to the Bacteroidetes phylum, are known for their efficient breakdown of complex carbohydrates and proteins. In support of this role is the observation that the levels of fecal amino acids, including the BCAA leucine, isoleucine and valine, the aromatic amino acids (tyrosine), and other amino acids (alanine, lysine, and methionine), and SCFA (acetate, propionate, and butyrate) have been positively correlated with the presence of *Prevotella*, *Alistipes* and *Barnesiella* species (Neis et al, 2015). Thus, a decrease of members of the genus *Alistipes* was identified as contributing to less efficient breakdown of complex carbohydrates and proteins, and lower levels of essential amino acids to help overcome auxotrophies in other members of the gut microbiome consortium.

Members of the genus *Bilophilia*, of which the most prominent intestinal isolate is *Bilophila wadsworthia*, a sulfate-reducing taxon, generally comprising <0.1% of the normal human GI microbiota (Baron, 1997) are associated with consumption of an animal-based diet. Given its unique ability to perform anaerobic respiration using taurine-derived sulfite as an electron acceptor (Da Silva et al, 2008), the observed shifts in *Bilophila* abundances were identified as reflecting the quantitative and/or qualitative changes in bile acid production in IBD patients. IBD patients characterized by dysbiosis of their gut microbiome due to inflammation were indeed found to have lower concentrations of secondary bile acids in the feces and periphery as well as more conjugated bile acids in the feces compared to healthy subjects (Duboc et al, 2013). While these findings fit remarkably well the observed decrease of members of the genus *Bilophilia*, other mechanistic hypotheses cannot be discarded, such as a lowered intestinal luminal pH as observed in patients with Ulcerative Colitis, which could also create a less favorable environment for *Bilophila*. Thus, a decrease of members of the genus *Bilophilia* was identified as resulting in lower levels of bile acid conversion in the gut of IBD patients compared to healthy individuals.

Overall, the Key Genera that are Lacking or Underrepresented in the Gut Microbiome of IBD Patients are Identified as Contributing Important Functionalities that are Beneficial for Gut Health and a Balanced Gut Microbiome.

The design of a microbial therapeutic consortium as described herein focuses on complementing key functionalities that are lacking or underrepresented in the dysbiotic gut microbiome of IBD patients as compared to healthy subjects, rather than trying to replace missing species. Based on the results described above as well as the literature, the critical functionalities identified for treatment of IBD and for general maintenance of a healthy gut microbiome are as follows: synthesis of short chain fatty acids, (SCFA), especially butyrate and propionate; synthesis of indole; bile salt deconjugation and conversion into secondary bile acids; breakdown of complex carbohydrates and proteins; and synthesis of antagonistic metabolites including bacteriocins to control (opportunistic) pathogenic microorganisms.

Example 2

Characterization of Strains for Metabolic Functionalities

First, various species of gut microorganisms were identified as target species in which to identify new strains for use as therapeutic formulations to improve animal and human health by providing key functionalities. The target bacterial species include both Gram-positive and Gram-negative species and cover members of the phyla Firmicutes, Actinobacteria, Proteobacteria, Bacteroidetes, and Verrucomicrobia. The species of bacterial strain was identified based on the 16S gene and RpoB gene DNA sequences. Using universal primers, the 16S and RpoB genes were partially amplified and sequenced. Subsequently, gene comparison against the NCBI GenBank database was used for species identification. Subsequently, the isolated gut bacteria can be identified using one or more of the screening assays provided below. Furthermore, strains with known properties, as described from the literature, can be included.

Siderophore Producing Strains:

Assay for production of siderophores is performed as followed. Strains are grown on full strength as well as ½ and ⅕$^{th}$ strength nonselective Gut Microbiota Medium (GMM) (Goodman et al, 2009). In parallel, the strains are also grown on the same media supplemented with 100 mg of ethylenediamine di(ohydroxyphenylacetic acid) (EDDHA) per ml as described by Hohnadel and Meyer (1988. Growth on EDDHA supplemented medium is indicative for siderophore synthesis.

Uptake of heterologous siderophores: Assays for uptake of heterologous siderophores were performed with full strength, ½ and ⅕$^{th}$ strength GMM agar medium supplemented with 100 mg of ethylenediamine di(ohydroxyphenylacetic acid) (EDDHA) per ml as described by Hohnadel and Meyer (1988). Plates were inoculated randomly with the help of sterile glass beads at a concentration of $10^{+6}$ cells per plate. Sterile paper disks (6 mm in diameter) were impregnated siderophore solutions and deposited, after drying because of siderophores solubilized in methanol (e.g., enterobactin, cepabactin, and pyochelin), at the surface of the inoculated agar. The ability of the siderophores to promote bacterial growth by competing for iron with EDDHA was checked after 3, 5 and 7 days of incubation at 37° C. Siderophores to be tested can include but are not limited to Aerobactin, Desferriaerobactin, Arthrobactin, Desferriarthrobactin, Fe-Carboxymycobactins, Coprogen, Desferricoprogen, Fusigen, Desferrifusigen, Ferrioxamine E, Desferrioxamine E, Ferrioxamine G, Desferrioxamine G, Fe-Rhodotorulic acid, Rhodotorulic acid (iron-free), Ferrichrome, Desferrichrome, Ferrichrome A, Desferrichrome A, Ferrichrysin, Desferrichrysin, Ferricrocin, Desferricrocin, Ferrirhodin, Desferrirhodin, Ferrirubin, Desferrirubin, Ornibactin (mixture C4, C6, C8), Desferriornibactin (mixture C4, C6, C8), Ornibactin C6, Desferriornibactin C6, Fe-Rhizoferrin, Rizoferrin (iron-free), Fe-Schizokinen, Schizokinen (iron-free), Triacetylfusarinine C, Desferritriacetylfusarinine C, Fe-Enterbactin, Enterbactin (iron-free), Fe-Salmochelin S4, Salmochelin S4 (iron-free), Fe-Yersiniabactin, Yersiniabactin (iron-free), Fe-Vibriobactin, Vibriobactin (iron-free), Fe-Bacillibactin, Bacillibactin (iron-free), Albomycin (ferric form), Pyoverdines (ferric or iron-free).

Synthesis of Butyrate, Propionate, Acetate:

Analysis of SCFA synthesis is performed using standard techniques, such as liquid chromatography-electrospray ionization-tandem mass spectrometry (LC-ESI-MS/MS) on cultures growing in appropriate media under fermentative conditions such as described by Narushima et al (2014). Fatty acids in the culture supernatant are derivatized with 2-nitrophenylhydrazine and purified by liquid/liquid extraction. Short chain fatty acid peaks are identified by both their specific MS/MS ion-transitions and comparison of the retention times with those of known short chain fatty acids in a standard solution. Synthesis of 4-amino-butyrate (gamma-aminobutyric acid; GABA): Analysis of GABA synthesis is performed using LC/MS-MS techniques on cultures growing in appropriate media under fermentative conditions as described previously (e.g. see Zazzeroni et al, 2009).

Synthesis of Indole:

Analysis of indole synthesis is performed using the Salkowski reagent and it is based on the oxidation of indole compounds by ferric salts (Mayer, 1958).

Assay for Synthesis of Antagonistic Metabolites:

For the testing of antagonism against bacterial and fungal pathogens, a plate assay is performed by spotting the bacterial isolate on a lawn of the pathogenic bacterium or fungus on GMM agar plates. Plates are incubated at 37° C. under anaerobic conditions, and checked regularly for growth behaviors such as growth inhibition, niche occupation, or no effect. Bacterial pathogens to be screened against include *Clostridium* species such as *C. difficile* and *C. perfringens*, *Vibrio* species such as *V. cholera* and *V. parahaemolyticus*, *Serratia* species including *S. marcescens*, *Klebsiella* species such as *K pneumoniae*, *Shigella* species such as *S. sonnei*, *Yersinia* species such as *Y. enterocolitica*, *Escherichia coli* (including enterotoxigenic, enteroinvasive, enteropathogenic and verotoxin-producing strains such as serotype 0157), *Salmonella* species such as *S. typhi* and *S. paratyphi*, *Campylobacter* species such as *C. jejuni* and *C. coli*, *Staphylococcus aureus* (MRSA), and *Pseudomonas aeruginosa*. Fungal pathogens to be screened against include *Candida* species, such as *C. albicans* and *C. auris*, *Pichia* species, *Cladosporium* (a known allergen and trigger for asthmatic attacks), and *Aureobasidium* (which can cause fungal infections in solid-organ transplant recipients).

EPS and LTA Production and Characterization:

To determine the synthesis of extracellular polysaccharides by the bacteria isolates, the methods described by Ortega-Morales et al (2007) are used. The synthesis of LTA is determined using ELISA assays. To further determine the structure of the LTA, the method described by Villeger et al (2014) is used.

Immuno Modulation:

To determine the immuno modulatory functionalities of the microorganisms, the protocols as described by Geva-Zatorsky et al (2017) can be used, as well as a series of commercially available test systems to determine the interactions of the microorganisms with various PRR receptors, including are the Toll-like receptors (TLRs), the C-type lectin receptors (CLRs), the nucleotide-binding oligomerization domain-like receptors (NLRs), the retinoic acid-inducible gene-I-like receptors (RLRs), and the AIM2-like receptor (ALR).

Example 3

Genome Sequencing and Annotation

In order to build a collection of well annotated genome sequences of strains isolated from the gut microbiome, bacterial genomsequences are either obtained via de novo sequencing, or from publicly available sources, such as but not limited to IMG (https://img.jgi.doe.gov/), RAST (http://www.nmpdr.org/FIG/wiki/view.cgi/FIG/RapidAnnotation-Server), and GenBank (https://www.ncbi.nlm nih.gov/genbank/).

Subsequently, genome annotation is performed on both de novo assembled genomes as well as downloaded genome sequences from public resources using the RAST annotation tool, followed by genome annotation of key competitive functions. Functionalities include, but are not limited to: synthesis of SCFA (propionate, butyrate, acetate), GABA synthesis and metabolism, indole synthesis, bile acid metabolism, siderophore biosynthesis and utilization of heterologous siderophores, synthesis of antagonistic metabolites including lantibiotics and bacteriocins, EPS and LTA synthesis.

The following families, genera and species are of particular interest:

Bacteria belonging to the Clostridiales, especially members of the *Clostridium* clusters IV, XIVa and XVIII: *Clostridium* cluster IV is composed of *Clostridium*, *Eubacterium*, *Ruminococcus* and *Anaerofilum* genera; Bacteria from the *Clostridium* cluster XIVa includes species belonging to the *Clostridium*, *Eubacterium*, *Ruminococcus*, *Coprococcus*, *Dorea*, *Lachnospira*, *Roseburia* and *Butyrivibrio* genera; and Bacteria from the *Clostridium* cluster XVIII includes the species *Clostridium ramosum* and *Clostridium spiroforme*.

Bacteria from the class Negativicutes
Bacteria from the orders Selenomonadales (families Selenomonadaceae and Sporomusaceae), Acidaminococcales (family Acidaminococcaceae), Vellionellales (family Vellionellaceae), and Verrucomicrobiales (family Verrucomicrobiaceae). Species of a genus selected from the group consisting of *Megamonas, Acidaminococcus, Succinispira, Megasphaera, Dialister, Pelosiunus, Veillonella*, and *Akkermansia*, especially *Acidamonas intestini, Megamonas funiformis, Megamonas hypermegale, Megamonas rupellensis* and *Akkermansia muciniphila*.
Bacteria from the families Prevotellaceae, Rikenellaceae, Porphyromonadaceae, Lactobacillaceae, and Bacteroidaceae; Species of a genus selected from the group consisting of *Rikenella, Alistipes, Anaerocella, Porphyromonas, Prevotella, Hallella*, and *Alloprevotella*, especially *Bacteroidia* species selected from the group consisting of *Alistipes putredinis, Bacteroides massiliensis*, and *Bacteroides stercoris;*
Species belonging to the genus *Marvinbryantia*.

Example 4

Building Strain Level Metabolic Models to Predict Key Auxotrophies

After genome annotation, the ModelSEED tool (Henry et al, 2010) is applied to construct draft genome-scale metabolic models. As an example, this was performed for 14 strains isolated from the human gut. These strains were chosen as examples based on having absent or underrepresented functionalities in IBD as described herein above and also based on the ability to provide metabolic interdependency to the consortium as described in further detail below. The ModelSEED was used to analyze the 14 individual strains for over 1100 metabolic reaction steps and to construct metabolic models for the individual strains. Subsequently, the strain level models were used to predict preferential carbon and nitrogen source utilization, as well as auxotrophies for essential nutrients including amino acids, vitamins and co-factors. Table 1 shows the summary statistics for the draft models, as well as statistics for all subsequent refinements to these models.

TABLE 1

High level statistics for the models created in ModelSEED for 14 strains isolated from the human gut microbiome. Draft refers to the reactions, compounds and genes out of the various strain ModelSEED models without curation; refined refers to the reactions, compounds and genes out of the various strain ModelSEED models following extensions based on expert curation and functional assignment.

| Strain | Draft reactions | Draft compounds | Draft genes | Refined reactions* | Refined compounds | Refined genes |
|---|---|---|---|---|---|---|
| *Clostridium scindens* ATCC 35704 | 1047 | 1212 | 783 | 1206 (177) | 1294 | 779 |
| Clostridiales 1 7 47FAA | 1217 | 1349 | 1423 | 1353 (157) | 1411 | 1416 |
| *Hungatella hathewayi* 12489931 | 1230 | 1370 | 1246 | 1361 (143) | 1427 | 1241 |
| *Clostridium symbiosum* WAL-14163 | 1146 | 1317 | 1026 | 1290 (168) | 1378 | 1019 |
| *Anaerotruncus colihominis* DSM 17241 | 1056 | 1223 | 821 | 1223 (190) | 1303 | 815 |
| Lachnospiraceae 3 1 57FAA CT1 | 1194 | 1362 | 1080 | 1350 (176) | 1438 | 1075 |
| *Clostridium asparagiforme* DSM 15981 | 1201 | 1341 | 1347 | 1347 (164) | 1411 | 1340 |
| *Clostridium bolteae* 903B3 | 1287 | 1411 | 1349 | 1421 (159) | 1472 | 1341 |
| *Dielma fastidiosa* | 859 | 1031 | 780 | 1091 (245) | 1178 | 773 |
| Lachnospiraceae 6163FAA | 990 | 1149 | 651 | 1144 (170) | 1225 | 647 |
| Lachnospiraceae 4137FAA | 1017 | 1179 | 684 | 1192 (190) | 1271 | 678 |
| *Clostridium* sp D5 | 1269 | 1393 | 1175 | 1398 (151) | 1447 | 1170 |
| *Erysipelatoclostridium ramosum* DSM1402 | 1053 | 1189 | 813 | 1192 (152) | 1269 | 809 |
| *Clostridium saccharogumia* DSM 17460 | 1034 | 1175 | 674 | 1173 (154) | 1252 | 670 |

*The number between parentheses indicates of reactions added to strain model during gap filling.

All models required some degree of gap filling to ensure that they are capable of synthesizing or acquiring all the small molecule building blocks required to produce new biomass. This gap filling was performed in silico mimicking a specific growth condition; it is preferable to perform gap filling mimicking minimal medium composition. The initial gap filling was therefore performed in glucose minimal medium. In this analysis, the synthesis pathways for all amino acids, vitamins, and cofactors are automatically assigned and subsequently, as part of a quality control process, manually reviewed in a model-driven fashion to determine which pathways were likely incomplete for each genome. The output of this analysis revealed substantial differences in auxotrophy across the 14 strains tested.

In addition, auxotrophic predictions can be confirmed in vitro using the Holliday grid (Miller 1972) or by growing the strains on defined media with or without the addition of a specific key metabolite. Similarly, predicted resistances of strains to clinically relevant antibiotics can be confirmed. In this manner, a data summary for each strain that provides an overview of critical carbon and nitrogen utilization and antibiotic resistances is produced.

Example 5

Random Mutagenesis to Obtain Auxotrophic Mutants

In order to use strains as part of a rationally designed consortium, it might be necessary to introduce additional auxotrophic mutations. This would make these strains dependent on other members of the consortium for specific metabolites, therefore creating a more stable consortium in the gut of the organism of interest. In order to obtain auxotrophic mutants, a culture of a microorganism of interest is diluted 50 to 100-fold in rich growth medium (such as GMM medium) and grown under optimal conditions until it reaches the exponential growth phase. Subsequently, the culture is exposed to a mutagenic product as described by Sadouk and Mergeay (1993). Mutagenic compounds that can be used include MNNG, N-methyl-N'-nitro-N-nitrosoguanidine and EMS, ethyl methane sulphonate. As a control and to estimate the mortality caused by exposure to the mutagenic compound, untreated culture is also processed. Dilutions of both treated and untreated cultures are plated on rich medium, such as GMM agar plates, and after incubation for 5 to 7 days under the appropriate growth conditions, colonies are counted. Ideally, the untreated cultures have a 100 to 1000-fold higher count than the cultures that were exposed to the mutagenic compound.

Colonies obtained from cultures exposed to mutagenic compounds are subsequently replica-plated on both a rich and a defined minimal growth medium. Colonies that fail to grow on the minimal medium are marked as auxotrophic. The type of auxotrophy is subsequently determined using the Holliday grid (Miller 1972). In addition, the reversion rate of the auxotrophic mutations is determined; this should ideally be below detection limit.

Example 6

Combining Strains into Rational Designed Consortia Based on Functionality

Using iterative computational approaches, the metabolic models of individual strains (which were selected for the presence of complementary functionalities for a healthy microbiome such as in EXAMPLE 4) are integrated into a series of community metabolic models for various artificial consortium configurations. By subsequently using flux balance analysis, these models can identify all critical strain interdependencies, as well as determine which critical auxotrophies should be addressed: either because the members of the consortium lack the genetic information to synthesize a critical metabolite, or because the ability to synthesize a critical metabolite is only possessed by a single or limited number of consortium members. This would result in the collapse the network in the gut of the organism of interest by putting too much pressure (energy cost) on a single strain to provide a critical metabolite to the other members of the consortium. This is shown by the example of the eight-strain consortium presented in Table 2.

TABLE 2

Predicted auxotrophies for members of a synthetic consortium comprised of eight strains.

| | Strain number | | | | | | | | |
| --- | --- | --- | --- | --- | --- | --- | --- | --- | --- |
| | 1 | 2 | 3 | 4 | 5 | 6 | 7 | 8 | |
| | Overall Auxotrophy count per strain | | | | | | | | |
| | 7 | 7 | 5 | 4 | 6 | 4 | 5 | 3 | Count |
| L-Tryptophan | | A | | | A | | | | 2 |
| L-Tyrosine | | A | | | | | | | 1 |
| L-Phenylalanine | | A | | | | | | | 1 |
| L-Valine | | | | | | | | | |
| L-Isoleucine | | | | | | | | | |
| L-Leucine | | | | | | | | | |
| L-Alanine | | | | | | | | | |
| L-Aspartate | | | | | | | | | |
| L-Asparagine | A | | | | A | | | | 2 |
| L-Glutamate | | | | | | | | | |
| L-Glutamine | | | | | | | | | |
| L-Serine | A | A | A | A | A | A | A | A | 8 |
| L-Threonine | | | A | | | | | | 1 |
| Glycine | | | | | | A | | | 1 |
| L-Methionine | | | | | | | | | |
| S-Adenosyl-L-methionine | | | | | | | | | |
| L-Cysteine | | | | | | | | | |
| L-Lysine | | | | | | | | | |
| L-Histidine | | | | A | | | | | 1 |
| L-Arginine | | | | | | | | | |
| L-Proline | | | | | | | | | |
| Putrescine | | | | | | | | | |
| Spermidine | A | A | A | | A | A | A | A | 7 |
| Pyridoxal phosphate | | | | | | | | | |
| Heme | A | | A | A | | | | | 3 |
| Cobalamin | | | A | | | | | | 1 |
| Niacin | | | | | | A | | A | 2 |
| Riboflavin | A | A | | | A | A | A | | 5 |
| Pantothenate | A | | | | | | | | 1 |
| Folate | A | A | | A | A | | A | | 5 |
| Thiamin | | | | | | | | | |
| Butyrate | P | | P | P | | P | | P | 5 |
| Propionate | | P | | | | P | | | 2 |
| GABA | | | P | | | | | | 1 |
| Bile acid | | P | | | P | | P | | 3 |
| Siderophore synthesis | | P | | P | | | P | | 3 |
| Hetero. Sid | P | P | P | P | | | | | 4 |
| Compl. Carbohydr./proteins | M | M | M | M | M | M | M | M | 7 |

Numbers in "bold" indicate the most frequently observed auxotrophies;
"A" in a cell indicates a compound for which a strain is predicted to be auxotrophic; "P" in a cell indicates an important functionality present in a strain; "M" in a cell indicates an important functionality missing in a strain.

Based on Table 2, the artificial consortium described in Table 2 would not be able to grow independently of other strains providing important metabolites. All eight strains are auxotrophic for L-serine so this amino acid needs to be provided. With the exception of strain 4, all seven other strains are auxotrophic for spermidine. It is very unlikely that strain 4 could synthesize sufficient spermidine to cover the needs of this consortium. Auxotrophies for riboflavin and folate are also commonly observed, so this consortium needs to be further optimized by including additional strains to provide sufficient amounts of critical metabolites for the consortium to optimally function. It should also be noticed that none of the 8 strains in this consortium was found to efficiently breakdown complex carbohydrates and proteins, making it mostly dependent on other strains for its carbon, nitrogen and energy needs. As a result, it is very unlikely that this consortium could successfully engraft and populate the gut sufficiently to perform in a dysbiotic gut environment.

Thus, one or more strains capable of breaking down complex carbohydrates and proteins is added to this consortium and the particular specie(s) selected is metabolically interdependent with the other members of the consortium as described in the methods provided herein.

Example 7

Adding Strains to Complement Auxotrophy and Address Critical Metabolic Dependencies Starting with the model described in EXAMPLE 4, in silico modeling is subsequently used to find the appropriate strains to complement the predicted and/or confirmed metabolic deficiencies. Specific metabolic interdependencies, defined via flux balance analysis, can be used to control the ratios of strains. For example, deficiencies in the synthesis of folate, aromatic amino acids, etc., provide critical auxotrophies that can be used to lock in specific strain ratios based on energy balances and thus interdependencies.

Some of the principles governing the rational design of a consortium are illustrated in Table 3.

TABLE 3

Predicted auxotrophies for members of a synthetic consortium comprised of 12 strains from EXAMPLE 4.

| | Strain number | | | | | | | | | | | | |
|---|---|---|---|---|---|---|---|---|---|---|---|---|---|
| | Original strains | | | | | | | | Added strains | | | | |
| | 1 | 2 | 3 | 4 | 5 | 6 | 7 | 8 | 9 | 10 | 11 | 12 | Aux count |
| | Overall Auxotrophy count per strain | | | | | | | | | | | | |
| | 8 | 7 | 6 | 4 | 6 | 5 | 6 | 4 | 4 | 4 | 4 | 4 | |
| L-Tryptophan | | A | | | A | | | | | | A | | 3 |
| L-Tyrosine | | | | | | | | | | | | A | 1 |
| L-Phenylalanine | | | | | | | | | | | | A | 1 |
| L-Valine | | | | | | | | | | | | | |
| L-Isoleucine | | | | | | | | | | | | | |
| L-Leucine | | | | | | | | | | | | | |
| L-Alanine | | | | | | | | | | | | | |
| L-Aspartate | | | | | | | | | | | | | |
| L-Asparagine | A | | | A | | | | | | | | | 2 |
| L-Glutamate | | | | | | | | | | | AM | | 1 |
| L-Glutamine | | | | | | | | | | | | | |
| L-Serine | A | A | A | A | A | A | A | A | | | | | 8 |
| L-Threonine | | | A | | | | | | A | | | | 2 |
| Glycine | | | | | | A | | | | A | | | 2 |
| L-Methionine | | | | | | | | | | | | | |
| S-Adenosyl-L-methionine | | | | | | | | | | | | | |
| L-Cysteine | | | | | | | | | | | | | |
| L-Lysine | | | | | | | | | AM | A | A | A | 4 |
| L-Histidine | | | A | | | | | | | AM | | | 2 |
| L-Arginine | | | | | | | | | | | | | |
| L-Proline | | | | | | | | | | | | | |
| Putrescine | | | | | | | A | | | | | | 1 |
| Spermidine | A | A | A | | A | A | A | A | | | | | 7 |
| Pyridoxal phosphate | | | | | | | | | | | | | |
| Heme | A | | A | A | | | | | | | A | | 4 |
| Cobalamin | | | A | | | | | | | A | | | 2 |
| Niacin | | | | | | A | | A | | | AM | | 3 |
| Riboflavin | A | A | | | A | A | A | | A | | | | 6 |
| Pantothenate | | | | | | | | | A | | | | 1 |
| Folate | A | A | | A | A | | A | | | | | AM | 6 |
| Thiamin | | | | | | | | | | A | | | 1 |
| Butyrate | P | | P | P | | P | | P | | | | | 5 |
| Propionate | | P | | | | P | | P | | | | | 3 |
| GABA | | | P | | | | | | | | | | 1 |
| Bile acid | | | P | | | P | | P | | | | | 3 |
| Siderophore synthesis | | | P | P | P | | | P | | | | | 4 |
| Hetero. Sid. uptake | P | P | P | P | | | | | | | | | 4 |
| Complex Carbohyd. | M | M | M | M | M | M | M | M | P | P | P | P | 4 |

Numbers in "bold" indicate the most frequently observed auxotrophies;

"A" in a cell indicates a compound for which a strain is predicted to be auxotrophic; "AM" indicate auxotrophies which were introduced using mutagenisis; "P" in a cell indicates an important functionality present in a strain; "M" in a cell indicates an important functionality missing in a strain.

To complement auxotrophy and address critical metabolic dependencies, four additional strains were selected as metabolic support strains and added to the consortium of EXAMPLE 6. All four strains were selected to be able to break down complex carbohydrates, and synthesize L-serine and spermidine. To stably integrate these strains into the original eight-strain consortium, the strains were also selected for being auxotrophic for several key metabolites. To further make sure that the additional four-strains would not outcompete the original eight-strains, all four new strains were selected to share a common auxotrophy for L-lysine, making them metabolically dependent on the original eight strains. Since the wild-type strain 9 had no auxotrophy for L-lysine, mutagenesis was used as described in EXAMPLE 5 to introduce this phenotype into strain 9.

Since the wild type versions of strains 11 and 12 only had two auxotrophies, mutagenesis was applied to introduce in each strain two additional auxotrophic markers, making the number of auxotrophies for these strains more in line with that of the other consortium members. Finally, since strains 1 and 2 had the highest number of auxotrophies, while not contributing a unique function to the consortium, it was decided to drop these strains. This resulted in an optimized consortium comprised of ten strains, that fully covered all key functionalities and that were predicted to form a stable functional consortium driven by interdependencies for critical metabolites.

Once a consortium of therapeutic plus metabolic support strains has been designed as described above by in silico modeling of strain metabolic interdependencies, complementarity of strains is confirmed by growing them together in non-selective medium such as GMM under optimal growth conditions (anaerobic, 37° C.). This can be done in liquid medium, starting with a fixed ratio of strains; changes in strain ratio can be determined via plating and phenotypic characterization, or via Quantitative PCR using strain specific primers. Complementarity of strains can also be tested on GMM agar plates, similar to the protocol used for screening of antagonistic functionalities.

Once a consortium had been rationally designed, in silico analysis is used to identify the minimal medium on which this consortium should be able to grow, reach a stable equilibrium (indicative for engrafting), and synthesize key metabolites, such as SCFA. This predictive model is subsequently confirmed by in vitro experimentation, where the various strains are combined in a single culture which is evaluated under a range of experimental conditions. These conditions can include initial strain ratios, batch versus steady state fermentation, carbon source (ranging from complex food polymers to simple carbon and nitrogen sources), iron limitation, heterologous siderophores, external disturbances such as antibiotics, other commensal as well as pathogenic microorganisms, etc. Changes in strain ratios over time and condition dependent equilibria are determined via quantitative PCR, while a suite of analytical techniques is used to analyze the synthesis of the therapeutic metabolites produced as a result of the key functionalites.

Example 8

Rational Design of a Microbial Therapeutic for the Treatment of IBD

Using the strategy outlined in the combination of EXAMPLES 1 to 7, a microbial therapeutic consortium was rationally designed to provide key functionalities that are lacking or underrepresented in the dysbiotic gut microbiome of IBD patients. These functionalities address both properties for inflammation and infection control. The following functionalities were included in the rational design process: butyrate synthesis and propionate synthesis for modulation of the immune response (e.g. affecting synthesis of the interleukins IL10, IL12 and IL23 to lower the (pre) inflammatory condition); indole synthesis to tighten the epithelial cell junctions and trigger AHR dependent synthesis of the anti-inflammatory interleukin-22 (IL22) (Hubbard et al, 2015b); deconjugation and conversion of bile salts into secondary bile acids; siderophore synthesis, heterologous siderophore uptake (incl. uptake of ferrichrome) to efficiently compete with (opportunistic) pathogens for the essential nutrient iron; and synthesis of antagonistic molecules, including bacteriocins.

Publicly available information, including an overview of major fermentation products produced by strains isolated from the human gut microbiome, was used to make an initial strain selection among the 773 strains currently present in the Virtual Metabolic Human strain database [http://vmh.uni.lu/#microbes/search]. Genome annotation and in silico modeling was subsequently performed to confirm the publicly available information for these fermentation products. Furthermore, in silico data mining and modeling of the annotated genomes for additional metabolic properties and key functionalities were used to narrow down the strain selection.

Specifically, the genome annotation platform, RAST, was used to confirm the presence of the key functionalities in the strains (see TABLE 4). Based on the presence of the key functionalities listed in the previous paragraph, a consortium of 14 strains was initially designed consisting of *Dialister succinatiphilus* DSM21274, *Megamonas funiformis* DSM19343, *Megamonas hypermegale* DSM1672, *Acidaminococcus intestini* DSM21505, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Anaerostipes hadrus* DSM 3319/ATCC 29173, *Clostridium symbiosum* ATCC14940, *Clostridium scindens* ATCC35704 and *Akkermansia muciniphila* ATCC BAA-835. Subsequently, four additional strains were added to provide additional metabolic support (*Clostridium bolteae* ATCC BAA-613, *Blautia producta* DSM2950, *Blautia hydrogenotrophica* DSM 10507) or to convert formate into acetate (*Marvinbryantia formatexigens* DSM14469). This resulted in an eighteen strain (listed in TABLE 4) rationally designed microbiome-based therapeutic for the treatment of IBD. This consortium is referred to as GUT-103. It should be noted that the design process purposely introduced redundancies in functionalities, this to increase the chances of establishment of the consortium or a subset of strains thereof under a broad range of conditions, thus addressing different degrees of gut microbiome dysbiosis as illustrated in FIG. 4.

More specifically, based on the annotation and modeling, it was concluded that several of the strains are capable of producing their own siderophore (*Anaerostipes caccae* DSM14662; *Clostridium bolteae* ATCC BAA-613), or possess uptake systems for heterologously produced siderophores, including the fungal siderophore Ferrichrome (*Dialister succinatiphilus* DSM21274, *Megamonas funiformis* DSM19343, *Megamonas hypermegale* DSM1672, *Blautia producta* DSM2950, *Anaerostipes caccae* DSM14662 and *Marvinbryantia formatexigens* DSM14469), and the Enterobacterial-type siderophores aerobactin (*Barnesiella intestinihominis* DSM21032) and enterobactin (*Bacteroides ster-* coris ATCC43183 and *Megamonas funiformis* DSM19343) (see Table 4). The presence of these heterologous siderophore uptake systems allows these strains to compete against opportunistic pathogenic fungi (including *Candida* sp. and *Pichia* species) and bacteria (including hemolytic and adherent/invasive *Escherichia coli* and *Klebsiella* species) that can thrive in the dysbiotic gut environment associated with IBD.

Key functionalities for bile salt identified for the members of the eighteen-strain rationally designed consortium for IBD control were confirmed using the genome annotation platform, RAST (Table 4). Based on the results it can be concluded that members of the eighteen-strain rationally designed consortium for IBD control cover a range of activities to deconjugate and subsequently modify bile salts into secondary bile acids. It should be specifically noted that putative bile acid 7-alpha-dehydratase activity, which was been previously reported for *Clostridium scindens* ATCC35704, was based on gene similarity also predicted to be present in strains *Blautia hydrogenotrophica* DSM10507 and *Anaerostipes caccae* DSM14662, representing species that belong to the Lachnospiraceae.

Key functionalities for bacteriocin and lantibiotic synthesis and resistance putatively identified for the members of the eighteen-strain rationally designed consortium for IBD control were confirmed using the genome annotation platform, RAST (Table 4).

The strains were also evaluated for their putative synthesis of indole. Strains *Bacteroides stercoris* ATCC43183 and *Akkermansia muciniphila* ATCC BAA-835 were found to possess a putative Tryptophanase (EC 4.1.99.1) gene that catalyzes the breakdown of tryptophan into indole, pyruvate and $NH_3$. Unexpectedly strain *Anaerostipes hadrus* DSM3319, which according to the VHM site is capable of producing indole, seems to lack a putative Tryptophanase gene, making it unlikely that this strain is an efficient indole producer. Alternatively, this strain synthesizes indole via a currently unknown pathway.

Based on genome annotation, *Blautia producta* DSM2950 was also predicted to produce butyrate, a phenotype not previously reported for this strain.

Further, the three strains, *Barnesiella intestinihominis* DSM21032, *Clostridium bolteae* ATCC BAA-613, and *Blautia hydrogenotrophica* DSM 10507, in addition to providing key functionalities underrepresented in IBD, were also included in the consortium for their ability to provide nutrients to other members of the GUT-103 consortium, i.e, metabolic support. For example, *Barnesiella intestinihominis* DSM21032, *Clostridium bolteae* ATCC BAA-613, and *Blautia hydrogenotrophica* DSM 10507, respectively, provide nine (of which 3 are unique), six (of which 2 are unique) and sixteen (of which 12 are unique) metabolites to facilitate growth and complement metabolic deficiencies of other members of the GUT-103 consortium.

TABLE 4

Summary of key functionalities identified for the members of the eighteen-strain rationally designed consortium for IBD control, referred to as the GUT-103 consortium.

| Strain | | Functionality underrepresented for IBD | | | | | |
|---|---|---|---|---|---|---|---|
| Species | Family | Butyrate | Propionate | Indole | Siderophore | Bile Salt | Anti-microbial |
| *Dialister succinatiphilus* DSM21274 | Veillonellaceae | | + | | Ferrichrome uptake | | |
| *Megamonas funiformis* DSM19343 | Selenomonadaceae | | + | | Ferrichrome and Enterobactin uptake | | |
| *Megamonas hypermegale* DSM1672 | Selenomonadaceae | | + | | Ferrichrome uptake | | |
| *Acidaminococcus intestini* DSM21505 | Acidaminococcaceae | + | | | | | |
| *Bacteroides massiliensis* DSM17679 | Bacteroidaceae | | + | | Heterologous uptake | | |
| *Bacteroides stercoris* ATCC43183/DSM19555 | Bacteroidaceae | | + | + | Heterologous incl. Enterobactin uptake | | |
| *Barnesiella intestinihominis* DSM21032 | Porphyromonadaceae | | + | | Heterologous incl. Aerobactin uptake | | |
| *Faecalibacterium prausnitzii* DSM17677 | Ruminococcaceae | + | | | Heterologous uptake | | Bacteriocin |
| *Subdoligranulum variabile* DSM15176 | Ruminococcaceae | + | | | | | Bacteriocin |
| *Anaerostipes caccae* DSM14662 | Lachnospiraceae | + | | | Heterologous uptake incl. Ferrichrome; Yersiniabactin synthesis | 7-α-DH, 7-α-HSD | Bacteriocin |
| *Anaerostipes hadrus* DSM 3319/ATCC 29173 | Lachnospiraceae | + | | + | | | |
| *Clostridium symbiosum* ATCC14940 | Lachnospiraceae | + | | | | 3-α-HSD, 7-α-HSD | |
| *Akkermansia muciniphila* ATCC BAA-835 | Akkermansiaceae | | + | + | Heterologous uptake | | |
| *Clostridium scindens* ATCC35704 | Lachnospiraceae | | | | | 7-α-DH | Bacteriocin |
| *Clostridium bolteae* ATCC BAA-613* | Lachnospiraceae | | | | Siderophore synthesis | 3-α-HSD, 7-α-HSD | Bacteriocin |
| *Blautia producta* DSM2950* | Lachnospiraceae | + | | | Heterologous incl. Ferrichrome uptake | | |

TABLE 4-continued

Summary of key functionalities identified for the members of the eighteen-strain rationally designed consortium for IBD control, referred to as the GUT-103 consortium.

| Strain | | Functionality underrepresented for IBD | | | | | |
|---|---|---|---|---|---|---|---|
| Species | Family | Butyrate | Propionate | Indole | Siderophore | Bile Salt | Anti-microbial |
| *Blautia hydrogenotrophia* DSM 10507* | Lachnospiraceae | | | | | 7-α-DH, 3-β-HSD | Bacteriocin |
| *Marvinbryantia formatexigens* DSM14469* | Lachnospiraceae | | | | Heterologous incl. Ferrichrome uptake | | |

Abbreviations: 7-α-DH: 7-alpha-dehydratase/dehydroxylase activity; 3-α-HSD: 3-alpha-hydroxysteroid dehydrogenase activity; 7-α-HSD: 7-alpha-hydroxysteroid dehydrogenase activity; 3-β-HSD: 3-beta-hydroxysteroid dehydrogenase activity.
*indicates strains that were added to provide additional redundancy for key functionalites and metabolic support (*Clostridium bolteae* ATCC BAA-613, *Blautia producta* DSM2950, *Blautia hydrogenotrophica* DSM 10507) or to convert formate into acetate (*Marvinbryantia formatexigens* DSM14469).

15

To build the GUT-103 consortium model for metabolic interdependency, computational models were first built for the individual GUT-103 strains (as described in EXAMPLE 4). All strain models required some degree of gap filling to ensure that they are capable of synthesizing or acquiring all the small molecule building blocks required to produce new biomass. This gap filling was performed in silico mimicking a specific growth condition; it is preferable to perform gap filling mimicking minimal medium composition. The initial gap filling was therefore performed in glucose minimal medium. The GUT-103 strains, and their most closely related reference strains, were experimentally confirmed to grow in rich medium, as no defined minimal medium is known for any of the strains. Thus, an auxotrophy analysis was performed to predict defined minimal media for each of the GUT-103 strains. In this analysis, the synthesis pathways for all amino acids, vitamins, and cofactors were computationally assigned and subsequently, as part of a quality control process, manually reviewed in a model-driven fashion to determine which pathways were likely incomplete for each genome. The output of this analysis revealed very substantial differences in auxotrophy across all of the GUT-103 strains (See Table 5).

TABLE 5

Predicted auxotrophies for members of a synthetic consortium comprised of the 18 strain GUT-103 consortium. The following strains, referred to by their strain number, are part of GUT-103: *Dialister succinatiphilus* DSM21274, *Megamonas funiformis* DSM19343, *Megamonas hypermegale* DSM1672, *Acidaminococcus intestini* DSM21505, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Anaerostipes hadrus* DSM 3319/ATCC 29173, *Clostridium symbiosum* ATCC14940, *Clostridium bolteae* ATCC BAA-613, *Blautia producta* DSM2950, *Blautia hydrogenotrophica* DSM 10507, *Marvinbryantia formatexigens* DSM14469, *Clostridium scindens* ATCC35704 and *Akkermansia muciniphila* ATCC BAA-835.

| | DSM21274 | DSM19343 | DSM 1672 | DSM21505 | DSM17679 | ATCC43183 | DSM21032 | DSM17677 | DSM15176 |
|---|---|---|---|---|---|---|---|---|---|
| Spermidine | A | | | A | A | A | A | | |
| Arginine | | | | | | | | | |
| Proline | | | | | | | | | |
| Glycine | | | | | | | | | |
| Serine | | | | A | | | | A | |
| Threonine | | | | | | | | | |
| Alanine | | | | | | | | | |
| Aspartate | | | | | | | | | |
| Asparagine | A | A | A | A | | | | | |
| Glutamate | | | | | | | | | |
| Tryptophan | | | | A | | | A | A | A |
| Tyrosine | | | | | | | | | |
| Phenylalanine | | | | | | | | | |
| Valine | | A | | | | | | | |
| Isoleucine | | A | | | | | | | |
| Leucine | | A | | | | | | | |
| Histidine | | | | | | | | | |
| Lysine | | | | | | | | | |
| Cysteine | A | | | A | | | | | |
| Methionine | | | | | | | | | |
| S-Adenosyl-methionine | | | | | | | | | |
| Folate | | | | | | | | A | A |
| Glutamine | | | | | | | | | |
| PAN | A | | | | | | | | |
| Niacin | A | | A | A | | | A | A | A |
| Heme | | | | A | A | A | A | A | A |
| Cbl | | | | A | | | A | A | |
| Thiamin | | | | | | | | | |
| Riboflavin | | | | | | | | A | A |
| Pyridoxal | | | | | | | | | |

TABLE 5-continued

Predicted auxotrophies for members of a synthetic consortium comprised of the 18 strain GUT-103 consortium. The following strains, referred to by their strain number, are part of GUT-103: *Dialister succinatiphilus* DSM21274, *Megamonas funiformis* DSM19343, *Megamonas hypermegale* DSM1672, *Acidaminococcus intestini* DSM21505, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Anaerostipes hadrus* DSM 3319/ATCC 29173, *Clostridium symbiosum* ATCC14940, *Clostridium bolteae* ATCC BAA-613, *Blautia producta* DSM2950, *Blautia hydrogenotrophica* DSM 10507, *Marvinbryantia formatexigens* DSM14469, *Clostridium scindens* ATCC35704 and *Akkermansia muciniphila* ATCC BAA-835.

| | DSM14662 | DSM3319 | ATCC14940 | ATCC BAA-613 | DSM2950 | DSM10507 | DSM14469 | ATCC35704 | ATCC BAA-835 |
|---|---|---|---|---|---|---|---|---|---|
| Spermidine | A | A | | | | | A | A | A |
| Arginine | | | | | | | | | |
| Proline | | | | | | | | | |
| Glycine | | | | | | | | | |
| Serine | | A | | | | | | | |
| Threonine | | | | | | | | | |
| Alanine | | | | | | | | | |
| Aspartate | | | | | | | | | |
| Asparagine | | | | | | | | | A | A |
| Glutamate | | | | | | | | | |
| Tryptophan | | | | | | | | | A | |
| Tyrosine | | | | | | | | | |
| Phenylalanine | | | | | | | | | |
| Valine | | | | | | | | | |
| Isoleucine | | | | | | | | | |
| Leucine | | | | | | | | | |
| Histidine | | | A | | | | | | |
| Lysine | | | | | | | | | |
| Cysteine | | | | | | | | | |
| Methionine | | | | | | | | | |
| S-Adenosyl-methionine | | | | | | | | | |
| Folate | | | A | | | | | | |
| Glutamine | | | | | | | | | |
| PAN | | | A | A | | | | | |
| Niacin | | | | | | A | | | |
| Heme | | | A | A | | | | | |
| Cbl | | A | | | | | | | |
| Thiamin | | | | | | | | | |
| Riboflavin | | | | | A | A | A | A | |
| Pyridoxal | | | | | | | | | |

"A" in a cell indicates a compound for which a strain is identified as auxotrophic.

As for the individual GUT-103 strain models, flux balance analysis was performed with the GUT-103 consortium model to predict the behavior and essentiality of each reaction in each strain while simulating growth in a specific medium condition. However, unlike the individual GUT-103 strain model simulations, all the fluxes in each strain of a consortium model are no longer independent. Instead, the activity of the reactions in one strain will impact the activity of the reactions in other strains via inter-strain interactions. Because of these inter-strain interactions, the GUT-103 consortium model simulates growth in a defined medium that is less complex than the defined medium computed for any of the individual GUT-103 strains. Reactions for synthesis of essential nutrients that are missing in one strain might be complemented by another strain in the consortium model, thus omitting the need to include this metabolite in the defined minimal growth medium. This result can be confirmed from flux balance analysis by running the model while minimizing the number of nutrients that are provided to the model. After this analysis was performed, it was found that the GUT-103 consortium model does indeed predict growth for the GUT-103 consortium in minimal medium, without the need to include additional nutrients, even though none of the GUT-103 consortium strains alone are predicted to be capable of growing in this medium. This finding confirms that the GUT-103 strains, after being integrated into a single consortium, can exchange metabolites to satisfy the auxotrophic requirements of all strains.

Finally, the flux profile generated by the GUT-103 consortium model was used to determine which inter-strain interactions are predicted to be active by the combined model. The modeling also confirmed that the GUT-103 individual strain models, when combined into a single compartmentalized consortium model, are capable of representing all therapeutic phenotypes simultaneously. To do so, the fluxes predicted for the consortium model were examined to ensure that all important therapeutic pathways are carrying flux. This analysis revealed that all predicted therapeutic functions could operate adequately when the entire consortium is growing together as a single consolidated system. Computational modeling also confirmed that many species displayed trophic interactions to ensure that the overall consortium could grow on minimal medium. The interaction data are displayed in tabular form in Table 6. This table shows all the compounds predicted by the GUT-103 consortium model to be exchanged by at least two GUT-103 strains during simulated growth on minimal medium. As this analysis shows, all strains in the GUT-103 consortium are predicted to interact with at least one other strain in the consortium; all strains are interacting with each other, often in a variety of ways. The interactions are induced not only by auxotrophic requirements, but also by resource balancing to maximize overall microbiome biomass production. For example, consider niacin, a metabolically expensive molecule to synthesize. Rather than having one strain produce all of the niacin needed by the auxotrophs, flux balance analysis divides the work among several strains. This further reinforces the view that the GUT-103 consortium can operate like a single "organ" in the gut microbiome, with individual cell-types intricately intertwined by numerous interactions.

TABLE 6

Nutrients exchanged between at least two species in the GUT-103 consortium as predicted by the 18 species GUT-103 consortium model.

| Compound | Consuming species | Generating species |
| --- | --- | --- |
| L-Histidine | Acidaminococcus intestini DSM 21505, Blautia producta DSM 2950, Megamonas hypermegale DSM 1672, Faecalibacterium prausnitzii DSM 17677, Clostridium bolteae ATCC BAA-613, Anaerostipes caccae DSM 14662, Bacteroides massiliensis DSM 17679, Anaerostipes hadrus DSM 3319, Megamonas funiformis DSM 19343, Clostridium symbiosum ATCC 14940, Bacteroides stercoris ATCC 43183, Dialister succinatiphilus DSM 21274, Akkermansia muciniphila ATCC BAA-835, Barnesiella intestinihominis DSM 21032, Clostridium scindens ATCC 35704, Marvinbryantia formatexigens DSM 14469, Subdoligranulum variabile DSM 15176 | Blautia hydrogenotrophica DSM 10507 |
| L-Glutamate | Clostridium symbiosum ATCC 14940, Clostridium bolteae ATCC BAA-613, Barnesiella intestinihominis DSM 21032 | Subdoligranulum variabile DSM 15176, Marvinbryantia formatexigens DSM 14469, Blautia hydrogenotrophica DSM 10507, Bacteroides stercoris ATCC 43183, Akkermansia muciniphila ATCC BAA-835, Anaerostipes caccae DSM 14662, Clostridium scindens ATCC 35704, Bacteroides massiliensis DSM 17679, Faecalibacterium prausnitzii DSM 17677, Blautia producta DSM 2950, Acidaminococcus intestini DSM 21505, Anaerostipes hadrus DSM 3319 |
| Glycine | Acidaminococcus intestini DSM 21505, Blautia hydrogenotrophica DSM 10507 | Clostridium symbiosum ATCC 14940, Clostridium bolteae ATCC BAA-613, Bacteroides stercoris ATCC 43183, Akkermansia muciniphila ATCC BAA-835, Dialister succinatiphilus DSM 21274, Barnesiella intestinihominis DSM 21032, Clostridium scindens ATCC 35704, Bacteroides massiliensis DSM 17679, Megamonas hypermegale DSM 1672, Megamonas funiformis DSM 19343, Faecalibacterium prausnitzii DSM 17677 |
| L-Tryptophan | Dialister succinatiphilus DSM 21274, Bacteroides stercoris ATCC 43183, Akkermansia muciniphila ATCC BAA-835, Clostridium symbiosum ATCC 14940, Clostridium scindens ATCC 35704, Barnesiella intestinihominis DSM 21032, Marvinbryantia formatexigens DSM 14469, Subdoligranulum variabile DSM 15176, Anaerostipes hadrus DSM 3319, Megamonas funiformis DSM 19343, Clostridium bolteae ATCC BAA-613, Anaerostipes caccae DSM 14662, Bacteroides massiliensis DSM 17679, Acidaminococcus intestini DSM 21505, Blautia producta DSM 2950, Megamonas hypermegale DSM 1672, Faecalibacterium prausnitzii DSM 17677 | Blautia hydrogenotrophica DSM 10507 |
| L-Phenylalanine | Anaerostipes hadrus DSM 3319, Megamonas funiformis DSM 19343, Clostridium symbiosum ATCC 14940, Bacteroides stercoris ATCC 43183, Dialister succinatiphilus DSM 21274, Akkermansia muciniphila ATCC BAA-835, Barnesiella intestinihominis DSM 21032, Clostridium scindens ATCC 35704, Marvinbryantia formatexigens DSM 14469, Subdoligranulum variabile DSM 15176, Acidaminococcus intestini DSM 21505, Blautia producta DSM 2950, Megamonas hypermegale DSM 1672, Faecalibacterium prausnitzii DSM 17677, Clostridium bolteae ATCC BAA-613, Anaerostipes caccae DSM 14662, Bacteroides massiliensis DSM 17679 | Blautia hydrogenotrophica DSM 10507 |

TABLE 6-continued

Nutrients exchanged between at least two species in the GUT-103 consortium as predicted by the 18 species GUT-103 consortium model.

| Compound | Consuming species | Generating species |
| --- | --- | --- |
| Putrescine | Barnesiella intestinihominis DSM 21032, Clostridium scindens ATCC 35704, Anaerostipes caccae DSM 14662, Clostridium symbiosum ATCC 14940, Akkermansia muciniphila ATCC BAA-835, Dialister succinatiphilus DSM 21274, Blautia hydrogenotrophica DSM 10507, Subdoligranulum variabile DSM 15176, Anaerostipes hadrus DSM 3319, Blautia producta DSM 2950, Megamonas funiformis DSM 19343, Megamonas hypermegale DSM 1672 | Acidaminococcus intestini DSM 21505, Bacteroides stercoris ATCC 43183, Bacteroides massiliensis DSM 17679, Faecalibacterium prausnitzii DSM 17677 |
| L-Proline | Clostridium scindens ATCC 35704, Clostridium symbiosum ATCC 14940, Bacteroides stercoris ATCC 43183, Dialister succinatiphilus DSM 21274, Akkermansia muciniphila ATCC BAA-835, Blautia hydrogenotrophica DSM 10507, Marvinbryantia formatexigens DSM 14469, Subdoligranulum variabile DSM 15176, Anaerostipes hadrus DSM 3319, Megamonas funiformis DSM 19343, Bacteroides massiliensis DSM 17679, Anaerostipes caccae DSM 14662, Acidaminococcus intestini DSM 21505, Blautia producta DSM 2950, Faecalibacterium prausnitzii DSM 17677, Megamonas hypermegale DSM 1672 | Clostridium bolteae ATCC BAA-613, Barnesiella intestinihominis DSM 21032 |
| Folate | Megamonas funiformis DSM 19343, Anaerostipes hadrus DSM 3319, Marvinbryantia formatexigens DSM 14469, Subdoligranulum variabile DSM 15176, Clostridium scindens ATCC 35704, Barnesiella intestinihominis DSM 21032, Akkermansia muciniphila ATCC BAA-835, Dialister succinatiphilus DSM 21274, Bacteroides stercoris ATCC 43183, Clostridium symbiosum ATCC 14940, Faecalibacterium prausnitzii DSM 17677, Megamonas hypermegale DSM 1672, Blautia producta DSM 2950, Bacteroides massiliensis DSM 17679, Anaerostipes caccae DSM 14662, Clostridium bolteae ATCC BAA-613 | Blautia hydrogenotrophica DSM 10507 |
| L-Valine | Anaerostipes caccae DSM 14662, Clostridium bolteae ATCC BAA-613, Bacteroides massiliensis DSM 17679, Acidaminococcus intestini DSM 21505, Blautia producta DSM 2950, Megamonas hypermegale DSM 1672, Faecalibacterium prausnitzii DSM 17677, Dialister succinatiphilus DSM 21274, Bacteroides stercoris ATCC 43183, Akkermansia muciniphila ATCC BAA-835, Clostridium symbiosum ATCC 14940, Clostridium scindens ATCC 35704, Barnesiella intestinihominis DSM 21032, Subdoligranulum variabile DSM 15176, Marvinbryantia formatexigens DSM 14469, Anaerostipes hadrus DSM 3319, Megamonas funiformis DSM 19343 | Blautia hydrogenotrophica DSM 10507 |
| Thiamin | Clostridium symbiosum ATCC 14940, Anaerostipes caccae DSM 14662, Clostridium scindens ATCC 35704, Megamonas hypermegale DSM 1672, Megamonas funiformis DSM 19343, Blautia producta DSM 2950, Acidaminococcus intestini DSM 21505, Anaerostipes hadrus DSM 3319 | Clostridium bolteae ATCC BAA-613, Faecalibacterium prausnitzii DSM 17677, Marvinbryantia formatexigens DSM 14469 |
| L-Methionine | Clostridium bolteae ATCC BAA-613, Anaerostipes caccae DSM 14662, Bacteroides massiliensis DSM 17679, Blautia producta DSM 2950, Acidaminococcus intestini DSM 21505, Megamonas hypermegale DSM 1672, Faecalibacterium prausnitzii DSM 17677, Clostridium symbiosum ATCC 14940, Akkermansia muciniphila ATCC BAA-835, Bacteroides stercoris ATCC 43183, Dialister succinatiphilus DSM 21274, Clostridium scindens ATCC 35704, Marvinbryantia formatexigens DSM 14469, Subdoligranulum variabile DSM 15176, Blautia hydrogenotrophica DSM 10507, Anaerostipes hadrus DSM 3319, Megamonas funiformis DSM 19343 | Barnesiella intestinihominis DSM 21032 |

TABLE 6-continued

Nutrients exchanged between at least two species in the GUT-103 consortium as predicted by the 18 species GUT-103 consortium model.

| Compound | Consuming species | Generating species |
| --- | --- | --- |
| L-Aspartate | *Megamonas funiformis* DSM 19343, *Megamonas hypermegale* DSM 1672, *Bacteroides massiliensis* DSM 17679, *Akkermansia muciniphila* ATCC BAA-835, *Dialister succinatiphilus* DSM 21274, *Bacteroides stercoris* ATCC 43183, *Anaerostipes caccae* DSM 14662, *Clostridium bolteae* ATCC BAA-613, *Subdoligranulum variabile* DSM 15176, *Marvinbryantia formatexigens* DSM 14469 | *Acidaminococcus intestini* DSM 21505 |
| Pyridoxal | *Anaerostipes hadrus* DSM 3319, *Acidaminococcus intestini* DSM 21505, *Megamonas funiformis* DSM 19343, *Faecalibacterium prausnitzii* DSM 17677, *Megamonas hypermegale* DSM 1672, *Clostridium scindens* ATCC 35704, *Bacteroides massiliensis* DSM 17679, *Anaerostipes caccae* DSM 14662, *Clostridium bolteae* ATCC BAA-613, *Clostridium symbiosum* ATCC 14940, *Dialister succinatiphilus* DSM 21274, *Marvinbryantia formatexigens* DSM 14469, *Subdoligranulum variabile* DSM 15176 | *Blautia hydrogenotrophica* DSM 10507 |
| L-Isoleucine | *Megamonas hypermegale* DSM 1672, *Faecalibacterium prausnitzii* DSM 17677, *Acidaminococcus intestini* DSM 21505, *Blautia producta* DSM 2950, *Anaerostipes caccae* DSM 14662, *Bacteroides massiliensis* DSM 17679, *Megamonas funiformis* DSM 19343, *Anaerostipes hadrus* DSM 3319, *Subdoligranulum variabile* DSM 15176, *Marvinbryantia formatexigens* DSM 14469, *Clostridium symbiosum* ATCC 14940, *Dialister succinatiphilus* DSM 21274, *Bacteroides stercoris* ATCC 43183, *Akkermansia muciniphila* ATCC BAA-83, *Barnesiella intestinihominis* DSM 21032, *Clostridium scindens* ATCC 35704 | *Blautia hydrogenotrophica* DSM 10507 |
| L-Lysine | *Megamonas funiformis* DSM 19343, *Anaerostipes hadrus* DSM 3319, *Marvinbryantia formatexigens* DSM 14469, *Subdoligranulum variabile* DSM 15176, *Dialister succinatiphilus* DSM 21274, *Bacteroides stercoris* ATCC 43183, *Akkermansia muciniphila* ATCC BAA-835, *Clostridium symbiosum* ATCC 14940, *Clostridium scindens* ATCC 35704, *Barnesiella intestinihominis* DSM 21032, *Megamonas hypermegale* DSM 1672, *Faecalibacterium prausnitzii* DSM 17677, *Blautia producta* DSM 2950, *Acidaminococcus intestini* DSM 21505, *Anaerostipes caccae* DSM 14662, *Bacteroides massiliensis* DSM 17679 | *Clostridium bolteae* ATCC BAA-613, *Blautia hydrogenotrophica* DSM 10507 |
| Spermidine | *Clostridium scindens* ATCC 35704, *Barnesiella intestinihominis* DSM 21032, *Akkermansia muciniphila* ATCC BAA-835, *Dialister succinatiphilus* DSM 21274, *Bacteroides stercoris* ATCC 43183, *Clostridium symbiosum* ATCC 14940, *Blautia hydrogenotrophica* DSM 10507, *Marvinbryantia formatexigens* DSM 14469, *Subdoligranulum variabile* DSM 15176, *Anaerostipes hadrus* DSM 3319, *Megamonas funiformis* DSM 19343, *Bacteroides massiliensis* DSM 17679, *Anaerostipes caccae* DSM 14662, *Blautia producta* DSM 2950, *Acidaminococcus intestini* DSM 21505, *Faecalibacterium prausnitzii* DSM 17677, *Megamonas hypermegale* DSM 1672 | *Clostridium bolteae* ATCC BAA-613 |
| L-Arginine | *Megamonas hypermegale* DSM 1672, *Faecalibacterium prausnitzii* DSM 17677, *Acidaminococcus intestini* DSM 21505, *Blautia producta* DSM 2950, *Anaerostipes caccae* DSM 14662, *Clostridium bolteae* ATCC BAA-613, *Bacteroides massiliensis* DSM 17679, *Megamonas funiformis* DSM 19343, *Anaerostipes hadrus* DSM 3319, *Subdoligranulum variabile* DSM 15176, *Marvinbryantia formatexigens* DSM 14469, *Clostridium symbiosum* ATCC 14940, | *Blautia hydrogenotrophica* DSM 10507, *Barnesiella intestinihominis* DSM 21032 |

TABLE 6-continued

Nutrients exchanged between at least two species in the GUT-103 consortium as predicted by the 18 species GUT-103 consortium model.

| Compound | Consuming species | Generating species |
|---|---|---|
| Riboflavin | *Akkermansia muciniphila* ATCC BAA-835, *Bacteroides stercoris* ATCC 43183, *Dialister succinatiphilus* DSM 21274, *Clostridium scindens* ATCC 35704 *Barnesiella intestinihominis* DSM 21032, *Clostridium scindens* ATCC 35704, *Clostridium symbiosum* ATCC 14940, *Dialister succinatiphilus* DSM 21274, *Akkermansia muciniphila* ATCC BAA-835, *Bacteroides stercoris* ATCC 43183, *Blautia hydrogenotrophica* DSM 10507, *Marvinbryantia formatexigens* DSM 14469, *Subdoligranulum variabile* DSM 15176, *Anaerostipes hadrus* DSM 3319, *Megamonas funiformis* DSM 19343, *Bacteroides massiliensis* DSM 17679, *Anaerostipes caccae* DSM 14662, *Acidaminococcus intestini* DSM 21505, *Blautia producta* DSM 2950, *Faecalibacterium prausnitzii* DSM 17677, *Megamonas hypermegale* DSM 1672 | *Clostridium bolteae* ATCC BAA-613 |
| L-Leucine | *Acidaminococcus intestini* DSM 21505, *Blautia producta* DSM 2950, *Faecalibacterium prausnitzii* DSM 17677, *Megamonas hypermegale* DSM 1672, *Bacteroides massiliensis* DSM 17679, *Clostridium bolteae* ATCC BAA-613, *Anaerostipes caccae* DSM 14662, *Anaerostipes hadrus* DSM 3319, *Megamonas funiformis* DSM 19343, *Clostridium scindens* ATCC 35704, *Barnesiella intestinihominis* DSM 21032, *Akkermansia muciniphila* ATCC BAA-835, *Dialister succinatiphilus* DSM 21274, *Bacteroides stercoris* ATCC 43183, *Clostridium symbiosum* ATCC 14940, *Marvinbryantia formatexigens* DSM 14469, *Subdoligranulum variabile* DSM 15176 | *Blautia hydrogenotrophica* DSM 10507 |
| L-Asparagine | *Blautia producta* DSM 2950, *Acidaminococcus intestini* DSM 21505, *Megamonas hypermegale* DSM 1672, *Faecalibacterium prausnitzii* DSM 17677, *Clostridium bolteae* ATCC BAA-613, *Anaerostipes caccae* DSM 14662, *Bacteroides massiliensis* DSM 17679, *Anaerostipes hadrus* DSM 3319, *Megamonas funiformis* DSM 19343, *Dialister succinatiphilus* DSM 21274, *Akkermansia muciniphila* ATCC BAA-835, *Bacteroides stercoris* ATCC 43183, *Clostridium symbiosum* ATCC 14940, *Clostridium scindens* ATCC 35704, *Marvinbryantia formatexigens* DSM 14469, *Subdoligranulum variabile* DSM 15176 | *Barnesiella intestinihominis* DSM 21032 |
| L-Alanine | *Faecalibacterium prausnitzii* DSM 17677, *Megamonas hypermegale* DSM 1672, *Anaerostipes hadrus* DSM 3319, *Blautia producta* DSM 2950, *Acidaminococcus intestini* DSM 21505, *Marvinbryantia formatexigens* DSM 14469, *Subdoligranulum variabile* DSM 15176, *Bacteroides massiliensis* DSM 17679, *Barnesiella intestinihominis* DSM 21032, *Bacteroides stercoris* ATCC 43183, *Akkermansia muciniphila* ATCC BAA-835, *Anaerostipes caccae* DSM 14662, *Clostridium bolteae* ATCC BAA-613 | *Dialister succinatiphilus* DSM 21274, *Blautia hydrogenotrophica* DSM 10507 |
| Heme | *Anaerostipes hadrus* DSM 3319, *Megamonas funiformis* DSM 19343, *Clostridium scindens* ATCC 35704, *Barnesiella intestinihominis* DSM 21032, *Dialister succinatiphilus* DSM 21274, *Akkermansia muciniphila* ATCC BAA-835, *Bacteroides stercoris* ATCC 43183, *Clostridium symbiosum* ATCC 14940, *Marvinbryantia formatexigens* DSM 14469, *Subdoligranulum variabile* DSM 15176, *Blautia producta* DSM 2950, *Acidaminococcus intestini* DSM 21505, *Faecalibacterium prausnitzii* DSM 17677, *Megamonas hypermegale* DSM 1672, *Bacteroides massiliensis* DSM 17679, *Anaerostipes caccae* DSM 14662, *Clostridium bolteae* ATCC BAA-613 | *Blautia hydrogenotrophica* DSM 10507 |

TABLE 6-continued

Nutrients exchanged between at least two species in the GUT-103 consortium as predicted by the 18 species GUT-103 consortium model.

| Compound | Consuming species | Generating species |
| --- | --- | --- |
| L-Cysteine | Blautia producta DSM 2950, Acidaminococcus intestini DSM 21505, Faecalibacterium prausnitzii DSM 17677, Megamonas hypermegale DSM 1672, Bacteroides massiliensis DSM 17679, Anaerostipes caccae DSM 14662, Clostridium bolteae ATCC BAA-613, Anaerostipes hadrus DSM 3319, Megamonas funiformis DSM 19343, Clostridium scindens ATCC 35704, Clostridium symbiosum ATCC 14940, Bacteroides stercoris ATCC 43183, Akkermansia muciniphila ATCC BAA-835, Dialister succinatiphilus DSM 21274, Subdoligranulum variabile DSM 15176, Marvinbryantia formatexigens DSM 14469 | Barnesiella intestinihominis DSM 21032, Blautia hydrogenotrophica DSM 10507 |
| Niacin | Anaerostipes caccae DSM 14662, Clostridium bolteae ATCC BAA-613, Clostridium symbiosum ATCC 14940, Dialister succinatiphilus DSM 21274, Marvinbryantia formatexigens DSM 14469, Blautia hydrogenotrophica DSM 10507, Blautia producta DSM 2950, Acidaminococcus intestini DSM 21505, Anaerostipes hadrus DSM 3319, Megamonas hypermegale DSM 1672, Megamonas funiformis DSM 19343, Faecalibacterium prausnitzii DSM 17677 | Clostridium scindens ATCC 35704, Bacteroides massiliensis DSM 17679, Barnesiella intestinihominis DSM 21032, Bacteroides stercoris ATCC 43183, Akkermansia muciniphila ATCC BAA-835, Subdoligranulum variabile DSM 15176 |
| L-Glutamine | Megamonas funiformis DSM 19343, Faecalibacterium prausnitzii DSM 17677, Megamonas hypermegale DSM 1672, Anaerostipes hadrus DSM 3319, Acidaminococcus intestini DSM 21505, Blautia producta DSM 2950, Blautia hydrogenotrophica DSM 10507, Marvinbryantia formatexigens DSM 14469, Subdoligranulum variabile DSM 15176, Anaerostipes caccae DSM 14662, Bacteroides stercoris ATCC 43183, Dialister succinatiphilus DSM 21274, Akkermansia muciniphila ATCC BAA-835 | Barnesiella intestinihominis DSM 21032 |
| L-Threonine | Faecalibacterium prausnitzii DSM 17677, Megamonas hypermegale DSM 1672, Acidaminococcus intestini DSM 21505, Blautia producta DSM 2950, Bacteroides massiliensis DSM 17679, Anaerostipes caccae DSM 14662, Clostridium bolteae ATCC BAA-613, Megamonas funiformis DSM 19343, Anaerostipes hadrus DSM 3319, Blautia hydrogenotrophica DSM 10507, Marvinbryantia formatexigens DSM 14469, Subdoligranulum variabile DSM 15176, Clostridium scindens ATCC 35704, Clostridium symbiosum ATCC 14940, Dialister succinatiphilus DSM 21274, Akkermansia muciniphila ATCC BAA-835, Bacteroides stercoris ATCC 43183 | Barnesiella intestinihominis DSM 21032 |
| L-Serine | Marvinbryantia formatexigens DSM 14469, Clostridium scindens ATCC 35704, Bacteroides massiliensis DSM 17679, Barnesiella intestinihominis DSM 21032, Bacteroides stercoris ATCC 43183, Anaerostipes caccae DSM 14662, Clostridium bolteae ATCC BAA-613, Clostridium symbiosum ATCC 14940, Faecalibacterium prausnitzii DSM 17677, Megamonas funiformis DSM 19343, Anaerostipes hadrus DSM 3319, Acidaminococcus intestini DSM 21505, Blautia producta DSM 2950 | Blautia hydrogenotrophica DSM 10507 |

TABLE 6-continued

Nutrients exchanged between at least two species in the GUT-103 consortium as predicted by the 18 species GUT-103 consortium model.

| Compound | Consuming species | Generating species |
|---|---|---|
| L-Tyrosine | Akkermansia muciniphila ATCC BAA-835, Dialister succinatiphilus DSM 21274, Bacteroides stercoris ATCC 43183, Clostridium symbiosum ATCC 14940, Clostridium scindens ATCC 35704, Barnesiella intestinihominis DSM 21032, Marvinbryantia formatexigens DSM 14469, Subdoligranulum variabile DSM 15176, Anaerostipes hadrus DSM 3319, Megamonas funiformis DSM 19343, Anaerostipes caccae DSM 14662, Clostridium bolteae ATCC BAA-613, Bacteroides massiliensis DSM 17679, Acidaminococcus intestini DSM 21505, Blautia producta DSM 2950, Megamonas hypermegale DSM 1672, Faecalibacterium prausnitzii DSM 17677 | Blautia hydrogenotrophica DSM 10507 |

Based on the results of Table 6, *Blautia hydrogenotrophica* DSM 10507 has three auxotrophies, and depends for its growth on other members of the GUT-103 consortium for riboflavin, niacin and spermidine. In the case of *Clostridium bolteae* ATCC BAA-613 it should be noted that this strain has a limited number of auxotrophies, and depends for its growth on other members of the GUT-103 consortium for heme. Therefore, at least one but possibly two additional auxotrophies can be introduced in this strain to make sure that this strain will not outcompete the other seventeen members of the GUT-103 consortium (as also described in EXAMPLES 5 and 7). The same can also be considered for *Anaerostipes caccae* DSM 14662 and *Megamonas funiformis* DSM 19343 which also had a single auxotrophy.

Finally, based on in silico modeling, the contribution of *Blautia producta* DSM2950 to provide critical nutrients to the other members of the GUT-103 consortium seems very limited under the conditions set in this simulation for growth on minimal glucose medium, making this strain a candidate to be omitted from the GUT-103 consortium. However, since *Blautia producta* DSM2950 was predicted to produce butyrate it was decided to keep this strain as part of the consortium, despite the finding that flux analysis on the GUT-103 consortium from which *Blautia producta* DSM2950 was omitted, showed that the remaining 17 strains continued to interact as a stable consortium with all exchanges of critical metabolites between consortium members being covered. This exemplifies the principle of functional redundancy as part of the consortium design process, which allows for the consortium to function with minimal functional penalty in case one of its members is omitted or exhibits minimum growth in vivo.

To evaluate the efficacy of the GUT-103 consortium to prevent or treat IBD, a preclinical study was performed using a validated animal model based on ex-germ-free (sterile) IL-10−/− 129SvEv mice where colitis was induced by inoculating the animals with a consortium of three human enteric bacteria as previously described (Sellon et al, 1998; Eun et al, 2014). This consortium of human *Escherichia coli* LF82 (a human Ileal Crohn's disease isolate), *Enterococcus faecalis* OG1RF and *Ruminococus gnavus* ATCC 29149 is referred to as the EER consortium. Inoculation of IL10−/− mice with the EER consortium results after 2 weeks in a chronic, bacterial antigen-specific Th1/Th17 driven inflammatory immune response. Strain *Dialister succinatiphilus* DSM21274 was not included in the GUT-103 consortium, as it was not available. The key functions of strain DSM21274, the synthesis of propionate and ferrichrome, are also provided by other members of the consortium. Furthermore, strain DSM21274 did not appear to provide a unique metabolite to the consortium, thus omitting this strain was expected to have a minimal effect on the performance of the GUT-103 consortium. The design of the experiment is provided below:

1. GUT-103 consortium, comprised of seventeen strains, alone served as a control to confirm the lack of induction of colitis and TH1/17 immune activation by this consortium;
2. Three-strain enteric bacterial consortium comprised of *Escherichia coli* LF82, *Enterococcus faecalis* OG1RF, and *Ruminococcus gnavus* ATCC 29149 (EER consortium). The EER consortium has a known time line for causing disease and served as a positive control;
3. GUT-103 consortium+EER consortium in a prevention protocol. The EER consortium is administered after the GUT-103 consortium has had time to get established, e.g. 48 hours or up to 2 weeks after application of the GUT-103 consortium;
4. GUT-103 consortium+EER consortium in a therapeutic protocol. The GUT-103 consortium was applied 2 weeks after administration of the EER consortium in a therapeutic protocol (delayed therapy after onset of disease).

All GUT-103 consortium strains were grown individually, subsequently mixed, and provided at a dose of $2.0 \times 10^{+7}$ cfu per strain in a total volume of 300 The strain mixture was provided three times via oral gavage on days 1, 3 and 7 to six germ-free IL-10−/− mice. Indices of treatment outcome were blinded histologic scores, weekly lipocalin levels, IL12P40 as a measure for inflammation potential of fecal microbiome, and interferon gamma secretion by mesenteric lymph node cells stimulated by fecal lysates from each group after colonization. RpoB gene-based consortium composition analysis was performed on fecal samples collected after 2, 3 and 4 weeks for all three studies (before introducing the GUT-103 to the mice treated with the EER consortiums in treatment 3) and at the end of each study.

Analysis of Establishment of GUT-103 in the IL-10−/− Mice Model

In a first experiment, the ability of the GUT-103 consortium (the seventeen strains in Table 4 omitting *Dialister*

*succinatiphilus* DSM21274) to become established in the intestinal tract of the germ-free IL-10–/– mice was determined. One week after the last application of the GUT-103 consortium, stool samples from six individual mice were collected, the DNA of the gut microbiome was extracted, and the establishment of the individual strains was determined as the percentage of the total consortium composition using quantitative PCR with strain specific primers designed on the rpoB gene. The results of this analysis are presented in Table 7.

tium. The first consortium subset of strains is comprised of *Bacteroides massiliensis* DSM17679, *Blautia producta* DSM2950, and *Akkermansia muciniphila* ATCC BAA-835 (referred to as GUT-103 consortium subset 1). These three bacteria form a stable network that can break down complex food polymers (DSM17679) and mucus (ATCC BAA-835), and provides synthesis of butyrate, propionate and indole, each of which have a key role in interacting with the host to reduce the inflammatory pathology, such as that associated with IBD. In addition, the three strains can complement each

TABLE 7

Composition of the gut microbiome of IL-10–/– mice as determined one week after the last oral gavage with the seventeen strain GUT-103 consortium. The percentage of each strain was determined by quantitative PCR using strain specific primers on the rpoB gene. The data represent the average consortium composition. The comment section describes the key functions that each of the established strains provide to the consortium.

| Species | Strain | Percentage in consortium after last gavage | Comment |
|---|---|---|---|
| *Megamonas hypermegale* | ATCC 25560 | 0.00% | |
| *Bacteroides stercoris* | ATCC 43183 | 0.00% | |
| *Anaerostipes hadrus* | ATCC 29173 | 0.02% | |
| *Clostridium symbiosum* | ATCC 14940 | 1.54% | Bile acid conversion: 3-α-HSD, 7-α-HSD |
| *Clostridium bolteae* | ATCC BAA-613 | 0.79% | Bile acid conversion: 3-α-HSD, 7-α-HSD; bacteriocin; siderophore synthesis |
| *Blautia producta* | ATCC 27340/ DSM2950 | 37.46% | Principal engine for secondary metabolite synthesis: butyrate; heterologous siderophore uptake, incl. ferrichrome |
| *Clostridium scindens* | ATCC 35704 | 1.09% | Bile acid conversion: 7-α-DH; bacteriocin |
| *Akkermansia muciniphila* | ATCC BAA-835 | 36.66% | Principal engine for secondary metabolite synthesis: propionate, indole; heterologous siderophore uptake |
| *Megamonas funiformis* | DSM19343 | 0.60% | Secondary metabolite synthesis: propionate; heterologous siderophore uptake, incl. ferrichrome and enterobactin |
| *Acidaminococcus intestini* | DSM21505 | 0.00% | |
| *Bacteroides massiliensis* | DSM17679 | 21.17% | Principal engine for secondary metabolite synthesis: propionate; conversion of complex carbon and nitrogen containing food polymers; heterologous siderophore uptake |
| *Barnesiella intestinihominis* | DSM21032 | 0.00% | |
| *Faecalibacterium prausnitzii* | DSM17677 | 0.00% | |
| *Subdoligranulum variabile* | DSM15176 | 0.23% | Secondary metabolite synthesis: butyrate; bacteriocin |
| *Anaerostipes caccae* | DSM14662 | 0.25% | Bile acid conversion: 7-α-DH, 7-α-HSD; bacteriocin; heterologous siderophore uptake, incl. ferrichrome, and yersiniabactin synthesis |
| *Blautia hydrogenotrophica* | DSM10507 | 0.00% | |
| *Marvinbryantia formatexigens* | DSM14469 | 0.00% | |

Based on the data from Table 7, it is noted that the consortium that became established covers all of the key functions that were determined upfront as being underrepresented or missing from the dysbiotic gut microbiome in IBD patients and as essential for maintenance of a healthy gut microbiome, i.e., synthesis of butyrate, synthesis of propionate, synthesis of indole, deconjugation of bile salt and conversion of bile acid into secondary bile acids, synthesis of at least one bacteriocin, synthesis of a siderophore, uptake of a heterologously produced siderophore, and breakdown of complex carbohydrates and proteins. This is despite that fact that several members of the GUT-103 consortium did not become established at detectable levels, confirming the importance of functional redundancy as part of the design process. More detailed analysis reveals that two subsets of strains can be identified in the consortium that became established after gavage with the GUT-103 consorothers auxotrophies, thus creating a stable network of interdependent strains that forms the driver of the engrafted consortium two weeks after the initial gavage. For example, both *Bacteroides massiliensis* DSM17679 and *Akkermansia muciniphila* ATCC BAA-835 are auxotrophic for spermidine (see also Table 5), and this essential nutrient is provided by *Blautia producta* DSM2950. Details of the roles and metabolic interdependencies between *Bacteroides massiliensis* DSM17679, *Blautia producta* DSM2950, and *Akkermansia muciniphila* ATCC BAA-835 are described in FIG. 5.

The GUT-103 consortium subset 1 can be used for other applications beyond IBD, such as treatment of diabetes or oncology therapies that require the establishment of strains to cover missing functionalities such as indole, butyrate and propionate synthesis, or in the case of *Akkermansia muciniphila*, produce LPS with immunestimulatory properties (see EXAMPLE 10).

The second subset of strains is comprised of *Clostridium symbiosum* ATCC 14940, *Clostridium bolteae* ATCC BAA-613, and *Clostridium scindens* ATCC 35704, and with lower representation of *Subdoligranulum variabile* DSM15176 and *Anaerostipes caccae* DSM14662 (referred to as GUT-103 consortium subset 2). Consortium subset 2 covers the conversion of bile salts in secondary bile acids and steroids, and also contributes to the management of ferric iron via the synthesis of siderophores and the uptake of several heterologously produced siderophores, including a putative yersiniabactin siderophore insensitive to inhibition by Lipocalin-2 (*Anaerostipes caccae* DSM14662). GUT-103 consortium subset 2 is metabolically supported by the GUT-103 consortium subset 1. The complete set of strains that were found to have become engrafted in the gut microbiome of the IL-10–/– mice are referred to as GUT-103 consortium subset 1+GUT-103 consortium subset 2.

*Megamonas funiformis* DSM19343, which was found to have asparagine as a single auxotrophy, also became established at low level. This strain is most likely benefiting from the asparagine flux between *Blautia producta* DSM2950 and *Akkermansia muciniphila* ATCC BAA-835, and could be an opportunistic colonizer. However, this strain is capable of acquiring several heterologous siderophores, including enterobactin and ferrichrome. *Megamonas hypermegale* ATCC 25560, *Bacteroides stercoris* ATCC 43183, *Anaerostipes hadrus* ATCC29173, *Acidaminococcus intestini* DSM21505, *Barnesiella intestinihominis* DSM21032, *Faecalibacterium prausnitzii* DSM17677, *Blautia hydrogenotrophica* DSM10507 and *Marvinbryantia formatexigens* DSM14469 did not become established at significant levels under the conditions of the IL-10–/– mouse model. However, the low abundance of these strains did not seem to affect the performance of the established consortium, which covered the key functionalities identified as missing or underrepresented in the gut microbiome of IBD patients.

In another experiment to evaluate establishment in the mice gut, the GUT-103 consortium was inadvertently contaminated with *Enterococcus faecalis* OG1RF and *Ruminococcus gnavus* ATCC 29149. The results are shown in Table 8 below. Surprisingly, the results showed that in addition to the establishment of the GUT-103 consortium subset 1 as described above, the strain *Bacteroides stercoris* ATCC43183 also became established as a dominant member. From the point of metabolic interdependencies, this strain has the same auxotrophies as the closely related strain *Bacteroides massiliensis* DSM17679, which is part of GUT-103 consortium subset 1. Strain ATCC43183 provides additional indole synthesis and the uptake of heterologous siderophores, incl. enterobactin, to the consortium. Thus, the GUT-103 consortium subset 1 can be extended with *Bacteroides stercoris* ATCC 43183. In addition to *Bacteroides stercoris* ATCC 43183 becoming established, several additional strains also became established at more elevated percentages as shown below in Table 8. The most significant decrease was observed for *Blautia producta* ATCC 27340/DSM2950. However, the loss of butyrate synthesis associated with the decrease of *Blautia producta* ATCC 27340/DSM2950 was compensated by the increase of other butyrate synthesizing strains, such as *Subdoligranulum variabile* DSM15176. Based on the data, GUT-103 consortium subset 2 can be extended to include *Megamonas funiformis* DSM19343.

These data show the preservation of functionality due to the functional redundancy of the strains in the GUT-103 consortium.

TABLE 8

Composition of the gut microbiome of IL-10–/– mice as determined one week after the last oral gavage with the seventeen strain GUT-103 consortium and the GUT-103 consortium contaminated with *Enterococcus faecalis* OG1RF and *Ruminococcus gnavus* ATCC 29149 (referred to as GUT-103 + ER). The percentage of each strain was determined by quantitative PCR using strain specific primers on the rpoB gene. The data represent the average consortium composition.

| Strain | GUT-103 | GUT-103 + ER |
|---|---|---|
| *Megamonas hypermegale* ATCC 25560 | 0.00% | 0.00% |
| *Bacteroides stercoris* ATCC 43183 | 0.00% | 7.81% |
| *Anaerostipes hadrus* ATCC 29173 | 0.02% | 0.26% |
| *Clostridium symbiosum* ATCC 14940 | 1.54% | 0.68% |
| *Clostridium boltea* ATCC BAA-613 | 0.79% | 2.25% |
| *Blautia producta* ATCC 27340/DSM2950 | 37.46% | 15.36% |
| *Clostridium scindens* ATCC 35704 | 1.09% | 4.07% |
| *Akkermansia muciniphila* ATCC BAA-835 | 36.66% | 27.66% |
| *Megamonas funiformis* DSM19343 | 0.60% | 2.68% |
| *Acidaminococcus intestini* DSM21505 | 0.00% | 0.58% |
| *Bacteroides massiliensis* DSM17679 | 21.17% | 15.53% |
| *Barnesiella intestinihominis* DSM21032 | 0.00% | 3.30% |
| *Faecalibacterium prausnitzii* DSM17677 | 0.00% | 0.00% |
| *Subdoligranulum variabile* DSM15176 | 0.23% | 5.19% |
| *Anaerostipes caccae* DSM14662 | 0.25% | 0.24% |
| *Blautia hydrogenotrophica* DSM10507 | 0.00% | 0.00% |
| *Marvinbryantia formatexigens* DSM14469 | 0.00% | 0.00% |
| *Enterococcus faecalis* OG1RF | N.A. | 10.78% |
| *Ruminococcus gnavus* ATCC 29149 | N.A. | 3.60% |

Analysis of the Therapeutic Effect of GUT-103 in the IL-10–/– Mice IBD Model

The ability of the GUT-103 consortium (the seventeen strains in Table 4) to therapeutically treat chronic, immune-mediated experimental colitis as a model of IBD was determined by comparing the level of inflammation in ex-germ-free IL-10–/– mice selectively colonized with GUT-103 (negative control for experimental colitis), EER (positive control for the onset of colitis), and EER plus GUT-103 (therapeutic protocol with GUT-103 being applied 2 weeks after the onset of colitis induced by EER application) as described herein above. The results are described below.

Evaluation of Microbiome Composition

The establishment of the EER strains, the GUT-103 consortium, and the EER strains plus GUT-103 consortium (therapeutic protocol) as part of the gut microbiome was evaluated on a weekly basis using quantitative PCR with strain specific primers designed on the rpoB gene as described above. The results of this analysis are presented in Table 9.

Based on the data from Table 9 it can be concluded that the application of GUT-103 to germ free strain 129 IL10–/– knockout mice resulted within 7 days after the last gavage in the establishment of a stable consortium that was dominated by *Bacteroides massiliensis* DSM17679, *Blautia producta* DSM2950, and *Akkermansia muciniphila* ATCC BAA-835, together referred to as the GUT-103 consortium subset 1. Overall, the composition of the established GUT-103 consortium, including the presence of the GUT-103 consortium subset 1 and subset 2, did not show significant differences between days 14, 21 and 28. Application of the EER consortium strains to germ free strain 129 IL10–/– knockout mice resulted within 7 days after the last gavage in the establishment of a stable consortium that included all tree strains: *Escherichia coli* LF82, *Enterococcus faecalis*

OG1RF, and *Ruminococcus gnavus* ATCC 29149. It was noticed that 28 days after the first gavage, the relative proportion of *Escherichia coli* LF82 started to decrease.

Application of the GUT-103 consortium as three gavages on days 15, 17 and 21 to EER colonized IL10−/− knockout mice resulted on day 21 in the establishment of the GUT-103 consortium at the expense of the EER consortium strains. One week after the start of the GUT-103 gavages, as determined on day 21, the total percentage of the EER consortium had dropped from 100% before gavage with GUT-103 to 31.3%; it decreased further to 16.8% on day 28. This result shows that the GUT-103 consortium is capable of replacing an established consortium of inflammation-inducing strains. In addition, the composition of the GUT-103 consortium that becomes established in the EER colonized strain 129 IL10−/− knockout mice strongly resembles that of the GUT-103 consortium that becomes established in the germ-free strain IL10−/− knockout mice, including the presence of both the consortium GUT-103 subset 1 and subset 2. These results demonstrate the resilience of the rationally designed GUT-103 consortium to become stably engrafted even when administered after establishment of pathogenic organisms.

Similar results for the establishment of the EER strains, the GUT-103 consortium, and the EER strains plus GUT-103 consortium (therapeutic protocol) were obtained when this experiment was performed in strain 129 germ free wild type mice, which do not develop colitis, further confirming the capability of the rationally designed GUT-103 consortium to become stably engrafted under a range of conditions, with and without experimental colitis (data not shown).

TABLE 9

Composition of the gut microbiome of strain 129 IL-10−/− knockout mice as determined 14, 21 and 28 days after the start of the experiment to determine the therapeutic effect of the GUT-103 consortium to treat experimental colitis in the model where the EER consortium is used to induce chronic, T cell mediated inflammation of the colon. On day 1, eight mice were inoculated via oral gavage with the GUT-103 consortium (GUT-103 protocol) and sixteen mice were inoculated via oral gavage with the EER consortium (EER protocol) as described above. The gavage procedure was repeated on day 3 and day 7. After 2 weeks from the start of the experiment, the average community composition was determined for both conditions. Subsequently, half of the EER treated mice received three gavages (on day 15, 17 and 21) with the GUT-103 consortium; this treatment is referred to as the EER + GUT-103 therapeutic protocol. The percentage of each strain was determined by quantitative PCR using strain specific primers recognizing the rpoB gene. The data represent the average consortium composition.

| | GUT-103 protocol | | | EER protocol | | | EER + GUT-103 therapeutic protocol | | |
|---|---|---|---|---|---|---|---|---|---|
| | % Average Consortium Composition | | | | | | | | |
| GUT103 and EER strains | Day 14 | Day 21 | Day 28 | Day 14* | Day 21 | Day 28 | Day 14* | Day 21 | Day 28 |
| *Megamonas hypermegale* ATCC 25560 | 0.00% | 0.00% | 0.01% | N.A. | N.A. | N.A. | N.A. | 0.03% | 0.00% |
| *Bacteroides stercoris* ATCC 43183 | 9.34% | 3.30% | 5.73% | N.A. | N.A. | N.A. | N.A. | 1.18% | 2.89% |
| *Anaerostipes hadrus* ATCC 29173 | 0.33% | 2.13% | 0.89% | N.A. | N.A. | N.A. | N.A. | 0.00% | 0.00% |
| *Clostridium symbiosum* ATCC 14940 | 0.81% | 1.11% | 1.08% | N.A. | N.A. | N.A. | N.A. | 0.60% | 0.80% |
| *Clostridium boltea* ATCC BAA-613 | 2.71% | 3.04% | 2.71% | N.A. | N.A. | N.A. | N.A. | 1.10% | 1.69% |
| *Blautia producta* ATCC 27340 | 18.50% | 21.67% | 17.38% | N.A. | N.A. | N.A. | N.A. | 14.15% | 13.33% |
| *Clostridium scindens* ATCC 35704 | 4.89% | 5.26% | 4.50% | N.A. | N.A. | N.A. | N.A. | 3.37% | 3.12% |
| *Akkermansia muciniphila* ATCC BAA-835 | 33.03% | 38.49% | 31.38% | N.A. | N.A. | N.A. | N.A. | 28.54% | 28.33% |
| *Megamonas funiformis* DSM19343 | 1.22% | 2.45% | 3.72% | N.A. | N.A. | N.A. | N.A. | 0.35% | 1.48% |
| *Acidaminococcus intestini* DSM21505 | 0.21% | 0.25% | 0.53% | N.A. | N.A. | N.A. | N.A. | 0.49% | 0.37% |
| *Bacteroides massiliensis* DSM17679 | 18.57% | 15.57% | 25.80% | N.A. | N.A. | N.A. | N.A. | 12.71% | 21.67% |
| *Barnesiella intestinihominis* DSM21032 | 3.91% | 1.68% | 4.12% | N.A. | N.A. | N.A. | N.A. | 2.53% | 4.62% |
| *Faecalibacterium prausnitzii* DSM17677 | 0.00% | 0.00% | 0.00% | N.A. | N.A. | N.A. | N.A. | 0.00% | 0.00% |
| *Subdoligranulum variabile* DSM15176 | 6.19% | 4.79% | 1.73% | N.A. | N.A. | N.A. | N.A. | 3.37% | 4.54% |
| *Anaerostipes caccae* DSM14662 | 0.29% | 0.27% | 0.41% | N.A. | N.A. | N.A. | N.A. | 0.30% | 0.38% |
| *Blautia hydrogenotrophia* DSM10507 | 0.00% | 0.00% | 0.00% | N.A. | N.A. | N.A. | N.A. | 0.00% | 0.00% |
| *Marvinbryantia formatexigens* DSM14469 | 0.00% | 0.00% | 0.01% | N.A. | N.A. | N.A. | N.A. | 0.00% | 0.00% |

TABLE 9-continued

Composition of the gut microbiome of strain 129 IL-10−/− knockout mice as determined 14, 21 and 28 days after the start of the experiment to determine the therapeutic effect of the GUT-103 consortium to treat experimental colitis in the model where the EER consortium is used to induce chronic, T cell mediated inflammation of the colon. On day 1, eight mice were inoculated via oral gavage with the GUT-103 consortium (GUT-103 protocol) and sixteen mice were inoculated via oral gavage with the EER consortium (EER protocol) as described above. The gavage procedure was repeated on day 3 and day 7. After 2 weeks from the start of the experiment, the average community composition was determined for both conditions. Subsequently, half of the EER treated mice received three gavages (on day 15, 17 and 21) with the GUT-103 consortium; this treatment is referred to as the EER + GUT-103 therapeutic protocol. The percentage of each strain was determined by quantitative PCR using strain specific primers recognizing the rpoB gene. The data represent the average consortium composition.

| GUT103 and EER strains | GUT-103 protocol | | | EER protocol | | | EER + GUT-103 therapeutic protocol | | |
| --- | --- | --- | --- | --- | --- | --- | --- | --- | --- |
| | Day 14 | Day 21 | Day 28 | Day 14* | Day 21 | Day 28 | Day 14* | Day 21 | Day 28 |
| *Escherichia coli* LF82 | N.A. | N.A. | N.A. | 37.62% | 43.37% | 11.55% | 37.62% | 9.67% | 1.75% |
| *Enterococcus faecalis* OG1RF | N.A. | N.A. | N.A. | 32.09% | 28.23% | 46.04% | 32.09% | 18.40% | 9.01% |
| *Ruminococcus gnavus* ATCC 29149 | N.A. | N.A. | N.A. | 30.29% | 28.40% | 42.41% | 30.29% | 3.22% | 6.02% |
| Total | 100.00 | 100.00 | 100.00 | 100.00 | 100.00 | 100.00 | 100.00 | 100.00 | 100.00 |

N.A. indicates that the strain was not applied and not detected by quantitative PCR.
The *indicates that the same data were used.

Evaluation of Inflammatory Parameters

The progression of the level of lipocalin 2 secreted in the stool of selectively colonized gnotobiotic 129 IL10−/− knock-out mice was evaluated in function of time after gavage of the IL10−/− knockout mice with the GUT-103 consortium, the EER consortium, and the EER plus GUT-103 consortia in the therapeutic protocol (2 week delay in administering GUT-103). Lipocalin 2 is a rapid indicator for distal intestinal inflammation; the higher the levels of lipocalin in the stool, the more severe the degree of gut inflammation. The results are presented in FIGS. 6A-6D. For all treatments, an increase of lipocalin 2 levels in the stool samples was observed 2 weeks after the first gavage due to an immunological reaction caused by the introduction of bacteria in the gut of IL10−/− knock-out mice that were previously germ free (compare FIGS. 6A and 6B). After four weeks (see FIG. 6D), the average lipocalin 2 levels in the stool of IL10−/− knock-out mice treated with GUT-103, EER, and EER plus GUT-103 were 4.2 ng/g, 579.2 ng/g and 78.9 ng/g, respectively. This indicates that the application of GUT-103 two weeks after the initial gavage with EER resulted in a reversal of the level of colonic inflammation, showing the therapeutic effect of the GUT-103 consortium to treat chronic experimental colitis.

In addition to the levels of Lipocalin 2, the in vivo synthesis of IFNγ by $T_H1$ cells in cecal tissue from gnotobiotic strain 129 IL10−/− knock-out mice inoculated with the GUT-103 consortium, the EER consortium, and the EER plus GUT-103 consortia in the therapeutic protocol was determined as previously described (Sellon et al, 1998). The level of IFNγ spontaneous secretion is a very good indicator of the level of immune activation and inflammation of the colonic tissue. In summary, cultures of colon fragments were prepared and cultured in 1 ml of complete medium containing antibiotics and an antimycotic agent. The cultures were incubated at 37° for 18 h with no stimulation. Culture supernatants were collected and stored at −20° C. until being assayed. IFNγ was measured by enzyme-linked immunosorbent assay (ELISA) with a commercially available antibody, similar to the IL12P40 assay described by Sellon et al (1998). The results of this test are presented in FIG. 7 and show that inoculation of germ free strain 129 IL10−/− knock-out mice with the EER consortium results in statistically significantly higher levels of IFNγ synthesis (430 pg/ml IFNγ) compared to IL10−/− mice inoculated with GUT-103 (80 pg/ml IFNγ). This result further confirms that inoculation of germ free strain 129 IL10−/− knock-out mice with the EER consortium results in immune-modulated chronic inflammation, while inoculation with the GUT-103 consortium does not result in an inflammatory response. Application of the GUT-103 consortium to strain 129 IL10−/− knock-out mice that have an established EER community and resulting inflammation in their gut results in a statistically significant decrease in IFNγ synthesis (mean 150 pg/ml IFNγ, compared to 430 pg/ml IFNγ). These results further confirm the therapeutic effect of the GUT-103 consortium to treat chronic, immune-modulated ulcerative colitis.

The degree of colitis was further examined by histological scoring (Sellon et al, 1998). Mice were killed four weeks after initial gavage. At necropsy, sections of colon (proximal, transverse, and distal) and cecum were fixed in 10% neutral buffered formalin. Duodenal and gastric tissue samples were taken from representative animals. The fixed tissue was embedded in paraffin and stained with H&E. The severity of inflammation was assessed blindly by a single individual and confirmed by an independent observer using a well-validated scale. Histological scores (0 to 4) were based on the degree of lamina propria and submucosal mononuclear cellular infiltration, crypt hyperplasia, goblet cell depletion, and architectural distortion. The mean (±standard deviation) histological scores for 129 IL10−/− knock-out mice treated with GUT-103, EER, and EER plus GUT-103 were 0.9±0.65, 3.5±1.4 and 2.167±0.91, respectively. This further confirms that the application of GUT-103 two weeks after the initial gavage with EER resulted in a reversal of established inflammation, showing the therapeutic effect of the GUT-103 consortium to treat experimental colitis.

Example 9

Rational Design of a Microbiome-Based Therapeutic for the Treatment of Type-2 Diabetes Using the strategy outlined in the combination of EXAMPLES 1 to 7, a microbial therapeutic consortium was rationally designed by providing key functionalities that are lacking or underrepresented in the dysbiotic gut microbiome of patients developing or suffering from Type-2 diabetes. The following functionalities have been found to be underrepresented or absent from the gut microbiome of patients suffering from (the onset of) Type-2 diabetes, allowing for the rational design of a biotherapeutic:

Scfa Synthesis:

Decreases in butyrate-producing organisms were observed in patients with type-2 diabetes (Qin et al, 2012), a disease which is characterized by low-grade inflammation. To address this, *Blautia producta* DSM2950 and *Akkermansia muciniphila* ATCC BAA-835 (which produces the SCFA propionate) were included (see Example 8).

Indole Synthesis:

Indole plays a key role in modulating the barrier integrity of the intestinal epithelial layer, by this process having a beneficial effect on chronic inflammation, which has also been implemented in the obesity-diabetes association (Luft et al, 2013). Indole is also recognized by the human AHR receptor (Hubbard et al, 2015a), which results in AHR dependent activation and transcription of target genes, including the anti-inflammatory interleukin-22 (IL22) (Hubbard et al, 2015b). To address this, *Akkermansia muciniphila* ATCC BAA-835 was included.

Bile Acid Conversion:

Bile acid levels and distribution are altered in type-2 diabetes and increased following bariatric procedures, in parallel with reduced body weight and improved insulin sensitivity and glycemic control (Ma and Patti, 2014). GUT-103 consortium subset 2 consisting of *Clostridium symbiosum* ATCC 14940, *Clostridium bolteae* ATCC BAA-613, *Clostridium scindens* ATCC 35704, *Subdoligranulum variabile* DSM15176, and *Anaerostipes caccae* DSM14662 (see Example 8), identified as responsible for the conversion of bile salts in secondary bile acids and steroids, was included to provide this function.

Synthesis of endocrine molecules from endogenous and exogenous steroids, including conversion of the dietary lignan secoisolariciresinol diglucoside (SDG) into enterolactone, an antidiabetic chemical. Key is to include secoisolariciresinol diglucoside as a prebiotic/symbiotic in the diet (Zhou et al, 2017). Conversion of SDG into enterolactone follows a four-step process described by Clavel et al (2006, 2007), where each step seems to depend on different microorgansims. Based on this work, strains *Clostridium saccharogumia* DSM17460, *Clostridium ramosum* DSM1402, *Blautia producta* DSM2950 (instead of DSM3507, whose genome sequence is not available), *Clostridium scindens* ATCC35704 (DSM5676) and *Lactonifactor longoviformis* DSM17459, which provide the key functionalities to convert secoisolariciresinol diglucoside into enterolactone, were included in the GUT-104 consortium. In order for the GUT-104 consortium to be effective, it can be administered in combination with a diet rich in the plant lignan secoisolariciresinol diglucoside. Alternatively, secoisolariciresinol diglucoside can be administered as a prebiotic/symbiotic in the diet (Zhou et al, 2017).

By following a similar strategy as described in EXAMPLE 8, a consortium consisting of 13 strains was designed to provide a therapeutic intervention at the early onset or during the progression of Type-2 diabetes. The two strains, *Clostridium bolteae* ATCC BAA-613, *Blautia hydrogenotrophica* DSM 10507, in addition to providing key functionalities underrepresented in diabetes, were also included in the consortium for their ability to provide nutrients to other members of the GUT-104 consortium. This consortium, referred to as GUT-104, is described in TABLE 10. The design process purposely introduced redundancies in functionalities, this to increase the chances of establishment of the consortium or a subset of strains thereof under a broad range of conditions, thus addressing different degrees of gut microbiome dysbiosis.

TABLE 10

Key functionalities tor the members of a thirteen-strain rationally designed consortium for treatment of Type-2 diabetes.

| Strain | | | | Key Underrepresented Functionalities in Diabetes | | | | |
|---|---|---|---|---|---|---|---|---|
| Species | Family | Butyrate | Propionate | Indole | Siderophore | Bile Salt | Anti-microbial | SDG conversion |
| *Clostridium saccharoguma* DSM17460 | Erysipelotrichace | | | | | | | O-deglycosylation |
| *Clostridium ramosum* DSM1402 | Erysipelotrichace | | | | | | | O-deglycosylation |
| *Blautia producta* DSM2950 | Lachnospiraceae | + | | | Heterologous, incl. Ferrichrome uptake | | | O-demethylation |
| *Clostridium scindens* ATCC35704 (DSM5676) | Lachnospiraceae | | | | | 7-α-DH | Bacteriocin | Dehydroxylation |
| *Lactonifactor longoviformis* DSM17459 | Lachnospiraceae | | | | | | Bacteriocin | Dehydrogenation |
| *Anaerostipes caccae* DSM14662 | Lachnospiraceae | + | | | Heterologous, incl. Ferrichrome uptake; Yersiniabactin synthesis | 7-α-DH, 7-α-HSD | Bacteriocin | |
| *Anaerostipes hadrus* DSM 3319/ATCC 29173 | Lachnospiraceae | + | | + | | | | |
| *Clostridium symbiosum* ATCC14940 | Lachnospiraceae | + | | | | 3-α-HSD 7-a-HSD | | |
| *Clostridium bolteae* ATCC BAA-613* | Lachnospiraceae | | | | Siderophore synthesis | 3-α-HSD 7-α-HSD | Bacteriocin | |
| *Blautia hydrogenotrphia* DSM 10507* | Lachnospiraceae | | | | | 7-α-DH, 3-β-HSD | Bacteriocin | |

TABLE 10-continued

Key functionalities for the members of a thirteen-strain rationally designed consortium for treatment of Type-2 diabetes.

| Strain | | | | Key Underrepresented Functionalities in Diabetes | | | | |
|---|---|---|---|---|---|---|---|---|
| Species | Family | Butyrate | Propionate | Indole | Siderophore | Bile Salt | Anti-microbial | SDG conversion |
| *Faecalibacterim prausnitzii* DSM17677 | Ruminococcaceae | + | | | Heterologous uptake | | Bacteriocin | |
| *Subdoligranulm variabile* DSM15176 | Ruminococcaceae | + | | | | | Bacteriocin | |
| *Akkermansia muciniphila* ATCC BAA-835 | Akkermansiaceae | | + | + | Heterologous uptake | | | |

Abbreviations: 7-α-DH: 7-alpha-dehydratase/dehydroxylase activity; 3-α-HSD: 3-alpha-hydroxysteroid dehydrogenase activity; 7-α-HSD: 7-alpha-hydroxysteroid dehydrogenase activity; 3-β-HSD: 3-beta-hydroxysteroid dehydrogenase activity.
*indicates strains that were added to provide redundancy for key functionalites and additional metabolic support.

As part of the process to build the GUT-104 consortium model, computational models were first built for the individual GUT-104 strains (as described in EXAMPLE 4). All strain models required some degree of gap filling to ensure that they are capable of synthesizing or acquiring all the small molecule building blocks required to produce new biomass. This gap filling was performed in silico mimicking a specific growth condition; it is preferable to perform gap filling mimicking minimal medium composition. The initial gap filling was therefore performed in glucose minimal medium. The GUT-104 strains, and their most closely related reference strains, were experimentally confirmed to grow in rich medium, as no defined minimal medium is known for any of the strains. Thus, an auxotrophy analysis was performed to predict defined minimal media for each of the GUT-104 strains. In this analysis, the synthesis pathways for all amino acids, vitamins, and cofactors were computationally assigned and subsequently, as part of a quality control process, manually reviewed in a model-driven fashion to determine which pathways were likely incomplete for each genome. The output of this analysis revealed very substantial differences in auxotrophy across all of the GUT-104 strains (See Table 11).

TABLE 11

Predicted auxotrophies for members of a synthetic consortium comprised of the 13 strain GUT-104 consortium.
The following strains, referred to by their strain number, are part of GUT-104:
*Clostridium saccharogumia* DSM17460, *Clostridium ramosum* DSM1402,
*Blautia producta* DSM2950, *Clostridium scindens* ATCC35704 (DSM5676),
*Lactonifactor longoviformis* DSM17459, *Anaerostipes caccae* DSM14662,
*Anaerostipes hadrus* DSM3319/ATCC29173, *Clostridium symbiosum* ATCC14940,
*Clostridium bolteae* ATCC BAA-613, *Blautia hydrogenotrophica* DSM10507, *Faecalibacterium prausnitzii*
DSM17677, *Subdoligranulum variabile* DSM15176, and *Akkermansia muciniphila* ATCC BAA-835.

| | DSM17677 | DSM15176 | DSM14662 | DMS3319 | ATCC 14940 | ATCC BAA-613 | DSM2950 |
|---|---|---|---|---|---|---|---|
| Spermidine | | | A | A | | | |
| Arginine | | | | | | | |
| Proline | | | | | | | |
| Glycine | | | | | | | |
| Serine | A | | | | A | | |
| Threonine | | | | | | | |
| Alanine | | | | | | | |
| Aspartate | | | | | | | |
| Asparagine | | | | | | | |
| Glutamate | | | | | | | |
| Tryptophan | A | A | | | | | |
| Tyrosine | | | | | | | |
| Phenylalanine | | | | | | | |
| Valine | | | | | | | |
| Isoleucine | | | | | | | |
| Leucine | | | | | | | |
| Histidine | | | | | A | | |
| Lysine | | | | | | | |
| Cysteine | | | | | | | |
| Methionine | | | | | | | |
| S-Adenosyl-methionine | | | | | | | |
| Folate | A | A | | | A | | |
| Glutamine | | | | | | | |
| PAN | | | | | A | | A |
| Niacin | A | A | | | | | |
| Heme | A | A | | | A | A | |
| Cbl | A | | | A | | | |
| Thiamin | | | | | | | |
| Riboflavin | A | A | | | | | A |
| Pyridoxal | | | | | | | |

TABLE 11-continued

Predicted auxotrophies for members of a synthetic consortium comprised of the 13 strain GUT-104 consortium. The following strains, referred to by their strain number, are part of GUT-104:
Clostridium saccharogumia DSM17460, Clostridium ramosum DSM1402,
Blautia producta DSM2950, Clostridium scindens ATCC35704 (DSM5676),
Lactonifactor longoviformis DSM17459, Anaerostipes caccae DSM14662,
Anaerostipes hadrus DSM3319/ATCC29173, Clostridium symbiosum ATCC14940,
Clostridium bolteae ATCC BAA-613, Blautia hydrogenotrophica DSM10507, Faecalibacterium prausnitzii
DSM17677, Subdoligranulum variabile DSM15176, and Akkermansia muciniphila ATCC BAA-835.

|  | DSM10507 | ATCC35704 | ATCC BAA-835 | DSM17460 | DSM 1402 | DSM17459 |
|---|---|---|---|---|---|---|
| Spermidine | A | A | A | A |  |  |
| Arginine |  |  |  |  |  |  |
| Proline |  |  |  |  |  | A |
| Glycine |  |  |  |  |  |  |
| Serine |  |  |  |  |  |  |
| Threonine |  |  |  |  |  |  |
| Alanine |  |  |  |  |  |  |
| Aspartate |  |  |  |  |  |  |
| Asparagine |  | A | A |  |  |  |
| Glutamate |  |  |  |  |  |  |
| Tryptophan |  | A |  |  |  |  |
| Tyrosine |  |  |  |  |  |  |
| Phenylalanine |  |  |  |  |  |  |
| Valine |  |  |  |  |  |  |
| Isoleucine |  |  |  |  |  |  |
| Leucine |  |  |  |  |  |  |
| Histidine |  |  |  |  |  |  |
| Lysine |  |  |  |  |  |  |
| Cysteine |  |  |  |  |  |  |
| Methionine |  |  |  |  |  |  |
| S-Adenosyl-methionine |  |  |  |  |  |  |
| Folate |  |  |  | A | A | A |
| Glutamine |  |  |  |  |  |  |
| PAN |  |  |  |  |  | A |
| Niacin | A |  |  |  |  |  |
| Heme |  |  |  | A |  |  |
| Cbl |  |  |  | A | A |  |
| Thiamin |  |  |  |  |  | A |
| Riboflavin | A | A |  | A | A |  |
| Pyridoxal |  |  |  |  |  |  |

"A" in a cell indicates a compound for which a strain is identified as being auxotrophic.

As performed for the individual GUT-104 strain models, flux balance analysis with the GUT-104 consortium model predicts the behavior and essentiality of each reaction in each strain while simulating growth in a specific medium condition. However, unlike the individual GUT-104 strain model simulations, all the fluxes in each strain of a consortium model are no longer independent. Instead, the activity of reactions in one strain will impact the activity of reactions in other strains via inter-strain interactions. Because of these inter-strain interactions, the GUT-104 consortium model simulates growth in a defined medium that is less complex than the defined medium computed for any of the individual GUT-104 strains. The reactions for synthesis of essential nutrients that were missing in one strain might be complemented by another strain in the consortium model, thus omitting the need to include this metabolite in the defined minimal growth medium. This result can be confirmed from flux balance analysis by running the model while minimizing the number of nutrients that are provided to the model. After this analysis was performed, it was found that the GUT-104 consortium model does indeed predict growth for the GUT-104 consortium in minimal medium, without the need to include additional nutrients, even though none of the GUT-104 consortium strains individually is predicted to be capable of growing in this medium. This finding confirms that the GUT-104 strains, after being integrated into a single consortium, can exchange metabolites to satisfy the auxotrophic requirements of all strains.

Finally, the flux profile generated by the GUT-104 consortium model can be used to determine which inter-strain interactions are active by the combined model. In silico modeling also confirmed that all the GUT-104 strain models, when combined into a single compartmentalized consortium model, are capable of representing all therapeutic phenotypes simultaneously. To do so, the fluxes predicted for the consortium model were examined to ensure that all important therapeutic pathways were carrying flux. This analysis revealed that all predicted therapeutic functions could operate adequately when the entire consortium is growing together as a single consolidated system. Computational modeling also confirmed that many strains displayed trophic interactions to ensure that the overall consortium could grow on minimal medium. The interaction data are displayed in tabular form in Table 12. This table shows all the compounds predicted by the GUT-104 consortium model to be exchanged by at least two GUT-104 strains during simulated growth on minimal medium. As this analysis clearly shows, all strains in the GUT-104 consortium are predicted to interact with at least one other strain in the consortium. Thus, all strains are interacting with each other, often in variety of ways. The interactions are induced not only by auxotrophic requirements, but also by resource balancing to maximize overall microbiome biomass production. For example, consider niacin, a metabolically expensive molecule to synthesize. Rather than having one strain produce all of the niacin needed by the auxotrophs, flux balance analysis divides the work among several strains. This further reinforces the view that the GUT-104 consortium can operate like a single "organ" in the gut microbiome, with individual cell-types intricately intertwined by numerous interactions.

TABLE 12

Nutrients exchanged between at least two species in the GUT-104 consortium as predicted by the 13 species GUT-104 consortium model.

| Compound | Consuming species | Generating species |
| --- | --- | --- |
| L-Phenylalanine | Clostridium ramosum DSM 1402, Blautia producta DSM 2950, Anaerostipes hadrus DSM 3319, Faecalibacterium prausnitzii DSM 17677, Clostridium symbiosum ATCC 14940, Anaerostipes caccae DSM 14662, Lactonifactor longoviformis DSM 17459, Akkermansia muciniphila ATCC BAA-835, Clostridium scindens ATCC 35704, Subdoligranulum variabile DSM 15176, Blautia hydrogenotrophica DSM 10507, Clostridium saccharogumia DSM 17460 | Clostridium bolteae ATCC BAA-613 |
| Putrescine | Clostridium scindens ATCC 35704, Clostridium bolteae ATCC BAA-613, Clostridium symbiosum ATCC 14940, Anaerostipes caccae DSM 14662, Lactonifactor longoviformis DSM 17459, Akkermansia muciniphila ATCC BAA-835, Blautia hydrogenotrophica DSM 10507, Clostridium saccharogumia DSM 17460, Subdoligranulum variabile DSM 15176, Anaerostipes hadrus DSM 3319, Blautia producta DSM 2950 | Faecalibacterium prausnitzii DSM 17677 |
| L-Proline | Lactonifactor longoviformis DSM 17459, Akkermansia muciniphila ATCC BAA-835, Anaerostipes caccae DSM 14662, Clostridium bolteae ATCC BAA-613, Clostridium symbiosum ATCC 14940, Clostridium scindens ATCC 35704, Blautia hydrogenotrophica DSM 10507, Anaerostipes hadrus DSM 3319, Faecalibacterium prausnitzii DSM 17677 | Blautia producta DSM 2950 |
| Folate | Subdoligranulum variabile DSM 15176, Clostridium saccharogumia DSM 17460, Lactonifactor longoviformis DSM 17459, Akkermansia muciniphila ATCC BAA-835, Clostridium symbiosum ATCC 14940, Clostridium bolteae ATCC BAA-613, Anaerostipes caccae DSM 14662, Clostridium scindens ATCC 35704, Faecalibacterium prausnitzii DSM 17677, Blautia producta DSM 2950, Clostridium ramosum DSM 1402, Anaerostipes hadrus DSM 3319 | Blautia hydrogenotrophica DSM 10507 |
| L-Valine | Clostridium scindens ATCC 35704, Anaerostipes caccae DSM 14662, Clostridium symbiosum ATCC 14940, Lactonifactor longoviformis DSM 17459, Akkermansia muciniphila ATCC BAA-835, Blautia hydrogenotrophica DSM 10507, Clostridium saccharogumia DSM 17460, Subdoligranulum variabile DSM 15176, Anaerostipes hadrus DSM 3319, Clostridium ramosum DSM 1402, Blautia producta DSM 2950, Faecalibacterium prausnitzii DSM 17677 | Clostridium bolteae ATCC BAA-613 |
| Thiamin | Clostridium ramosum DSM 1402, Blautia producta DSM 2950, Anaerostipes hadrus DSM 3319, Clostridium saccharogumia DSM 17460, Lactonifactor longoviformis DSM 17459, Anaerostipes caccae DSM 14662, Clostridium symbiosum ATCC 14940, Clostridium scindens ATCC 35704 | Faecalibacterium prausnitzii DSM 17677, Clostridium bolteae ATCC BAA-613 |
| L-Methionine | Subdoligranulum variabile DSM 15176, Blautia hydrogenotrophica DSM 10507, Akkermansia muciniphila ATCC BAA-835, Lactonifactor longoviformis DSM 17459, Anaerostipes caccae DSM 14662, Clostridium bolteae ATCC BAA-613, Clostridium symbiosum ATCC 14940, Clostridium scindens ATCC 35704, Faecalibacterium prausnitzii DSM 17677, Clostridium ramosum DSM 1402, Anaerostipes hadrus DSM 3319 | Clostridium saccharogumia DSM 17460, Blautia producta DSM 2950 |
| L-Aspartate | Subdoligranulum variabile DSM 15176, Clostridium saccharogumia DSM 17460, Akkermansia muciniphila ATCC BAA-835, Clostridium ramosum DSM 1402, Anaerostipes caccae DSM 14662 | Clostridium symbiosum ATCC 14940, Clostridium bolteae ATCC BAA-613 |
| L-Glutamate | Blautia hydrogenotrophica DSM 10507, Clostridium symbiosum ATCC 14940, Clostridium scindens ATCC 35704 | Lactonifactor longoviformis DSM 17459, Blautia producta DSM 2950 |
| L-Histidine | Clostridium saccharogumia DSM 17460, Blautia hydrogenotrophica DSM 10507, Subdoligranulum variabile DSM 15176, Clostridium scindens ATCC 35704, Clostridium symbiosum ATCC 14940, Anaerostipes caccae DSM 14662, Akkermansia | Clostridium bolteae ATCC BAA-613 |

TABLE 12-continued

Nutrients exchanged between at least two species in the GUT-104 consortium as predicted by the 13 species GUT-104 consortium model.

| Compound | Consuming species | Generating species |
| --- | --- | --- |
| | *muciniphila* ATCC BAA-835, *Lactonifactor longoviformis* DSM 17459, *Faecalibacterium prausnitzii* DSM 17677, *Anaerostipes hadrus* DSM 3319, *Blautia producta* DSM 2950, *Clostridium ramosum* DSM 1402 | |
| Glycine | *Blautia hydrogenotrophica* DSM 10507, *Anaerostipes caccae* DSM 14662, *Clostridium symbiosum* ATCC 14940 | *Clostridium scindens* ATCC 35704, *Clostridium ramosum* DSM 1402, *Akkermansia muciniphila* ATCC BAA-835, *Clostridium saccharogumia* DSM 17460, *Subdoligranulum variabile* DSM 15176 |
| L-Tryptophan | *Lactonifactor longoviformis* DSM 17459, *Akkermansia muciniphila* ATCC BAA-835, *Clostridium symbiosum* ATCC 14940, *Anaerostipes caccae* DSM 14662, *Clostridium scindens* ATCC 35704, *Subdoligranulum variabile* DSM 15176, *Clostridium saccharogumia* DSM 17460, *Blautia hydrogenotrophica* DSM 10507, *Clostridium ramosum* DSM 1402, *Blautia producta* DSM 2950, *Anaerostipes hadrus* DSM 3319, *Faecalibacterium prausnitzii* DSM 17677 | *Clostridium bolteae* ATCC BAA-613 |
| Spermidine | *Clostridium saccharogumia* DSM 17460, *Blautia hydrogenotrophica* DSM 10507, *Clostridium scindens* ATCC 35704, *Akkermansia muciniphila* ATCC BAA-835, *Clostridium symbiosum* ATCC 14940, *Anaerostipes caccae* DSM 14662, *Faecalibacterium prausnitzii* DSM 17677, *Anaerostipes hadrus* DSM 3319 | *Clostridium ramosum* DSM 1402, *Blautia producta* DSM 2950 |
| L-Arginine | *Anaerostipes hadrus* DSM 3319, *Clostridium ramosum* DSM 1402, *Blautia producta* DSM 2950, *Faecalibacterium prausnitzii* DSM 17677, *Clostridium scindens* ATCC 35704, *Lactonifactor longoviformis* DSM 17459, *Akkermansia muciniphila* ATCC BAA-835, *Anaerostipes caccae* DSM 14662, *Clostridium symbiosum* ATCC 14940, *Clostridium saccharogumia* DSM 17460, *Blautia hydrogenotrophica* DSM 10507, *Subdoligranulum variabile* DSM 15176 | *Clostridium bolteae* ATCC BAA-613 |
| Pyridoxal | *Anaerostipes hadrus* DSM 3319, *Clostridium ramosum* DSM 1402, *Faecalibacterium prausnitzii* DSM 17677, *Clostridium scindens* ATCC 35704, *Clostridium symbiosum* ATCC 14940, *Anaerostipes caccae* DSM 14662, *Lactonifactor longoviformis* DSM 17459, *Blautia hydrogenotrophica* DSM 10507, *Clostridium saccharogumia* DSM 17460, *Subdoligranulum variabile* DSM 15176 | *Clostridium bolteae* ATCC BAA-613 |
| L-Isoleucine | *Clostridium saccharogumia* DSM 17460, *Blautia hydrogenotrophica* DSM 10507, *Subdoligranulum variabile* DSM 15176, *Clostridium scindens* ATCC 35704, *Lactonifactor longoviformis* DSM 17459, *Akkermansia muciniphila* ATCC BAA-835, *Clostridium symbiosum* ATCC 14940, *Anaerostipes caccae* DSM 14662, *Faecalibacterium prausnitzii* DSM 17677, *Anaerostipes hadrus* DSM 3319, *Blautia producta* DSM 2950, *Clostridium ramosum* DSM 1402 | *Clostridium bolteae* ATCC BAA-613 |
| L-Lysine | *Anaerostipes hadrus* DSM 3319, *Blautia producta* DSM 2950, *Clostridium ramosum* DSM 1402, *Faecalibacterium prausnitzii* DSM 17677, *Clostridium scindens* ATCC 35704, *Clostridium symbiosum* ATCC 14940, *Anaerostipes caccae* DSM 14662, *Lactonifactor longoviformis* DSM 17459, *Akkermansia muciniphila* ATCC BAA-835, *Clostridium saccharogumia* DSM 17460, *Blautia hydrogenotrophica* DSM 10507, *Subdoligranulum variabile* DSM 15176 | *Clostridium bolteae* ATCC BAA-613 |
| Heme | *Subdoligranulum variabile* DSM 15176, *Blautia hydrogenotrophica* DSM 10507, *Clostridium saccharogumia* DSM 17460, *Clostridium symbiosum* ATCC 14940, *Clostridium bolteae* ATCC BAA-613, *Anaerostipes caccae* DSM 14662, *Lactonifactor longoviformis* DSM 17459, *Akkermansia muciniphila* ATCC BAA-835, *Clostridium scindens* ATCC 35704, | *Blautia producta* DSM 2950 |

TABLE 12-continued

Nutrients exchanged between at least two species in the GUT-104 consortium as predicted by the 13 species GUT-104 consortium model.

| Compound | Consuming species | Generating species |
|---|---|---|
| | *Faecalibacterium prausnitzii* DSM 17677, *Clostridium ramosum* DSM 1402, *Anaerostipes hadrus* DSM 3319 | |
| L-Cysteine | *Akkermansia muciniphila* ATCC BAA-835, *Lactonifactor longoviformis* DSM 17459, *Clostridium symbiosum* ATCC 14940, *Anaerostipes caccae* DSM 14662, *Clostridium scindens* ATCC 35704, *Subdoligranulum variabile* DSM 15176, *Blautia hydrogenotrophica* DSM 10507, *Clostridium saccharogumia* DSM 17460, *Clostridium ramosum* DSM 1402, *Blautia producta* DSM 2950, *Anaerostipes hadrus* DSM 3319, *Faecalibacterium prausnitzii* DSM 17677 | *Clostridium bolteae* ATCC BAA-613 |
| Niacin | *Anaerostipes hadrus* DSM 3319, *Blautia producta* DSM 2950, *Faecalibacterium prausnitzii* DSM 17677, *Clostridium symbiosum* ATCC 14940, *Clostridium bolteae* ATCC BAA-613, *Anaerostipes caccae* DSM 14662, *Lactonifactor longoviformis* DSM 17459, *Clostridium saccharogumia* DSM 17460, *Blautia hydrogenotrophica* DSM 10507 | *Subdoligranulum variabile* DSM 15176, *Clostridium scindens* ATCC 35704, *Clostridium ramosum* DSM 1402, *Akkermansia muciniphila* ATCC BAA-835 |
| Riboflavin | *Blautia producta* DSM 2950, *Clostridium ramosum* DSM 1402, *Anaerostipes hadrus* DSM 3319, *Faecalibacterium prausnitzii* DSM 17677, *Anaerostipes caccae* DSM 14662, *Clostridium symbiosum* ATCC 14940, *Lactonifactor longoviformis* DSM 17459, *Akkermansia muciniphila* ATCC BAA-835, *Clostridium scindens* ATCC 35704, *Subdoligranulum variabile* DSM 15176, *Clostridium saccharogumia* DSM 17460, *Blautia hydrogenotrophica* DSM 10507 | *Clostridium bolteae* ATCC BAA-613 |
| L-Leucine | *Clostridium saccharogumia* DSM 17460, *Subdoligranulum variabile* DSM 15176, *Clostridium scindens* ATCC 35704, *Anaerostipes caccae* DSM 14662, *Clostridium symbiosum* ATCC 14940, *Lactonifactor longoviformis* DSM 17459, *Akkermansia muciniphila* ATCC BAA-835, *Faecalibacterium prausnitzii* DSM 17677, *Anaerostipes hadrus* DSM 3319, *Blautia producta* DSM 2950, *Clostridium ramosum* DSM 1402 | *Clostridium bolteae* ATCC BAA-613 |
| L-Asparagine | *Faecalibacterium prausnitzii* DSM 17677, *Anaerostipes hadrus* DSM 3319, *Blautia producta* DSM 2950, *Clostridium ramosum* DSM 1402, *Clostridium saccharogumia* DSM 17460, *Subdoligranulum variabile* DSM 15176, *Clostridium scindens* ATCC 35704, *Anaerostipes caccae* DSM 14662, *Clostridium symbiosum* ATCC 14940, *Akkermansia muciniphila* ATCC BAA-835, *Lactonifactor longoviformis* DSM 17459 | *Blautia hydrogenotrophica* DSM 10507 |
| L-Alanine | *Anaerostipes hadrus* DSM 3319, *Clostridium ramosum* DSM 1402, *Lactonifactor longoviformis* DSM 17459, *Akkermansia muciniphila* ATCC BAA-835, *Blautia producta* DSM 2950, *Clostridium saccharogumia* DSM 17460, *Faecalibacterium prausnitzii* DSM 17677 | *Subdoligranulum variabile* DSM 15176, *Clostridium symbiosum* ATCC 14940, *Clostridium scindens* ATCC 35704 |
| L-Serine | *Clostridium saccharogumia* DSM 17460, *Blautia hydrogenotrophica* DSM 10507, *Clostridium symbiosum* ATCC 14940, *Anaerostipes caccae* DSM 14662, *Clostridium bolteae* ATCC BAA-613, *Lactonifactor longoviformis* DSM 17459, *Clostridium scindens* ATCC 35704, *Faecalibacterium prausnitzii* DSM 17677 | *Subdoligranulum variabile* DSM 15176, *Blautia producta* DSM 2950, *Anaerostipes hadrus* DSM 3319 |
| L-Tyrosine | *Faecalibacterium prausnitzii* DSM 17677, *Anaerostipes hadrus* DSM 3319, *Clostridium ramosum* DSM 1402, *Blautia producta* DSM 2950, *Clostridium saccharogumia* DSM 17460, *Blautia hydrogenotrophica* DSM 10507, *Subdoligranulum variabile* DSM 15176, *Clostridium scindens* ATCC 35704, *Lactonifactor longoviformis* DSM 17459, *Akkermansia muciniphila* ATCC BAA-835, *Clostridium symbiosum* ATCC 14940, *Anaerostipes caccae* DSM 14662 | *Clostridium bolteae* ATCC BAA-613 |
| L-Glutamine | *Lactonifactor longoviformis* DSM 17459, *Akkermansia muciniphila* ATCC BAA-835, *Anaerostipes caccae* DSM 14662, *Clostridium symbiosum* ATCC 14940, *Clostridium* | *Clostridium bolteae* ATCC BAA-613, *Blautia hydrogenotrophica* DSM 10507 |

TABLE 12-continued

Nutrients exchanged between at least two species in the GUT-104 consortium as predicted by the 13 species GUT-104 consortium model.

| Compound | Consuming species | Generating species |
|---|---|---|
|  | *saccharogumia* DSM 17460, *Subdoligranulum variabile* DSM 15176, *Anaerostipes hadrus* DSM 3319, *Blautia producta* DSM 2950, *Clostridium ramosum* DSM 1402, *Faecalibacterium prausnitzii* DSM 17677 |  |
| L-Threonine | *Blautia hydrogenotrophica* DSM 10507, *Subdoligranulum variabile* DSM 15176, *Clostridium scindens* ATCC 35704, *Akkermansia muciniphila* ATCC BAA-835, *Lactonifactor longoviformis* DSM 17459, *Clostridium symbiosum* ATCC 14940, *Anaerostipes caccae* DSM 14662, *Faecalibacterium prausnitzii* DSM 17677, *Anaerostipes hadrus* DSM 3319 | *Clostridium saccharogumia* DSM 17460, *Clostridium ramosum* DSM 1402, *Blautia producta* DSM 2950, *Clostridium bolteae* ATCC BAA-613 |

Based on the results of Table 12, four strains provided one or several unique nutrients to other members of the GUT-104 consortium: *Blautia producta* DSM2950, *Clostridium bolteae* ATCC BAA-613, *Blautia hydrogenotrophica* DSM 10507, and *Faecalibacterium prausnitzii* DSM 17677, providing respectively seven (of which 2 are unique), sixteen (of which 12 are unique), three (of which 2 are unique), and two (of which 1 is unique) metabolites to other members of the GUT-103 consortium. In the case of *Clostridium bolteae* ATCC BAA-613 it should be noted that this strain has a limited number of auxotrophies, and depends for its growth on other members of the GUT-104 consortium for heme. Therefore, at least one but possible two additional auxotrophies can be introduced in this strain to make sure that this strain will not outcompete the other twelve members of the GUT-104 consortium (as also described in EXAMPLES 5 and 7). The same can also be considered for *Anaerostipes caccae* DSM 14662, which also has only a single auxotrophy.

Effects of GUT-104 on the Onset of Obesity and Metabolic Disorder

The effect of the GUT-104 consortium on the onset of Type-2 diabetes was evaluated in a C57 BL/6 mouse model, where the animals were placed on a high fat diet. GUT-103 was also included in this trail as a positive control for reducing inflammation, and as a negative control for glucose tolerance. As described herein above, GUT-103 was rationally designed to control inflammation, however, this consortium lacks the functionalities for the synthesis of endocrine molecules with antidiabetic activity from endogenous and exogenous steroids. Both the GUT-103 and GUT-104 consortia were prepared by mixing $2.0 \times 10^{+8}$ cfu of each strain in a total volume of 3.0 ml. Subsequently, 300 µl of each of the GUT-103, GUT-104, or 300 µl PBS (phosphate buffered solution) as a control were administered three times per week via oral gavage to the mice. The effects of GUT-104 compared to GUT-103 and PBS on body weight and fat, glucose tolerance, and colon health were determined in the C57 BL/6 mice that were placed on the high fat diet.

Effects of GUT-104 on Body Weight

The application of GUT-104, compared to the application of GUT-103 and PBS, resulted in a slower increase in body weight as measured over a forty two-day period (FIG. 8A). In addition, application of GUT-104 also resulted in a smaller epididymal fat pad, both in absolute weight (FIG. 8B) and as a function of total body weight (FIG. 8C). These results show that the application of GUT-104, compared to the application of GUT-103 and PBS, results in a decreased rate of the development of obesity in C57 BL/6 mice that were placed on a high fat diet.

Effects of GUT-104 on Glucose Tolerance

To determine the effects of the high fat diet on the onset of metabolic disorder in C57 BL/6 mice, which is similar to Type-2 diabetes, the effects of the application of the GUT-103 and GUT-104 consortia to lower the tolerance to glucose were measured by first fasting the animals for 5 hours, and then looking at the lowering of glucose from the blood after intraperitoneal injection of glucose. Compared to GUT-103 and PBS, the application of GUT-104 had no effect on the blood glucose levels of C57 BL/6 mice that were fasted for 5 hours (FIG. 9A). However, after intraperitoneal injection of glucose, mice treated with GUT-104 showed a faster drop in blood glucose levels, indicating that the application of GUT-104 resulted in better glucose tolerance compared to C57 BL/6 mice that received GUT-103 or PBS. This is shown in FIG. 9B.

Effects of GUT-104 on Colon Health

To determine the effects of the application of the GUT-103 and GUT-104 consortia on the onset of gut inflammation caused by a high fat diet in comparison to C57 BL/6 mice that received PBS, both the colon length (FIG. 10A) and colon weight (FIG. 10B) were measured after forty two days. In general, animals that suffer from an inflamed colon, induced by the stress of a high fat diet, will have a colon that is characterized by reduced mass/proliferation and increased fragility. After forty two days, C57 BL/6 mice that had received the GUT-103 or GUT-104 consortia showed a better developed colon compared to mice treated with PBS; specifically, their colon was longer and weighted more. These data indicate that both GUT-103 and GUT-104 provide protection against gut inflammation caused by a high fat diet.

Based on the comparison between GUT-103 and GUT-104 and the observed beneficial effects on gut health and decreased severity of metabolic disorder it can be concluded that the functional module comprised of *Clostridium saccharogumia* DSM17460, *Clostridium ramosum* DSM1402, *Blautia producta* DSM2950, *Clostridium scindens*

ATCC35704 (DSM5676) and *Lactonifactor longoviformis* DSM17459, which was designed to synthesize endocrine molecules from endogenous and exogenous steroids, can have a beneficial effect on the development and severity of the metabolic disorder. This module is referred to as GUT-104 consortium subset 3.

Further Optimization of GUT-104

Based on the data in Example 8, the GUT-104 consortium can be extended by including *Bacteroides massiliensis* DSM17679. This strain, together with *Blautia producta* DSM2950 and *Akkermansia muciniphila* ATCC BAA-835 forms a stable network that breaks down complex food polymers and mucus, and covers the synthesis of butyrate, propionate and indole (referred to as GUT-103 consortium subset 1, see Example 8). Another improvement to the GUT-104 consortium can include the addition of dietary fiber, such as inulin, as a prebiotic to the formulation. This, however, will also require the presence of strains in the GUT-104 consortium that can use inulin as a carbon and energy source, a process dependent on the presence of the enzyme β-fructofuranosidase. Based on genome annotation, this enzyme is present in *Faecalibacterium prausnitzii* DSM17677, a member of GUT-104. To broaden the number of strains with this activity to address functional redundancy during the rational design process, *Megamonas hypermegale* DSM1672 and/or *Megamonas funiformis* DSM19343 can also be included. Both *Megamonas hypermegale* DSM1672 and *Megamonas funiformis* DSM19343 were found to encode a putative (3-fructofuranosidase gene.

Example 10

Rational Design of a Microbial Therapeutic for the Treatment of Type-1 Diabetes

Using the strategy outlined in the combination of EXAMPLES 1 to 7, a microbial therapeutic consortium was rationally designed by providing key functionalities that are lacking or underrepresented in the dysbiotic gut microbiome of patients developing or suffering from Type-1 diabetes. The following functionalities have been found to be underrepresented or absent from the gut microbiome of pediatric patients suffering from (the onset of) Type-1 diabetes, allowing for the rational design of a biotherapeutic:

GABA Synthesis:

Long term administration of 4-amino-butyrate (GABA) was shown to induce alpha cell-mediated beta-like cell neogenesis, reversing chemically induced diabetes in vivo in mice studies (Ben-Othman et al, 2017). Bacteria that show glutamate decarboxylase activity, converting glutamate into 4-amino-butyrate, should have a positive effect on children prone to developing Type-1 diabetes, helping to delay the onset of the disease or reducing its severity. To address this *Bacteroides stercoris* ATCC 43183, *Bacteroides massiliensis* DSM17679 and *Barnesiella intestinihominis* DSM21032, which were found to possess a putative glutamate decarboxylase gene, were included in the consortium.

SCFA Synthesis:

Decreases in butyrate-producing organisms were observed in patients with type-1 diabetes (Endesfelder et al, 2016), and it was hypothesized that butyrate had a protective effect on the development of anti-islet cell autoantibodies. To address this, *Blautia producta* DSM2950 (butyrate synthesis) and *Akkermansia muciniphila* ATCC BAA-835 (propionate synthesis; part of the GUT-103 consortium subset 1, see Example 8) together with *Faecalibacterium prausnitzii* DSM17677 (butyrate synthesis) were included.

Indole Synthesis:

Indole plays a key role in modulating the barrier integrity of the intestinal epithelial layer, by this process having a beneficial effect on chronic inflammation, which has also been implemented in type-1 diabetes: individuals with type-1 diabetes show increased intestinal permeability and changes in the microvilli of the gut lining (Pellegrini et al, 2017, Vaarala et al, 2008). Both *Akkermansia muciniphila* ATCC BAA-835 and *Bacteroides stercoris* ATCC 43183 can putatively synthese indole, futher confirming the importance of these strains as part of the rationally designed consortium.

Bile Acid Conversion:

Bile acid levels and conversion are altered in type-1 and type-2 diabetes. Bile acids are involved in the regulation of hepatic glucose metabolism by FXR-mediated pathways. The expression of FXR itself is decreased in rat models of type-1 and type-2 diabetes (for general review, see Prawitt et al, 2011). GUT-103 consortium subset 2 comprised of *Clostridium symbiosum* ATCC 14940, *Clostridium bolteae* ATCC BAA-613, *Clostridium scindens* ATCC 35704, *Subdoligranulum variabile* DSM15176 and *Anaerostipes caccae* DSM14662 (see Example 8), which is key for the the conversion of bile salts in secondary bile acids and steroids, was included to provide this function.

LPS Biosynthesis:

Early exposure to certain types of LPS, such as produced by *Escherichia coli*, will help to educate the immune system, lowering the risk of autoimmune diseases such as type-1 diabetes. On the other hand, bacteria such as *Bacteroides dorei* produce LPS with immunoinhibitory properties; in children that were more susceptible to develop type-1 diabetes elevated levels of *Bacteroides dorei* were observed (Vatanen et al, 2016). *Akkermansia muciniphila* also produces LPS with immunestimulatory properties, futher confirming the importance of this species as part of the rationally designed consortium. *Megamonas funiformis* DSM19343, which encodes a putative β-fructofuranosidase gene important for the breakdown of dietary figers such as inulin, was also included in the consortium.

By following a similar strategy as described in EXAMPLE 8, a consortium consisting of 12 strains was designed to provide a therapeutic intervention at the early onset or during the progression of Type-1 diabetes. This consortium, referred to as GUT-107, is described in TABLE 13. The design process purposely introduced redundancies in functionalities to increase the chances of establishment of the consortium or a subset of strains thereof under a broad range of conditions. This can address different degrees of gut microbiome dysbiosis. All strains in GUT-107 are able to produce acetate as a fermentation end product. Combining GUT-107 with specialized diets designed to release large amounts of acetate or butyrate after bacterial fermentation in the colon, e.g. rich in high-amylose maize starch (HAMS) that has been acetylated (HAMSA) or butyrylated (HAMSB), can further enhance the beneficial effect of GUT-107 on the onset and development of type-1 diabetes: diets stimulating the microbial synthesis of either acetate or butyrate provided a high degree of protection from diabetes, even when administered after breakdown of immunotolerance; and acetate-plus butyrate-yielding diets were shown to enhance gut integrity and decrease serum concentration of diabetogenic cytokines such as IL-21 in the non-obese diabetic (NOD) mouse model (Mariño et al, 2017).

TABLE 13

Key functionalities for the members of a twelve-strain rationally designed consortium, referred to as GUT-107, for treatment of Type-1 diabetes.

| Species | Family | Butyrate | Propionate | Indole | GABA | Bile Salt | Siderophore |
|---|---|---|---|---|---|---|---|
| *Megamonas funiformis* DSM19343 | Selenomonadaceae | | + | | | | Ferrichrome and Enterobactin uptake |
| *Bacteroides massiliensis* DSM17679 | Bacteroidaceae | | + | | + | | Heterologous siderophore uptake |
| *Bacteroides stercoris* ATCC43183/DSM19555 | Bacteroidaceae | | + | + | + | | Heterologous siderophore uptake incl. Enterobactin |
| *Barnesiella intestinihominis* DSM21032 | Porphyromonadaceae | | + | | + | | Heterologous siderophore uptake incl. Aerobactin |
| *Faecalibacterium prausnitzii* DSM17677 | Ruminococcaceae | + | | | | | Heterologous siderophore uptake |
| *Subdoligranulum variabile* DSM15176 | Ruminococcaceae | + | | | | | |
| *Anaerostipes caccae* DSM14662 | Lachnospiraceae | + | | | | 7-α-DH, 7-α-HSD | Heterologous siderophore uptake incl. Ferrichrome; Yersiniabactin synthesis |
| *Clostridium symbiosum* ATCC14940 | Lachnospiraceae | + | | | | 3-α-HSD, 7-α-HSD | |
| *Akkermansia muciniphila* ATCC BAA-835 | Akkermansiaceae | | + | + | | | Heterologous siderophore uptake |
| *Clostridium scindens* ATCC35704 | Lachnospiraceae | | | | | 7-α-DH | |
| *Clostridium bolteae* ATCC BAA-613* | Lachnospiraceae | | | | | 3-α-HSD, 7-α-HSD | Siderophore synthesis |
| *Blautia producta* DSM2950* | Lachnospiraceae | + | | | | | Heterologous siderophore uptake incl. Ferrichrome |

Abbreviations: 7-α-DH: 7-alpha-dehydratase/dehydroxylase activity; 3-α-HSD: 3-alpha-hydroxysteroid dehydrogenase activity; 7-α-HSD: 7-alpha-hydroxysteroid dehydrogenase activity; 3-β-HSD: 3-beta-hydroxysteroid dehydrogenase activity.
*indicates strains that were added to provide redundancy for key functionalites and additional metabolic support.

As part of the process to build the GUT-107 consortium model, computational models were first built for the individual GUT-107 strains (as described in EXAMPLE 4). All strain models required some degree of gap filling to ensure that they are capable of synthesizing or acquiring all the small molecule building blocks required to produce new biomass. This gap filling was performed in silico mimicking a specific growth condition; it is preferable to perform gap filling mimicking minimal medium composition. The initial gap filling was therefore performed in glucose minimal medium. The GUT-107 strains, and their most closely related reference strains, were experimentally confirmed to grow in rich medium, as no defined minimal medium is known for any of the strains. Thus, an auxotrophy analysis was performed to predict defined minimal media for each of the GUT-107 strains. In this analysis, the synthesis pathways for all amino acids, vitamins, and cofactors were computationally assigned and subsequently, as part of a quality control process, manually reviewed in a model-driven fashion to determine which pathways were likely incomplete for each genome. The output of this analysis revealed very substantial differences in auxotrophy across all of the GUT-107 strains (See Table 14).

TABLE 14

Predicted auxotrophies for members of a synthetic consortium comprised of the 12 strain GUT-107 consortium. The following strains, referred to by their strain number, are part of GUT-107: *Megamonas funiformis* DSM19343, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Clostridium symbiosum* ATCC14940, *Clostridium bolteae* ATCC BAA-613, *Blautia producta* DSM2950, *Clostridium scindens* ATCC35704 and *Akkermansia muciniphila* ATCC BAA-835.

| | DSM19343 | DSM17679 | ATCC43183 | DSM21032 | DSM17677 | DSM15176 | DSM14662 |
|---|---|---|---|---|---|---|---|
| Spermidine | | A | | A | A | | A |
| Arginine | | | | | | | |
| Proline | | | | | | | |
| Glycine | | | | | | | |
| Serine | | | | | | A | |
| Threonine | | | | | | | |
| Alanine | | | | | | | |
| Aspartate | | | | | | | |

TABLE 14-continued

Predicted auxotrophies for members of a synthetic consortium comprised of the 12 strain GUT-107 consortium. The following strains, referred to by their strain number, are part of GUT-107: *Megamonas funiformis* DSM19343, *Bacteroides massiliensis* DSM17679, *Bacteroides stercoris* ATCC43183/DSM19555, *Barnesiella intestinihominis* DSM21032, *Faecalibacterium prausnitzii* DSM17677, *Subdoligranulum variabile* DSM15176, *Anaerostipes caccae* DSM14662, *Clostridium symbiosum* ATCC14940, *Clostridium bolteae* ATCC BAA-613, *Blautia producta* DSM2950, *Clostridium scindens* ATCC35704 and *Akkermansia muciniphila* ATCC BAA-835.

| | DSM19343 | DSM17679 | DSM19555 | DSM21032 | DSM17677 | DSM15176 |
|---|---|---|---|---|---|---|
| Asparagine | A | | | | | |
| Glutamate | | | | | | |
| Tryptophan | | | | A | A | A |
| Tyrosine | | | | | | |
| Phenylalanine | | | | | | |
| Valine | | | | | | |
| Isoleucine | | | | | | |
| Leucine | | | | | | |
| Histidine | | | | | | |
| Lysine | | | | | | |
| Cysteine | | | | | | |
| Methionine | | | | | | |
| S-Adenosyl-methionine | | | | | | |
| Folate | | | | | A | A |
| Glutamine | | | | | | |
| PAN | | | | | | |
| Niacin | | | | A | A | A |
| Heme | | A | A | A | A | A |
| Cbl | | | | A | A | |
| Thiamin | | | | | | |
| Riboflavin | | | | | A | A |
| Pyridoxal | | | | | | |

| | ATTC14940 | ATCC BAA-613 | DSM2950 | ATCC35704 | ATCC BAA-835 | NISLE-1917 |
|---|---|---|---|---|---|---|
| Spermidine | | | | A | A | |
| Arginine | | | | | | |
| Proline | | | | | | |
| Glycine | | | | | | |
| Serine | A | | | | | |
| Threonine | | | | | | |
| Alanine | | | | | | |
| Aspartate | | | | | | |
| Asparagine | | | | A | A | |
| Glutamate | | | | | | |
| Tryptophan | | | | A | | |
| Tyrosine | | | | | | |
| Phenylalanine | | | | | | |
| Valine | | | | | | |
| Isoleucine | | | | | | |
| Leucine | | | | | | |
| Histidine | A | | | | | |
| Lysine | | | | | | |
| Cysteine | | | | | | A |
| Methionine | | | | | | |
| S-Adenosyl-methionine | | | | | | |
| Folate | A | | | | | |
| Glutamine | | | | | | |
| PAN | A | | A | | | |
| Niacin | | | | | | |
| Heme | A | A | | | | |
| Cbl | | | | | | |
| Thiamin | | | | | | |
| Riboflavin | | | A | A | | |
| Pyridoxal | | | | | | |

"A" in a cell indicates a compound for which a strain is identified as auxotrophic.

To evaluate the efficacy of the GUT-107 consortium to prevent the onset or treat type-1 diabetes, a preclinical study is performed using a validated animal model based on ex-germ-free (sterile) non-obese diabetic (NOD) mice. In the NOD mouse model, the gut microbiome has been shown to have a direct, causal role in prevention/delay of the onset of autoimmune diabetes.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

REFERENCES

Antunes L. C. and B. B. Finlay (2011). "A comparative analysis of the effect of antibiotic treatment and enteric infection on intestinal homeostasis." Gut Microbes 2: 105-108.

Arpaia, N., C. Campbell, X. Fan, S. Dikiy, J. van der Veeken, P. deRoos, H. Liu, J. R. Cross, K. Pfeffer, P. J. Coffer and A. Y. Rudensky (2013). "Metabolites produced by commensal bacteria promote peripheral regulatory T-cell generation." Nature 504: 451-455.

Atarashi, K., T. Tanoue, K. Oshima, W. Suda, Y. Nagano, H. Nishikawa, S. Fukuda, T. Saito, S. Narushima, K. Hase, S. Kim, J. V. Fritz, P. Wilmes, S. Ueha, K. Matsushima, H. Ohno, B. OIle, S. Sakaguchi, T. Taniguchi, H. Morita, M. Hattori and K. Honda (2013). "Treg induction by a rationally selected mixture of Clostridia strains from the human microbiota." Nature 500(7461): 232-236.

Bansal, T., R. C. Alaniz, T. K. Wood and A. Jayaraman (2010). "The bacterial signal indole increases epithelial-cell tight-junction resistance and attenuates indicators of inflammation." Proc Natl Acad Sci USA 107: 228-233.

Bansal, T., D. Englert, J. Lee, M. Hegde, T. K. Wood, and A. Jayaraman (2007). "Differential effects of epinephrine, norepinephrine, and indole on Escherichia coli O157:H7 chemotaxis, colonization, and gene expression." Infect Immun 75:4597-4607. Baron, E. J. (1997). "*Bilophila wadsworthia*: a unique Gram-negative anaerobic rod." Anaerobe 3: 83-86.

Ben-Othman, N., Vieira, A., Courtney, M., Record, F., Gjernes, E., Avolio, F., Hadzic, B., Druelle, N., Napolitano, T., Navarro-Sanz, S., Silvano, S., Al-Hasani, K., Pfeifer, A., Lacas-Gervais, S., Leuckx, G., Marroqui, L., Thevenet, J., Dragsbaek Madsen, O., Eizirik, D. L., Heimberg, H., Kerr-Conte, J., Pattou, F., Mansouri, A. and Collombat, P. (2017). "Long-term GABA administration induces alpha cell-mediated beta-like cell neogenesis." Cell 168: 73-85.

Bereswill, S., A. Fischer, R. Plickert, L. M. Haag, B. Otto, A. A. Kuhl, J. I. Dasti, A. E. Zautner, M. Munoz, C. Loddenkemper, et al. (2011). "Novel murine infection models provide deep insights into the "menage a trois" of Campylobacter jejuni, microbiota and host innate immunity." PLoS One 6: e20953

Bhattacharjee, S. and W. J. Lukiw (2013). "Alzheimer's disease and the microbiome." Frontiers in Cellular Neuroscience 7: e153.

Boulangé, C. L., A. L. Neves, J. Chilloux, J. K. Nicholson and M.-E. Dumas (2016). "Impact of the gut microbiota on inflammation, obesity, and metabolic disease." Genome Medicine 8:42.

Canani, R. B., M. Di Costanzo, G. Bedogni, A. Amoroso, L. Cosenza, C. Di Scala, V. Granata and R. Nocerino (2017). "Extensively hydrolyzed casein formula containing Lactobacillus rhamnosus GG reduces the occurrence of other allergic manifestations in children with cow's milk allergy: 3-year randomized controlled trial." J Allergy Clin Immunol In press.

Canani, R. B., N. Sangwan, A. T. Stefka, R. Nocerino, L. Paparo, R. Aitoro, A. Calignano, A. A. Khan, J. A. Gilbert and C. R. Nagler (2016). "*Lactobacillus rhamnosus* GG-supplemented formula expands butyrate-producing bacterial strains in food allergic infants." ISME Journal 10: 742-750.

Cassidy, A., B. Hanley and R. M. Lamueal-Raventos (2000). "Isoflavones, lignans and stilbenes—origins, metabolism and potential importance to human health." J Sci Food Agr 80: 1044-1062.

Chen, J., K. P. Tan, W. E. Ward and L. U. Thompson (2003). "Exposure to flaxseed or its purified lignan during suckling inhibits chemically induced rat mammary tumorigenesis." Exp Biol Med (Maywood) 228(8): 951-958.

Chimerel, C., E. Emery, D. K. Summers, U. Keyser, F. M. Gribble, and F. Reimann (2014). "Bacterial metabolite indole modulates incretin secretion from intestinal enteroendocrine L cells." Cell Reports 9: 1202-1208.

Clavel, T., G. Henderson, W. Engst, J. Dore and M. Blaut (2006). "Phylogeny of human intestinal bacteria that activate the dietary lignan secoisolariciresinol diglucoside". FEMS Microbiol Ecol 55: 471-478.

Clavel, T., R. Lippman, F. Gavini, J. Dore and M. Blaut (2007). "*Clostridium saccharogumia* sp. nov. and *Lactonifactor longoviformis* gen. nov., sp. nov., two novel human faecal bacteria involved in the conversion of the dietary phytoestrogen secoisolariciresinol diglucoside". Systematic Applied Microbiology 30: 16-26.

Da Silva, S. M., S. S. Venceslau, C. L. V. Fernandes, F. M. Valente and I. A. Pereira (2008). "Hydrogen as an energy source for the human pathogen *Bilophila wadsworthia*." Antonie Van Leeuwenhoek 93: 381-390.

Dehghan, P., B. P. Gargari, M. A. Jafar-Abadi and A. Aliasgharzadeh (2014). Inulin controls inflammation and metabolic endotoxemia in women with type 2 diabetes mellitus: a randomized-controlled clinical trial. Int J Food Sci Nutr. 65:117-123.

De Souza, H. S. P. and C. Fiocchi (2016). "Immunopathogenesis of IBD: current state of the art." Nature Rev. Gastroenterology Hepatology 13: 13-27.

Downes, J., M. Munson and W. G. Wade (2003). "*Dialister invisus* sp. nov., isolated from the human oral cavity." Int J Syst Evol Microbiol 53: 1937-1940.

Duboc, H., S. Rajca, D. Rainteau, D. Benarous, M. A. Maubert, E. Quervain, G. Thomas, V. Barbu, L. Humbert, G. Despras, C. Bridonneau, F. Dumetz, J. P. Grill, J. Masliah, L. Beaugerie, J. Cosnes, O. Chazouilleres, R. Poupon, C. Wolf, J. M. Mallet, P. Langella, G. Trugnan, H. Sokol and P. Seksik (2013). "Connecting dysbiosis, bile-acid dysmetabolism and gut inflammation in inflammatory bowel diseases." Gut 62: 531-539.

Eeckhaut, V., B. Flahou, C. Romero, S. Van DerHeyden, F. Pasmans, F. Haesebrouck, R. Ducatelle and F. Van Immerseel (2009). "The anaerobic butyrate-producing strain Butyricicoccus pullicaecorum decreases colonic inflammation and ulceration in a TNBS-induced colitis rat model." In 5th Probiotics, Prebiotics and New Foods Congress, Rome, Italy. http://www.probiotics-prebiotics newfood.org/pdf/5th_Probiotics_Prebiotics_Newfood- .pdf.

Endesfelder, D., M. Engel, A. G. Davis-Richardson, A. N. Ardissone, P. Achenbach, S. Hummel, C. Winkler, M. Atkinson, D. Schatz, E. Triplett, A.-G. Ziegler and W. zu Castell (2016). "Towards a functional hypothesis relating anti-islet cell autoimmunity to the dietary impact on microbial communities and butyrate production." Microbiome 4:17. https://doi.org/10.1186/s40168-016-0163-4

Eun, C. S., Y. Mishima, S. Wohlgemuth, B. Liu, M. Bower, I. M. Carroll and R. B Sartor (2014). "Induction of bacterial antigen-specific colitis by a simplified human microbiota consortium in gnotobiotic interleukin-10-/- mice". Infect Immun 82(6): 2239-2246.

Evrensel, A. and M. E. Ceylan (2015). "The Gut-Brain Axis: The Missing Link in Depression." Clinical Psychopharmacology and Neuroscience 13(3): 239-244. Fasano, A. (2011). "Zonulin and its regulation of intestinal barrier function: the biological door to inflammation, autoimmunity, and cancer". Physiological Reviews 91: 151-175.

Field, D., P. D. Cotter, C. Hill and R. P. Ross (2015). "Bioengineering Lantibiotics for Therapeutic Success." Frontiers in Microbiology 6: e1363.

Furusawa, Y., Y. Obata, S. Fukuda, T. A. Endo, G. Nakato, D. Takahashi, Y. Nakanishi, C. Uetake, K. Kato, T. Kato, M. Takahashi, N. N. Fukuda, S. Murakami, E. Miyauchi, S. Hino, K. Atarashi, S. Onawa, Y. Fujimura, T. Lockett, J. M. Clarke, D. L. Topping, M. Tomita, S. Hori, O. Ohara, T. Morita, H. Koseki, J. Kikuchi, K. Honda, K. Hase and H. Ohno (2013). "Commensal microbe-derived butyrate induces the differentiation of colonic regulatory T cells." Nature 504: 446-450.

Geva-Zatorsky, N., E. Sefik, L. Kua, L. Pasman, T. G. Tan, A. Ortiz-Lopez, T. B. Yanortsang, L. Yang, R. Jupp, D. Mathis, C. Benoist and D. L. Kasper (2017). "Mining the human gut microbiota for immunomodulatory organisms." Cell 168: 1-16.

Gevers, D., S. Kugathasan, L. A. Denson, Y. Vazquez-Baeza, W. Van Treuren, B. Ren, E. Schwager, D. Knights, S. J. Song, M. Yassour, X. C. Morgan, A. D. Kostic, C. Luo, A. Gonzalez, D. McDonald, Y. Haberman, T. Walters, S. Baker, J. Rosh, M. Stephens, M. Heyman, J. Markowitz, R. Baldassano, A. Griffiths, F. Sylvester, D. Mack, S. Kim, W. Crandall, J. Hyams, C. Huttenhower, R. Knight and R. J. Xavier (2014). "The Treatment-Naive Microbiome in New-Onset Crohn's Disease." Cell Host & Microbe 15: 382-392.

Gevers, D., S. Kugathasan, D. Knights, A. D. Kostic, R. Knight and R. J. Xavier (2017). "A Microbiome Foundation for the Study of Crohn's Disease." Cell Host & Microbe 21: 301-304.

Giel J. L., J. A. Sorg, A. L. Sonenshein, et al. (2010) "Metabolism of bile salts in mice influences spore germination in Clostridium difficile." PLoS One 5: e8740.

Goodman, A. L., et al. (2009) "Identifying genetic determinants needed to establish a human gut symbiont in its habitat." Cell Host Microbe 6: 279-289.

Göker, M., S. Gronow, A. Zeytun, M. Nolan, S. Lucas, A. Lapidus, N. Hammon, S. Deshpande, J. F. Cheng, S. Pitluck, K. Liolios, I. Pagani, N. Ivanova, K. Mavromatis, G. Ovchinikova, A. Pati, R. Tapia, C. Han, L. Goodwin, A. Chen, K. Palaniappan, M. Land, L. Hauser, C. D. Jeffries, E. M. Brambilla, M. Rohde, J. C. Detter, T. Woyke, J. Bristow, V. Markowitz, P. Hugenholtz, J. A. Eisen, N. C. Kyrpides and H. P. Klenk (2011). "Complete genome sequence of Odoribacter splanchnicus type strain (1651/6)." Stand Genomic Sci 2: 200-209.

Halfvarson, J., C. J. Brislawn, R. Lamendella, Y. Vázquez-Baeza, W. A. Walters, L. M. Bramer, M. D'Amato, F. Bonfiglio, D. McDonald, A. Gonzalez, E. E. McClure, M. F. Dunklebarger, R. Knight and J. K. Jansson (2017). "Dynamics of the human gut microbiome in inflammatory bowel disease." Nature Microbiol. 2: e17004.

Hazenberg, M. P., J. P. van de Merwe, A. S. Pena, A. M. Pennock-Schröder and L. M. van Lieshout (1987). "Antibodies to Coprococcus comes in sera of patients with Crohn's disease. Isolation and purification of the agglutinating antigen tested with an ELISA technique." J Clin Lab Immunol 23(3): 143-148.

Henry, C. S., M. DeJongh, A. A. Best, P. M. Frybarger, B. Linsay, R. L. Stevens (2010). "High-throughput generation, optimization and analysis of genome-scale metabolic models." Nature Biotechnology 28: 977-982.

Hohnadel, D. and J. M. Meyer (1988). "Specificity of pyoverdine-mediated iron uptake among fluorescent Pseudomonas strains." J. Bacteriol. 170: 4865-4873. Holmstrom, K., M. D. Collins, T. Moller, E. Falsen and P. A. Lawson (2004). "Subdoligranulum variabile gen. nov., sp. nov. from human feces." Anaerobe 10: 197-203.

Honda, K., K. Atarashi, K. Itoh and T. Tanoue (2015). Composition for inducing proliferation or accumulation of regulatory T cells. T. U. o. Tokyo. Japan. U.S. Pat. No. 9,415,079 B2. Hubbard, T. D., I. A. Murray, W. H. Bisson, T. S. Lahoti, K. Gowda, S. G. Amin, A. D. Patterson and G. H. Perdew (2015a). Adaptation of the human aryl hydrocarbon receptor to sense microbiota-derived indoles. Scientific Reports 5: 12689. doi:10.1038/srep12689.

Hubbard, T. D., I. A. Murray and G. H. Perdew (2015b). Indole and tryptophan metabolism: endogenous and dietary routes to Ah receptor activation. Drug Metab Dispos. 43(10): 1522-1535.

Joossens, M., G. Huys, M. Cnockaert, P. De Vos, K. Verbeke, P. Rutgeerts, P. Vandamme, Vermeire and S. (2011). "Dysbiosis of the faecal microbiota in patients with Crohn's disease and their unaffected relatives." Gut 60: 631-637.

Kang, D. D., J. Jeff Froula, R. Rob Egan and Z. Wang (2015). "MetaBAT, an efficient tool for accurately reconstructing single genomes from complex microbial communities." PeerJ 3: e1165.

Kortman, G. A. M., M. Raffatellu, D. W. Swinkels and H. Tjalsma (2014). "Nutritional iron turned inside out: intestinal stress from a gut microbial perspective." FEMS Microbiol Rev 38: 1202-1234.

Li, Q. and J.-M. Zhou (2016). "The microbiota-gut-brain axis and its potential therapeutic role in autism spectrum disorder" Neuroscience 324: 131-139.

Louis, P and F. H J (2009). "Diversity, metabolism and microbial ecology of butyrate-producing bacteria from the human large intestine." FEMS. Microbiol Lett. (294): 1-8.

Louis, P., P. Young, G. Holtrop and H. J. Flint (2010). "Diversity of human colonic butyrate-producing bacteria revealed by analysis of the butyryl-CoA:acetate CoA-transferase gene." Environ. Microbiol. 12: 304-314.

Luft, V. C., M. I. Schmidt, J. S. Pankow, D. Couper, C. M. Ballantyne, J. H. Young and B. B. Duncan (2013). "Chronic inflammation role in the obesity-diabetes association: a case-cohort study". Diabetology & Metabolic Syndrome 5 (31): 1-8.

Ma, H. and M. E. Patti (2014). "Bile Acids, Obesity, and the Metabolic Syndrome." Best Pract Res Clin Gastroenterol. 28(4): 573-583.

Mariño, E., J. L. Richards, K. H. McLeod, D. Stanley, Y. A. Yap, J. Knight, C. McKenzie, J. Kranich, A. C. Oliveira, F. J. Rossello, B. Krishnamurthy, C. M. Nefzger, L Macia, A. Thorburn, A. G. Baxter, G. Morahan, L. H. Wong, J. M. Polo, R. J. Moore, T. J. Lockett, J. M. Clarke, D. L. Topping, L. C. Harrison and C. R. Mackay (2017). "Gut microbial metabolites limit the frequency of autoimmune T cells and protect against type 1 diabetes." Nature Immunology 18: 552-562.

Martinez, I., J. M. Lattimer, K. L. Hubach, J. A. Case, J. Yang, C. G. Weber, J. A. Louk, D. J. Rose, G. Kyureghian, D. A. Peterson, M. D. Haub and J. Walter (2013). "Gut microbiome composition is linked to whole grain-induced immunological improvements." ISME Journal 7: 269-280.

Mayer, A. M. (1958). "Determination of Indole Acetic Acid by the Salkowsky Reaction." Nature 182: 1670-1671.

Mazzoli, R. and E. Pessione (2016). "The Neuro-endocrinological Role of Microbial Glutamate and GABA Signaling." Front. Microbiol. 7: e1934.

Miller, J. H. (1972). "Experiments in molecular genetics". Cold Spring Harbor Laboratory Press, Cold Spring Harbor, N.Y.

Moos, W. H., D. V. Faller, D. N. Harpp, I. Kanara, J. Pernokas, W. R. Powers and K. Steliou (2016). "Microbiota and Neurological Disorders: A Gut Feeling." BioResearch Open Access 5: 137-145.

Morgan, X. C., T. L. Tickle, H. Sokol, D. Gevers, K. L. Devaney, D. V. Ward, J. A. Reyes, S. A. Shah, N. LeLeiko, S. B. Snapper, A. Bousvaros, J. Korzenik, B. E. Sands, R. J. Xavier and C. Huttenhower (2012). "Dysfunction of the intestinal microbiome in inflammatory bowel disease and treatment." Genome Biol 13(9): R79. doi: 10.1186/gb-2012-1113-1189-r1179.

Narushima, S., Y. Sugiura, K. Oshima, K. Atarashi, M. Hattori, M. Suematsu and K. Honda (2014). "Characterization of the 17 strains of regulatory T cell-inducing human-derived Clostridia." Gut Microbes 5(3): 333-339.

Neis, E. P. J. G., C. H. C. Dejong and S. S. Rensen (2015). "The role of microbial amino acid metabolism in host metabolism." Nutrients 7: 2930-2946.

Ning, C., X. Wang, S. Gao, J. Mu, Y. Wang, S. Liu, J. Zhu and X. Meng (2017). Chicory inulin ameliorates type 2 diabetes mellitus and suppresses JNK and MAPK pathways in vivo and in vitro. Mol. Nutr. Food Res. 61(8). doi: 10.1002/mnfr.201600673. O'Callaghan, A. and D. van Sinderen (2016). "Bifidobacteria and their role as members of the human gut microbiota." Frontiers in Microbiology 7.

Ortega-Morales B. O., J. L. Santiago-Garcia, M. J. Chan-Bacab, X. Moppert, E. Miranda-Tello, M. L. Fardeau, J. C. Carrero, P. Bartolo-Perez, A. Valadez-Gonzalez and J. Guezennec (2007). "Characterization of extracellular polymers synthesized by tropical intertidal biofilm bacteria." Journal of Applied Microbiology 102: 254-264.

Paun, A. and J. S. Danska (2016). "Modulation of type 1 and type 2 diabetes risk by the intestinal microbiome." Pediatr Diabetes 17(7): 469-477.

Pellegrini, S., V. Sordi, A. M. Bolla, D. Saita, R. Ferrarese, F. Canducci, M. Clementi, F. Invernizzi, A. Mariani, R. Bonfanti, G. Barera, P. A. Testoni, C. Doglioni, E. Bosi and L. Piemonti (2017). "Duodenal mucosa of patients with type 1 diabetes shows distinctive inflammatory profile and microbiota." J Clin Endocrinol Metab 102: 1468-1477.

Peng, Y., H. C. Leung, S. M. Yiu and F. M. Chin (2012). "IDBA-UD: a de novo assembler for single-cell and metagenomic sequencing data with highly uneven depth." Bioinformatics 28(11): 1420-1428.

Pitt, J. M., M. Vétizou, N. Waldschmitt, G. Kroemer, M. Chamaillard, I. Gomperts Boneca and L. Zitvogel (2016). "Fine-Tuning Cancer Immunotherapy: Optimizing the Gut Microbiome." Cancer Res 76(16): 1-6.

Prasad, K. (1999). "Reduction of serum cholesterol and hypercholesterolemic atherosclerosis in rabbits by secoisolariciresinol diglucoside isolated from flaxseed." Circulation 99(10): 1355-1362.

Prasad, K. (2001). "Secoisolariciresinol diglucoside from flaxseed delays the development of type 2 diabetes in Zucker rat." J Lab Clin Med. 138(1): 32-39.

Prawitt, J. S. Caron, and B. Staels (2011). "Bile acid metabolism and the pathogenesis of type 2 diabetes." Curr Diab Rep. 11(3): 160-166.

Qin, J., Y. Li, Z. Cai, S. Li, J. Zhu, F. Zhang, S. Liang, W. Zhang, Y. Guan, D. Shen, et al. (2012). "A metagenome-wide association study of gut microbiota in type 2 diabetes." Nature 490: 55-60.

Ridlon, J. M., S. Ikegawa, J. M. P. Alves, B. Zhou, A. Kobayashi, T. Iida, K. Mitamura, G. Tanabe, M. Serrano, A. De Guzman, P. Cooper, G. A. Buck, and P. B. Hylemon (2013). "*Clostridium scindens*: a human gut microbe with a high potential to convert glucocorticoids into androgens." Journal of Lipid Research 54: 2437-2449.

Rogers, G. B., D. J. Keating, R. L. Young, M.-L. Wong, J. J Licinio and S. Wesselingh (2016). "From gut dysbiosis to altered brain function and mental illness: mechanisms and pathways." Molecular Psychiatry 21: 738-748.

Sadouk, A. and M. Mergeay (1993). "Chromosome mapping in *Alealigenes eutrophus* CH34". Molecular and General Genetics MGG 240: 181-187.

Sartor, B. R. and G D. Wu (2017). "Roles for intestinal bacteria, viruses, and fungi in pathogenesis of inflammatory bowel diseases and therapeutic approaches". Gastroenterology 152 (2): 327-339.e4.

Schwabe, R. F. and C. Jobin (2013). "The microbiome and cancer." Nature Reviews Cancer 13: 800-812.

Seekatz, A. M. R., K. Santhosh, K. Young, V. B. (2016). "Dynamics of the fecal microbiome in patients with recurrent and nonrecurrent *Clostridium difficile* infection." Genome Medicine 8:47.

Segata, N., D. Bornigen, X. C. Morgan and C. Huttenhower (2013). "PhyloPhlAn is a new method for improved phylogenetic and taxonomic placement of microbes." Nature Comms 4

Sellon, R. K., S. Tonkonogy, M. Schultz, L. A. Dieleman, W. Grenther, E. Balish, D. A. Rennick, and R. B. Sartor (1998). "Resident enteric bacteria are necessary for development of spontaneous colitis and immune system activation in interleukin-10-deficient mice." Infection Immunity 66: 5224-5231.

Shaw, K. A., M. Bertha, T. Hofmekler, P. Chopra, T. Vatanen, A. Srivatsa, J. Prince, A. Kumar, C. Sauer, M. E. Zwick, G. A. Satten, A. D. Kostic, J. G. Mulle, R. J. Xavier and S. Kugathasan (2016). "Dysbiosis, inflammation, and response to treatment: a longitudinal study of pediatric subjects with newly diagnosed inflammatory bowel disease." Genome Medicine 8: e75.

Shetty, S. A., N. P. Marathe, V. Lanjekar, D. Ranade and Y. S. Shouche (2013). "Comparative genome analysis of *Megasphaera* sp. reveals niche specialization and its potential role in the human gut." PLoS ONE 8: e79353.

Smith, P. M., M. R. Howitt, N. Panikov, M. Michaud, C. A. Gallini, M. Bohlooly-Y, J. N. Glickman and W. S. Garrett (2013). "The microbial metabolites, short chain fatty acids, regulate colonic Treg cell homeostasis." Science 341: 569-573.

Sokol, H., B. Pigneur, L. Watterlot, O. Lakhdari, L. G. Bermúdez-Humarán, J. J. Gratadoux, S. Blugeon, C. Bridonneau, J. P. Furet, G. Corthier, C. Grangette, N. Vasquez, P. Pochart, G. Trugnan, G. Thomas, H. M. Blottière, J. Doré, P. Marteau, P. Seksik and P. Langella (2008). "*Faecalibacterium prausnitzii* is an anti-inflammatory commensal bacterium identified by gut microbiota analysis of Crohn disease patients." Proc Natl Acad Sci USA 105(43): 16731-16736.

Sun, J. and I. Kato (2016). "Gut microbiota, inflammation and colorectal cancer." Genes & Diseases 3: 130-143.

Truong, D. T., E. A. Franzosa, T. L. Tickle, M. Scholz, G. Weingart, E. Pasolli, A. Tett, C. Huttenhower and N. Segata (2015). "MetaPhlAn2 for enhanced metagenomic taxonomic profiling." Nature Methods 12: 902-903.

Vaarala, O., M. A. Atkinson and J. Neu (2008). "The "perfect storm" for type 1 diabetes: the complex interplay between intestinal microbiota, gut permeability, and mucosal immunity." Diabetes 57: 2555-2562.

Vanderhaeghen, S., C. Lacroix and C. Schwab (2015). "Methanogen communities in stools of humans of different age and health status and co-occurrence with bacteria." FEMS Microbiol Lett 362: fnv092

Van Immerseel, F., R. Ducatelle, M. De Vos, N. Boon, T. Van De Wiele, K. Verbeke, P. Rutgeerts, B. Sas, P. Louis and H. J. Flint (2010). "Butyric acid-producing anaerobic bacteria as a novel probiotic treatment approach for inflammatory bowel disease." Journal of Medical Microbiology 59: 142-143.

Vatanen, T., A. D. Kostic, E. d'Hennezel, H. Siljander, E. A. Franzosa, M. Yassour, R. Kolde, H. Vlamakis, T. D. Arthur, A.-M. Hamalainen, A. Peet, V. Tillmann, R. Uibo, S. Mokurov, N. Dorshakova, J. Ilonen, S. M. Virtanen, S. J. Szabo, J. A. Porter, H. Landesmaki, C. Huttenhower, D. Gevers, T. W. Cullen, M. Knip, on behalf of the DIABIMMUNE Study Group, and R. J. Xavier (2016)."Variation in microbiome LPS immunogenicity contributes to autoimmunity in humans." Cell 165: 842-853.

Vernia, P., P. L. Fracasso, V. Casale, G. Villotti, A. Marcheggiano, V. Stigliano, P. Pinnaro, V. Bagnardi and R. Caprilli (2000). "Topical butyrate for acute radiation proctitis: randomised, crossover trial." Lancet 356: 1232-1235.

Vernia, P., V. Annese, G. Bresci, G. d'Albasio, R. D'Inca, S. Giaccari, M. Ingrosso, C. Mansi, G. Riegler, D. Valpiani, et al. (2003). "Topical butyrate improves efficacy of 5-ASA in refractory distal Ulcerative Colitis: results of a multicentre trial." Eur J Clin Invest 33: 244-248.

Villeger R., N. Saad, K. Grenier, X. Falourd, L. Foucat, M. C. Urdaci, P. Bressollier and T.-S. Ouk (2014). "Characterization of lipoteichoic acid structures from three probiotic *Bacillus* strains: involvement of D-alanine in their biological activity." Antonie van Leeuwenhoek 106: 693-706.

Vuong, H. E. H., E. Y. (2017). "Emerging Roles for the Gut Microbiome in Autism Spectrum Disorder." Biological Psychiatry 5: 411-423.

Willing, B. P., J. Dicksved, J. Halfvarson, A. F. Andersson, M. Lucio, Z. Zheng, G. Jämerot, C. Tysk, J. K. Jansson and L. Engstrand (2010). "A pyrosequencing study in twins shows that gastrointestinal microbial profiles vary with inflammatory bowel disease phenotypes." Gastroenthology 139: 1844-1854.

Wright, E. K., M. A. Kamm, S M. Teo, M. Inouye, J. Wagner and C. D. Kirkwood (2015). "Recent Advances in Characterizing the Gastrointestinal Microbiome in Crohn's Disease: A Systematic Review." Inflamm Bowel Dis 21: 1219-1228.

Zazzeroni, R., A. Homan, E. Thain (2009). "Determination of γ-aminobutyric acid in food matrices by isotope dilution hydrophilic interaction chromatography coupled to mass spectrometry." Journal of Chromatographic Science 47: 564-568.

Zhou, F., K. Furuhashi, M. J. Son, M. Toyozaki, F. i Yoshizawa, Y. Miura and K. Yagasaki (2017). "Antidiabetic effect of enterolactone in cultured muscle cells and in type 2 diabetic model db/db mice." Cytotechnology 69: 493-502.

Zitomersky, N. L., B. J. Atkinson, S. W. Franklin, P. D. Mitchell, S. B. Snapper, L. E. Comstock and A. Bousvaros (2013). "Characterization of adherent bacteroidales from intestinal biopsies of children and young adults with inflammatory bowel disease." PLoS ONE 8: e63686.

---

That which is claimed:

1. A method for rational design of microbial consortia for benefiting the health of an organism, the method comprising:
   providing genome annotation for a plurality of microbial strains, wherein based on the genome annotation each strain in the plurality has at least one functionality in a set of functionalities comprising:
   synthesis of butyrate, synthesis of propionate, synthesis of indole, deconjugation of bile salt and conversion of bile acid into secondary bile acids, synthesis of a siderophore, uptake of a heterologously produced siderophore, and synthesis of at least one bacteriocin, wherein each of the functionalities in the set of functionalities is present in the plurality of microbial strains;
   creating for each strain in the plurality, based on the genome annotation, an in silico individual metabolic model and, based on the individual metabolic models, predicting an auxotrophic profile for one or a combination of essential nutrients consisting of amino acids, vitamins, or co-factors for each strain;
   obtaining one or more community metabolic models for all or a subset of the plurality of strains through integration in silico of the individual metabolic models, wherein integration of the individual models comprises modeling exchange of the one or a combination of essential nutrients between the strains within each of the one or more community metabolic models;
   determining, based on the community metabolic models, a metabolic interdependency between the strains;
   designating members of the plurality of strains as being part of a designed microbial consortium based on all members of the designed microbial consortium having the metabolic interdependency,
   wherein the metabolic interdependency requires each of the strains to have at least one auxotrophy for the one or a combination of essential nutrients and each to be dependent on at least one of the other strains in the designed microbial consortium for growth,
   wherein each of the functionalities in the set of functionalities is retained and each functionality is present in more than one strain in the designed microbial consortium; and
   combining ex vivo a biologically pure culture of each of the microbial strains in the designed microbial consortium, wherein the designed microbial consortium benefits the health of the organism.

2. The method of claim 1, wherein the metabolic interdependency requires each of the strains in the designed microbial consortium to have at least two auxotrophies for the one or a combination of essential nutrients.

3. The method of claim 1, wherein the organism is a human or an animal and the set of functionalities further comprises synthesis of indole-3-propionate and indole-3-aldehyde and synthesis of 4-amino butyrate (gamma-aminobutyric acid; GABA).

4. The method of claim 1, wherein the organism is a human or an animal and the set of functionalities further comprises: synthesis of indole-3-propionate and indole-3-aldehyde and synthesis of 4-amino butyrate (gamma-aminobutyric acid; GABA), and wherein the health benefited is one or a combination of Ulcerative Colitis, Crohn's Disease, Inflammatory Bowel Disease, or Irritable Bowel Syndrome.

5. The method of claim 1, wherein the organism is a human or an animal and wherein the set of functionalities further comprises: synthesis of indole-3-propionate and indole-3-aldehyde, synthesis of 4-amino butyrate (gamma-amino-butyric acid; GABA), and conversion of secoisolariciresinol diglucoside (SDG) to enterodiol and enterolactone and wherein the health benefited is Type-2 Diabetes.

6. The method of claim 1, further comprising:
   creating one or more additional in silico individual metabolic models corresponding to one or more metabolic support microbial strains and, based on the one or more additional individual metabolic models, predicting an auxotrophic profile for the one or a combination of essential nutrients consisting of amino acids, vitamins, or co-factors for the one or more metabolic support microbial strains, wherein obtaining the one or more community metabolic models includes integration of the one or more additional individual metabolic models corresponding to the one or more metabolic support microbial strains to enhance the metabolic interdependency of the designed microbial consortium, and wherein the one or more metabolic support microbial strain(s) does not necessarily have the at least one functionality.

7. The method of claim 1, wherein the plurality of microbial strains comprises strains from one or a combination of the species: *Megamonas funiformis, Megamonas hypermegale, Acidaminococcus intestini, Bacteroides massiliensis, Bacteroides stercoris, Barnesiella intestinihominis, Faecalibacteriumprausnitzii, Subdoligranulum variabile, Anaerostipes caccae, Anaerostipes hadrus, Clostridium symbiosum, Clostridium scindens, Clostridium bolteae, Clostridium saccharogumia, Clostridium ramosum, Blautia producta, Blautia hydrogenotrophica, Marvinbryantia formatexigens, Lactonifactor longoviformis,* or *Akkermansia muciniphila.*

8. The method of claim 1, wherein the plurality of microbial strains comprises strains from species of: *Megamonas funiformis, Megamonas hypermegale, Acidaminococcus intestini, Bacteroides massiliensis, Bacteroides stercoris, Barnesiella intestinihominis, Faecalibacterium prausnitzii, Subdoligranulum variabile, Anaerostipes caccae, Anaerostipes hadrus, Clostridium symbiosum, Clostridium bolteae, Blautia hydrogenotrophica, Marvinbryantia formatexigens, Clostridium scindens, Blautia producta,* and *Akkermansia muciniphila.*

9. The method of claim 1, further comprising administering to an animal or a human the combined biologically pure cultures of the plurality of microbial strains in the designed microbial consortium.

10. The method of claim 9, wherein the health benefited is for the treatment of Ulcerative Colitis, Crohn's Disease, Inflammatory Bowel Disease, Irritable Bowel Syndrome, or diabetes.

* * * * *

SEQUENCE LISTING

```
<160> NUMBER OF SEQ ID NOS: 21

<210> SEQ ID NO 1
<211> LENGTH: 1521
<212> TYPE: DNA
<213> ORGANISM: Dialister succinatiphilus
<220> FEATURE:
<221> NAME/KEY: misc_feature
<222> LOCATION: (1)..(1521)
<220> FEATURE:
<221> NAME/KEY: misc_feature
<222> LOCATION: (1)..(1521)
<223> OTHER INFORMATION: DSM21274 16S rRNA gene

<400> SEQUENCE: 1
gacgaacgct ggcggcgtgc ttaacacatg caagtcgaac gagaggacaa gagaagcttg      60
cttcttttgg aatcgagtgg caaacgggtg agtaacacgt aaacaacctg ccttcaggat     120
ggggacaaca gacggaaacg actgctaata ccgaatacgc ttgggagacc gcatgatctt     180
ccaaggaaag ggtggcctct acctgtaagc tatcgcctga agagggtttt gcgtctgatt     240
aggcagttgg tgaggtaacg gcccaccaaa cctacgatca gtagccggtc tgagaggatg     300
aacggccaca ctggaactga gacacggtcc agactcctac gggaggcagc agtggggaat     360
cttccgcaat gggcgaaagc ctgacggagc aacgccgcgt gagtgatgac ggccttcggg     420
```

```
ttgtaaagct ctgtgatcgg ggacgaacgg tccgtaagct aataccttat ggaagtgacg    480
gtacccgaat agcaagccac ggctaactac gtgccagcag ccgcggtaat acgtaggtgg    540
caagcgttgt ccggaattat tgggcgtaaa gcgcgcgcag gcggctttct aagtccatct    600
taaaagtgcg gggcttaacc ccgtgatggg atggaaactg gaagctgga gtatcggaga     660 ggaaagtgga attcctagtg tagcggtgaa atgcgtagag attaggaaga acaccggtgg    720
cgaaggcgac tttctggacg acaactgacg ctgaggcgcg aaagcgtggg gagcaaacag    780
gattagatac cctggtagtc cacgccgtaa acgatgaata ctaggtgtag gaggtatcga    840 cccttctgt gccggagcta acacaataag tattccgcct gggaagtacg atcgcaagat     900
taaaactcaa aggaattgac ggggcccgc acaagcggtg gagtatgtgg tttaattcga     960
cgcaacgcga gaaccttac caggtcttga cattgatcgc cattcacaga aatgtgaagt    1020
tctccttcgg gagacgagaa aacaggtggt gcacggctgt cgtcagctcg tgtcgtgaga   1080
tgttgggtta agtcccgcaa cgagcgcaac ccctatctta tgttaccagc acgttatggt   1140
ggggactcat gagagaccgc cgcggacaac gcggaggaag gtggggatga cgtcaagtca   1200
tcatgcccct tatgacctgg gctacacacg tactacaatg ggtgtcaaca agagaagcg    1260 aaaccgcgag gtggagcgaa cctcaaaaac acaccccag ttcagattgc aggctgcaac    1320
ccgcctgcat gaagtaggaa tcgctagtaa tcgcgggtca gcataccgcg gtgaatacgt   1380
tcccgggcct tgtacacacc gcccgtcaca ctatgagagt cggaaacacc cgaagccggt    1440
gaggtaaccg caaggagcca gccgtcgaag gtggagctga tgattggagt gaagtcgtaa    1500
caaggtagcc gtatcggaag g                                              1521
```

<210> SEQ ID NO 2
<211> LENGTH: 1342
<212> TYPE: DNA
<213> ORGANISM: Megamonas funiformis
<220> FEATURE:
<221> NAME/KEY: misc_feature
<222> LOCATION: (1)..(1342)
<223> OTHER INFORMATION: DSM19343 16S rRNA gene

<400> SEQUENCE: 2

```
ctttgacata agcttccgct tgaagatgag cttgcgtctg attagctagt tggtgagggt     60
aaaggcccac caaggcgacg atcagtagcc ggtctgagag gatgaacggc cacattggga    120
ctgagacacg gcccagactc ctacgggagg cagcagtggg gaatcttccg caatgggcga    180
aagcctgacg gagcaacgcc gcgtgaacga tgaaggtctt aggatcgtaa agttctgttg    240
ttagggacga aggataagga ttataataca gtctttgttt gacggtacct aacgaggaag    300
ccacggctaa ctacgtgcca gcagccgcgg taatacgtag gcggcaagcg ttgtccggaa    360
ttattgggcg taaagggagc gcaggcggga aactaagcgg atcttaaaag tgcggggctc    420
aaccccgtga tggggtccga actggtttttc ttgagtgcag gagaggaaag cggaattccc    480
agtgtagcgg tgaaatgcgt agatattggg aagaacacca gtggcgaagg cggctttctg    540
gactgtaact gacgctgagg ctcgaaagct agggtagcga acgggattag ataccccggt    600
agtcctagcc gtaaacgatg gatactaggt gtggaggta tcgactcctt ccgtgccgga    660
gttaacgcaa taagtatccc gcctggggag tacggccgca aggttgaaac tcaaaggaat    720
tgacgggggc ccgcacaagc ggtggagtat gtggtttaat tcgacgcaac gcgaagaacc    780
ttaccaagac ttgacattga ttgaaagact tagagataag ttccttctct tcggagaaca    840
agaaaacagg tggtgcatgg ctgtcgtcag ctcgtgtcgt gagatgttgg gttaagtccc    900
```

```
gcaacgagcg caaccccuat actatgttgc cagcatttcg gatgggaact catagtagac   960
tgccgcggac aacgcggagg aaggcgggga tgacgtcaag tcatcatgcc ccttacgtct  1020
tgggctacac acgtactaca atgggatgaa cagagggaag cgaaatcgcg aggtggagcg  1080
gatccctaaa agcatctctc agttcggatt gtaggctgaa actcgcctac atgaagtcgg  1140
aatcgctagt aatcgcaggt cagcatactg cggtgaatac gttcccgggc cttgtacaca  1200
ccgcccgtca caccacgaaa gtcattcaca cccgaagccg gctaagggcc tatggtaccg  1260
accgtctaag gtgggggcga tgattgggt gaagtcgtaa caaggtagcc gtatcggaag  1320
gtgcggctgg atcacctcct ta                                          1342
```

<210> SEQ ID NO 3
<211> LENGTH: 1518
<212> TYPE: DNA
<213> ORGANISM: Megamonas hypermegale
<220> FEATURE:
<221> NAME/KEY: misc_feature
<222> LOCATION: (1)..(1518)
<223> OTHER INFORMATION: DSM1672 16S rRNA gene

<400> SEQUENCE: 3

```
cctggctcag gacgaacgct ggcggcgtgc ttaacacatg caagtcgaac ggggtgttta    60
tttcggtaaa caccaagtgg cgaacgggtg agtaacgcgt aagcaatcta ccttcaagat   120
ggggacaaca cttcgaaagg ggtgctaata ccgaatgaat gagagatgac cgcatggata   180
tttctctaaa ggaggcctct gaaaatgctt ccgcttgaag atgagcttgc gtctgattag   240
ctagttggtg agggtaaagg cccaccaagg cgacgatcag tagccggtct gagaggatga   300
acggccacat tgggactgag acacggccca gactcctacg ggaggcagca gtggggaatc   360
ttccgcaatg ggcgaaagcc tgacggagca acgccgcgtg aacgaagaag gtcttaggat   420
cgtaaagttc tgttgttagg ggcgaagggc aacattttga ataagggtgt tgtttgacgg   480
tacttaacga ggaagccacg gctaactacg tgccagcagc cgcggtaata cgtaggcggc   540
aagcgttgtc cggaattatt gggcgtaaag ggagcgcagg cgggaagtta agcggacttt   600
aaaagtgcgg ggctcaaccc cgtgaggggg tccgaactga ctttcttgag tgcaggagag   660
ggaagcggaa ttcctagtgt agcggtgaaa tgcgtagata ttaggaagaa caccagtggc   720
gaaggcggct ttctggactg taactgacgc tgaggctcga agctagggt agcgaacggg   780 attagatacc ccggtagtcc tagccgtaaa cgatggatac taggtgtggg aggtatcgac   840
cccttccgtg ccggagttaa cgcaataagt atcccgcctg gggagtacgg ccgcaaggtt   900
gaaactcaaa ggaattgacg ggggcccgca caagcggtgg agtatgtggt ttaattcgac   960
gcaacgcgaa gaaccttacc aagacttgac atcgactgac gtagttagag ataagtattt  1020
ttacttcggt aaacaggaag acaggtggtg catggctgtc gtcagctcgt gtcgtgagat  1080
gttgggttaa gtcccgcaac gagcgcaacc cctatactat gttgccagca cgtaaaggtg  1140
ggaactcata gtagactgcc gcggacaacg cggaggaagg cggggatgac gtcaagtcat  1200
catgcccctt acgtcttggg ctacacacgt actacaatgg gatgaacaga gggaagcgaa  1260
gtcgcgaggc agagcggaac cctaaaagca tctctcagtt cggattgcag gctgaaactc  1320
gcctgcatga agtcggaatc gctagtaatc gcaggtcagc atactgcggt gaatacgttc  1380
ccgggccttg tacaccgcc cgtcacacc acgaaagtca ttcacacccg aagccggcta  1440
agggccgaaa ggaaccgacc gtcgaaggtg ggggcgatga ttggggtgaa gtcgtaacaa  1500
```

```
ggtagccgta tcggaagg                                                 1518
```

<210> SEQ ID NO 4
<211> LENGTH: 1439
<212> TYPE: DNA
<213> ORGANISM: Acidaminococcus intestine
<220> FEATURE:
<221> NAME/KEY: misc_feature
<222> LOCATION: (1)..(1439)
<223> OTHER INFORMATION: DSM21505 16S rRNA gene

<400> SEQUENCE: 4

```
gcggagactt atttcggtaa gttcttagtg gcgaacgggt gagtaacgcg tgggcaacct    60
gccctccagt tgggacaac  attccgaaag ggatgctaat accgaatgtg ctccctcctc   120
cgcatggagg agggaggaaa gatggcctct gcttgcaagc tatcgctgga agatgggccc   180
gcgtctgatt agctagttgg tgggtaacg  gctcaccaag gcgatgatca gtagccggtc   240
tgagaggatg aacggccaca ttggactga  gacacggccc aaactcctac gggaggcagc   300
agtgggaat  cttccgcaat ggacgaaagt ctgacggagc aacgccgcgt gagtgatgaa   360
ggtcttcgga ttgtaaaact ctgttgttag ggacgaaagc accgtgttcg aacaggtcat   420
ggtgttgacg gtacctaacg aggaagccac ggctaactac gtgccagcag ccgcggtaat   480
acgtaggtgg caagcgttgt ccggaattat tgggcgtaaa gagcatgtag gcgggctttt   540
aagtctgacg tgaaaatgcg gggcttaacc ccgtatggcg ttggatactg gaagtcttga   600
gtgcaggaga ggaaagggga attcccagtg tagcggtgaa atgcgtagat attgggagga   660
acaccagtgg cgaaggcgcc tttctggact gtgtctgacg ctgagatgcg aaagccaggg   720
tagcaaacgg gattagatac cccggtagtc ctggccgtaa acgatggata ctaggtgtag   780
gaggtatcga ccccttctgt gccggagtta acgcaataag tatcccgcct ggggactacg   840
atcgcaagat tgaaactcaa aggaattgac ggggcccgc  acaagcggtg gagtatgtgg   900
tttaattcga cgcaacgcga agaaccttac caaggcttga cattgagtga aagacctaga   960
gataggtccc tcccttcggg gacacgaaaa caggtggtgc atggctgtcg tcagctcgtg  1020
tcgtgagatg ttgggttaag tcccgcaacg agcgcaaccc ctatcctatg ttaccagcgc  1080
gtaatggcgg ggactcatag gagactgcca gggataactt ggaggaaggc ggggatgacg  1140
tcaagtcatc atgcccctta tgtcttgggc tacacacgta ctacaatggt cggcaacaaa  1200
gggcagcgaa accgcgaggt ggagcaaatc ccagaaaccc gaccccagtt cggatcgtag  1260
gctgcaaccc gcctacagtg aagttggaat cgctagtaat cgcaggtcag catactgcgg  1320
tgaatacgtt cccgggcctt gtacacaccg cccgtcacac cacgaaagtt ggtaacaccc  1380
gaagccggtg agataaccctt ttaggagtca gctgtctaag gtggggccga tgattgggg   1439
```

<210> SEQ ID NO 5
<211> LENGTH: 1478
<212> TYPE: DNA
<213> ORGANISM: Bacteroides massiliensis
<220> FEATURE:
<221> NAME/KEY: misc_feature
<222> LOCATION: (1)..(1478)
<223> OTHER INFORMATION: DSM17679 16S rRNA gene

<400> SEQUENCE: 5

```
ggctcaggat gaacgctagc tacaggctta acacatgcaa gtcgaggggc agcatggtct    60
tagcttgcta aggccgatgg cgaccggcgc acgggtgagt aacgcgtatc caacctgcct   120
tacactcttg gacagccttc tgaaagggag attaatacaa gatgttatca tgagtaagca   180
```

```
ttttcgcatg attaaaggtt taccggtgta agatggggat gcgttccatt agatagtagg      240
cggggtaacg gcccacctag tcttcgatgg ataggggttc tgagaggaag gtcccccaca      300
ttggaactga gacacggtcc aaactcctac ggggaggcagc agtgaggaat attggtcaat     360
ggacgagagt ctgaaccagc caagtagcgt gaaggatgaa ggttctatgg attgtaaact      420
tcttttatac gggaataaac ggatccacgt gtggattttt gcatgtaccg tatgaataag     480
gatcggctaa ctccgtgcca gcagccgcgg taatacggag gatccgagcg ttatccggat     540
ttattgggtt taaagggagc gtagatgggt tgttaagtca gttgtgaaag tttgcggctc     600
aaccgtaaaa ttgcaattga tactggcagt cttgagtaca gttgaggtag gcggaattcg     660
tggtgtagcg gtgaaatgct tagatatcac gaagaactcc gattgcgaag gcagcttact     720
aacctgtaac tgacattgat gctcgaaagt gtgggtatca aacaggatta gataccctgg     780
tagtccacac ggtaaacgat gaatactcgc tgtaggcgat atacggtctg cggccaagcg     840
aaagcattaa gtattccacc tggggagtac gccggcaacg tgaaactcaa aggaattga    900 cgggggcccg cacaagcgga ggaacatgtg gtttaattcg atgatacgcg aggaaccttta   960 cccgggctta aattgcaacc gaatatggcg gaaacgctat agctagcaat agcggttgtg   1020
aaggtgctgc atggttgtcg tcagctcgtg ccgtgaggtg tcggcttaag tgccataacg    1080
agcgcaaccc ttgccgatag ttactaacag gtcatgctga ggactctgtc gggactgcca   1140
tcgtaagatg tgaggaaggt ggggatgacg tcaaatcagc acggccctta cgtccggggc    1200
tacacacgtg ttacaatggg gggtacagag ggctgctacc acgcaagtgg atgccaatcc    1260
caaaaacctc tctcagttcg gattgaagtc tgcaacccga cttcatgaag ctggattcgc    1320
tagtaatcgc gcatcagcca cggcgcggt aatacgttcc cgggccttgt acacaccgcc     1380
cgtcaagcca tgggagccgg gggtacctga agtgcgtaac cgcaaggagc gccctagggt    1440
aaaactggtg actggggcta agtcgtaaca aggtaacc                           1478
```

<210> SEQ ID NO 6
<211> LENGTH: 1476
<212> TYPE: DNA
<213> ORGANISM: Bacteroides stercoris
<220> FEATURE:
<221> NAME/KEY: misc_feature
<222> LOCATION: (1)..(1476)
<223> OTHER INFORMATION: ATCC43183 / DSM19555 16S rRNA gene

<400> SEQUENCE: 6

```
tggctcagga tgaacgctag ctacaggctt aacacatgca agtcgagggg cagcatcatc      60
aaagcttgct ttgatggatg gcgaccggcg cacgggtgag taacacgtat ccaacctgcc     120
gacaacactg ggatagcctt tcgaaagaaa gattaatacc ggatggcata gttttcccgc    180
atgggatgat tattaaagaa tttcggttgt cgatggggat gcgttccatt aggcagttgg    240
cggggtaacg gcccaccaaa cctacgatgg ataggggttc tgagaggaag gtcccccaca    300
ttggaactga gacacggtcc aaactcctac ggggaggcagc agtgaggaat attggtcaat    360
ggacgagagt ctgaaccagc caagtagcgt gaaggatgac tgccctatgg gttgtaaact    420
tcttttatac gggaataaag tgagccacgt gtggcttttt gtatgtaccg tatgaataag    480
gatcggctaa ctccgtgcca gcagccgcgg taatacggag gatccgagcg ttatccggat    540
ttattgggtt taaagggagc gtaggcgggt tgttaagtca gttgtgaaag tttgcggctc    600
aaccgtaaaa ttgcagttga tactggcgac cttgagtgca acagaggtag gcggaattcg    660
```

```
tggtgtagcg gtgaaatgct agatatcac gaagaactcc gattgcgaag gcagcttact      720
ggattgtaac tgacgctgat gctcgaaagt gtgggtatca acaggatta gatacactgg      780
tagtccacac agtaaacgat gaatactcgc tgttggcgat atacagtcag cggccaagcg      840
aaagcattaa gtattccacc tggggagtac gccggcaacg gtgaaactca aaggaattga     900
cggggcccg cacaagcgga ggaacatgtg gtttaattcg atgatacgcg aggaaccta      960
cccgggctta aattgcaact gactgaatcg gaaacggttc tttcttcgga cagttgtgaa    1020
ggtgctgcat ggttgtcgtc agctcgtgcc gtgaggtgtc ggcttaagtg ccataacgag    1080
cgcaacccct acgggtagtt accatcaggt tatgctgggg actctacccg gactgccgtc    1140
gtaagatgtg aggaaggtgg ggatgacgtc aaatcagcac ggcccttacg tccggggcta    1200
cacacgtgtt acaatggggg gtacagaagg cagctacacg cgacgtggt gctaatcccg     1260
aaagcctctc tcagttcgga ttggagtctg caacccgact ccatgaagct ggattcgcta    1320
gtaatcgcgc atcagccacg gcgcggtgaa tacgttcccg ggccttgtac acaccgcccg    1380
tcaagccatg aaagccgggg gtacctgaag tacgtaaccg cgaggagcgt cctagggtaa    1440
aactggtgat tggggctaag tcgtaacaag gtaacc                              1476
```

<210> SEQ ID NO 7
<211> LENGTH: 1484
<212> TYPE: DNA
<213> ORGANISM: Barnesiella intestinihominis
<220> FEATURE:
<221> NAME/KEY: misc_feature
<222> LOCATION: (1)..(1484)
<223> OTHER INFORMATION: DSM21032 16S rRNA gene

<400> SEQUENCE: 7

```
gatgaacgct agcgacaggc ctaacacatg caagtcgagg ggcagcgggg aggtagcaat      60
acctttgccg gcgaccggcg cacgggtgag taacacgtat gcaatccacc tgtaacaggg     120
ggataacccg gagaaatccg gactaatacc ccataatatg ggcgctccgc atggagagtt     180
cattaaagag agcaattttg gttacagacg agcatgcgct ccattagcca gttggcgggg     240
taacggccca ccaaagcgac gatggatagg ggttctgaga ggaaggtccc ccacattgga    300
actgagacac ggtccaaact cctacgggag gcagcagtga ggaatattgg tcaatggtcg    360
gcagactgaa ccagccaagt cgcgtgaggg aagacggccc tacggttgt aaacctcttt     420
tgtcggagag taaagtacgc tacgtgtagc gtattgcaag tatccgaaga aaaagcatcg    480
gctaactccg tgccagcagc cgcggtaata cggaggatgc gagcgttatc cggatttatt    540
gggtttaaag ggtgcgtagg cggcacgcca agtcagcggt gaaatttccg ggctcaaccc    600
ggagtgtgcc gttgaaactg gcgagctaga gtacacaaga ggcaggcgga atgcgtggtg    660
tagcggtgaa atgcatagat atcacgcaga accccgattg cgaaggcagc ctgctagggt    720
gaaacagacg ctgaggcacg aaagcgtggg tatcgaacag gattagatac cctggtagtc    780
cacgcagtaa acgatgaata ctaactgttt gcgatacaat gtaagcggta cagcgaaagc    840
gttaagtatt ccacctgggg agtacgccgg caacggtgaa actcaaagga attgacgggg    900
gcccgcacaa gcgaggaac atgtggttta attcgatgat acgcgaggaa ccttacccgg     960
gctcaaacgc aggggaatg tcggtgaaag ccggcagcta gtaatagtca cctgcgaggt    1020
gctgcatggt tgtcgtcagc tcgtgccgtg aggtgtcggc ttaagtgcca taacgagcgc    1080
aacccctatc gacagttact aacgggtgaa gccgaggact ctgtcgagac tgccggcgca    1140
agccgcgagg aaggtgggga tgacgtcaaa tcagcacggc ccttacgtcc ggggcgacac    1200
```

```
acgtgttaca atggcaggta cagaaggcag ccagtcagca atgacgcgcg aatcccgaaa    1260
acctgtctca gttcggattg gagtctgcaa cccgactcca tgaagctgga ttcgctagta    1320
atcgcgcatc agccatggcg cggtgaatac gttcccgggc cttgtacaca ccgcccgtca    1380
agccatggaa gccgggagta cctgaagcat gcaaccgcaa ggagcgtacg aaggtaatac    1440
cggtaactgg ggctaagtcg taacaaggta gccgtaccgg aagg                    1484
```

```
<210> SEQ ID NO 8
<211> LENGTH: 1462
<212> TYPE: DNA
<213> ORGANISM: Faecalibacterium prausnitzii
<220> FEATURE:
<221> NAME/KEY: misc_feature
<222> LOCATION: (1)..(1462)
<223> OTHER INFORMATION: DSM17677 16S rRNA gene

<400> SEQUENCE: 8
```

```
gatcctggct caggcgaacg ctggcggcgc gcctaacaca tgcaagtcga acgagcgaga      60
gagagcttgc tttctcaagc gagtggcgaa cgggtgagta acgcgtgagg aacctgcctc     120
aaagaggggg acaacagttg gaaacgactg ctaataccgc ataagcccac gacccggcat     180
cgggtagagg gaaaaggagc aatccgcttt gagatggcct cgcgtccgat tagctagttg     240
gtgaggtaac ggcccaccaa ggcgacgatc ggtagccgga ctgagaggtt gaacggccac     300
attgggactg agacacggcc cagactccta cgggaggcag cagtggggaa tattgcacaa     360
tgggggaaac cctgatgcag cgacgccgcg tggaggaaga aggtcttcgg attgtaaact     420
cctgttgttg aggaagataa tgacggtact caacaaggaa gtgacggcta actacgtgcc     480
agcagccgcg gtaaaacgta ggtcacaagc gttgtccgga attactgggt gtaaagggag     540
cgcaggcggg aaggcaagtt ggaagtgaaa tccatgggct caacccatga actgctttca     600
aaactgtttt tcttgagtag tgcagaggta ggcggaattc ccggtgtagc ggtggaatgc     660
gtagatatcg gaggaacac cagtggcgaa ggcggcctac tgggcaccaa ctgacgctga     720
ggctcgaaag tgtgggtagc aaacaggatt agataccctg gtagtccaca ctgtggccga     780
tgtttactag gtgttggagg attgacccct tcagtgccgc agttaacaca ataagtaatc     840
cacctgggga gtacgaccgc aaggttgaaa ctcaaaggaa ttgacggggg cccgcacaag     900
cagtggagta tgtggtttaa ttcgacgcaa cgcgaagaac cttaccaagt cttgacatcc     960
tgcgacgcac atagaaatat gtgtttcctt cgggacgcag agacaggtgg tgcatggttg    1020
tcgtcagctc gtgtcgtgag atgttgggtt aagtcccgca acgagcgcaa cccttatggt    1080
cagttactac gcaagaggac tctggccaga ctgccgttga caaaacggag gaaggtgggg    1140
atgacgtcaa atcatcatgc cctttatgac ttgggctaca cacgtactac aatggcgtta    1200
aacaaagaga agcaagaccg cgaggtggag caaaactcag aaacaacgtc ccagttcgga    1260
ctgcaggctg caactcgcct gcacgaagtc ggaattgcta gtaatcgcag atcagcatgc    1320
tgcggtgaat acgttcccgg gccttgtaca caccgcccgt cacaccatga gagccggggg    1380
gacccgaagt cggtagtcta accgcaagga ggacgccgcc gaaggtaaaa ctggtgattg    1440
gggtgaagtc gtaacaaggt ac                                             1462
```

```
<210> SEQ ID NO 9
<211> LENGTH: 1428
<212> TYPE: DNA
<213> ORGANISM: Subdoligranulum variabile
<220> FEATURE:
```

<221> NAME/KEY: misc_feature
<222> LOCATION: (1)..(1428)
<223> OTHER INFORMATION: DSM15176 16S rRNA gene
<220> FEATURE:
<221> NAME/KEY: misc_feature
<222> LOCATION: (1189)..(1189)
<223> OTHER INFORMATION: n at position 1189 can be nucleotide a, t, c,
    or g

<400> SEQUENCE: 9

```
tgcaagtcga acggagttat ttcggttgaa gttttcggat ggatactggt ttaacttagt    60
ggcgaacggg tgagtaacgc gtgagtaacc tgccctggag tggggacaa cagttggaaa    120
cgactgctaa taccgcataa gcccacgatc cggcatcgga ttgagggaaa aggatttatt    180
cgcttcagga tggactcgcg tccaattagc tagttggtga ggtaacggcc caccaaggcg    240
acgattggta gccggactga gaggttgaac ggccacattg ggactgagac acggcccaga    300
ctcctacggg aggcagcagt gggggatatt gcacaatggg ggaaaccctg atgcagcgac    360
gccgcgtgga ggaagaaggt tttcggattg taaactcctg tcgttaggga cgaatcttga    420
cggtacctaa caagaaagca ccggctaact acgtgccagc agccgcggta aaacgtaggg    480
tgcaagcgtt gtccggaatt actgggtgta aaggagcgc aggcggaccg gcaagttgga    540
agtgaaatct atgggctcaa cccataaatt gctttcaaaa ctgctggcct tgagtagtgc    600
agaggtaggt ggaattcccg gtgtagcggt ggaatgcgta gatatcggga ggaacaccag    660
tggcgaaggc gacctactgg gcaccaactg acgctgaggc tcgaaagcat gggtagcaaa    720
caggattaga taccctggta gtccatgccg taaacgatga ttactaggtg ttggaggatt    780
gacccccttca gtgccgcagt taacacaata agtaatccac ctggggagta cgaccgcaag    840
gttgaaactc aaaggaattg acgggggccc gcacaagcag tggagtatgt ggtttaattc    900
gaagcaacgc gaagaacctt accaggtctt gacatccgat gcatagtgca gagatgcatg    960
aagtccttcg ggacatcgag acaggtggtg catggttgtc gtcagctcgt gtcgtgagat    1020
gttgggttaa gtcccgcaac gagcgcaacc cttattgcca gttactacgc aagaggactc    1080
tggcgagact gccgttgaca aaacggagga aggtggggat gacgtcaaat catcatgccc    1140
tttatgacct gggctacaca cgtactacaa tggcgtttaa caaagagang caagaccgcg    1200
aggtggagca aaactcaaaa acaacgtctc agttcagatt gcaggctgca actcgcctgc    1260
atgaagtcgg aattgctagt aatcgcggat cagcatgccg cggtgaatac gttcccgggc    1320
cttgtacaca ccgcccgtca caccatgaga gccgggggg acccgaagtc ggtaagtaag    1380
tctaaccgca aggaggacgc cgccgaaggt aaaactggtg attgggtg               1428
```

<210> SEQ ID NO 10
<211> LENGTH: 1456
<212> TYPE: DNA
<213> ORGANISM: Anaerostipes caccae
<220> FEATURE:
<221> NAME/KEY: misc_feature
<222> LOCATION: (1)..(1456)
<223> OTHER INFORMATION: DSM14662 16S rRNA gene

<400> SEQUENCE: 10

```
gcgcttaata catgtcaagt cgaacgaagc atttaggatt gaagttttcg gatggatttc    60
ctatatgact gagtggcgga cgggtgagta acgcgtgggg aacctgccct atacaggggg    120
ataacagctg gaaacggctg ctaataccgc ataagcgcac agaatcgcat gattcagtgt    180
gaaaagccct ggcagtatag gatggtcccg cgtctgatta gctggttggt gaggtaacgg    240
```

| | | |
|---|---|---|
| ctcaccaagg cgacgatcag tagccggctt gagagagtga acggccacat tgggactgag | 300 | |
| acacggccca aactcctacg ggaggcagca gtggggaata ttgcacaatg ggggtaaacc | 360 | |
| ctgatgcagc gacgccgcgt gagtgaagaa gtatttcggt atgtaaagct ctatcagcag | 420 | |
| ggaagaaaac agacggtacc tgactaagaa gccccggcta actacgtgcc agcagccgcg | 480 | |
| gtaatacgta gggggcaagc gttatccgga attactgggt gtaaagggtg cgtaggtggc | 540 | |
| atggtaagtc agaagtgaaa gcccggggct aaccccggg actgcttttg aaactgtcat | 600 | |
| gctggagtgc aggagaggta agcggaattc ctagtgtagc ggtgaaatgc gtagatatta | 660 | |
| ggaggaacac cagtggcgaa ggcggcttac tggactgtca ctgacactga tgcacgaaag | 720 | |
| cgtggggagc aaacaggatt agataccctg gtagtccacg ccgtaaacga tgaatactag | 780 | |
| gtgtcgggc cgtagaggct tcggtgccgc agcaaacgca gtaagtattc cacctgggga | 840 | |
| gtacgttcgc aagaatgaaa ctcaaaggaa ttgacgggga cccgcacaag cggtggagca | 900 | |
| tgtggtttaa ttcgaagcaa cgcgaagaac cttacctggt cttgacatcc caatgaccga | 960 | |
| accttaaccg gtttttctt tcgagacatt ggagacaggt ggtgcatggt tgtcgtcagc | 1020 | |
| tcgtgtcgtg agatgttggg ttaagtcccg caacgagcgc aaccctatc tttagtagcc | 1080 | |
| agcatttaag gtgggcactc tagagagact gccaggata acctggagga aggtggggac | 1140 | |
| gacgtcaaat catcatgccc cttatggcca gggctacaca cgtgctacaa tggcgtaaac | 1200 | |
| aaagggaagc gaagtcgtga ggcgaagcaa atcccgaaaa taacgtctca gttcggattg | 1260 | |
| tagtctgcaa ctcgactaca tgaagctgga atcgctagta atcgtgaatc agaatgtcac | 1320 | |
| ggtgaatacg ttcccgggtc ttgtacacac cgcccgtcac accatgggag tcagtaacgc | 1380 | |
| ccgaagtcag tgacccaacc gcaaggaggg agctgccgaa ggtgggaccg ataactgggg | 1440 | |
| tgaagtcgta acaagg | 1456 | |

<210> SEQ ID NO 11
<211> LENGTH: 1616
<212> TYPE: DNA
<213> ORGANISM: Anaerostipes hadrus
<220> FEATURE:
<221> NAME/KEY: misc_feature
<222> LOCATION: (1)..(1616)
<223> OTHER INFORMATION: DSM 3319 / ATCC 29173 16S rRNA gene

<400> SEQUENCE: 11

| | | |
|---|---|---|
| tttgatcctg gctcaggatg aacgctggcg gcgtgcttaa cacatgcaag tcgaacgaaa | 60 | |
| caccttattt gattttcttc ggaactgaag atttggtgat tgagtggcgg acgggtgagt | 120 | |
| aacgcgtggg taacctgccc tgtacagggg gataacagtc agaaatgact gctaataccg | 180 | |
| cataagacca cagcaccgca tggtgcaggg gtaaaaactc cggtggtaca ggatggaccc | 240 | |
| gcgtctgatt agctggttgg tgaggtaacg gctcaccaag gcgacgatca gtagccggct | 300 | |
| tgagagagtg aacggccaca tgggactga gacacggccc aaactcctac gggaggcagc | 360 | |
| agtggggaat attgcacaat gggggaaacc ctgatgcagc gacgccgcgt gagtgaagaa | 420 | |
| gtatctcggt atgtaaagct ctatcagcag ggaagaaaat gacggtacct gactaagaag | 480 | |
| ccccggctaa ctacgtgcca gcagccgcgg taatacgtag ggggcaagcg ttatccggaa | 540 | |
| ttactgggtg taaagggtgc gtaggtggta tggcaagtca gaagtgaaaa cccagggctt | 600 | |
| aactctggga ctgcttttga aactgtcaga ctggagtgca ggagaggtaa gcggaattcc | 660 | |
| tagtgtagcg gtgaaatgcg tagatattag gaggaacatc agtggcgaag gcggcttact | 720 | |
| ggactgaaac tgacactgag gcacgaaagc gtggggagca aacaggatta gataccctgg | 780 | |

```
tagtccacgc cgtaaacgat gaatactagg tgtcggggcc gtaggggctt cggtgccgca      840
gccaacgcag taagtattcc acctgggagg tacgttcgca agaatgaaac tcaaaggaat      900
tgacggggac ccgcacaagc ggtggagcat gtggtttaat tcgaagcaac gcgaagaacc      960
ttacctggtc ttgacatcct tctgaccggt ccttaaccgg accttttcctt cgggacagga    1020 gagacaggtg gtgcatggtt gtcgtcagct cgtgtcgtga gatgttgggt taagtcccgc    1080
aacgagcgca accctatctt tagtagcca gcatataagg tgggcactct agagagactg     1140
ccagggataa cctggaggaa ggtggggacg acgtcaaatc atcatgcccc ttatgaccag     1200
ggctacacac gtgctacaat ggcgtaaaca gagggaagca gcctcgtgag agtgagcaaa     1260
tcccaaaaat aacgtctcag ttcggattgt agtctgcaac tcgactacat gaagctggaa     1320
tcgctagtaa tcgcgaatca gaatgtcgcg gtgaatacgt tcccgggtct tgtacacacc     1380
gcccgtcaca ccatgggagt cagtaacgcc cgaagtcagt gacccaaccg taaggaggga     1440
gctgccgaag gcgggaccga taactggggt gaagtcgtaa caaggtagcc gtatcggaag     1500
gtgcggctgg atcacctcct ttctaatccc gcggccatgg cggccgggag catgcgacgt     1560
cgggcccaat tcgccctata gtgagtcgta ttacaattca ctggccgtcg tttaaa        1616
```

<210> SEQ ID NO 12  
<211> LENGTH: 1492  
<212> TYPE: DNA  
<213> ORGANISM: Clostridium symbiosum  
<220> FEATURE:  
<221> NAME/KEY: misc_feature  
<222> LOCATION: (1)..(1492)  
<223> OTHER INFORMATION: ATCC14940 16S rRNA gene  
<220> FEATURE:  
<221> NAME/KEY: misc_feature  
<222> LOCATION: (66)..(66)  
<223> OTHER INFORMATION: n at position 66 can be nucleotide a, t, c, or g  
<220> FEATURE:  
<221> NAME/KEY: misc_feature  
<222> LOCATION: (199)..(199)  
<223> OTHER INFORMATION: n at position 199 can be nucleotide a, t, c, or g

<400> SEQUENCE: 12

```
agagtttgat cctggctcag gatgaacgct ggcggcgtgc ctaacacatg caagtcgaac       60
gaagcnattt aacggaagtt ttcggatgga agttgaattg actgagtggc ggacgggtga      120
gtaacgcgtg gtaacctgc cttgtactgg gggacaacag ttagaaatga ctgctaatac      180
cgcataagcg cacagtatng catgatacag tgtgaaaaac tccggtggta caagatggac      240
ccgcgtctga ttagctagtt ggtaaggtaa cggcttacca aggcgacgat cagtagccga     300
cctgagaggg tgaccggcca cattgggact gagacacggc ccaaactcct acggaggca     360 gcagtgggga atattgcaca atgggcgaaa gcctgatgca gcgacgccgc gtgagtgaag    420
aagtatttcg gtatgtaaag ctctatcagc agggaagaaa atgacggtac ctgactaaga    480
agccccggct aactacgtgc cagcagccgc ggtaatacgt aggggggcaag cgttatccgg   540 atttactggg tgtaaaggga gcgtagacgg taaagcaagt ctgaagtgaa agcccgcggc   600
tcaactgcgg gactgctttg gaaactgttt aactggagtg tcgagaggt aagtggaatt    660 cctagtgtag cggtgaaatg cgtagatatt aggaggaaca ccagtggcga aggcgactta    720
ctggacgata actgacgttg aggctcgaaa gcgtggggag caaacaggat tagataccct    780
ggtagtccac gccgtaaacg atgaatacta ggtgttgggg agcaaagctc ttcggtgccg   840
```

-continued

```
tcgcaaacgc agtaagtatt ccacctgggg agtacgttcg caagaatgaa actcaaagga      900
attgacgggg acccgcacaa gcggtggagc atgtggttta attcgaagca acgcgaagaa      960
ccttaccagg tcttgacatc gatccgacgg gggagtaacg tccccttccc ttcggggcgg     1020
agaagacagg tggtgcatgg ttgtcgtcag ctcgtgtcgt gagatgttgg gttaagtccc     1080
gcaacgagcg caacccttat tctaagtagc cagcggttcg gccgggaact cttgggagac     1140
tgccagggat aacctggagg aaggtgggga tgacgtcaaa tcatcatgcc ccttatgatc     1200
tgggctacac acgtgctaca atggcgtaaa caaagagaag caagaccgcg aggtggagca     1260
aatctcaaaa ataacgtctc agttcggact gcaggctgca actcgcctgc acgaagctgg     1320
aatcgctagt aatcgcgaat cagaatgtcg cggtgaatac gttcccgggt cttgtacaca     1380
ccgcccgtca caccatggga gtcagtaacg cccgaagtca gtgacccaac cgcaaggagg     1440
gagctgccga aggcgggacc gataactggg gtgaagtcgt aacaaggtaa cc             1492
```

<210> SEQ ID NO 13
<211> LENGTH: 1498
<212> TYPE: DNA
<213> ORGANISM: Clostridium boltea
<220> FEATURE:
<221> NAME/KEY: misc_feature
<222> LOCATION: (1)..(1498)
<223> OTHER INFORMATION: ATCC BAA-613 16S rRNA gene

<400> SEQUENCE: 13

```
agagtttgat cctggctcag gatgaacgct ggcggcgtgc ctaacacatg caagtcgaac       60
gaagcaatta aaatgaagtt ttcggatgga tttttaattg actgagtggc ggacgggtga      120
gtaacgcgtg gataacctgc ctcacactgg gggataacag ttagaaatga ctgctaatac      180
cgcataagcg cacagtgccg catggtacag tgtgaaaaac tccggtggtg tgagatggat      240
ccgcgtctga ttagccagtt ggcggggtaa cggcccacca aagcgacgat cagtagccga      300
cctgagaggg tgaccggcca cattgggact gagacacggc ccaaactcct acggaggca      360
gcagtgggga atattgcaca atgggcgaaa gcctgatgca gcgacgccgc gtgagtgaag      420
aagtatttcg gtatgtaaag ctctatcagc agggaagaaa atgacggtac ctgactaaga      480
agccccggct aactacgtgc cagcagccgc ggtaatacgt aggggcaag cgttatccgg      540
atttactggg tgtaaaggga gcgtagacgg cgaagcaagt ctgaagtgaa acccagggc      600
tcaaccctgg gactgctttg gaaactgttt tgctagagtg tcggagaggt aagtggaatt      660
cctagtgtag cggtgaaatg cgtagatatt aggaggaaca ccagtggcga aggcggctta      720
ctggacgata actgacgttg aggctcgaaa gcgtggggag caaacaggat tagataccct      780
ggtagtccac gccgtaaacg atgaatgcta ggtgttgggg gcaaagccc ttcggtgccg      840
tcgcaaacgc agtaagcatt ccgcctgggg agtacgttcg caagaatgaa actcaaagga      900
attgacgggg acccgcacaa gcggtggagc atgtggttta attcgaagca acgcgaagaa      960
ccttaccaag tcttgacatc ctcttgaccg gcgtgtaacg cgccttccc ttcggggcaa     1020
gagagacagg tggtgcatgg ttgtcgtcag ctcgtgtcgt gagatgttgg gttaagtccc     1080
gcaacgagcg caacccttat ccttagtagc cagcaggtag agctgggcac tctagggaga     1140
ctgccaggga taacctggag gaaggtgggg atgacgtcaa atcatcatgc ccttatgat     1200
ttgggctaca cacgtgctac aatggcgtaa acaaagggaa gcaaggcagt gatgtggagc     1260
aaatcccaaa ataacgtcc cagttcggac tgtagtctgc aacccgacta cacgaagctg     1320
gaatcgctag taatcgcgaa tcagaatgtc gcggtgaata cgttcccggg tcttgtacac     1380
```

```
accgcccgtc acaccatggg agtcagcaac gcccgaagtc agtgacccaa ctcgcaagag   1440
agggagctgc cgaaggcggg gcaggtaact ggggtgaagt cgtaacaagg taaccgta    1498

<210> SEQ ID NO 14
<211> LENGTH: 1427
<212> TYPE: DNA
<213> ORGANISM: Blautia producta
<220> FEATURE:
<221> NAME/KEY: misc_feature
<222> LOCATION: (1)..(1427)
<223> OTHER INFORMATION: DSM2950 16S rRNA gene

<400> SEQUENCE: 14
tatcctggct caggatgaac gctggcggcg tgcttaacac atgcaagtcg agcgaagcac     60
taagacagat ttcttcggat tgaagccttt gtgactgagc ggcggacggg tgagtaacgc    120
gtgggtagcc tacctcatac aggggaataa cagttagaaa tgactgctaa taccgcataa    180
gcgcacagga ccgcatggtc tggtgtgaaa actccggtg gtatgagatg acccgcgtc    240 tgattagcta gttggagggg taacggccca ccaaggcgac gatcagtagc cggcctgaga    300
gggtgaacgg ccacattggg actgagacac ggcccagact cctacgggag gcagcagtgg    360
ggaatattgc acaatggggg gaaccctgat gcagcgacgc cgcgtgaagg aagaagtatc    420
tcggtatgta aacttctatc agcagggaag aaaatgacgg tacctgacta agaagccccg    480
gctaactacg tgccagcagc cgcggtaata cgtaggggc aagcgttatc cggatttact    540
gggtgtaaag ggagcgtaga cggaagagca agtctgatgt gaaaggctgg ggcttaaccc    600
caggactgca ttggaaactg ttgttctaga gtgccggaga ggtaagcgga attcctagtg    660
tagcggtgaa atgcgtagat attaggagga acaccagtgg cgaaggcggc ttactggacg    720
gtaactgacg ttgaggctcg aaagcgtggg gagcaaacag gattagatac cctggtagtc    780
cacgccgtaa acgatgaata ctaggtgtcg ggtggctaag ccattcggtg ccgcagcaaa    840
cgcaataagt attccacctg gggagtacgt tcgcaagaat gaaactcaaa ggaattgacg    900
gggacccgca caagcggtgg agcatgtggt ttaattcgaa gcaacgcgaa gaaccttacc    960
aagtcttgac atccctctga ccgycccgta acggggrttt ccttcgggg cagaggagac   1020 aggtggtgca tggttgtcgt cagctcgtgt cgtgagatgt tgggttaagt cccgcaacga   1080 gcgcaacccct tatccttagt agccagcaya tgatggtggg cactctaggg agactgccgg   1140
ggataacccg agggaaggcg gggacgacgt caaatcatca tgccccttat gatttgggct   1200
acacacgtgc tacaatggcg taaacaaagg gaagcgagag agcgatgttg agcgaatccc   1260
aaaaataacg tcccagttcg gactgcagtc tgcaactcga ctgcacgaag ctggaatcgc   1320
tagtaatcgc ggatcagaat gccgcggtga atacgttccc gggtcttgta cacaccgccc   1380
gtcacaccat gggagtcagt aacgcccgaa gtcagtgacc taaccga            1427

<210> SEQ ID NO 15
<211> LENGTH: 1458
<212> TYPE: DNA
<213> ORGANISM: Blautia hydrogenotrophica
<220> FEATURE:
<221> NAME/KEY: misc_feature
<222> LOCATION: (1)..(1458)
<223> OTHER INFORMATION: DSM 10507 16S rRNA gene
<220> FEATURE:
<221> NAME/KEY: misc_feature
<222> LOCATION: (1416)..(1416)
<223> OTHER INFORMATION: n at position 1416 can be nucleotide a, t, c,
      or g
```

<400> SEQUENCE: 15

```
gatgaacgct ggcggcgtgc ttaacacatg caagtcgaac gaagcgatag agaacggaga      60
tttcggttga agttttctat tgactgagtg gcggacgggt gagtaacgcg tgggtaacct     120
gccctataca gggggataac agttagaaat gactgctaat accgcataag cgcacagctt     180
cgcatgaagc ggtgtgaaaa actgaggtgg tataggatgg acccgcgttg gattagctag     240
ttggtgaggt aacggcccac caaggcgacg atccatagcc ggcctgagag ggtgaacggc     300
cacattggga ctgagacacg gcccaaactc ctacgggagg cagcagtggg gaatattgca     360
caatggggga accctgatgc agcgacgccg cgtgaagga agaagtatct cggtatgtaa      420
acttctatca gcagggaaga aagtgacggt acctgactaa gaagccccgg ctaattacgt     480
gccagcagcc gcggtaatac gtaaggggca agcgttatcc ggatttactg ggtgtaaagg     540
gagcgtagac ggtttggcaa gtctgatgtg aaaggcatgg gctcaacctg tggactgcat     600
tggaaactgt cagacttgag tgccggagag gcaagcggaa ttcctagtgt agcggtgaaa     660
tgcgtagata ttaggaggaa caccagtggc gaaggcggcc tgctggacgg taactgacgt     720
tgaggctcga aagcgtgggg agcaaacagg attagatacc ctggtagtcc acgctgtaaa     780
cgatgaatac taggtgtcgg gtggcaaagc cattcggtgc cgcagcaaac gcaataagta     840
ttcccacctg gggagtacgt tcgcaagaat gaaactcaaa ggaattgacg ggacccgca      900
caagcggtgg agcatgtggt ttaattcgaa gcaacgcgaa gaaccttacc aaatcttgac     960
atccctctga ccgggaagta atgttcccctt tcttcggaa cagaggagac aggtggtgca    1020
tggttgtcgt cagctcgtgt cgtgagatgt tgggttaagt cccgcaacga gcgcaaccct    1080
tattcttagt agccagcagg tagagctggg cactctaggg agactgccag ggataacctg    1140
gaggaaggtg gggatgacgt caaatcatca tgccccttat gatttgggct acacacgtgc    1200
tacaatggcg taaacaaagg gaagcgaagg ggtgacctgg agcaaatctc aaaaataacg    1260
tctcagttcg gattgtagtc tgcaactcga ctacatgaag ctggaatcgc tagtaatcgc    1320
gaatcagaat gtcgcggtga atacgttccc gggtcttgta cacaccgccc gtcacaccat    1380
gggagtcagt aacgcccgaa gtcagtgacc caaccnaaag gagggagctg ccgaaggtgg    1440
gactgataac tggggtga                                                  1458
```

<210> SEQ ID NO 16
<211> LENGTH: 1456
<212> TYPE: DNA
<213> ORGANISM: Marvinbryantia formatexigens
<220> FEATURE:
<221> NAME/KEY: misc_feature
<222> LOCATION: (1)..(1456)
<223> OTHER INFORMATION: DSM14469 16S rRNA gene

<400> SEQUENCE: 16

```
tggcggcgtg cttaacacat gcaagtcgag cgaagcattt taaatgaagt tttcggacgg      60
aatttaaaat gactgagcgg cggacgggtg agtaacgcgt ggataacctg ccttatacag     120
ggggataaca gccagaaatg gctgctaata ccgcataagc gcacggtacc gcatggtaca     180
gtgtgaaaaa ctccggtggt ataagatggg tccgcgttgg attaggcagt tggcggggta     240
aaggcccacc aaaccgacga tccatagccg gcctgagagg gtggacggcc acattgggac     300
tgagacacgg cccagactcc tacgggaggc agcagtgggg aatattgcac aatggggaa      360
accctgatgc agcgacgccg cgtgggtgaa gaagtatttc ggtatgtaaa gccctatcag     420
```

```
cagggaagaa aatgacggta cctgaccaag aagccccggc taactacgtg ccagcagccg    480
cggtaatacg taggggggcaa gcgttatccg gatttactgg gtgtaaaggg agcgtagacg    540
gccatgcaag tctggtgtga aaggcggggg ctcaacccccc ggactgcatt ggaaactgta    600
tggcttgagt gccggagagg taagcggaat tcctggtgta gcggtgaaat gcgtagatat    660
caggaggaac accagtggcg aaggcggctt actggacggt aactgacgtt gaggctcgaa    720
agcgtgggga gcaaacagga ttagataccc tggtagtcca cgccgtaaac gatgaatacc    780
aggtgtcggg ggacacggtc cttcggtgcc gcagcaaacg cactaagtat tccacctggg    840
gagtacgttc gcaagaatga aactcaaagg aattgacggg gacccgcaca agcggtggag    900
catgtggttt aattcgaagc aacgcgaaga accttaccag gtcttgacat ccggacgacc    960
ggacagtaac gtgtccttcc cttcggggcg tccgagacag gtggtgcatg gttgtcgtca    1020
gctcgtgtcg tgagatgttg ggttaagtcc cgcaacgagc gcaacccctg ttcccagtag    1080
ccagcattca ggatgggcac tctggggaga ctgccaggga taacctggag gaaggcgggg    1140
atgacgtcaa atcatcatgc cccttatgat ctgggctaca cacgtgctac aatggcgtga    1200
acagagggaa gcgaacccgc gaggggggagc aaatcccaga ataacgtcc cagttcggat    1260 tgtagtctgc aacccggcta catgaagctg gaatcgctag taatcgcgga tcagcatgcc    1320
gcggtgaata cgttcccggg tcttgtacac accgcccgtc acaccatggg agtcggaaat    1380
gcccgaagtc agtgacccaa ccggaaggag ggagctgccg aaggcggggc cggtaactgg    1440
ggtgaagtcg taacaa    1456

<210> SEQ ID NO 17
<211> LENGTH: 1529
<212> TYPE: DNA
<213> ORGANISM: Clostridium scindens
<220> FEATURE:
<221> NAME/KEY: misc_feature
<222> LOCATION: (1)..(1529)
<223> OTHER INFORMATION: ATCC35704 16S rRNA gene

<400> SEQUENCE: 17
gagagtttga tcctggctca ggatgaacgc tggcggcgtg cctaacacat gcaagtcgaa    60
cgaagcgcct ggccccgact tcttcggaac gaggagcctt gcgactgagt ggcggacggg    120
tgagtaacgc gtgggcaacc tgccttgcac tgggggataa cagccagaaa tggctgctaa    180
taccgcataa gaccgaagcg ccgcatggcg cggcggccaa agccccggcg gtgcaagatg    240
ggcccgcgtc tgattaggta gttggcgggg taacggccca ccaagccgac gatcagtagc    300
cgacctgaga gggtgaccgg ccacattggg actgagacac ggcccagact cctacgggag    360
gcagcagtgg ggaatattgc acaatggggg aaaccctgat gcagcgacgc cgcgtgaagg    420
atgaagtatt tcggtatgta aacttctatc agcagggaag aagatgacgg tacctgacta    480
agaagccccg gctaactacg tgccagcagc cgcggtaata cgtaggggcc aagcgttatc    540
cggatttact gggtgtaaag ggagcgtaga cggcgatgca agccagatgt gaaagcccgg    600
ggctcaaccc cgggactgca tttggaactg cgtggctgga gtgtcggaga ggcaggcgga    660
attcctagtg tagcggtgaa atgcgtagat attaggagga acaccagtgg cgaaggcggc    720
ctgctggacg atgactgacg ttgaggctcg aaagcgtggg gagcaaacag gattagatac    780
cctggtagtc cacgccgtaa acgatgacta ctaggtgtcg ggtggcaagg ccattcggtg    840
ccgcagcaaa cgcaataagt agtccacctg gggagtacgt tcgcaagaat gaaactcaaa    900
ggaattgacg gggacccgca caagcggtgg agcatgtggt ttaattcgaa gcaacgcgaa    960
```

```
gaaccttacc tgatcttgac atcccgatgc caaagcgcgt aacgcgctct ttcttcggaa    1020
catcggtgac aggtggtgca tggttgtcgt cagctcgtgt cgtgagatgt tgggttaagt    1080
cccgcaacga gcgcaacccc tatcttcagt agccagcatt ttggatgggc actctggaga    1140
gactgccagg gagaacctgg aggaaggtgg ggatgacgtc aaatcatcat gccccttatg    1200
accagggcta cacacgtgct acaatggcgt aaacaaaggg aggcgaaccc gcgagggtgg    1260
gcaaatccca aaataacgt ctcagttcgg attgtagtct gcaactcgac tacatgaagt    1320
tggaatcgct agtaatcgcg aatcagaatg tcgcggtgaa tacgttcccg ggtcttgtac    1380
acaccgcccg tcacaccatg ggagtcagta acgcccgaag ccggtgaccc aacccgtaag    1440
ggagggagcc gtcgaaggtg ggaccgataa ctggggtgaa gtcgtaacaa ggtagccgta    1500
tcggaaggtg cggctggatc acctccttc                                     1529
```

```
<210> SEQ ID NO 18
<211> LENGTH: 1433
<212> TYPE: DNA
<213> ORGANISM: Akkermansia muciniphila
<220> FEATURE:
<221> NAME/KEY: misc_feature
<222> LOCATION: (1)..(1433)
<223> OTHER INFORMATION: ATCC BAA-835 rRNA gene

<400> SEQUENCE: 18
```

```
aacgaacgct ggcggcgtgg ataagacatg caagtcgaac gagagaattg ctagcttgct      60
aataattctc tagtggcgca cgggtgagta acacgtgagt aacctgcccc cgagagcggg     120
atagccctgg gaaactggga ttaataccgc atagtatcga aagattaaag cagcaatgcg     180 cttgggatg gctcgcggc ctattagtta gttggtgagg taacggctca ccaaggcgat      240
gacgggtagc cggtctgaga ggatgtccgg ccacactgga actgagacac ggtccagaca     300
cctacgggtg gcagcagtcg agaatcattc acaatggggg aaaccctgat ggtgcgacgc     360
cgcgtggggg aatgaaggtc ttcggattgt aaaccctgt catgtgggag caaattaaaa     420
agatagtacc acaagaggaa gagacggcta actctgtgcc agcagccgcg gtaatacaga     480
ggtctcaagc gttgttcgga atcactgggc gtaaagcgtg cgtaggctgt ttcgtaagtc     540
gtgtgtgaaa ggcgcgggct caacccgcgg acggcacatg atactgcgag actagagtaa     600 tggagggga accggaattc tcggtgtagc agtgaaatgc gtagatatcg agaggaacac     660
tcgtggcgaa ggcgggttcc tggacattaa ctgacgctga ggcacgaagg ccaggggagc     720
gaaagggatt agataccct gtagtcctgg cagtaaacgg tgcacgcttg gtgtgcgggg     780
aatcgacccc ctgcgtgccg gagtaacgcg ttaagcgtgc cgcctgggga gtacggtcgc     840
aagattaaaa ctcaaagaaa ttgacgggga cccgcacaag cggtggagta tgtggcttaa     900
ttcgatgcaa cgcgaagaac cttacctggg cttgacatgt aatgaacaac atgtgaaagc     960
atgcgactct tcggaggcgt tacacaggtg ctgcatggcc gtcgtcagct cgtgtcgtga    1020
gatgtttggt taagtccagc aacgagcgca acccctgttg ccagttacca gcacgtgaag    1080
gtggggactc tggcgagact gcccagatca actgggagga aggtggggac gacgtcaggt    1140
cagtatggcc cttatgccca gggctgcaca cgtactacaa tgcccagtac agaggggcc     1200 gaagccgcga ggcggaggaa atcctaaaaa ctgggcccag ttcggactgt aggctgcaac    1260
ccgcctacac gaagccggaa tcgctagtaa tggcgcatca gctacggcgc cgtgaatacg    1320
ttcccgggtc ttgtacacac cgcccgtcac atcatggaag ctggtcgcac ccgaagtatc    1380
```
tgaagccaac cgcaaggagg cagggtccta aggtgagact ggtaactggg atg        1433

<210> SEQ ID NO 19
<211> LENGTH: 1484
<212> TYPE: DNA
<213> ORGANISM: Clostridium saccharogumia
<220> FEATURE:
<221> NAME/KEY: misc_feature
<222> LOCATION: (1)..(1484)
<223> OTHER INFORMATION: DSM17460 16S rRNA gene

<400> SEQUENCE: 19
aagagtttga tcctggctca ggatgaacgc tggcggcgtg cctaatacat gcaagtcgaa        60
cgcgggcagt aatgtccgag tggcgaacgg gtgagtaaga cataagtaac ctgcccttta       120
caggggata actattggaa acgatagcta agaccgcata ggtaaagata ccgcatggta        180
ggtttattaa aagtgccaag gcactggtag aggatggact tatggcgcat tagctggttg       240
gtgaggtaac ggctcaccaa ggcgacgatg cgtagccgac ctgagagggt gaccggccac       300
actgggactg agacacggcc cagactccta cgggaggcag cagtagggaa ttttcggcaa       360
tgggggaac cctgaccgag caacgccgcg tgaaggagga aggtcttcgg actgtaaact       420
tctgttataa aggaagaaag gcggatacag gaatggtat ccgagtgacg gtactttatg        480
aggaagccac ggctaactac gtgccagcag ccgcggtaat acgtaggtgg caagcgttat       540
ccggaattat tgggcgtaaa gagggagcag gcggcagcaa gggtctgtgg tgaaagactg       600
aagcttaact tcagtaagcc atagaaaccg gcagctaga gtgcaggaga ggatcgtgga        660
attccatgtg tagcggtgaa atgcgtagat atatggagga acaccagtgg cgaaggcgac       720
gatctggcct gcaactgacg ctcagtcccg aaagcgtggg gagcaaatag gattagatac       780
cctagtagtc cacgccgtaa acgatgagta ctaagtgttg ggagtcaaat ctcagtgctg       840
cagttaacgc agtaagtact ccgcctgagt agtacgttcg caagaatgaa actcaaagga       900
attgacgggg gcccgcacaa gcggtggagc atgtggttta attcgaagca acgcgaagaa       960
ccttaccagg tcttgacata tcataaagg ctccagagat ggagagatag gtatatggga       1020
tacaggtggt gcatggttgt cgtcagctcg tgtcgtgaga tgttgggtta agtcccgcaa      1080
cgagcgcaac ccttatcgtt agttaccatc attaagttgg ggactctagc gagactgcca      1140
gtgacaagct ggaggaaggc ggggatgacg tcaaatcatc atgccccctta tgacctgggc      1200
tacacacgtg ctacaatgga tggagcagag ggaagcgaag ccgcgaggtg gagcgaaacc      1260
cagaaaacca ttctcagttc ggattgtagt ctgcaactcg actacatgaa gttggaatcg      1320
ctagtaatcg cgaatcagca tgtcgcggtg aatacgttct cgggccttgt acacaccgcc      1380
cgtcacacca tgagagttga taacacccga agccggtggc ctaaccgcaa ggagggagct      1440
gtctaaggtg ggattgatga ttggggtgaa gtcgtaacaa gggt                       1484

<210> SEQ ID NO 20
<211> LENGTH: 1519
<212> TYPE: DNA
<213> ORGANISM: Clostridium ramosum
<220> FEATURE:
<221> NAME/KEY: misc_feature
<222> LOCATION: (1)..(1519)
<223> OTHER INFORMATION: DSM1402 16S rRNA gene

<400> SEQUENCE: 20
gagagtttga tcctggctca ggatgaacgc tggcggcgtg cctaatacat gcaagtcgaa        60
cgcgagcact tgtgctcgag tggcgaacgg gtgagtaata cataagtaac ctgccctaga       120

```
caggggggata actattggaa acggatagct aagaccgcat aggtacggac actgcatggt    180
gaccgtatta aaagtgcctc aaagcactgg tagaggatgg acttatggcg cattagctgg    240
ttggcggggt aacggcccac caaggcgacg atgcgtagcc gacctgagag ggtgaccggc    300
cacactggga ctgagacacg gcccagactc ctacgggagg cagcagtagg gaattttcgg    360
caatggggga aaccctgacc gagcaacgcc gcgtgaagga agaaggtttt cggattgtaa    420
acttctgtta taaagaagaa cggcggctac aggaaatggt agccgagtga cggtacttta    480
ttttagaaag ccacggctaa ctacgtgcca gcagccgcgg taatacgtag gtggcaagcg    540
ttatccggaa ttattgggcg taaagaggga gcaggcggca gcaagggtct gtggtgaaag    600
cctgaagctt aacttcagta agccatagaa accaggcagc tagagtgcag gagaggatcg    660
tggaattcca tgtgtagcgg tgaaatgcgt agatatatgg aggaacacca gtggcgaagg    720
cgacgatctg gcctgcaact gacgctcagt cccgaaagcg tggggagcaa ataggattag    780
ataccctagt agtccacgcc gtaaacgatg agtactaagt gttggatgtc aaagttcagt    840
gctgcagtta acgcaataag tactccgcct gagtagtacg ttcgcaagaa tgaaactcaa    900
aggaattgac gggggccgca caagcggtgg agcatgtggt ttaattcgaa gcaacgcgaa    960
gaaccttacc aggtcttgac atactcataa aggctccaga gatggagaga tagctatatg    1020
agatacaggt ggtgcatggt tgtcgtcagc tcgtgtcgtg agatgttggg ttaagtcccg    1080
caacgagcgc aaccctttatc gttagttacc atcattaagt tggggactct agcgagactg    1140
ccagtgacaa gctggaggaa ggcggggatg acgtcaaatc atcatgcccc ttatgacctg    1200
ggctacacac gtgctacaat ggatggtgca gagggaagcg aaccgcgagg tgaagcaaaa    1260
cccataaaaa ccattctcag ttcggattgt agtctgcaac tcgactacat gaagttggaa    1320
tcgctagtaa tcgcgaatca gcatgtcgcg gtgaatacgt tctcgggcct tgtacacacc    1380
gcccgtcaca ccacgagagt tgataacacc cgaagccggt ggcctaaccg caaggaagga    1440
gctgtctaag gtgggattga tgattggggt gaagtcgtaa caaggtatcc ctacgggaac    1500
gtgcggctgg atcacctcc                                                 1519
```

<210> SEQ ID NO 21
<211> LENGTH: 1438
<212> TYPE: DNA
<213> ORGANISM: Lactonifactor longoviformis
<220> FEATURE:
<221> NAME/KEY: misc_feature
<222> LOCATION: (1)..(1438)
<223> OTHER INFORMATION: DSM17459 16S rRNA gene

<400> SEQUENCE: 21

```
gagtttgatt atggctcagg atgaacgctg gcggcgtgct taacacatgc aagtcgaacg     60
aagcatatag agacgagtat ttcggtatga gtaactatat gactgagtgg cggacgggtg    120
agtaacgcgt ggataacctg cctcatacag ggggataaca gttagaaatg actgctaata    180
ccgcataagc gcacagtgct gcatggcaca gtgtgaaaag ctccggcggt atgagatgga    240
tccgcgtttg attagctagt tggtggggta aaggcctacc aaggcgacga tcaatagccg    300
acctgagagg gtgaccggcc acattgggac tgagacacgc ccaaactcct acgggaggc    360 agcagtgggg aatattgcac aatggggaa accctgatgc agcgacgccg cgtgaaggaa    420
gaagtatttc ggtatgtaaa cttctatcag caggaagaa aatgacggta cctgactaag    480
aagccccggc taattacgtg ccagcagccg cggtaatacg taaggggcaa gcgttatccg    540
```

-continued

```
gatttactgg gtgtaaaggg agcgtagacg gcagtgcaag tctgatgtga aagcccgggg    600
ctcaaccccg ggactgcatt ggaaactgtg cagctagagt gtcggagagg taagtggaat    660
tcctagtgta gcggtgaaat gcgtagatat taggaggaac accagtggcg aaggcggctt    720
actggacgat aactgacgtt gaggctcgaa agcgtgggga gcaaacagga ttagataccc    780
tggtagtcca cgccgtaaac gatgaatact aggtgtcggg cgccaaaggc gttcggtgcc    840
gcagcaaacg caataagtat tccacctggg gagtacgttc gcaagaatga aactcaaagg    900
aattgacggg gacccgcaca agcggtggag catgtggttt aattcgaagc aacgcgaaga    960
accttaccaa gtcttgacat ctgcctgacc ggtccgtaac aggaccccttc cttcgggaca   1020 ggcaagacag gtggtgcatg gttgtcgtca gctcgtgtcg tgagatgttg ggttaagtcc   1080
cgcaacgagc gcaaccctta tccttagtag ccagcaggta gagctgggca ctctagggag   1140
actgccaggg acaacctgga ggaaggtggg gatgacgtca aatcatcatg ccccttatga   1200
tttgggctac acacgtgcta caatggcgta aacaaaggga agcgaagggg tgacctgaag   1260
caaatcccaa aaataacgtc tcagttcgga ttgtagtctg caactcgact acatgaagct   1320
ggaatcgcta gtaatcgcga atcagaatgt cgcggtgaat acgttccccgg gtcttgtaca   1380 caccgcccgt cacaccatgg gagtcggata tgcccgaagc cggtgaccga acccgaaa     1438
```